United States Patent
Gotoh et al.

(10) Patent No.: US 9,676,686 B2
(45) Date of Patent: Jun. 13, 2017

(54) LIQUID CRYSTAL COMPOSITION CONTAINING NITROGEN-CONTAINING CYCLIC COMPOUND AND LIQUID CRYSTAL DISPLAY DEVICE

(71) Applicants: JNC CORPORATION, Tokyo (JP); JNC PETROCHEMICAL CORPORATION, Tokyo (JP)

(72) Inventors: Yasuyuki Gotoh, Tokyo (JP); Kazuo Okumura, Chiba (JP)

(73) Assignees: JNC CORPORATION, Tokyo (JP); JNC PETROCHEMICAL CORPORATION, Tokyo (JP)

( * ) Notice: Subject to any disclaimer, the term of this patent is extended or adjusted under 35 U.S.C. 154(b) by 0 days.

(21) Appl. No.: 14/994,150

(22) Filed: Jan. 13, 2016

(65) Prior Publication Data
US 2016/0208172 A1  Jul. 21, 2016

(30) Foreign Application Priority Data
Jan. 15, 2015  (JP) ................... 2015-005929

(51) Int. Cl.
| | |
|---|---|
| G02F 1/1333 | (2006.01) |
| C07C 13/28 | (2006.01) |
| C09K 19/34 | (2006.01) |
| C09K 19/30 | (2006.01) |
| C07D 207/12 | (2006.01) |
| C07D 223/08 | (2006.01) |
| C07D 207/14 | (2006.01) |
| C07D 223/12 | (2006.01) |
| C07D 403/12 | (2006.01) |
| C07D 405/14 | (2006.01) |
| C07D 403/14 | (2006.01) |
| C09K 19/32 | (2006.01) |
| C09K 19/04 | (2006.01) |
| C09K 19/18 | (2006.01) |

(52) U.S. Cl.
CPC ............ *C07C 13/28* (2013.01); *C07D 207/12* (2013.01); *C07D 207/14* (2013.01); *C07D 223/08* (2013.01); *C07D 223/12* (2013.01); *C07D 403/12* (2013.01); *C07D 403/14* (2013.01); *C07D 405/14* (2013.01); *C09K 19/3003* (2013.01); *C09K 19/3066* (2013.01); *C09K 19/3068* (2013.01); *C09K 19/32* (2013.01); *C09K 19/3402* (2013.01); *C09K 19/3483* (2013.01); *C09K 2019/0466* (2013.01); *C09K 2019/181* (2013.01); *C09K 2019/301* (2013.01); *C09K 2019/3009* (2013.01); *C09K 2019/3016* (2013.01); *C09K 2019/3019* (2013.01); *C09K 2019/3021* (2013.01); *C09K 2019/3042* (2013.01); *C09K 2019/3077* (2013.01); *C09K 2019/3083* (2013.01); *C09K 2019/3422* (2013.01); *C09K 2019/3425* (2013.01)

(58) Field of Classification Search
CPC ............ C09K 19/3068; C09K 19/3066; C09K 19/3003; C09K 19/32; C09K 19/3483; C09K 2019/3422; C09K 2019/3425; C09K 2019/3083; C09K 2019/3077; C09K 2019/0466; C09K 2019/181; C09K 2019/3009; C09K 2019/301; C09K 2019/3016; C09K 2019/3019; C09K 2019/3021; C09K 2019/3042; G02F 1/1333; C07C 13/28; C07D 207/12; C07D 223/12; C07D 207/14; C07D 403/12; C07D 405/14
USPC .............. 252/299.01, 299.6, 299.61; 428/1.1
See application file for complete search history.

(56) References Cited
U.S. PATENT DOCUMENTS 4,111,901 A   9/1978  Hechenbleikner

*Primary Examiner* — Geraldina Visconti
(74) *Attorney, Agent, or Firm* — Jianq Chyun IP Office

(57) ABSTRACT

The disclosure shows a liquid crystal composition that contains a compound having an effect of preventing photolysis of the liquid crystal composition and having high solubility in the liquid crystal composition, and that satisfies at least one of characteristics such as high maximum temperature, low minimum temperature, small viscosity, suitable optical anisotropy, large positive or negative dielectric anisotropy, large specific resistance, high stability to ultraviolet light or heat, and a suitable elastic constant, etc. and so on.

The disclosure shows a liquid crystal composition that contains a compound having the following azolidine ring (Q-1) or azepane ring (Q-2), a liquid crystal display device and so on.

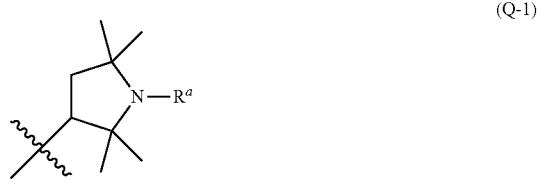

(Q-1)

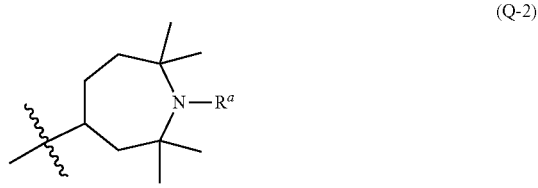

(Q-2)

18 Claims, No Drawings

LIQUID CRYSTAL COMPOSITION CONTAINING NITROGEN-CONTAINING CYCLIC COMPOUND AND LIQUID CRYSTAL DISPLAY DEVICE

CROSS-REFERENCE TO RELATED APPLICATION

This application claims the priority benefit of Japan application serial no. 2015-005929, filed on Jan. 15, 2015. The entirety of the above-mentioned patent application is hereby incorporated by reference herein and made a part of this specification.

FIELD OF THE INVENTION

The invention relates to a liquid crystal composition that contains a nitrogen-containing cyclic compound, and a liquid crystal display device. More specifically, the invention relates to a liquid crystal composition that contains a compound having an azolidine ring or azepane ring, and a liquid crystal display device. The invention also relates to a compound having an azepane ring.

DESCRIPTION OF THE RELATED ART

For liquid crystal display devices, a classification based on an operating mode of liquid crystal molecules includes phase change (PC), twisted nematic (TN), super twisted nematic (STN), electrically controlled birefringence (ECB), optically compensated bend (OCB), in-plane switching (IPS), vertical alignment (VA), fringe field switching (FFS), and field-induced photo-reactive alignment (FPA) modes, etc. A classification based on a driving mode of the device includes passive matrix (PM) and active matrix (AM). The PM type is classified into static type and multiplex type, etc.; the AM type is classified into thin-film transistor (TFT) type and metal insulator metal (MIM) type, etc. The TFT type is classified into amorphous silicon and polycrystal silicon. The latter is classified into a high temperature type and a low temperature type according to a production process. A classification based on a light source includes a reflective type utilizing natural light, a transmissive type utilizing backlight, and a transflective type utilizing both natural light and backlight.

A liquid crystal display device contains a liquid crystal composition having a nematic phase. This composition has suitable characteristics. By improving the characteristics of this composition, an AM device having good characteristics can be obtained. The following Table 1 summarizes a relationship of the characteristics between two aspects. The characteristics of the composition are further described based on a commercially available AM device. A temperature range of the nematic phase relates to a temperature range in which the device can be used. A preferred maximum temperature of the nematic phase is about 70° C. or higher, and a preferred minimum temperature of the nematic phase is about −10° C. or lower. Viscosity of the composition relates to response time of the device. Short response time is preferred for displaying moving images on the device. A shorter response time even by one millisecond is desirable. Accordingly, small viscosity in the composition is preferred, and small viscosity at low temperature is more preferred.

TABLE 1

Characteristics of Composition and AM Device

| No | Characteristics of composition | Characteristics of AM device |
|---|---|---|
| 1 | Wide temperature range of a nematic phase | Wide usable temperature range |
| 2 | Small viscosity | Short response time |
| 3 | Suitable optical anisotropy | Large contrast ratio |
| 4 | Large positive or negative dielectric anisotropy | Low threshold voltage; small electric power consumption Large contrast ratio |
| 5 | Large specific resistance | Large voltage holding ratio; large contrast ratio |
| 6 | High stability to ultraviolet light and heat | Long service life |
| 7 | Large elastic constant | Large contrast ratio; short response time |

Optical anisotropy of the composition relates to the contrast ratio of the device. Depending on the mode of the device, large optical anisotropy or small optical anisotropy, namely suitable optical anisotropy, is required. A product (Δn×d) of the optical anisotropy (Δn) of the composition and a cell gap (d) of the device is designed so as to maximize the contrast ratio. A suitable value of the product depends on the type of the operating mode. A composition having large optical anisotropy is preferred for a device having a small cell gap. Large dielectric anisotropy in the composition contributes to a low threshold voltage, small electric power consumption and a large contrast ratio in the device. Accordingly, large positive or negative dielectric anisotropy is preferred. Large specific resistance in the composition contributes to a large voltage holding ratio and a large contrast ratio in the device. Accordingly, a composition having large specific resistance not only at room temperature but also at high temperature at an early stage is preferred. A composition having large specific resistance not only at room temperature but also at high temperature after a long-time use is preferred. Stability of the composition to ultraviolet light or heat relates to service life of the device. When the stability is high, the device has long service life. Such characteristics are preferred in an AM device for use in liquid crystal projectors and liquid crystal TVs, etc.

In a polymer sustained alignment (PSA)-type liquid crystal display device, a liquid crystal composition containing a polymer is used. First of all, the composition to which a small amount of a polymerizable compound is added is poured into the device. Next, while a voltage is applied between substrates of the device, the composition is irradiated with ultraviolet light. The polymerizable compound is polymerized so as to generate a polymer network structure in the composition. In this composition, since it becomes possible to control the alignment of liquid crystal molecules by the polymer, the response time of the device is shortened and image burn-in is improved. Such an effect of the polymer can be expected in the devices having a mode such as a TN mode, an ECB mode, an OCB mode, an IPS mode, a VA mode, an FFS mode, or an FPA mode.

A liquid crystal composition is prepared by mixing liquid crystal compounds. Additives such as a polymerizable compound, a polymerization initiator, a polymerization inhibitor, an optically active compound, an antioxidant, an ultraviolet absorbent, a light stabilizer, a heat stabilizer and a defoamer are added to this composition if necessary. Among them, the light stabilizer has an effect of preventing the liquid crystal compounds from being decomposed by light from a backlight or the sun. Due to this effect, the high voltage holding ratio of the device is maintained, and service life of the device is thus increased. A hindered amine light stabilizer (HALS) is suitable for such purposes. However, development of a more excellent light stabilizer has been expected.

PRIOR-ART DOCUMENTS

Patent Documents

[Patent Document 1] U.S. Pat. No. 4,111,901

SUMMARY OF THE INVENTION

Problems to be Solved

A first subject of the invention is to provide a liquid crystal composition that contains a compound having an effect of preventing photolysis of the liquid crystal composition and having high solubility in the liquid crystal composition, and that satisfies at least one of characteristics such as high maximum temperature of a nematic phase, low minimum temperature of a nematic phase, small viscosity, suitable optical anisotropy, large positive or negative dielectric anisotropy, large specific resistance, high stability to ultraviolet light or heat, and a suitable elastic constant, etc. This subject is especially to provide a liquid crystal composition stable to light. A second subject is to provide a liquid crystal display device that contains this composition and that has a wide usable temperature range, short response time, a high voltage holding ratio, a low threshold voltage, a large contrast ratio, and long service life. A third subject is to provide a compound that has an effect of preventing photolysis of a liquid crystal composition and that has high solubility in the liquid crystal composition.

Means for Solving the Problems

The invention relates to a liquid crystal composition that contains at least one compound (1) selected from the group consisting of compounds represented by formulae (1-1) to (1-4), and at least one compound selected from the group consisting of compounds represented by formulae (2) to (4), and to a liquid crystal display device that contains this composition, and so on.

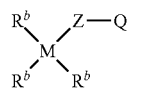

(1-1)

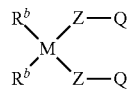

(1-2)

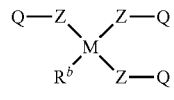

(1-3)

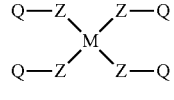

(1-4)

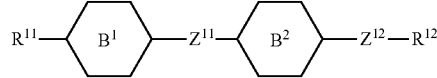

(2)

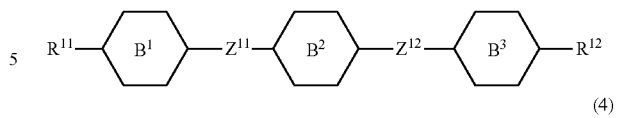

(3)

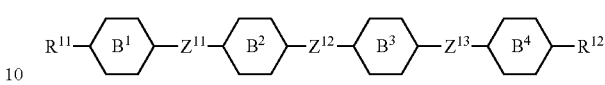

(4)

Moreover, definitions of symbols in formulae (1-1) to (1-4) and formulae (2) to (4) are described in item 1.

Effects of the Invention

A first advantage of the invention is to provide a liquid crystal composition that contains a compound having an effect of preventing photolysis of the liquid crystal composition and having high solubility in the liquid crystal composition, and that satisfies at least one of characteristics such as high maximum temperature of a nematic phase, low minimum temperature of a nematic phase, small viscosity, suitable optical anisotropy, large positive or negative dielectric anisotropy, large specific resistance, high stability to ultraviolet light or heat, and a suitable elastic constant, etc. This advantage is especially to provide a liquid crystal composition stable to light. A second advantage is to provide a liquid crystal display device that contains this composition and that has a wide usable temperature range, short response time, a high voltage holding ratio, a low threshold voltage, a large contrast ratio, and long service life. A third advantage is to provide a compound that has an effect of preventing photolysis of a liquid crystal composition and that has high solubility in the liquid crystal composition.

DESCRIPTION OF THE EMBODIMENTS

The terms in this specification are defined as follows. Liquid crystal compound is a generic term for compounds having a liquid crystal phase such as nematic phase or smectic phase etc., or compounds having no liquid crystal phase but are added for adjusting characteristics of a composition such as maximum temperature, minimum temperature, viscosity, and dielectric anisotropy. These compounds have a six-membered ring such as 1,4-cyclohexylene or 1,4-phenylene, and a rod-like molecular structure. A liquid crystal composition is prepared by mixing such liquid crystal compounds. The ratio (content) of the liquid crystal compound is expressed by a weight percentage (wt %) based on the weight of the liquid crystal composition. Additives such as a polymerizable compound, a polymerization initiator, a polymerization inhibitor, an optically active compound, an antioxidant, an ultraviolet absorbent, a light stabilizer, a heat stabilizer and a defoamer are added to this composition if necessary. Similarly to the liquid crystal compound, a ratio (amount added) of the additive is expressed by a weight percentage (wt %) based on the weight of the liquid crystal composition. Parts per million (ppm) may also be used.

Liquid crystal display device is a generic term for liquid crystal display panels and liquid crystal display modules. Liquid crystal compound, liquid crystal composition and liquid crystal display device are sometimes simply referred to as compound, composition, and device, respectively. A clearing point is the transition temperature between a liquid crystal phase and an isotropic phase in a liquid crystal compound. The minimum temperature of a liquid crystal phase is the transition temperature between solids and a liquid crystal phase (a smectic phase, a nematic phase or the like) in a liquid crystal compound. The maximum temperature of a nematic phase is the transition temperature between a nematic phase and an isotropic phase in a liquid crystal composition, and is sometimes simply referred to as maximum temperature. The minimum temperature of a nematic phase is sometimes simply referred to as minimum temperature.

In formulae (2) to (15), the symbols B' and C', etc. surrounded by hexagons respectively correspond to ring B' and ring C', etc. The symbol of the terminal group $R^{11}$ is used in a plurality of compounds. In these compounds, the two groups represented by arbitrary two $R^{11}$'s may be the same or different. For example, in one case, $R^{11}$ represents ethyl in both compounds (2) and (3). In another case, $R^{11}$ represents ethyl in the compound (2), and represents propyl in the compound (3). This rule also applies to symbols such as other terminal groups, rings, and linking groups, etc.

Compounds represented by formulae (1-1) to (1-4) are sometimes simply referred to as compound (1). A compound represented by formula (8) is sometimes simply referred to as a compound (8). "Compound (8)" means one compound represented by formula (8), a mixture of two compounds represented by formula (8), or a mixture of three or more compounds represented by formula (8). This rule also applies to compounds represented by other formulae. In formula (8), when i is 2, two $D^1$'s are present. In this compound, the two groups represented by the two $D^1$'s may be the same or different. This rule also applies to arbitrary two $D^1$'s when i is greater than 2. This rule also applies to other symbols. Two Q's are present in formula (1-2). In this compound, the two groups represented by the two Q's may be the same or different. This rule also applies to formula (1-3) and so on in which more than two Q's are present. This rule also applies to other symbols.

The expression "at least one 'A'" means the number of 'A' is arbitrary. The expression "at least one 'A' is optionally replaced with 'B'" means that when the number of 'A' is one, the position of 'A' is arbitrary, and when the number of 'A' is two or more, the positions of 'A' can be freely selected without any restriction. The expression "at least one A is optionally replaced with B, C or D" means that at least one A is replaced with B, at least one A is replaced with C or at least one A is replaced with D, and also means that a plurality of A's are replaced with at least two of B, C and D. For example, the scope of "alkyl in which at least one —CH$_2$— (or —CH$_2$CH$_2$—) is optionally replaced with —O— (or —CH=CH—)" includes alkyl, alkenyl, alkoxy, alkoxyalkyl, alkoxyalkenyl and alkenyloxyalkyl. Moreover, it is undesirable that two successive —CH$_2$— be replaced with —O— to form —O—O—, and it is also undesirable that —CH$_2$— in a methyl moiety (—CH$_2$—H) in alkyl or the like be replaced with —O— to form —O—H.

Halogen includes fluorine, chlorine, bromine and iodine. The halogen is preferably fluorine or chlorine, and more preferably fluorine. In a liquid crystal compound, alkyl is straight or branched, and does not include cyclic alkyl. Generally, straight alkyl is preferred to branched alkyl. The same rules also apply to terminal groups such as alkoxy and alkenyl, etc. To raise the maximum temperature of a nematic phase, the stereo configuration of 1,4-cyclohexylene is preferably trans rather than cis. 2-fluoro-1,4-phenylene means the following two divalent groups. In a chemical formula, fluorine may be leftward (L) or rightward (R). This rule also applies to an asymmetrical divalent group such as tetrahydropyran-2,5-diyl, which is formed by removing two hydrogens from a ring.

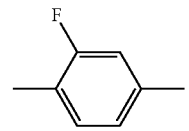

(L)

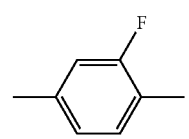

(R)

The invention includes the following items.

Item 1 is a liquid crystal composition that contains at least one compound (1) selected from the group consisting of compounds represented by formulae (1-1) to (1-4) and at least one compound selected from the group consisting of compounds represented by formulae (2) to (4).

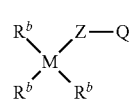

(1-1)

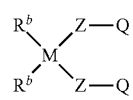

(1-2)

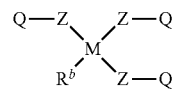

(1-3)

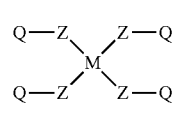

(1-4)

In formulae (1-1) to (1-4),

M is a tetravalent aliphatic hydrocarbon group having 1 to 20 carbons or a tetravalent aromatic hydrocarbon group having 1 to 20 carbons, wherein at least one —CH$_2$— in these groups is optionally replaced with —O— or —S—, one or two —CH=CH— in these groups are optionally replaced with —CH=N—, and at least one hydrogen in these groups is optionally replaced with fluorine or chlorine;

Z is a single bond, —O—, —COO—, or —OCO—;

Q is a monovalent group represented by formula (Q-1) or (Q-2), wherein $R^a$ is hydrogen, —O., —OH, or —R$^1$;

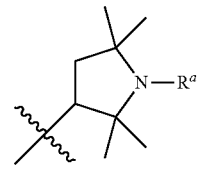

(Q-1)

-continued

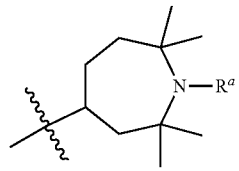
(Q-2)

$R^b$ is hydrogen, fluorine, or —$R^2$; and
$R^1$ and $R^2$ are independently alkyl having 1 to 20 carbons, arylalkyl having 1 to 20 carbons, or aryl having 1 to 20 carbons, wherein at least one —$CH_2$— in the alkyl is optionally replaced with —O—, —CO—, —COO—, or —OCO—, and —$CH_3$ located at a terminal of the alkyl is optionally replaced with —$NHR^3$ or —$NR^4R^5$, wherein $R^3$, $R^4$ and $R^5$ are independently alkyl having 1 to 10 carbons.

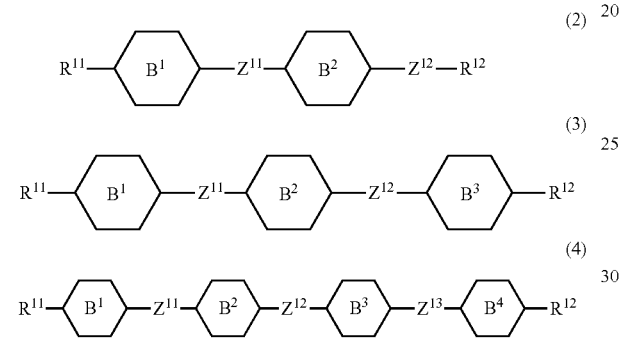

In formulae (2) to (4),
$R^{11}$ and $R^{12}$ are independently alkyl having 1 to 10 carbons or alkenyl having 2 to 10 carbons, wherein at least one —$CH_2$— in the alkyl or alkenyl is optionally replaced with —O—, and at least one hydrogen in the alkyl or alkenyl is optionally replaced with fluorine; ring $B^1$, ring $B^2$, ring $B^3$, and ring $B^4$ are independently 1,4-cyclohexylene, 1,4-phenylene, 2-fluoro-1,4-phenylene, 2,5-difluoro-1,4-phenylene, or pyrimidine-2,5-diyl; and $Z^{11}$, $Z^{12}$, and $Z^{13}$ are independently a single bond, —$CH_2CH_2$—, —CH═CH—, —C≡C—, or —COO—.

Item 2 is the liquid crystal composition described in item 1, wherein in formulae (1-1) to (1-4) described in item 1, at least one Q is a monovalent group represented by formula (Q-2).

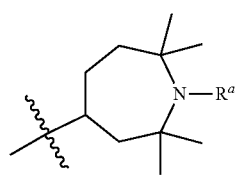
(Q-2)

In formula (Q-2), $R^a$ is hydrogen, —O., —OH, or —$R^1$; and $R^1$ is alkyl having 1 to 20 carbons, arylalkyl having 1 to 20 carbons, or aryl having 1 to 20 carbons, wherein at least one —$CH_2$— in the alkyl is optionally replaced with —O—, —CO—, —COO—, or —OCO—, and —$CH_3$ located at a terminal of the alkyl is optionally replaced with —$NHR^3$ or —$NR^4R^5$, wherein $R^3$, $R^4$ and $R^5$ are independently alkyl having 1 to 10 carbons.

Item 3 is the liquid crystal composition described in item 1 or item 2, and contains a compound represented by any one of formulae (1-1a) to (1-4a).

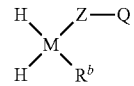
(1-1a)

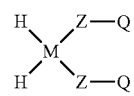
(1-2a)

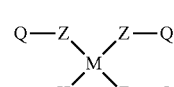
(1-3a)

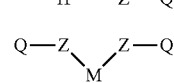
(1-4a)

In formulae (1-1a) to (1-4a),

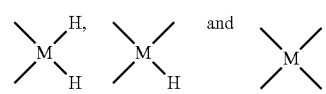

are divalent, trivalent or tetravalent groups, formed by removing hydrogen from alkane having 1 to 15 carbons, alkane having 1 to 15 carbons in which at least one —$CH_2$— is replaced with —O—, cyclohexane, bicyclohexane, decahydronaphthalene, tetrahydropyran, dioxane, benzene, benzene in which at least one hydrogen is replaced with fluorine, biphenyl, naphthalene, pyridine, or pyrimidine;
Z is a single bond, —O—, —COO—, or —OCO—;
Q is a monovalent group represented by formula (Q-1) or (Q-2), wherein $R^a$ is hydrogen, —O., —OH, or —$R^1$;

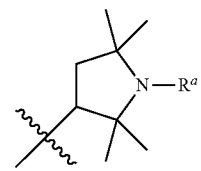
(Q-1)

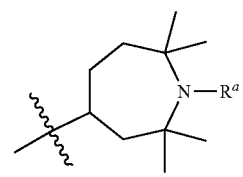
(Q-2)

$R^b$ is hydrogen, fluorine, or —$R^2$; and
$R^1$ and $R^2$ are independently alkyl having 1 to 20 carbons, arylalkyl having 1 to 20 carbons, or aryl having 1 to 20 carbons, wherein at least one —$CH_2$— in the alkyl is optionally replaced with —O—, and —$CH_3$ located at a terminal of the alkyl is optionally replaced with —$NHR^3$ or —$NR^4R^5$, wherein $R^3$, $R^4$ and $R^5$ are independently alkyl having 1 to 10 carbons.

Item 4 is the liquid crystal composition described in item 3, wherein in formulae (1-1a) to (1-4a) described in item 3,

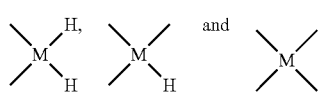
are independently any one of a divalent group represented by formulae (M-1) to (M-7), a trivalent group represented by formulae (M-8) to (M-23), and a tetravalent group represented by formulae (M-24) to (M-42), wherein c is an integer of 0 to 16.
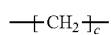 (M-1)
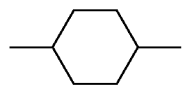 (M-2)
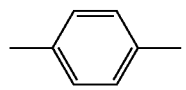 (M-3)
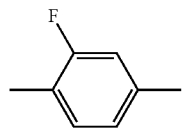 (M-4)
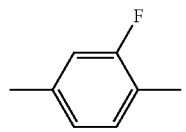 (M-5)
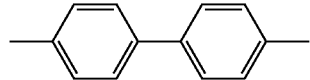 (M-6)
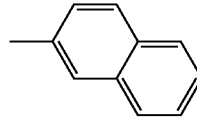 (M-7)
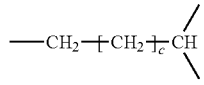 (M-8)
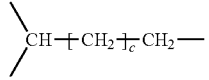 (M-9)
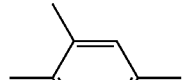 (M-10)
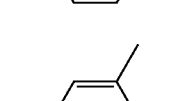 (M-11)
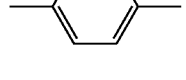 (M-12)
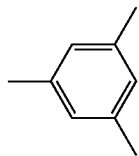 (M-13)
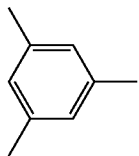 (M-14)
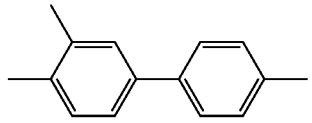 (M-15)
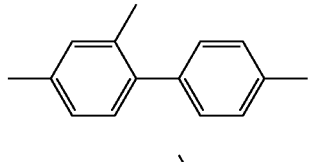 (M-16)
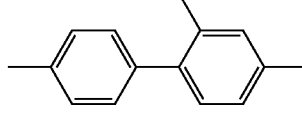 (M-17)
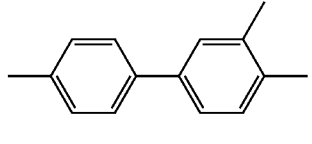 (M-18)
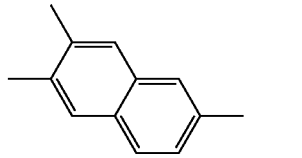 (M-19)
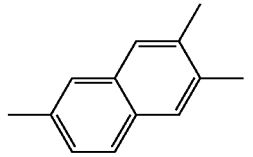 (M-20)
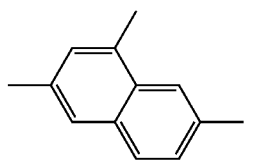 (M-21)
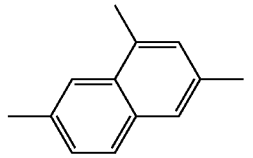

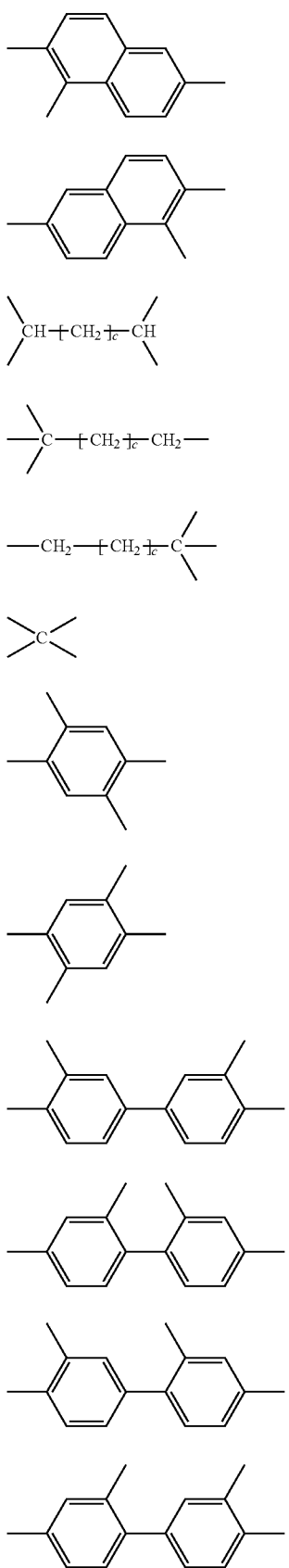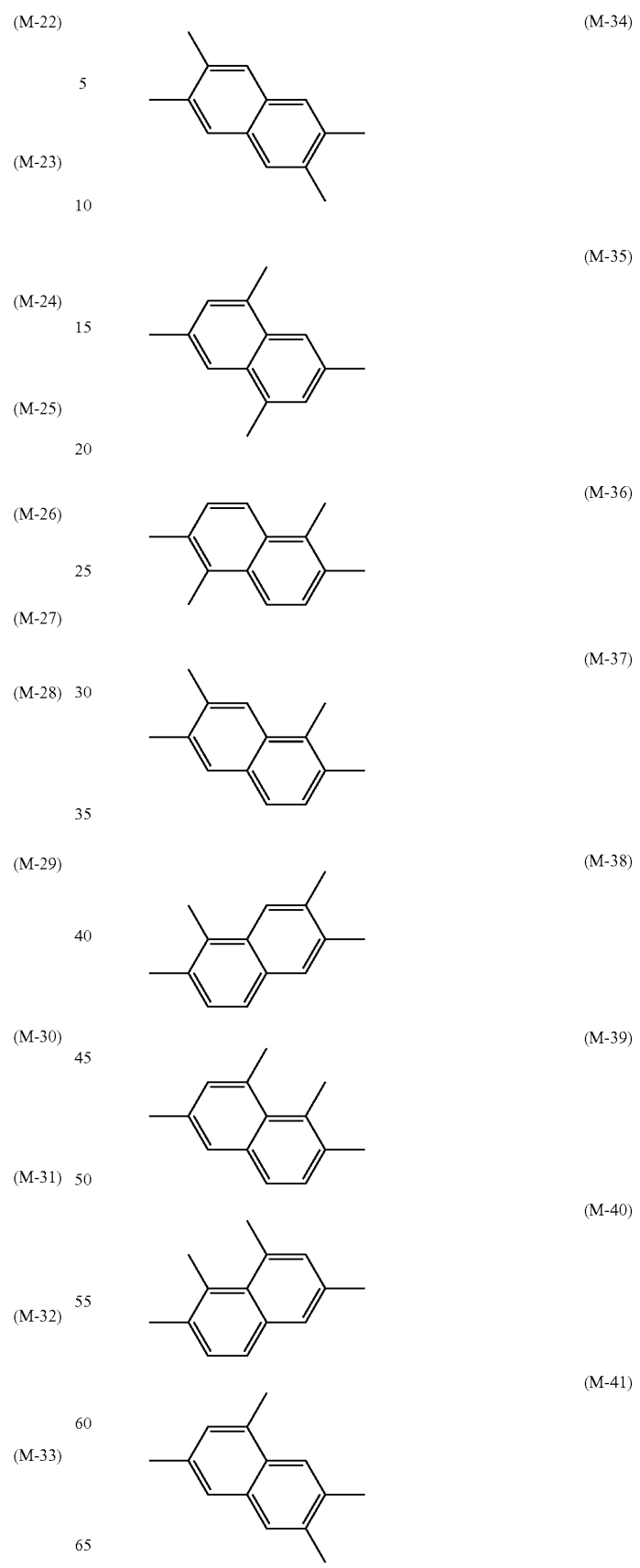

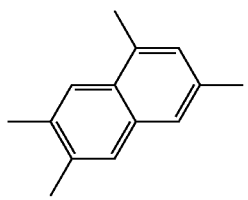
(M-42)
Item 5 is the liquid crystal composition described in any one of items 1 to 4, and contains a compound represented by any one of formulae (1a) to (1s).
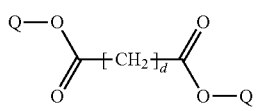
(1a)
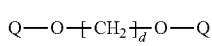
(1b)
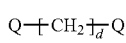
(1c)
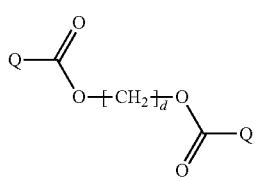
(1d)
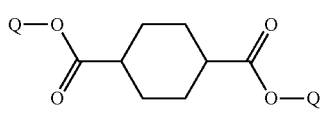
(1e)
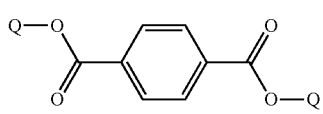
(1f)
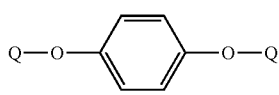
(1g)
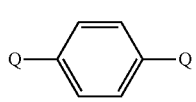
(1h)
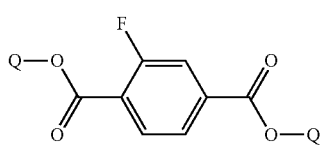
(1i)
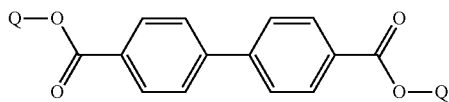
(1j)
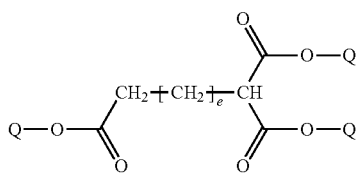
(1k)
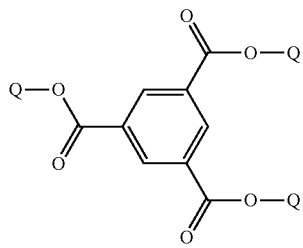
(1l)
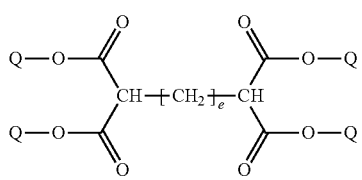
(1m)
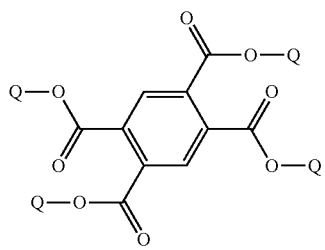
(1n)
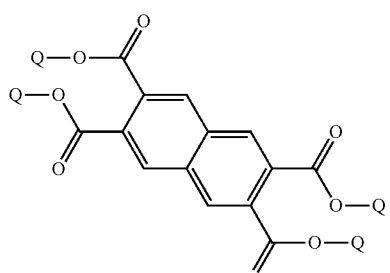
(1o)
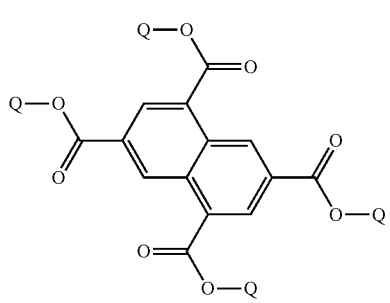
(1p)
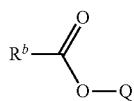
(1q)
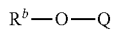
(1r)
$R^4-N-Q$
$\quad\ \ |$
$\quad\ R^5$
(1s)
In formulae (1a) to (1s),
d is an integer of 1 to 14;
e is an integer of 0 to 13;
Q is a monovalent group represented by formula (Q-1) or (Q-2), wherein $R^a$ is hydrogen, —O., —OH, or —$R^1$;

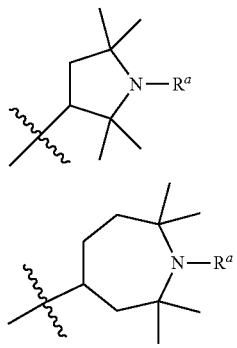

(Q-1)

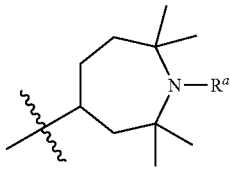

(Q-2)

$R^b$ is hydrogen or $—R^2$;
$R^1$ and $R^2$ are independently alkyl having 1 to 20 carbons, arylalkyl having 1 to 20 carbons, or aryl having 1 to 20 carbons, wherein at least one $—CH_2—$ in the alkyl is optionally replaced with $—O—$; and $R^4$ and $R^5$ are independently alkyl having 1 to 10 carbons.

Item 6 is the liquid crystal composition described in item 5, wherein in formulae (Q-1) and (Q-2) described in item 5, $R^a$ is hydrogen, $—O.$, $—OH$, alkyl having 1 to 10 carbons, or alkoxy having 1 to 10 carbons.

Item 7 is the liquid crystal composition described in any one of items 1 to 6, and contains a compound represented by any one of formulae (1a-1), (1f), (1h), and (1n).

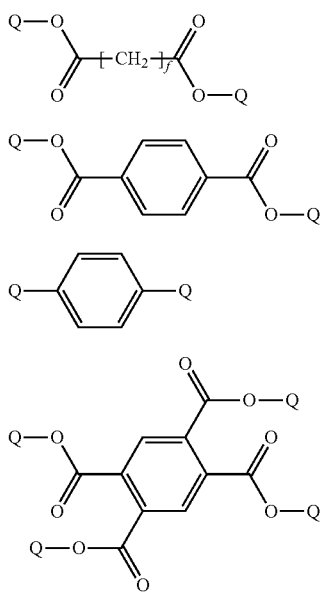

In formulae (1a-1), (1f), (1h), and (1n),
f is an integer of 1 to 12; and
Q is a monovalent group represented by formula (Q-1) or (Q-2), wherein $R^a$ is hydrogen or alkyl having 1 to 15 carbons.

Item 8 is the liquid crystal composition described in any one of items 1 to 7, further containing at least one compound selected from the group consisting of compounds represented by formulae (5) to (7).

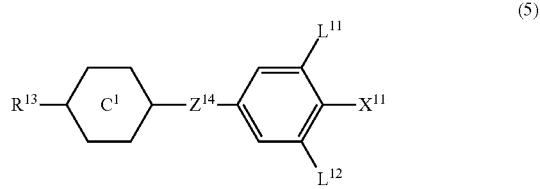

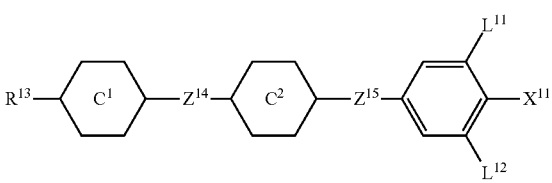

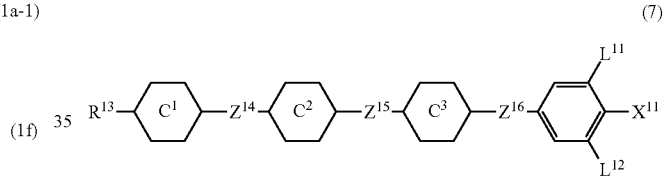

In formulae (5) to (7),
$R^{13}$ is alkyl having 1 to 10 carbons or alkenyl having 2 to 10 carbons, wherein at least one $—CH_2—$ in the alkyl and alkenyl is optionally replaced with $—O—$, and at least one hydrogen in the alkyl and alkenyl is optionally replaced with fluorine;
$X^{11}$ is fluorine, chlorine, $—OCF_3$, $—OCHF_2$, $—CF_3$, $—CHF_2$, $—CH_2F$, $—OCF_2CHF_2$, or $—OCF_2CHFCF_3$; ring $C^1$, ring $C^2$ and ring $C^3$ are independently 1,4-cyclohexylene, 1,4-phenylene in which at least one hydrogen is optionally replaced with fluorine, tetrahydropyran-2,5-diyl, 1,3-dioxane-2,5-diyl, or pyrimidine-2,5-diyl;
$Z^{14}$, $Z^{15}$, and $Z^{16}$ are independently a single bond, $—CH_2CH_2—$, $—CH=CH—$, $—C≡C—$, $—COO—$, $—CF_2O—$, $—OCF_2—$, $—CH_2O—$, or $—(CH_2)_4—$; and $L^{11}$ and $L^{12}$ are independently hydrogen or fluorine.

Item 9 is the liquid crystal composition described in any one of items 1 to 8, further containing at least one compound selected from the group consisting of compounds represented by formula (8).

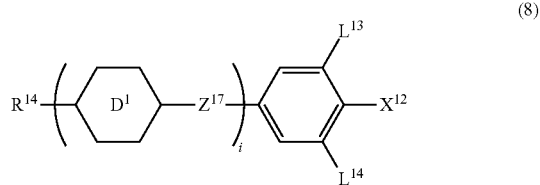

In formula (8), $R^{14}$ is alkyl having 1 to 10 carbons or alkenyl having 2 to 10 carbons, wherein at least one —CH$_2$— in the alkyl and alkenyl is optionally replaced with —O—, and at least one hydrogen in the alkyl and alkenyl is optionally replaced with fluorine;

$X^{12}$ is —C≡N or —C≡C—C≡N;

ring $D^1$ is 1,4-cyclohexylene, 1,4-phenylene in which at least one hydrogen is optionally replaced with fluorine, tetrahydropyran-2,5-diyl, 1,3-dioxane-2,5-diyl, or pyrimidine-2,5-diyl;

$Z^{17}$ is a single bond, —CH$_2$CH$_2$—, —C≡C—, —COO—, —CF$_2$O—, —OCF$_2$—, or —CH$_2$O—;

$L^{13}$ and $L^{14}$ are independently hydrogen or fluorine; and i is 1, 2, 3, or 4.

Item 10 is the liquid crystal composition described in any one of items 1 to 9, further containing at least one compound selected from the group consisting of compounds represented by formulae (9) to (15).

—CH$_2$— in the alkyl and alkenyl is optionally replaced with —O—, and at least one hydrogen in the alkyl and alkenyl is optionally replaced with fluorine;

ring $E^1$, ring $E^2$, ring $E^3$, and ring $E^4$ are independently 1,4-cyclohexylene, 1,4-cyclohexenylene, 1,4-phenylene in which at least one hydrogen is optionally replaced with fluorine, tetrahydropyran-2,5-diyl, or decahydronaphthalene-2,6-diyl;

ring $E^5$ and ring $E^6$ are independently 1,4-cyclohexylene, 1,4-cyclohexenylene, 1,4-phenylene, tetrahydropyran-2,5-diyl, or decahydronaphthalene-2,6-diyl;

$Z^{18}$, $Z^{19}$, $Z^{20}$, and $Z^{21}$ are independently a single bond, —CH$_2$CH$_2$—, —COO—, —CH$_2$O—, —OCF$_2$—, or —OCF$_2$CH$_2$CH$_2$—;

$L^{15}$ and $L^{16}$ are independently fluorine or chlorine;

$S^{11}$ is hydrogen or methyl;

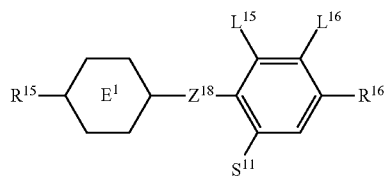

(9)

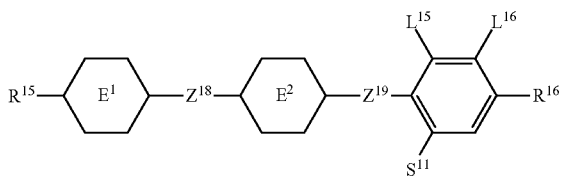

(10)

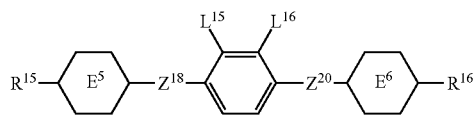

(11)

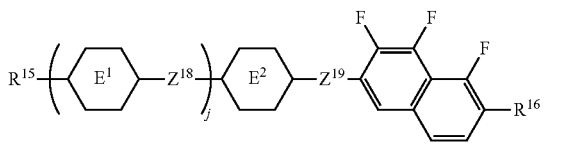

(12)

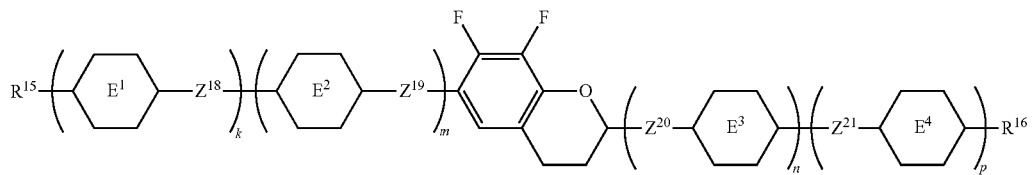

(13)

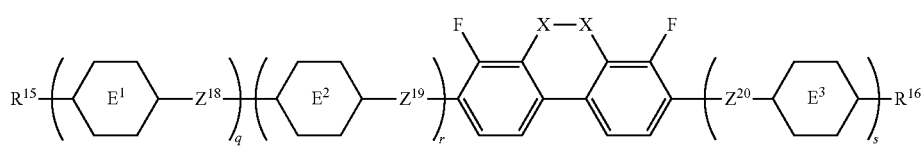

(14)

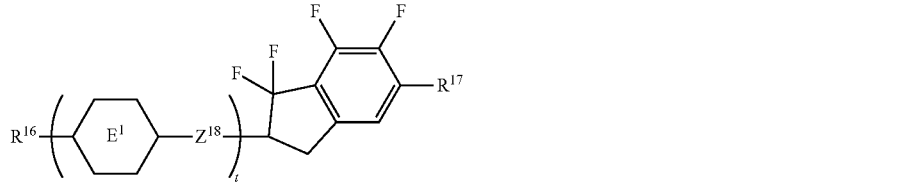

(15)

In formulae (9) to (15), $R^{15}$ and $R^{16}$ are independently alkyl having 1 to 10 carbons or alkenyl having 2 to 10 carbons, wherein at least one —CH$_2$— in the alkyl and alkenyl is optionally replaced with —O—, and at least one hydrogen in the alkyl and alkenyl is optionally replaced with fluorine;

$R^{17}$ is hydrogen, fluorine, alkyl having 1 to 10 carbons, or alkenyl having 2 to 10 carbons, wherein at least one X is —CHF— or —CF$_2$—; and j, k, m, n, p, q, r and s are independently 0 or 1, the sum of k, m, n and p is 1 or 2, the sum of q, r and s is 0, 1, 2, or 3, and t is 1, 2, or 3.

Item 11 is at least one compound selected from the group consisting of compounds represented by formulae (1-1) to (1-4).

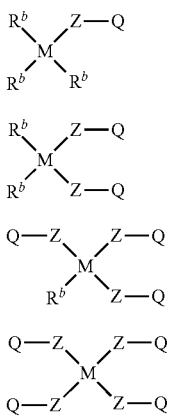 (1-1)

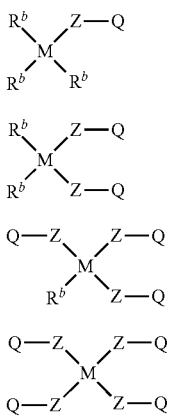 (1-2)

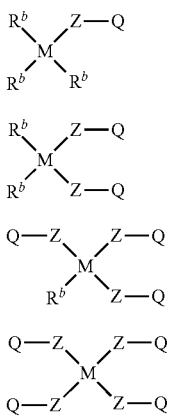 (1-3)

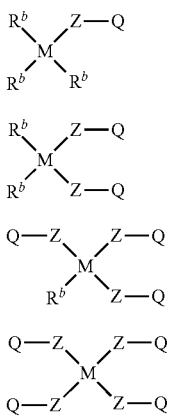 (1-4)

In formulae (1-1) to (1-4),

M is a tetravalent aliphatic hydrocarbon group having 1 to 20 carbons or a tetravalent aromatic hydrocarbon group having 1 to 20 carbons, wherein at least one —$CH_2$— in these groups is optionally replaced with —O— or —S—, one or two —CH=CH— in these groups are optionally replaced with —CH=N—, and at least one hydrogen in these groups is optionally replaced with fluorine or chlorine;

Z is a single bond, —O—, —COO—, or —OCO—;

Q is a monovalent group represented by formula (Q-1) or (Q-2), and at least one Q is a monovalent group represented by formula (Q-2), wherein $R^a$ is hydrogen, —O·, —OH, or —$R^1$;

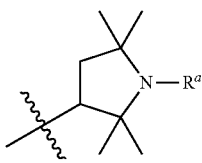 (Q-1)

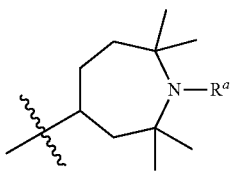 (Q-2)

$R^b$ is hydrogen, fluorine, or —$R^2$; and $R^1$ and $R^2$ are independently alkyl having 1 to 20 carbons, arylalkyl having 1 to 20 carbons, or aryl having 1 to 20 carbons, wherein at least one —$CH_2$— in the alkyl is optionally replaced with —O—, —CO—, —COO—, or —OCO—, and —$CH_3$ located at a terminal of the alkyl is optionally replaced with —$NHR^3$ or —$NR^4R^5$, wherein $R^3$, $R^4$ and $R^5$ are independently alkyl having 1 to 10 carbons.

Item 12 is the compound described in item 11, represented by any one of formulae (1-1a) to (1-4a).

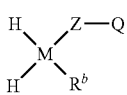 (1-1a)

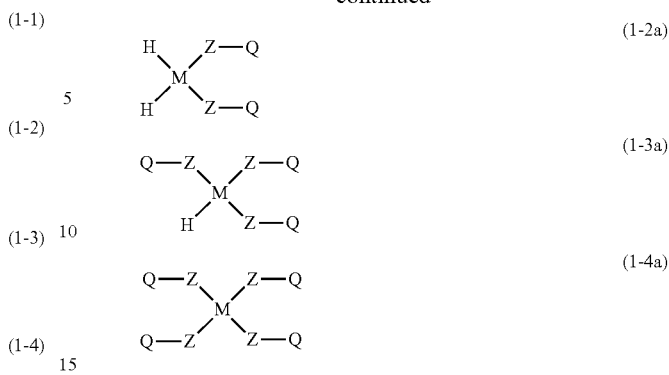

(1-2a)

(1-3a)

(1-4a)

In formulae (1-1a) to (1-4a),

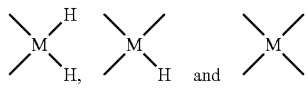

are divalent, trivalent or tetravalent groups, formed by removing hydrogen from alkane having 1 to 15 carbons, alkane having 1 to 15 carbons in which at least one —$CH_2$— is replaced with —O—, cyclohexane, bicyclohexane, decahydronaphthalene, tetrahydropyran, dioxane, benzene, benzene in which at least one hydrogen is replaced with fluorine, biphenyl, naphthalene, pyridine, or pyrimidine;

Z is a single bond, —O—, —COO—, or —OCO—;

Q is a monovalent group represented by formula (Q-1) or (Q-2), and at least one Q is a monovalent group represented by formula (Q-2), wherein $R^a$ is hydrogen, —O·, —OH, or —$R^1$;

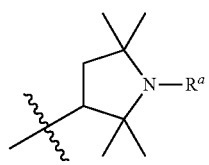 (Q-1)

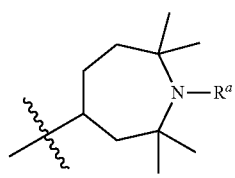 (Q-2)

$R^b$ is hydrogen, fluorine, or —$R^2$; and $R^1$ and $R^2$ are independently alkyl having 1 to 20 carbons, arylalkyl having 1 to 20 carbons, or aryl having 1 to 20 carbons, wherein at least one —$CH_2$— in the alkyl is optionally replaced with —O—, and —$CH_3$ located at a terminal of the alkyl is optionally replaced with —$NHR^3$ or —$NR^4R^5$, wherein $R^3$, $R^4$ and $R^5$ are independently alkyl having 1 to 10 carbons.

Item 13 is the compound described in item 12, wherein in formulae (1-1a) to (1-4a) described in item 12,
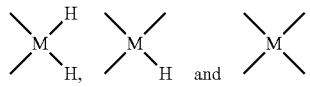
are independently any one of a divalent group represented by formulae (M-1) to (M-7), a trivalent group represented by formulae (M-8) to (M-23), and a tetravalent group represented by formulae (M-24) to (M-42), wherein c is an integer of 0 to 16.
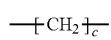 (M-1)
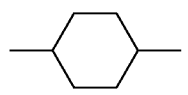 (M-2)
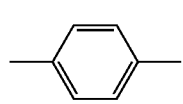 (M-3)
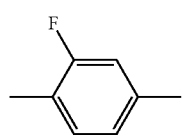 (M-4)
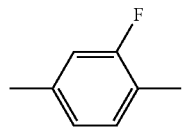 (M-5)
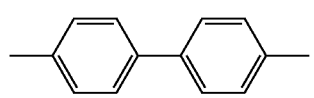 (M-6)
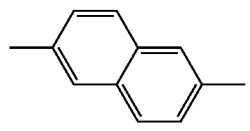 (M-7)
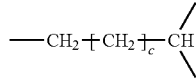 (M-8)
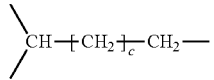 (M-9)
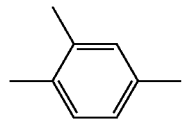 (M-10)
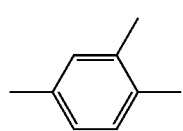 (M-11)
-continued
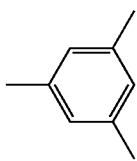 (M-12)
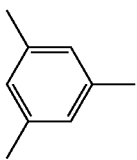 (M-13)
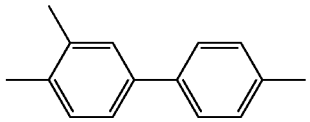 (M-14)
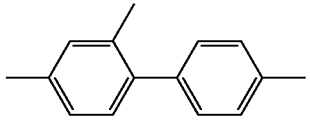 (M-15)
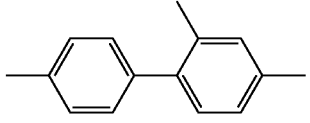 (M-16)
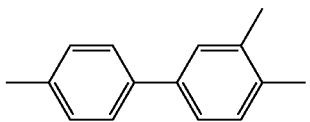 (M-17)
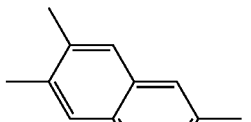 (M-18)
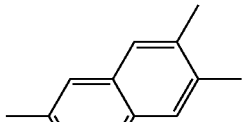 (M-19)
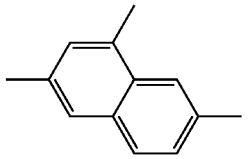 (M-20)
(M-21)

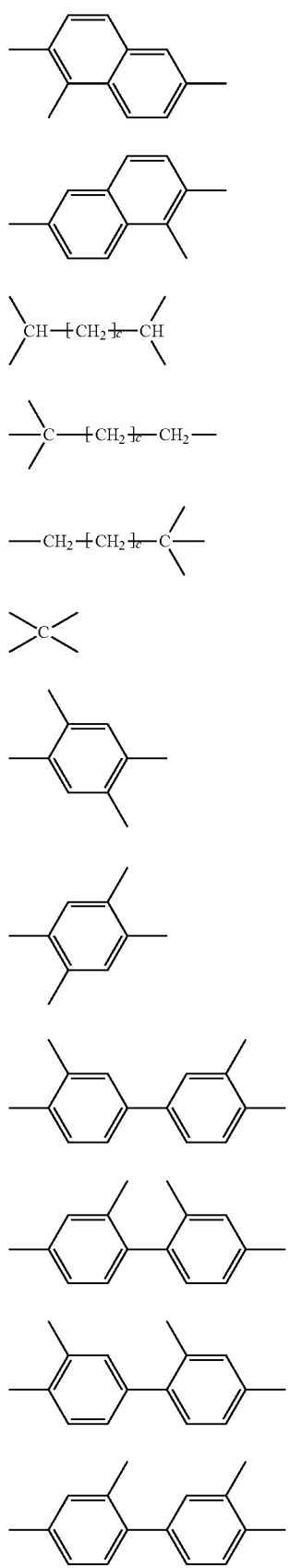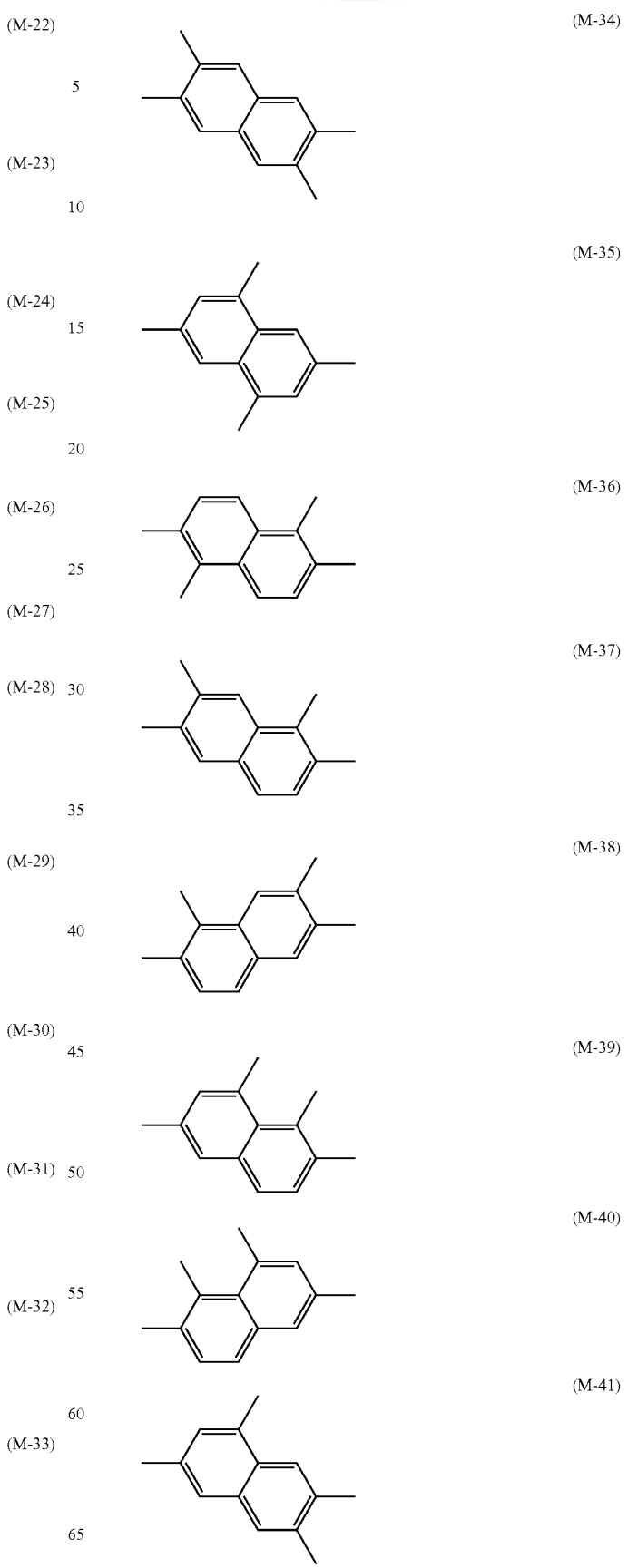

(M-42)
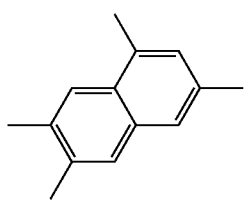
Item 14 is the compound described in any one of items 11 to 13, represented by any one of formulae (1a) to (1s).
(1a)
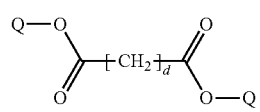
(1b)
$Q-O-(CH_2)_d-O-Q$
(1c)
$Q-(CH_2)_d-Q$
(1d)
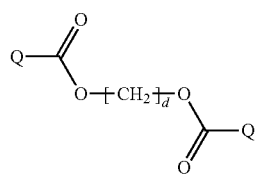
(1e)
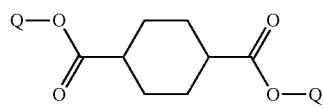
(1f)
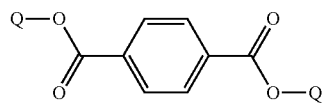
(1g)
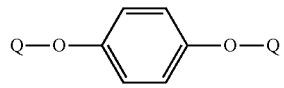
(1h)
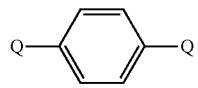
(1i)
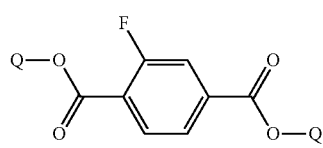
(1j)
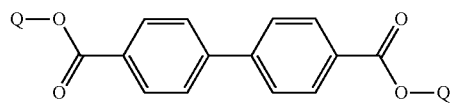
(1k)
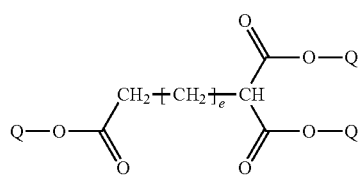
(1l)
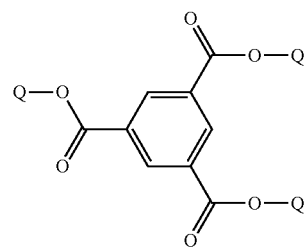
(1m)
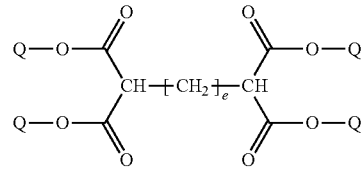
(1n)
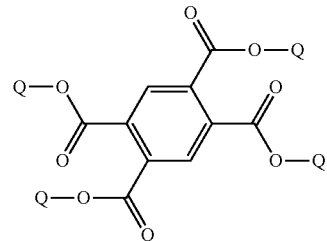
(1o)
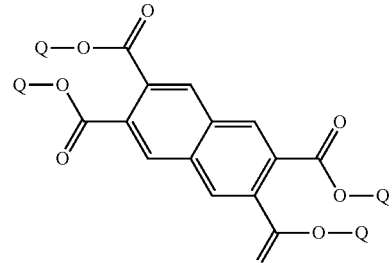
(1p)
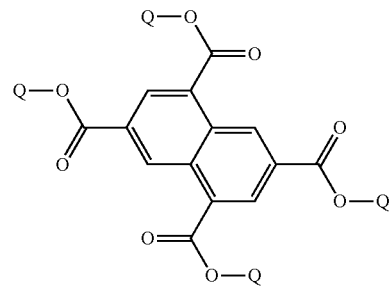
(1q)
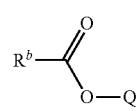
(1r)
$R^b-O-Q$
(1s)
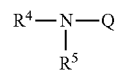
In formulae (1a) to (1s),
d is an integer of 1 to 14;
e is an integer of 0 to 13;

Q is a monovalent group represented by formula (Q-1) or (Q-2), and at least one Q is a monovalent group represented by formula (Q-2), wherein $R^a$ is hydrogen, —O., —OH, or —$R^1$;

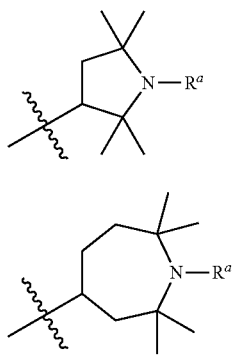

(Q-1)

(Q-2)

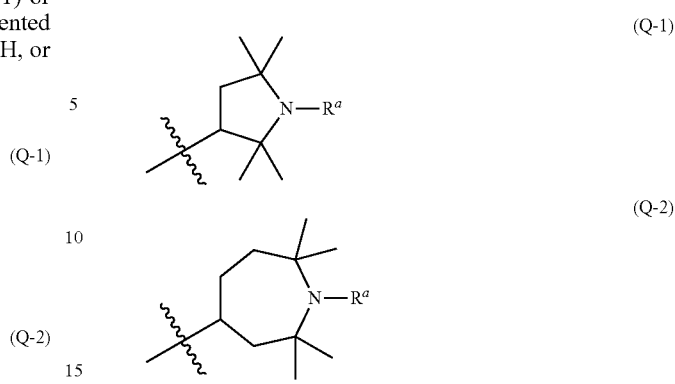

(Q-1)

(Q-2)

$R^b$ is hydrogen or —$R^2$;

$R^1$ and $R^2$ are independently alkyl having 1 to 20 carbons, arylalkyl having 1 to 20 carbons, or aryl having 1 to 20 carbons, wherein at least one —$CH_2$— in the alkyl is optionally replaced with —O—; and $R^4$ and $R^5$ are independently alkyl having 1 to 10 carbons.

Item 15 is the compound described in item 14, wherein in formulae (Q-1) and (Q-2) described in item 14, $R^a$ is hydrogen, —O., —OH, alkyl having 1 to 10 carbons, or alkoxy having 1 to 10 carbons.

Item 16 is the compound described in item 11, represented by any one of formulae (1a-1), (1f), (1h), and (1n).

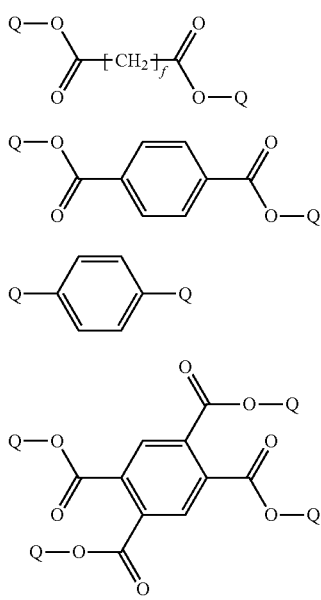

(1a-1)

(1f)

(1h)

(1n)

In formulae (1a-1), (1f), (1h), and (1n), f is an integer of 1 to 12; and

Q is a monovalent group represented by formula (Q-1) or (Q-2), and at least one Q is a monovalent group represented by formula (Q-2), wherein $R^a$ is hydrogen or alkyl having 1 to 15 carbons;

Item 17 is a liquid crystal composition containing at least one compound described in any one of items 11 to 16.

Item 18 is a liquid crystal display device containing at least one liquid crystal composition described in any one of items 1 to 10 and 17.

The invention also includes the following items: (a) the liquid crystal composition containing one compound, two compounds or three or more compounds selected from the group consisting of additives such as polymerizable compounds, polymerization initiators, polymerization inhibitors, optically active compounds, antioxidants, ultraviolet absorbents, light stabilizers, heat stabilizers and defoamers; (b) a polymerizable composition prepared by adding a polymerizable compound to the liquid crystal composition; (c) a liquid crystal composite prepared by polymerizing the polymerizable composition; (d) a polymer sustained alignment (PSA)-type liquid crystal display device containing the liquid crystal composite; (e) a use of the compounds (1-1) to (1-4) as a light stabilizer; (f) a use of the compounds (1-1) to (1-4) as a heat stabilizer; (g) a combined use of a light stabilizer different from the compounds (1-1) to (1-4) and the compounds (1-1) to (1-4); and h) a use of the liquid crystal composition as an optically active composition, achieved by adding an optically active compound to the liquid crystal composition.

Embodiments of the compounds (1-1) to (1-4), synthesis of these compounds, the liquid crystal composition and the liquid crystal display device will be described in sequence. Moreover, the compounds represented by formulae (1-1) to (1-4) are sometimes simply referred to as compound (1).

1. Embodiments of Compound (1)

The compound (1) has a monovalent group represented by formula (Q-1) or a monovalent group represented by formula (Q-2). This compound may also have both groups. This compound has such an azolidine ring (Q-1) or azepane ring (Q-2), and is thus useful as a hindered amine light stabilizer.

(Q-1)

-continued

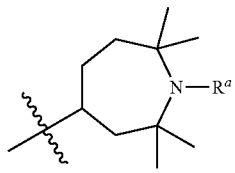
(Q-2)

The azolidine ring or the azepane ring is characterized in that a carbon next to a nitrogen has two methyls. Due to these methyls, the nitrogen undergoes steric hindrance, and reactivity will thus be controlled. Accordingly, the compound (1) is suitable for trapping a decomposition product generated by a photoreaction of a liquid crystal compound. This compound can be added to a liquid crystal composition because of its high solubility in the liquid crystal composition (see Example 3). The liquid crystal composition is a mixture of a liquid crystal compound. The compound (1) has an effect of preventing this liquid crystal compound from being decomposed by light from a backlight or the sun. The compound (1) may also have an effect as a heat stabilizer.

When a liquid crystal display device is used for a long time, the liquid crystal compound tends to be decomposed by light so as to generate a decomposition product. This product is unfavorable to the device due to being an impurity. There is a possibility that this impurity may cause phenomena such as a decrease in the contrast ratio, occurrence of display unevenness, or image burn-in. Since these phenomena can be easily recognized by visual observation, even if their extent is small, they are very noticeable. Accordingly, a light stabilizer with less formation of impurities than conventional light stabilizers even by only 1% is preferred. The compound (1) is such a light stabilizer.

Preferred examples of the compound (1), i.e., the compounds (1-1) to (1-4), are described. Preferred examples of an organic group M, a linking group Z, a monovalent group Q, and $R^b$ in the compound (1) are also applicable to sub-formulae of the compound (1). By a suitable combination of the types of these compounds and groups, the characteristics can be arbitrarily adjusted. The compound (1) may contain an isotope such as $^2H$ (deuterium) and $^{13}C$ in an amount larger than the natural abundance since there is no large difference in characteristics of the compound.

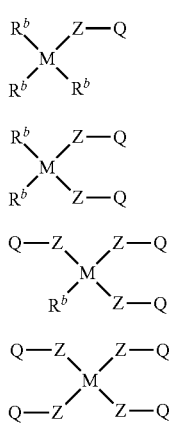

(1-1)

(1-2)

(1-3)

(1-4)

In view of high solubility in the liquid crystal composition, the compound (1-1) is preferred. In view of easy synthesis, the compounds (1-1) and (1-2) are preferred. In view of low volatility, the compounds (1-1), (1-2) and (1-3) are preferred. In view of the effect per unit weight, the compounds (1-3) and (1-4) are preferred, and the compound (1-4) is more preferred. In view of the balance between characteristics, the compounds (1-2) and (1-3) are preferred.

In formulae (1-1) to (1-4), M is a tetravalent aliphatic hydrocarbon group having 1 to 20 carbons or a tetravalent aromatic hydrocarbon group having 1 to 20 carbons, wherein at least one —$CH_2$— in these groups is optionally replaced with —O— or —S—, one or two —CH=CH— in these groups are optionally replaced with —CH=N—, and at least one hydrogen in these groups is optionally replaced with fluorine or chlorine.

M is preferably a tetravalent group formed by removing four hydrogens from alkane (having 1 to 15 carbons), alkane in which at least one —$CH_2$— is replaced with —O—, cyclohexane, bicyclohexane, decahydronaphthalene, tetrahydropyran, dioxane, benzene, benzene in which at least one hydrogen is replaced with fluorine, biphenyl, naphthalene, pyridine, or pyrimidine. M is more preferably the groups (M-1) to (M-42) described in item 4. In the divalent group (M-1), when c is 0, this group means a single bond.

In formulae (1-1) to (1-4), Z is a single bond, —O—, —COO—, or —OCO—. Z is more preferably —O—, —COO—, or —OCO—, and most preferably —COO— or —OCO—.

In formulae (1-1) to (1-4), Q is a monovalent group represented by formula (Q-1) or (Q-2), wherein $R^a$ is hydrogen, —O., —OH, or —$R^1$, and a wavy line indicates a bonding site.

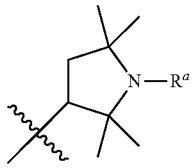
(Q-1)

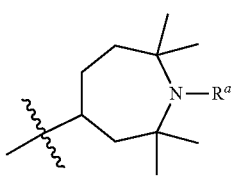
(Q-2)

Formula (Q-1) has reduced symmetry as compared to a monovalent group of a corresponding N-containing six-membered ring. This means that the compound having formula (Q-1) has higher solubility in the liquid crystal composition. Formula (Q-2) has reduced symmetry as compared to a monovalent group of a corresponding N-containing six-membered ring. This means that the compound having formula (Q-2) has higher solubility in the liquid crystal composition. A synthetic intermediate of formulae (Q-1) and (Q-2) is a corresponding alcohol. In view of a short synthesis route, formula (Q-2) is preferred.

In formula (Q-1) or (Q-2), $R^a$ is hydrogen, —O. (oxygen radical), —OH, or —$R^1$. $R^a$ is preferably hydrogen, —O., —OH, or —$R^1$, more preferably hydrogen, —O., or —$R^1$, and most preferably hydrogen or —$R^1$.

In formulae (1-1) to (1-4), $R^b$ is hydrogen, fluorine, or —$R^2$. $R^b$ is preferably hydrogen or —$R^2$, and most preferably hydrogen.

$R^1$ and $R^2$ are independently alkyl having 1 to 20 carbons, arylalkyl having 1 to 20 carbons, or aryl having 1 to 20 carbons, wherein at least one —CH$_2$— in the alkyl is optionally replaced with —O—, —CO—, —COO—, or —OCO—, and —CH$_3$ located at a terminal of the alkyl is optionally replaced with —NHR$^3$ or —NR$^4$R$^5$, wherein R$^3$, R$^4$ and R$^5$ are independently alkyl having 1 to 10 carbons. The alkyl may be straight, branched, or cyclic, and is preferably straight.

$R^1$ and $R^2$ are preferably alkyl having 1 to 15 carbons, wherein at least one —CH$_2$— in the alkyl is optionally replaced with —O—, —CO—, —COO—, —OCO—, or —NHR$_3$—, and —CH$_3$ located at a terminal of the alkyl is optionally replaced with —NHR$^3$ or —NR$^4$R$^5$. $R^1$ and $R^2$ are more preferably alkyl, alkoxyalkyl, acyloxyalkyl, alkoxycarbonylalkyl, alkylaminoalkyl, dialkylaminoalkyl, alkoxy, alkoxyalkoxy, acyloxy, alkoxycarbonyl, alkylamino, or dialkylamino. $R^1$ and $R^2$ are particularly preferably alkyl, alkoxyalkyl, acyloxyalkyl, alkoxycarbonylalkyl, or alkoxy, and most preferably alkyl.

$R^1$ and $R^2$ are also preferably arylalkyl having 1 to 15 carbons, wherein at least one —CH$_2$— in the alkyl is optionally replaced with —O—, —CO—, —COO—, —OCO—, or —NHR$_3$—. $R^1$ and $R^2$ are more preferably benzyl, styryl, cinnamyl, 3-phenylpropyl, cumyl, or trityl, and most preferably benzyl.

$R^1$ and $R^2$ are also preferably aryl having 1 to 15 carbons. $R^1$ and $R^2$ are more preferably phenyl, tolyl, xylyl, cumenyl, mesityl, 1-naphthyl, or 2-naphthyl, and most preferably phenyl.

With reference to the above preferred examples, by suitably selecting a combination of the organic group M, the linking group Z, the monovalent group Q, and R$^b$, the compound (1) having intended characteristics can be obtained. Preferred examples of the compound (1) include the compound described in item 5. More specific examples of the compound (1) are described in items 6 and 7.

2. Synthesis of Compound (1)

A synthesis method of the compound (1) is described. This compound can be synthesized by a suitable combination of methods in organic synthetic chemistry. The methods for introducing target organic group M, linking group Z, monovalent group Q and monovalent group R$^b$ into starting materials are described in books such as Houben-Weyl, Methoden der Organische Chemie (Georg-Thieme Verlag, Stuttgart), Organic Syntheses (John Wiley & Sons, Inc.), Organic Reactions (John Wiley & Sons, Inc.), Comprehensive Organic Synthesis (Pergamon Press), and New Experimental Chemistry Course (Shin Jikken Kagaku Koza, in Japanese) (Maruzen Co., Ltd.), etc.

2-1. Synthetic Intermediate

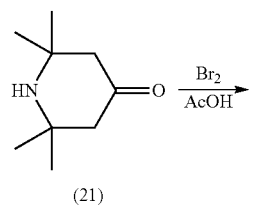

(21)

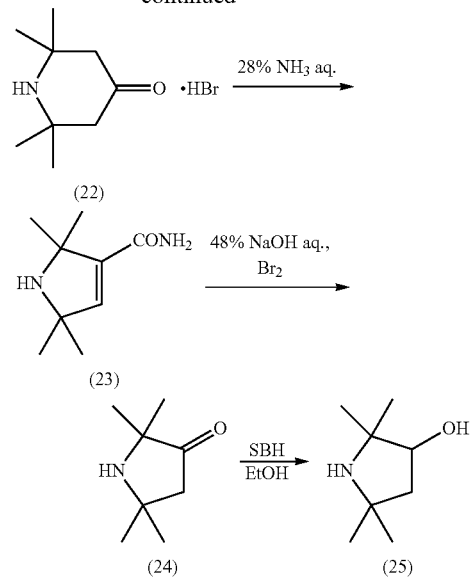

2,2,5,5-tetramethylpyrrolidin-3-ol (25) is synthesized as follows. A commercially available ketone (21) is reacted with bromine in acetic acid to obtain a hydrobromide (22). Next, the resultant is treated with 28% ammonia water to obtain an amide (23). The amide is derived into a ketone (24) using bromine and 48% sodium hydroxide aqueous solution and then reduced using sodium borohydride (SBH), thereby obtaining an alcohol (25). This alcohol is converted into a bromide or carboxylic acid if necessary, and is then used as a synthetic intermediate.

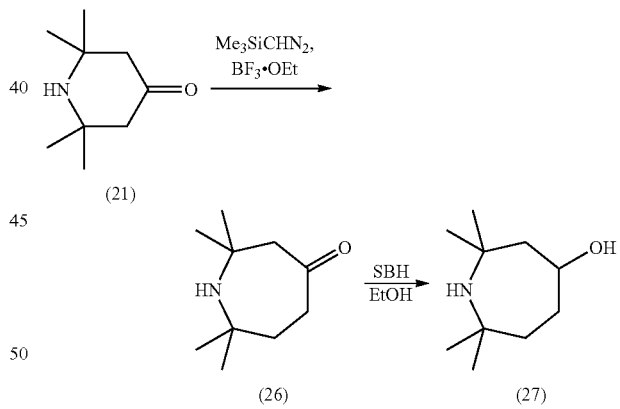

2,2,7,7-tetramethylazepan-4-ol (27) is synthesized as follows. A commercially available ketone (21) is reacted with trimethylsilyldiazomethane in the presence of a boron trifluoride ether complex to obtain a ketone (26). The ketone (26) is reduced using sodium borohydride (SBH), thereby obtaining an alcohol (27). The alcohol (27) is converted into a bromide or carboxylic acid if necessary, and is then used as a synthetic intermediate.

2-2. Synthesis Examples

Synthesis methods of compounds (1A) to (1H) are shown. The symbol R$^a$ in each compound has the same meaning as described in item 1.

(1) Compound (1A)

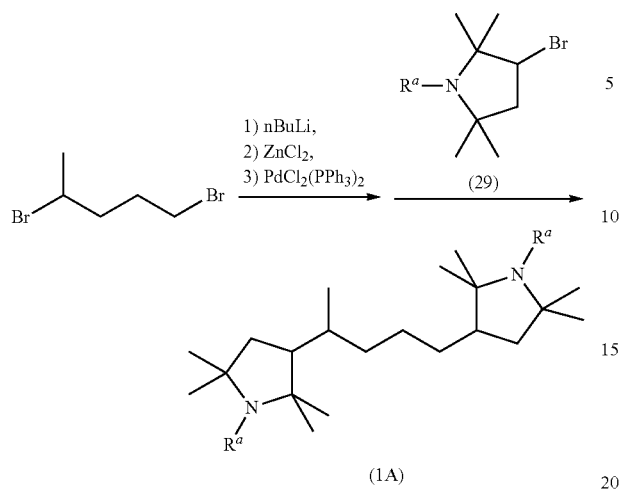

1,4-dibromopentane (28) is reacted with n-butyllithium and then with zinc chloride. By reacting this reaction intermediate with a bromide (29) in the presence of a dichlorobis(triphenylphosphine)palladium catalyst, the compound (1A) is synthesized.

(2) Compound (1B)


1,4-dibromobenzene (30) is reacted with n-butyllithium and then with zinc chloride. By reacting this reaction intermediate with a bromide (31) in the presence of a dichlorobis(triphenylphosphine)palladium catalyst, the compound (1B) is synthesized.

(3) Compound (1C)

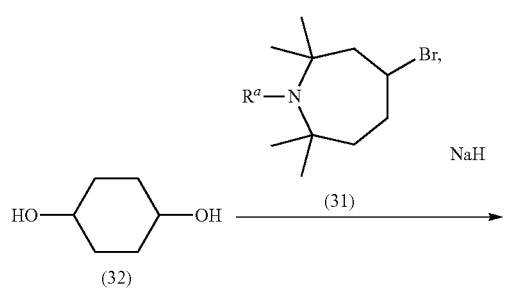

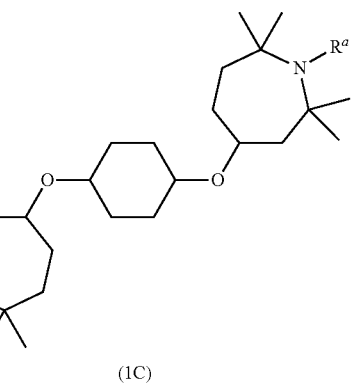

By reacting 1,4-cyclohexanediol (32) with the bromide (31) in the presence of sodium hydride, the compound (1C) is synthesized.

(4) Compound (1D)

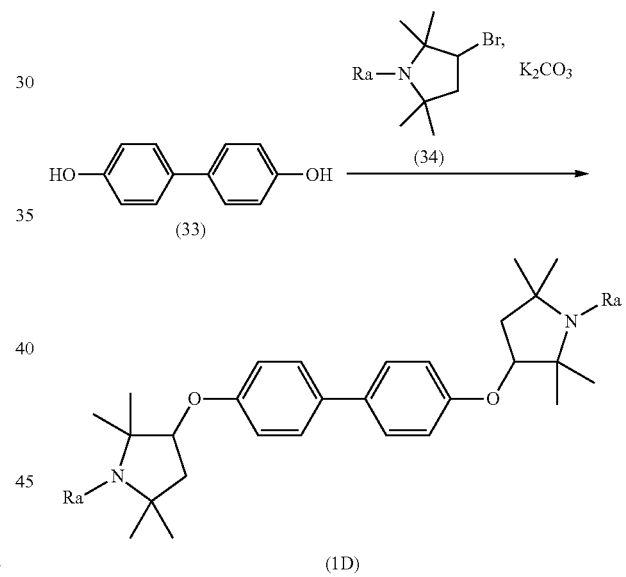

By reacting 4,4'-biphenol (33) with a bromide (34) in the presence of potassium carbonate, the compound (1D) is synthesized.

(5) Compound (1E)

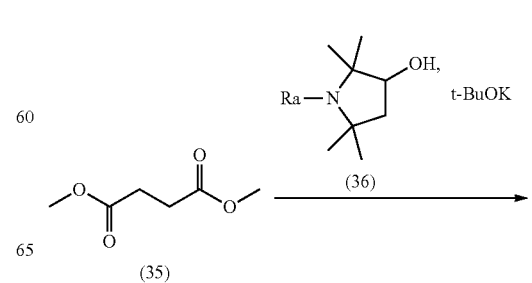

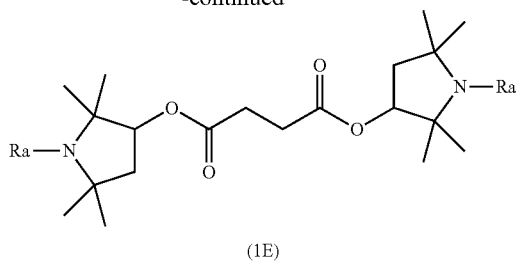

(1E)

By reacting dimethyl succinate (35) with piperidinol (36) in the presence of potassium tert-butoxide, the compound (1E) is synthesized.

(6) Compound (1F)

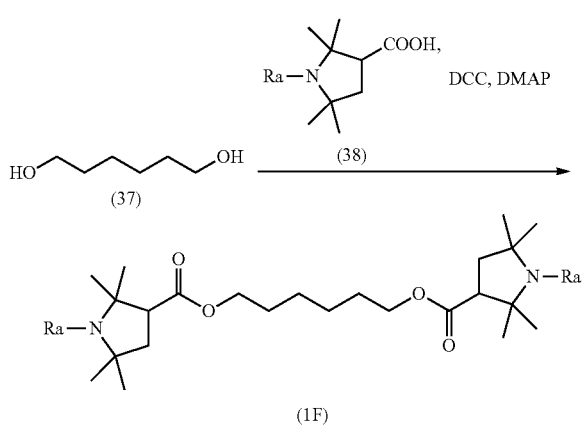

(1F)

By dehydrating 1,6-hexanediol (37) and carboxylic acid (38) in the presence of 1,3-dicyclohexylcarbodiimide (DCC) and 4-dimethylaminopyridine (DMAP), the compound (1F) is synthesized.

(7) Compound (1G)

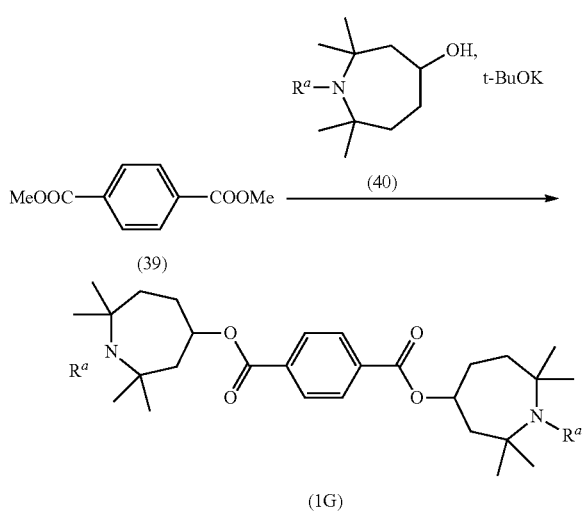

(1G)

By reacting dimethyl terephthalate (39) with piperidinol (40) in the presence of potassium tert-butoxide, the compound (1G) is synthesized.

(8) Compound (1H)

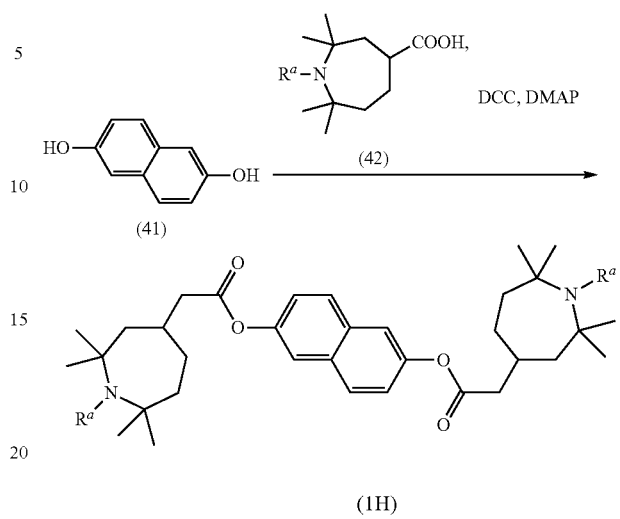

(1H)

By dehydrating 2,6-naphthalenediol (41) and carboxylic acid (42) in the presence of 1,3-dicyclohexylcarbodiimide (DCC) and 4-dimethylaminopyridine (DMAP), the compound (1H) is synthesized.

3. Liquid Crystal Composition 3-1. Component Compounds

The liquid crystal composition of the invention contains at least one of the compounds (1-1) to (1-4), i.e., at least one compound (1), as a component A. The compound (1) is suitable for preventing the liquid crystal composition from being decomposed by light or heat. Preferably, this composition contains the compound (1) as the component A, and further contains a liquid crystal compound selected from components B, C, D and E shown below. The component B includes compounds (2) to (4). The component C includes compounds (5) to (7). The component D includes a compound (8). The component E includes compounds (9) to (15). This composition may contain other liquid crystal compounds different from the compounds (2) to (15). In preparing this composition, it is preferred to select the components B, C, D and E by taking positive or negative dielectric anisotropy and the magnitude of dielectric anisotropy, etc. into consideration. The composition in which the components are suitably selected has high maximum temperature, low minimum temperature, small viscosity, suitable (large or small) optical anisotropy, large positive or negative dielectric anisotropy, large specific resistance, stability to ultraviolet light or heat, and a suitable (large or small) elastic constant.

A preferred ratio of the compound (1) based on the weight of the liquid crystal composition is about 0.01 wt % or more in order to maintain high stability to ultraviolet light, and is about 5 wt % or less in order to enable the compound (1) to dissolve in the liquid crystal composition. The ratio is more preferably about 0.05 to 2 wt %, and most preferably about 0.05 to 1 wt %.

The component B is a compound in which two terminal groups are alkyl or the like. Preferred examples of the component B include compounds (2-1) to (2-11), compounds (3-1) to (3-19) and compounds (4-1) to (4-7). In the compounds as the component B, $R^{11}$ and $R^{12}$ are independently alkyl having 1 to 10 carbons or alkenyl having 2 to 10 carbons, wherein at least one —$CH_2$— in the alkyl or alkenyl is optionally replaced with —O—, and at least one hydrogen in the alkyl or alkenyl is optionally replaced with fluorine.
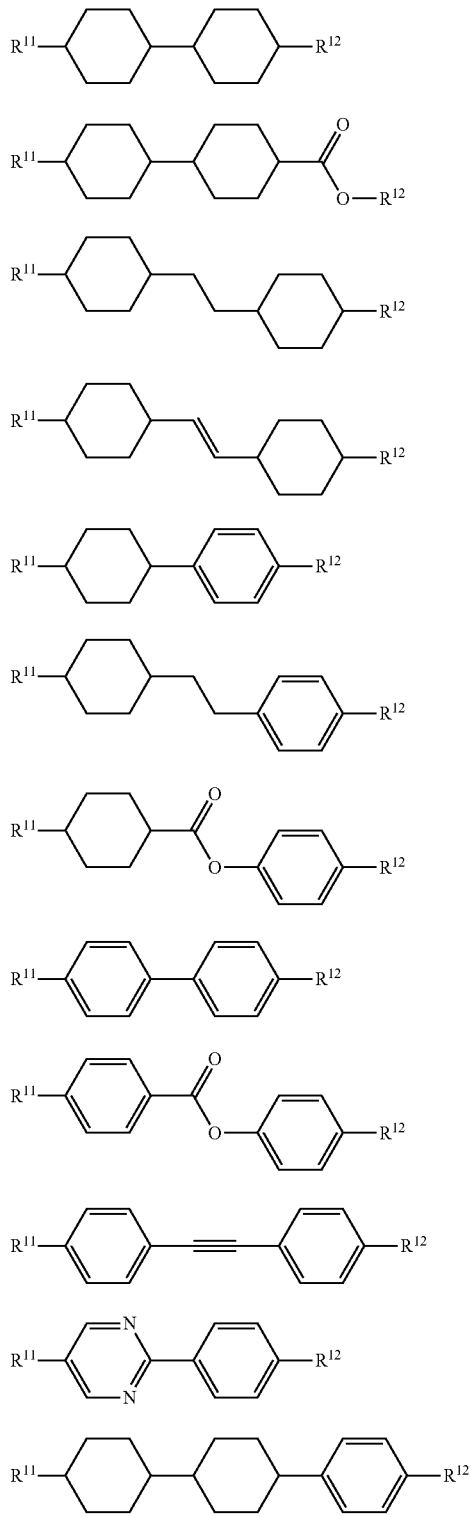
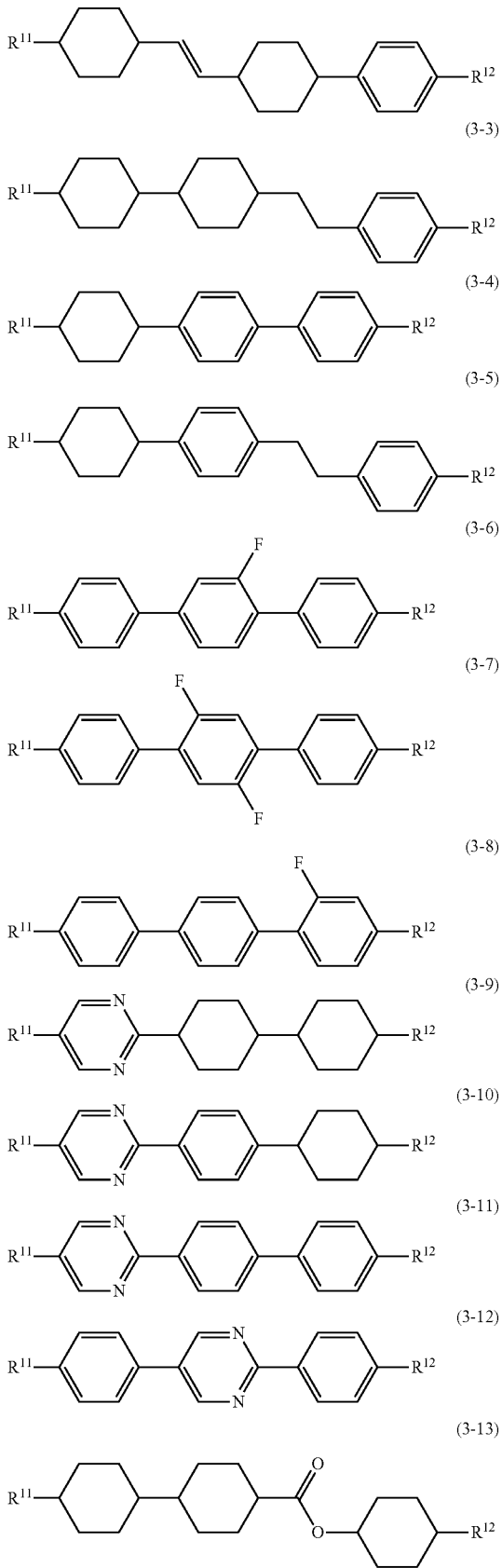

-continued (3-14) 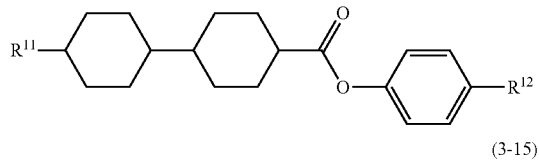

(3-15) 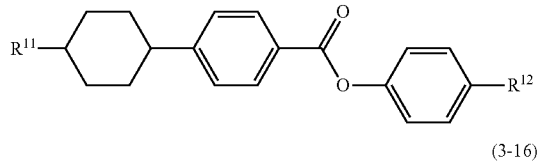

(3-16) 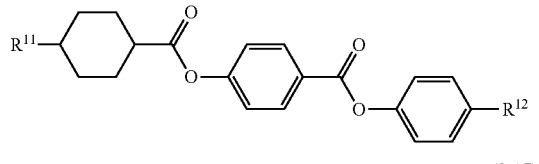

(3-17) 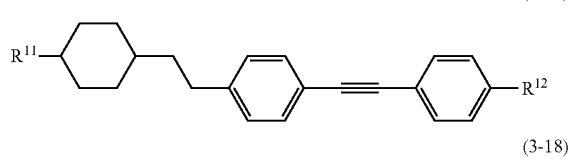

(3-18) 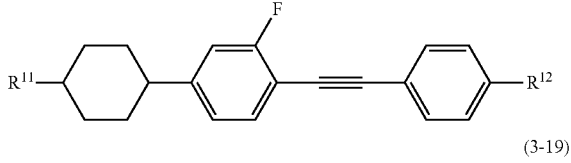

(3-19) 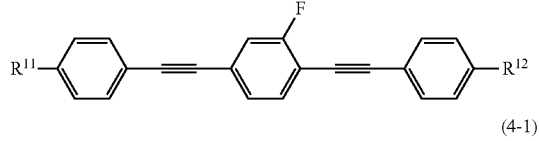

(4-1) 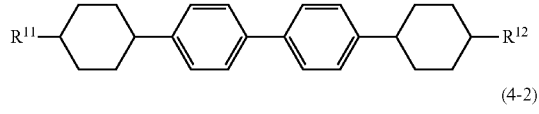

(4-2) 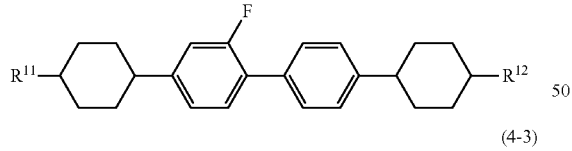

(4-3) 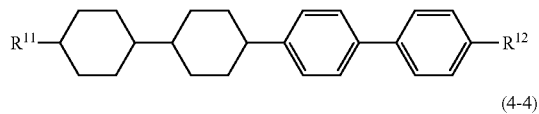

(4-4) 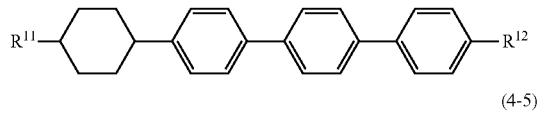

(4-5) 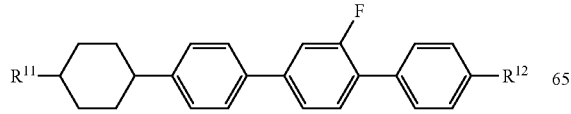

(4-6) 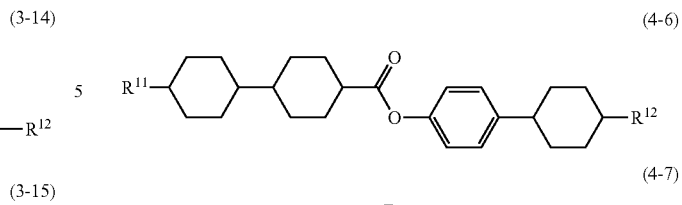

(4-7) 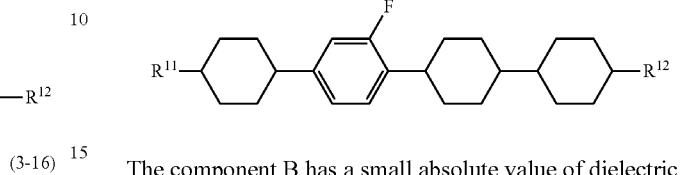

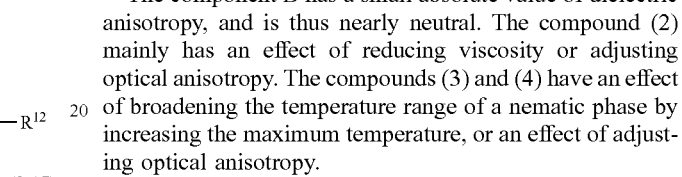

The component B has a small absolute value of dielectric anisotropy, and is thus nearly neutral. The compound (2) mainly has an effect of reducing viscosity or adjusting optical anisotropy. The compounds (3) and (4) have an effect of broadening the temperature range of a nematic phase by increasing the maximum temperature, or an effect of adjusting optical anisotropy.

As the content of the component B is increased, the viscosity of the composition is reduced and the dielectric anisotropy is reduced. Therefore, the content is preferably as high as possible as long as a required value of threshold voltage of the device is satisfied. In preparing the composition for use in modes such as IPS and VA, etc., the content of the component B is preferably 30 wt % or more, more preferably 40 wt % or more, based on the weight of the liquid crystal composition.

The component C is a compound having halogen or a fluorine-containing group in the right terminal. Preferred examples of the component C include compounds (5-1) to (5-16), compounds (6-1) to (6-113) and compounds (7-1) to (7-57). In the compounds as the component C, $R^{13}$ is alkyl having 1 to 10 carbons or alkenyl having 2 to 10 carbons, wherein at least one —$CH_2$— in the alkyl and alkenyl is optionally replaced with —O—, and at least one hydrogen in the alkyl and alkenyl is optionally replaced with fluorine; and $X^{11}$ is fluorine, chlorine, —$OCF_3$, —$OCHF_2$, —$CF_3$, —$CHF_2$, —$CH_2F$, —$OCF_2CHF_2$, or —$OCF_2CHFCF_3$.

(5-1) 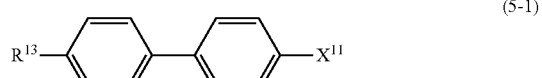

(5-2) 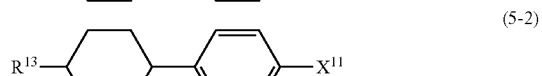

(5-3) 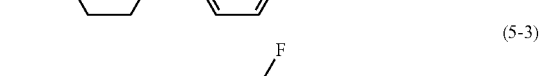

(5-4) 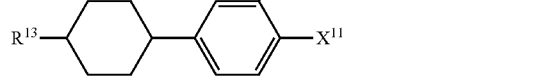

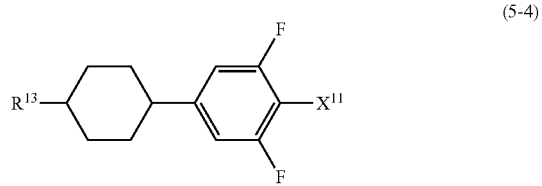

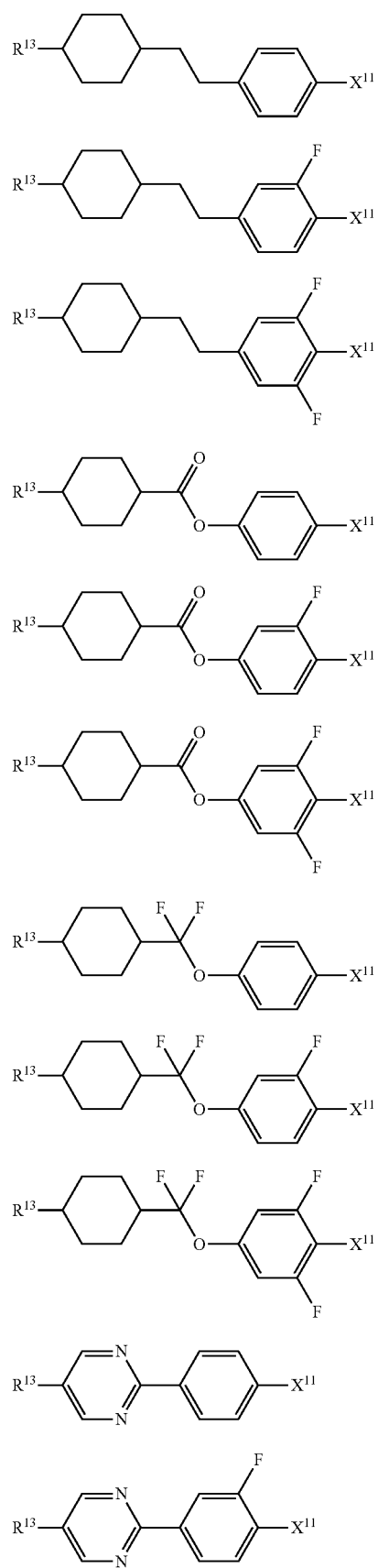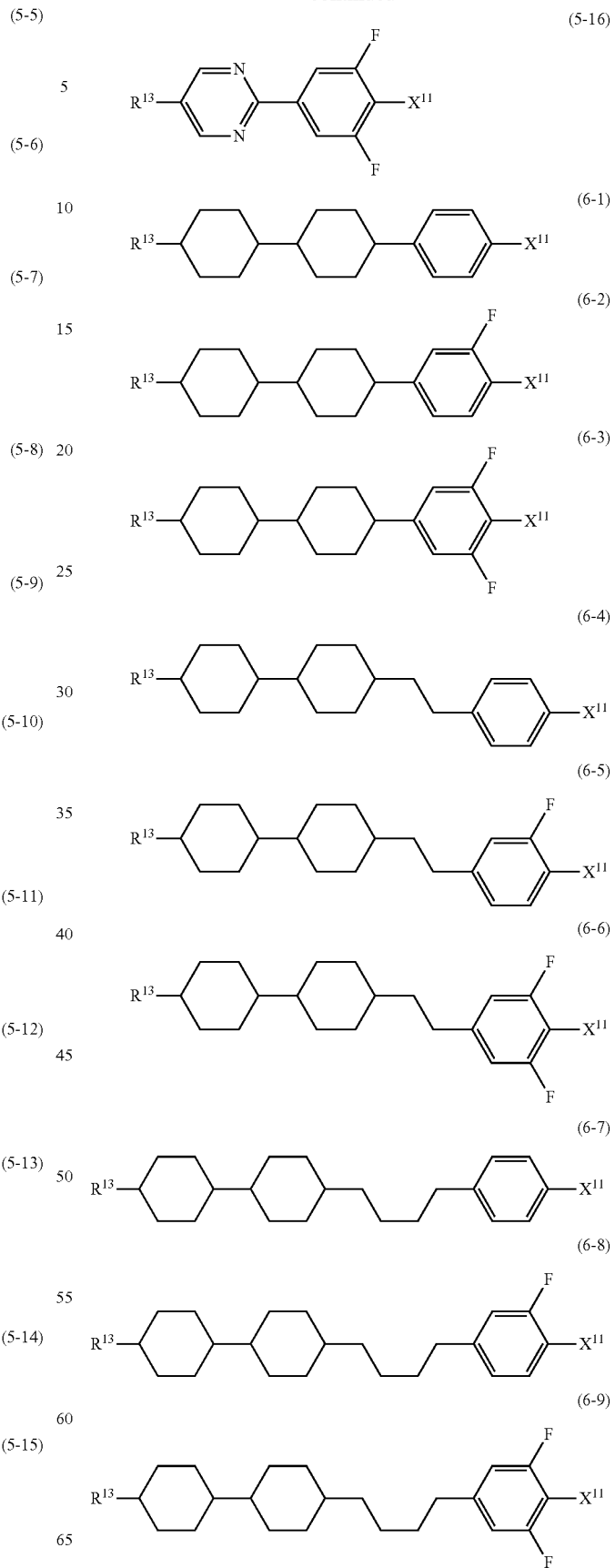

(6-10) 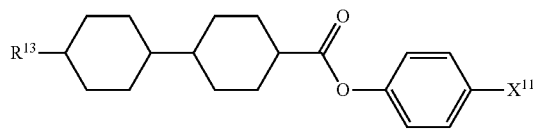
(6-11) 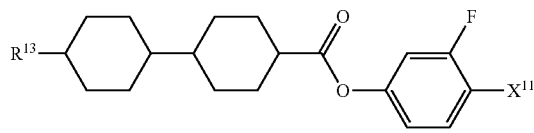
(6-12) 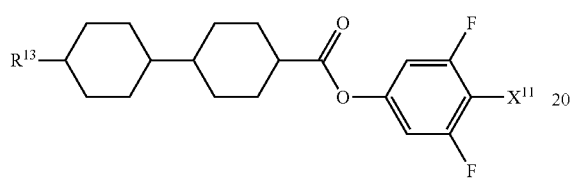
(6-13) 
(6-14) 
(6-15) 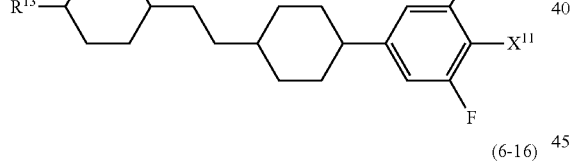
(6-16) 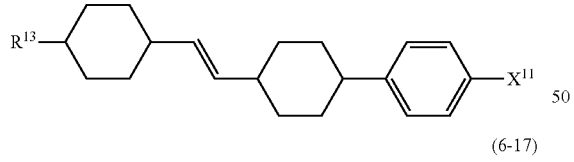
(6-17) 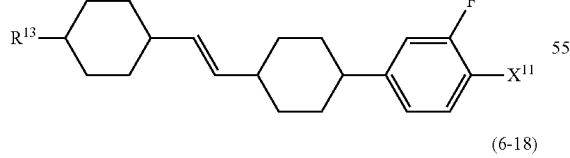
(6-18) 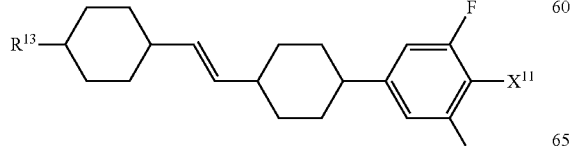
(6-19) 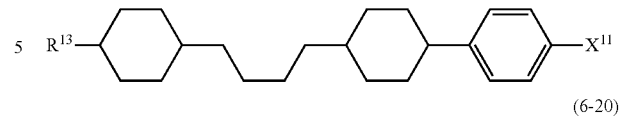
(6-20) 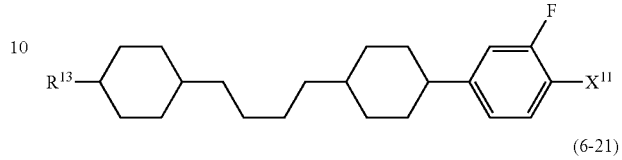
(6-21) 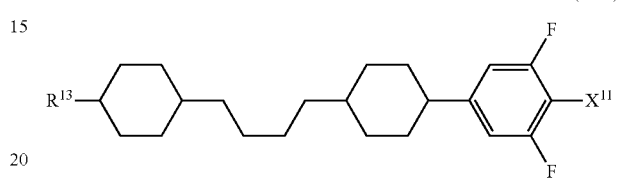
(6-22) 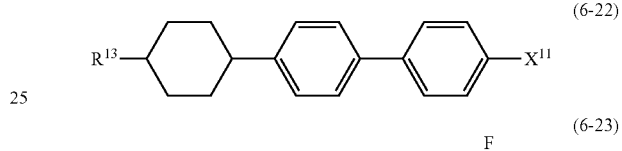
(6-23) 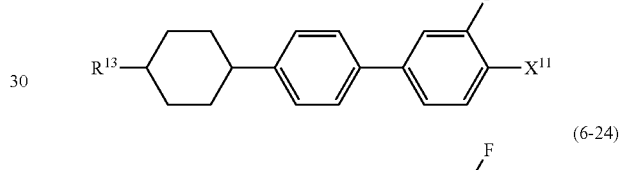
(6-24) 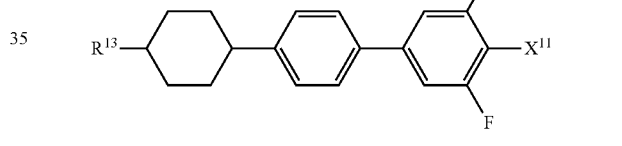
(6-25) 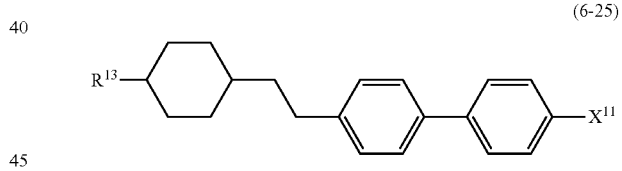
(6-26) 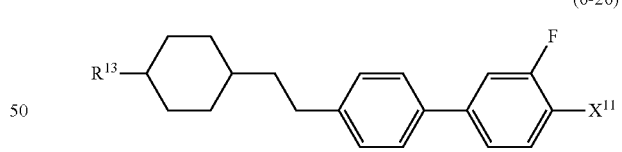
(6-27) 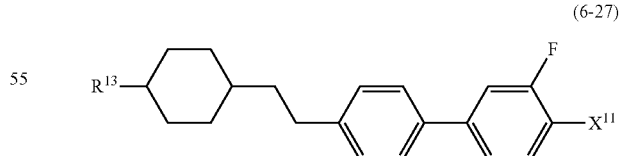
(6-28) 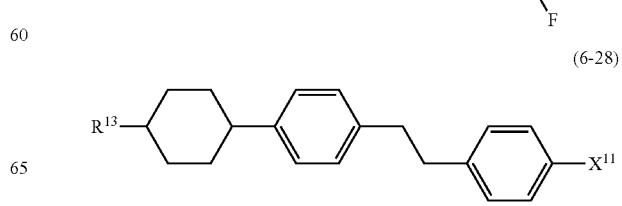

(6-29) 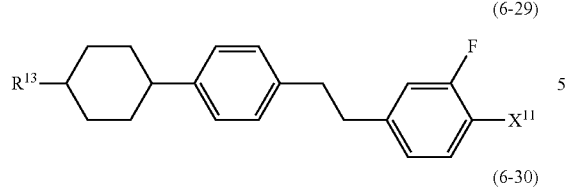
(6-30) 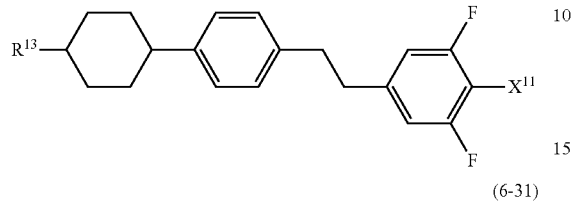
(6-31) 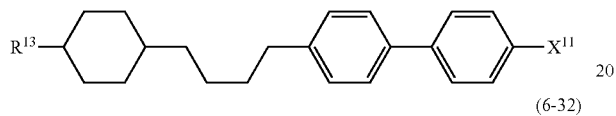
(6-32) 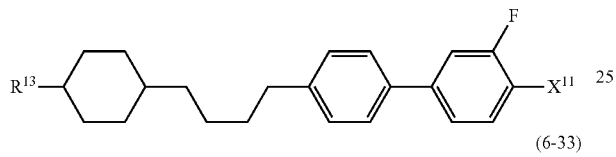
(6-33) 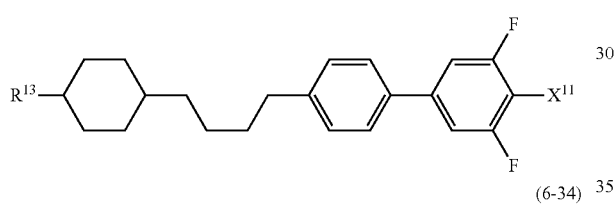
(6-34) 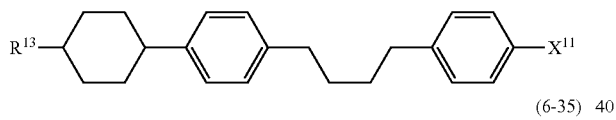
(6-35) 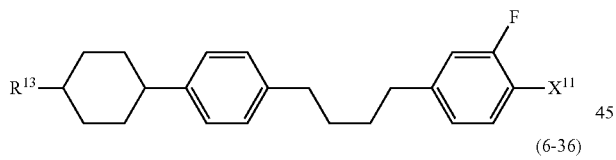
(6-36) 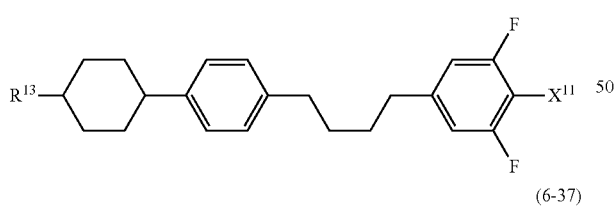
(6-37) 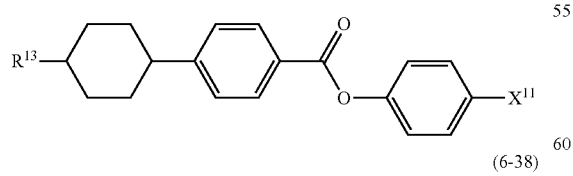
(6-38) 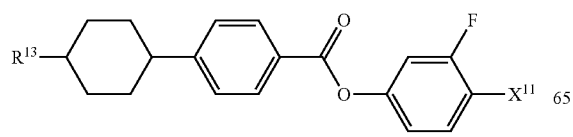
(6-39) 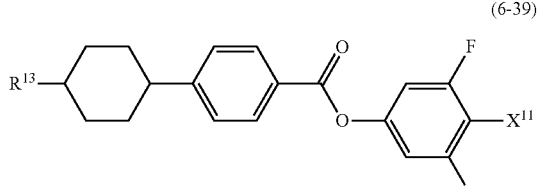
(6-40) 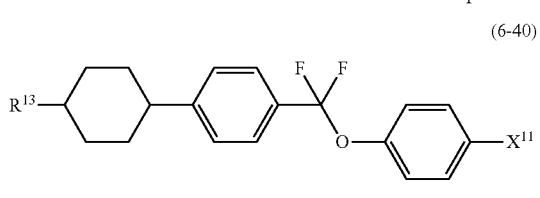
(6-41) 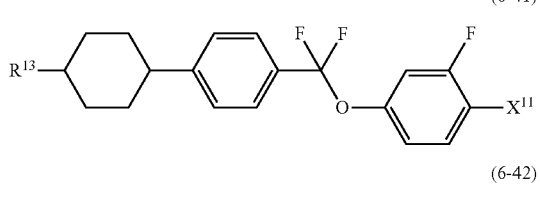
(6-42) 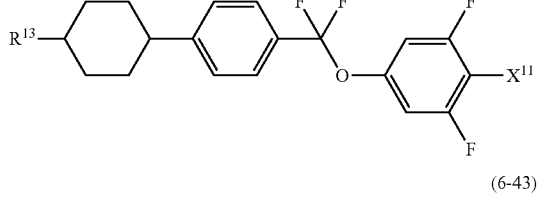
(6-43) 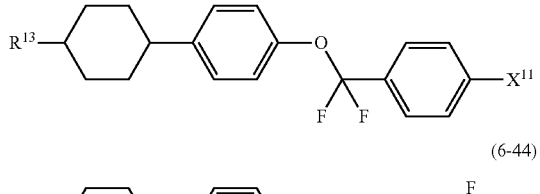
(6-44) 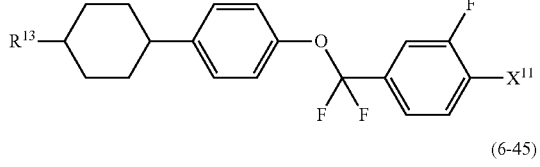
(6-45) 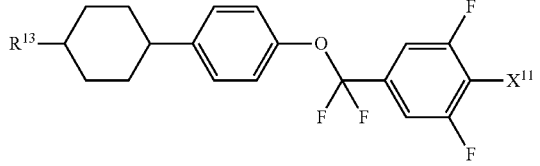
(6-46) 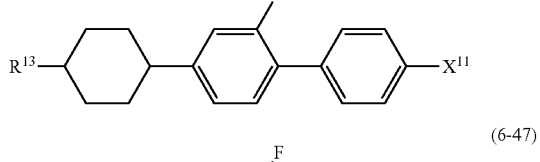
(6-47)

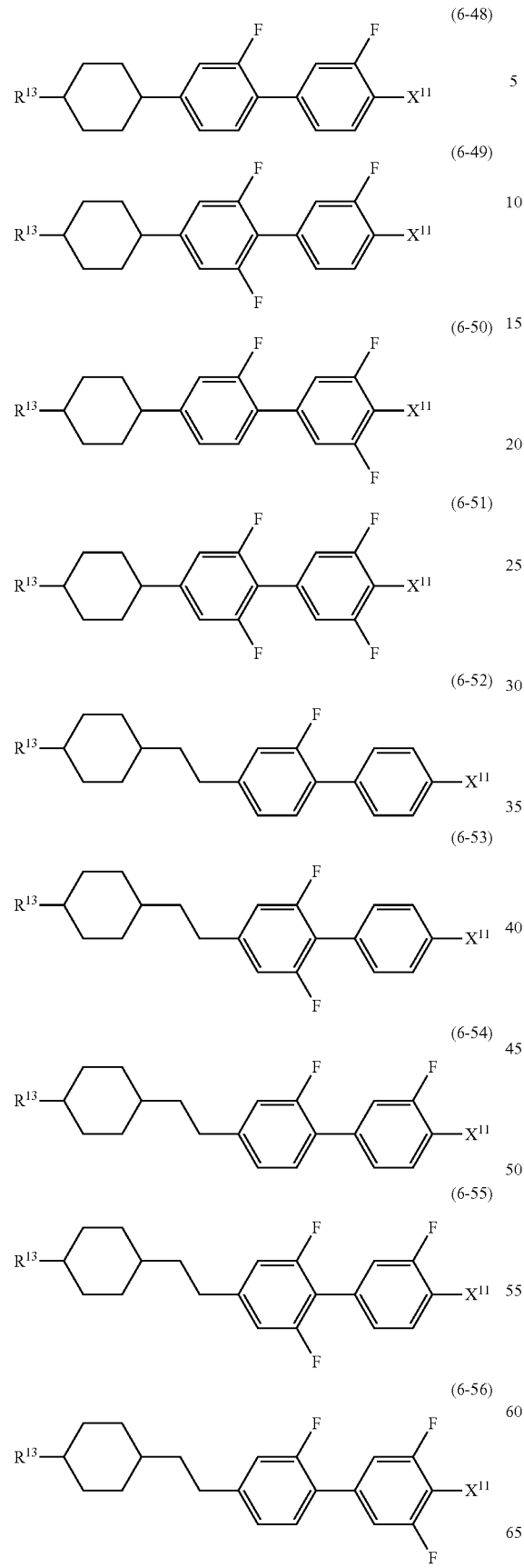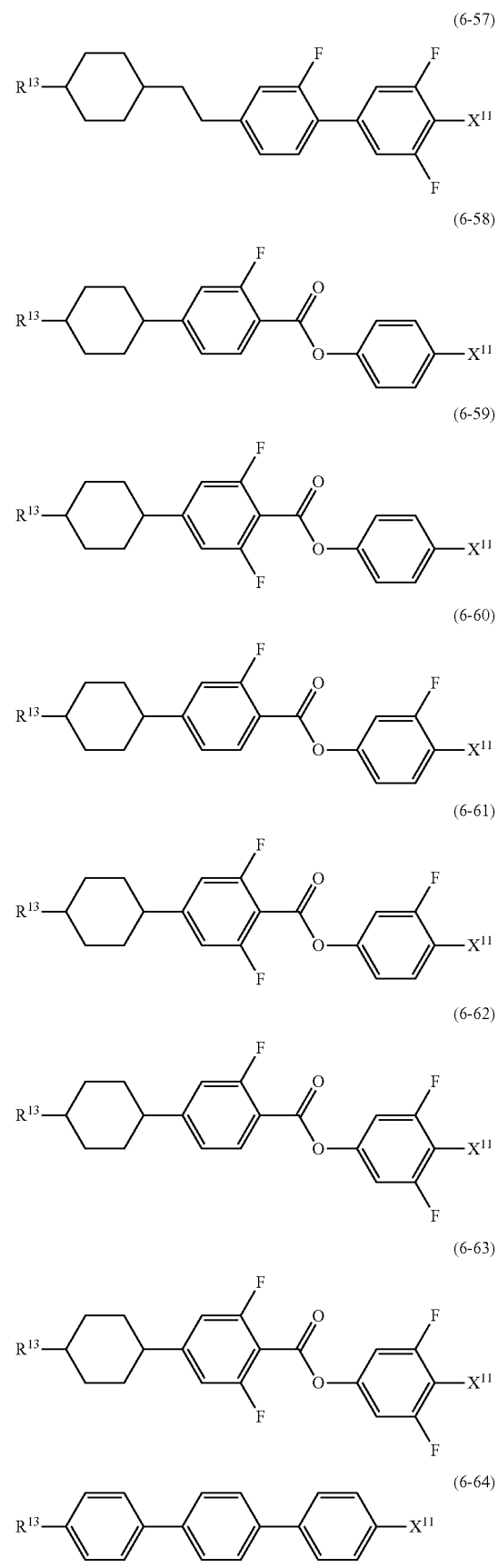

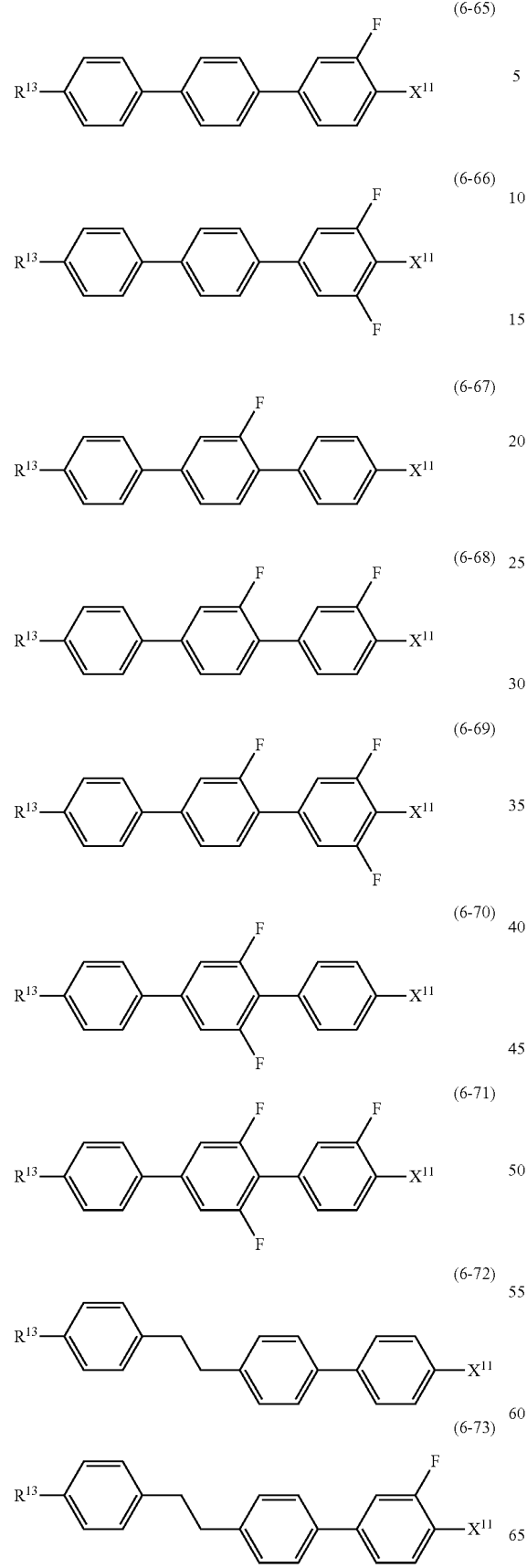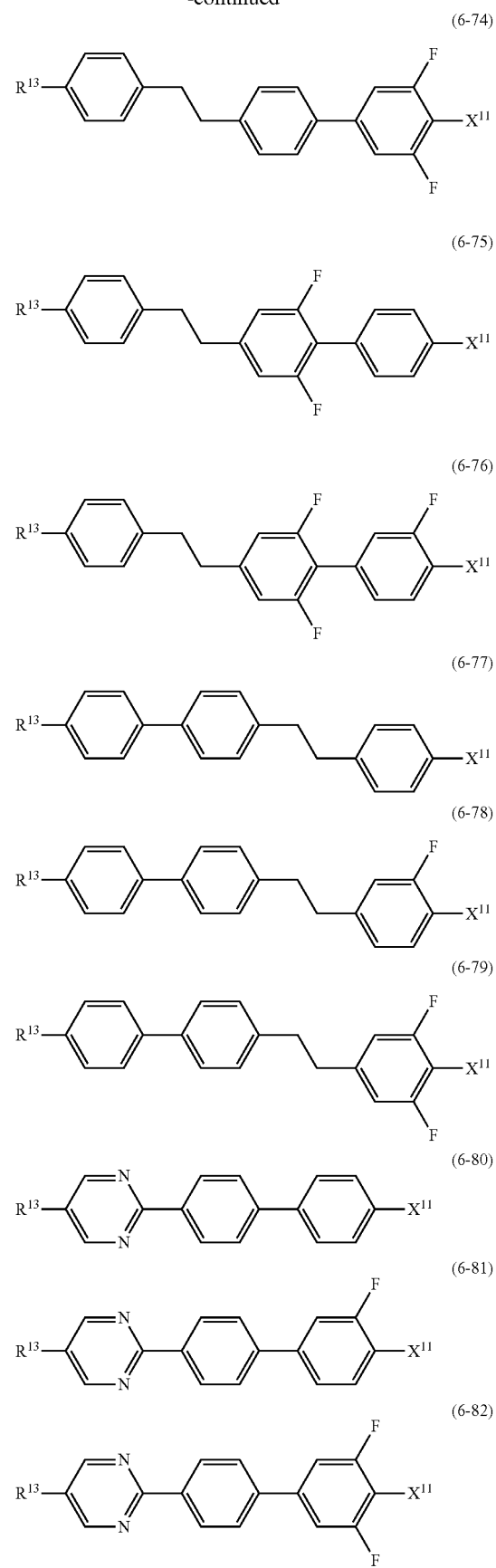

(6-83)
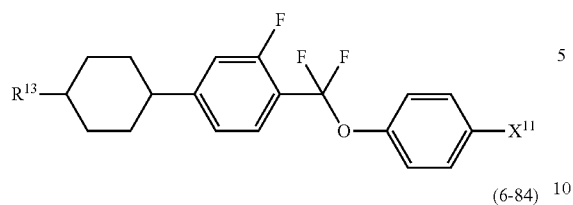
(6-84)
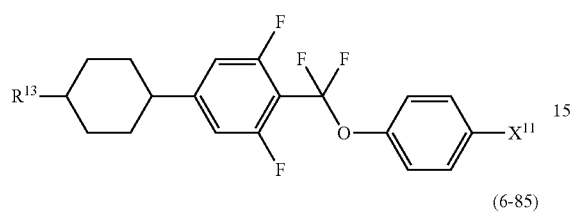
(6-85)
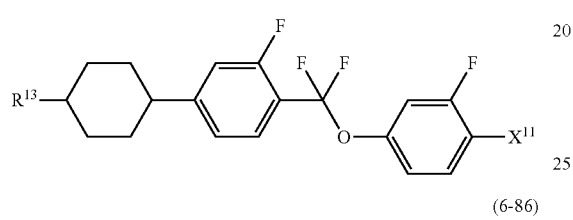
(6-86)
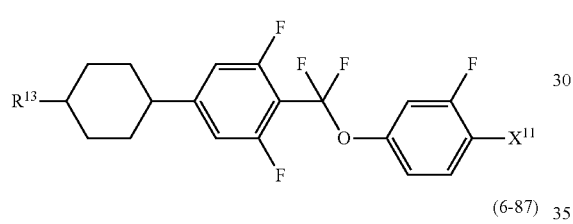
(6-87)
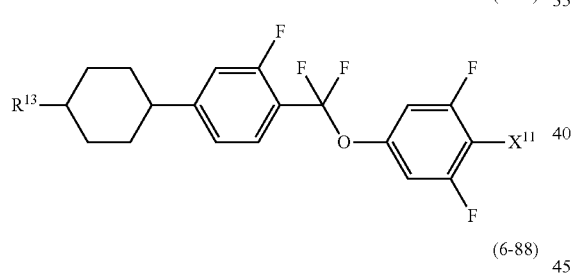
(6-88)
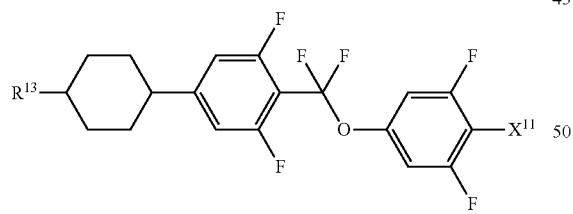
(6-89)
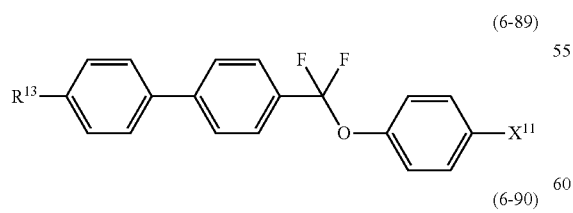
(6-90)
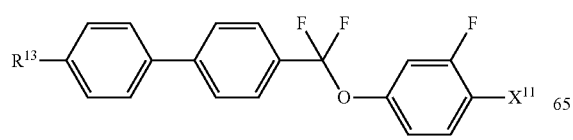
(6-91)
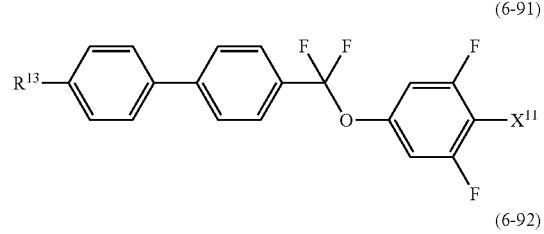
(6-92)
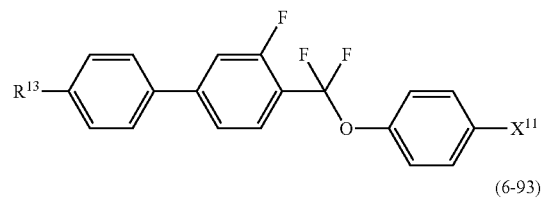
(6-93)
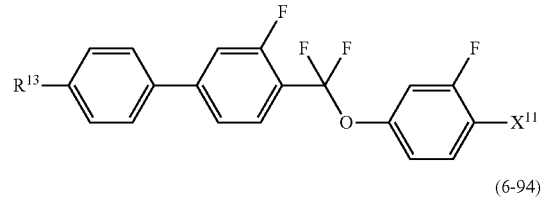
(6-94)
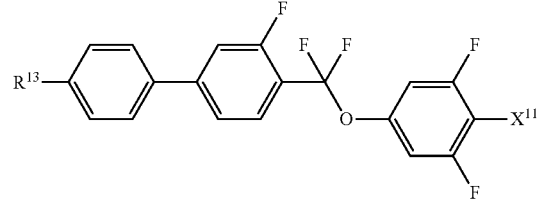
(6-95)
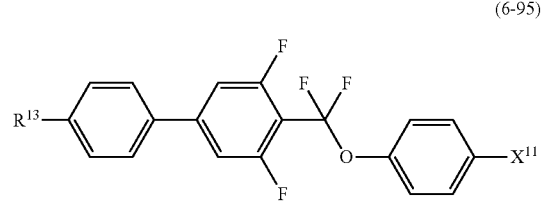
(6-96)
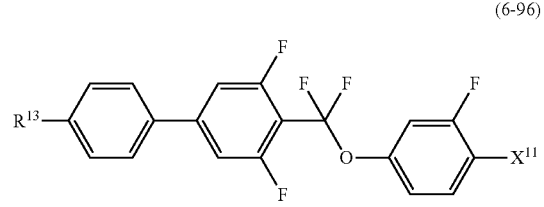
(6-97)
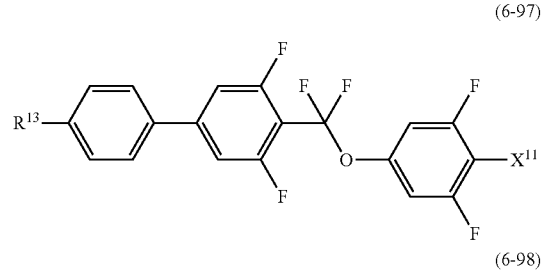
(6-98)
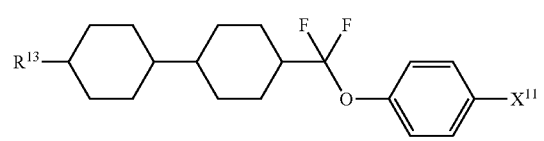

(6-99)
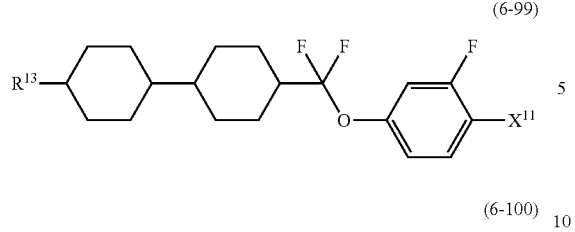
(6-100)
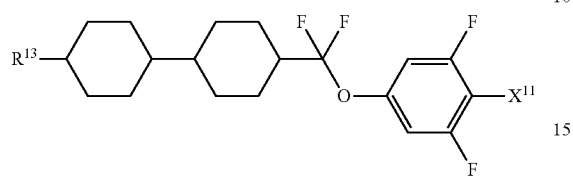
(6-101)
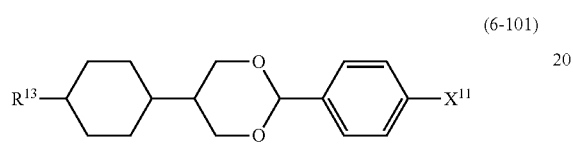
(6-102)
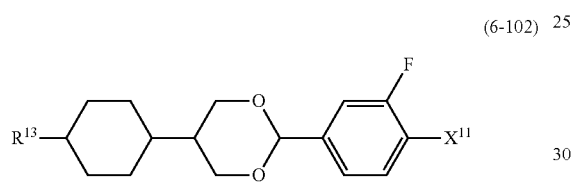
(6-103)
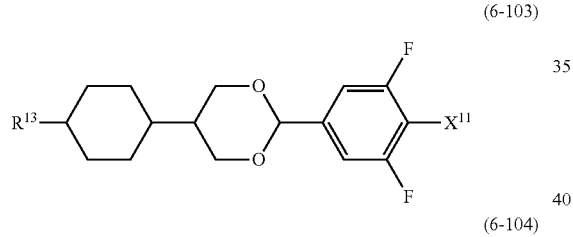
(6-104)
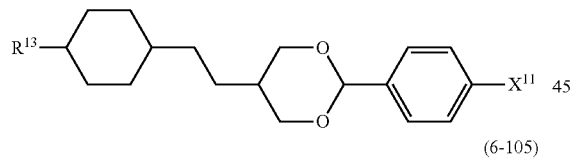
(6-105)
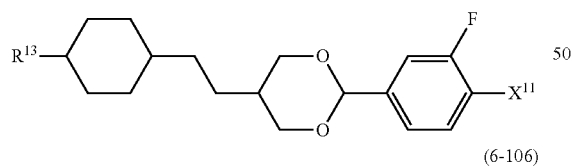
(6-106)
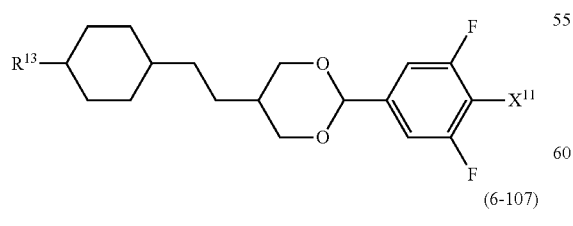
(6-107)
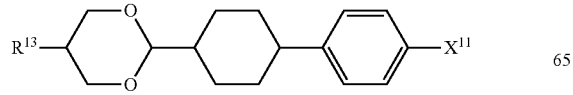
(6-108)
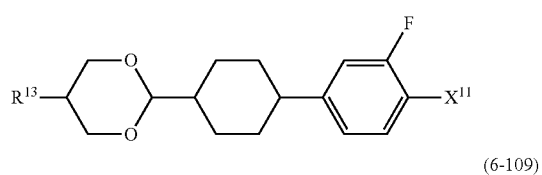
(6-109)
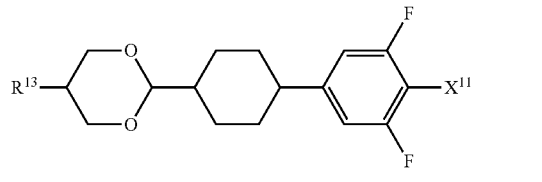
(6-110)
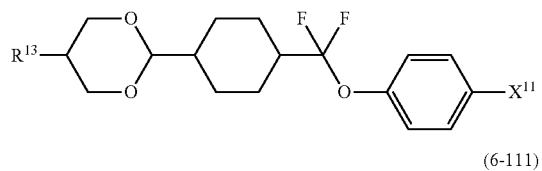
(6-111)
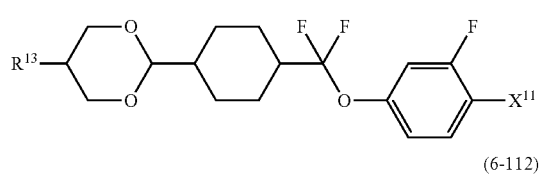
(6-112)
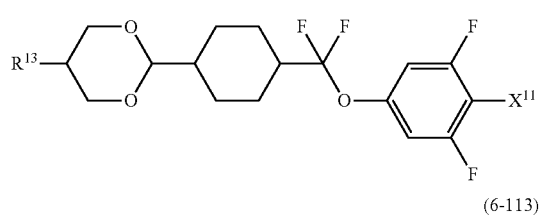
(6-113)
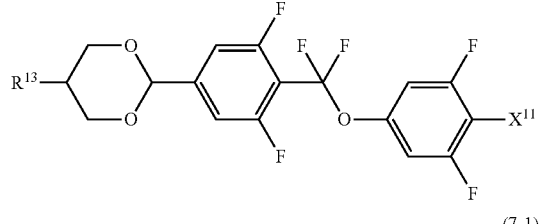
(7-1)
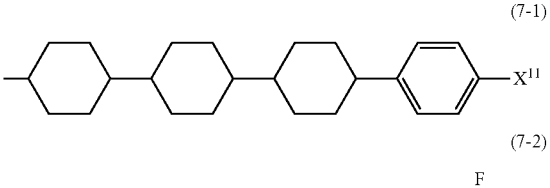
(7-2)
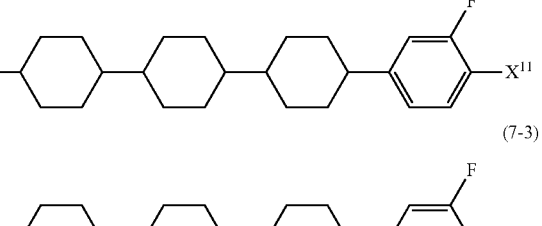
(7-3)
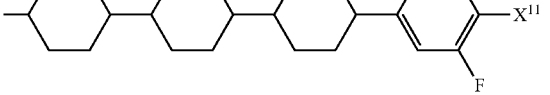

(7-4) 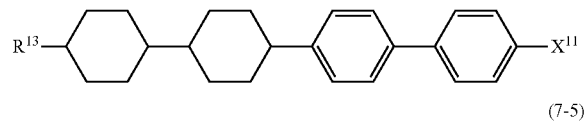
(7-5) 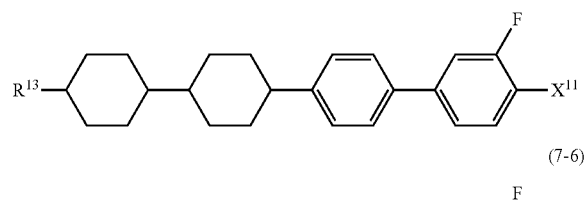
(7-6) 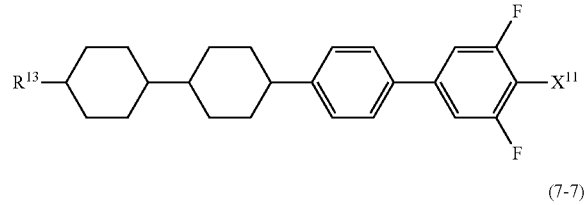
(7-7) 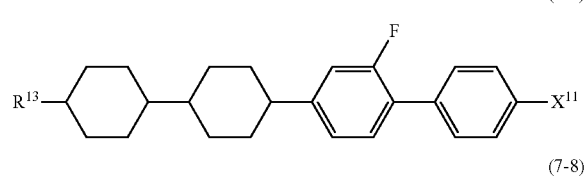
(7-8) 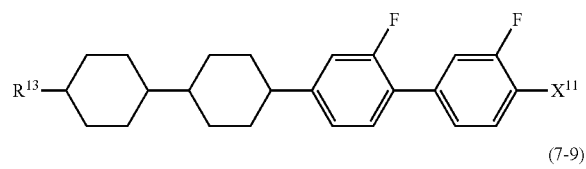
(7-9) 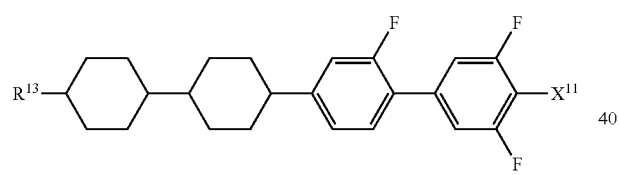
(7-10) 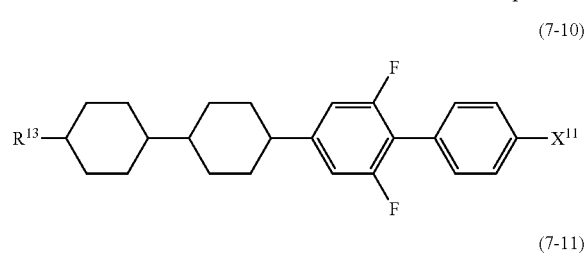
(7-11) 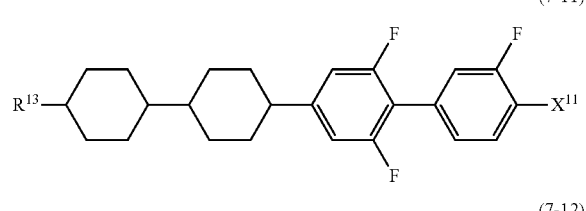
(7-12) 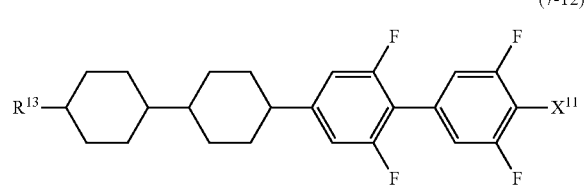
(7-13) 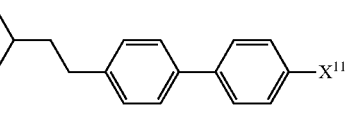
(7-14) 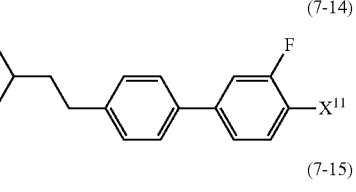
(7-15) 
(7-16) 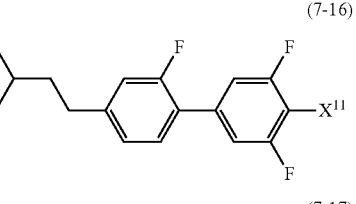
(7-17) 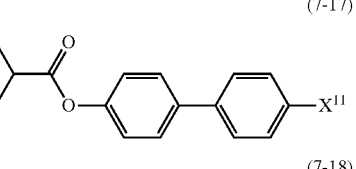
(7-18) 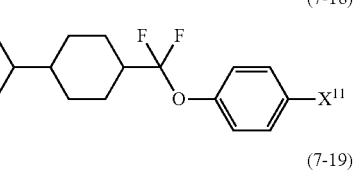
(7-19) 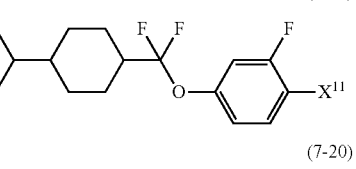
(7-20) 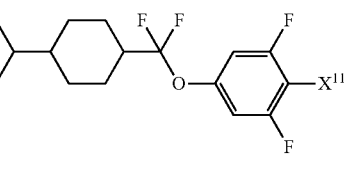
(7-21) 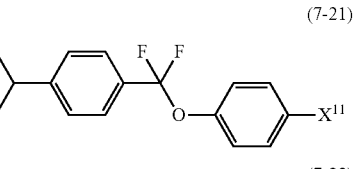
(7-22) 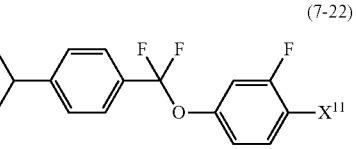

(7-23) 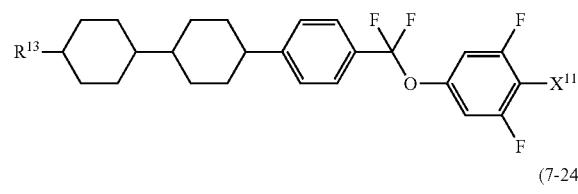
(7-24) 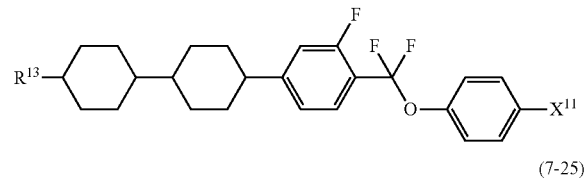
(7-25) 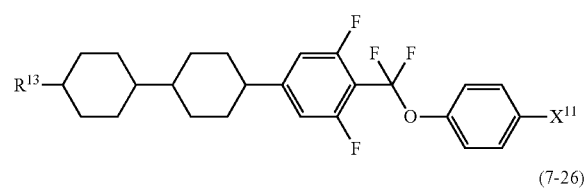
(7-26) 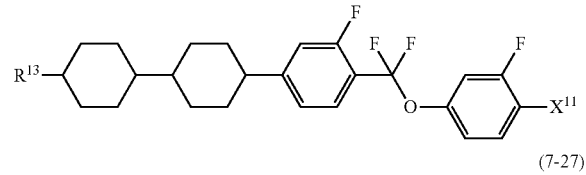
(7-27) 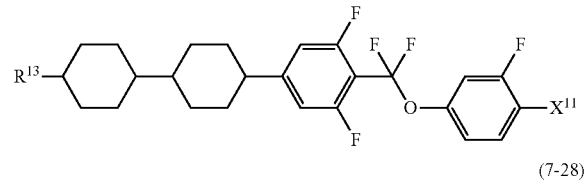
(7-28) 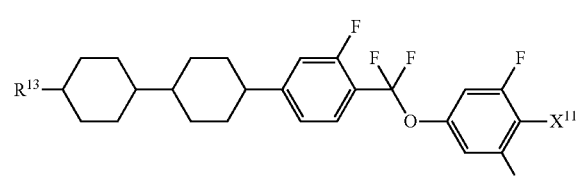
(7-29) 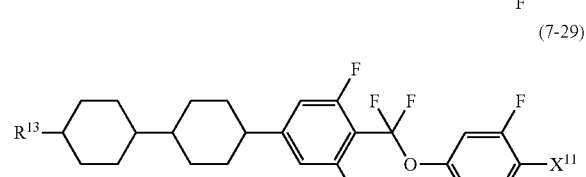
(7-30) 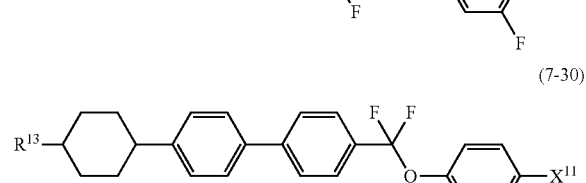
(7-31) 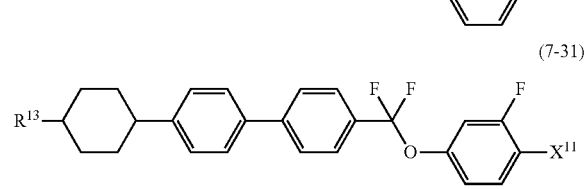
(7-32) 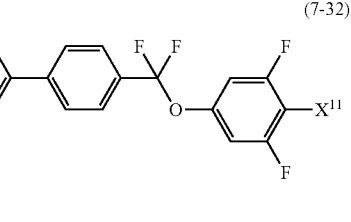
(7-33) 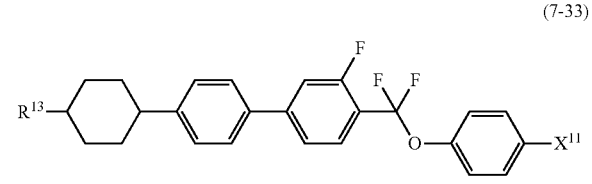
(7-34) 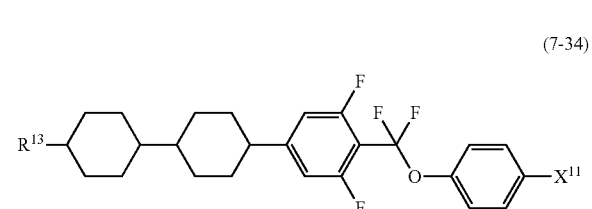
(7-35) 
(7-36) 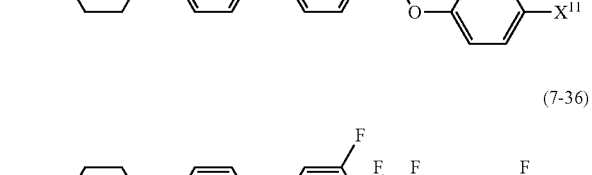
(7-37) 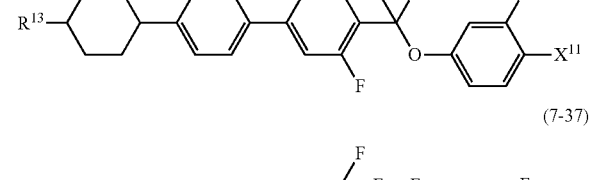
(7-38) 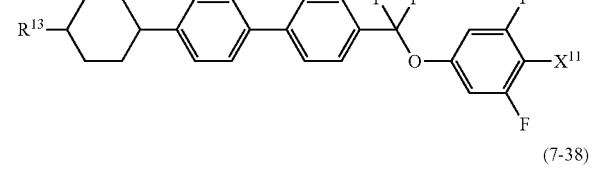
(7-39) 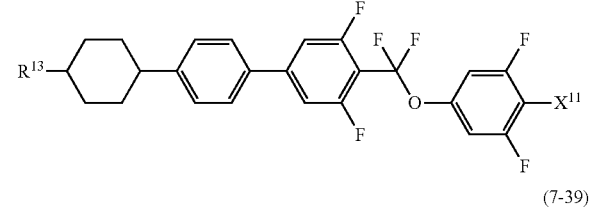

(7-40)
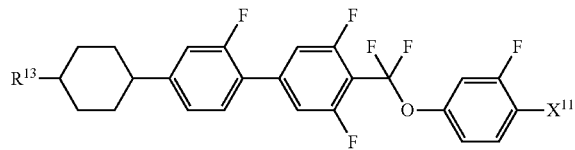
(7-41)
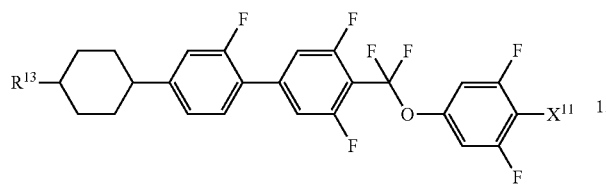
(7-42)
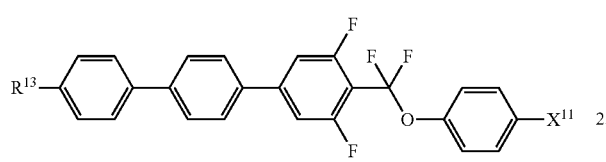
(7-43)
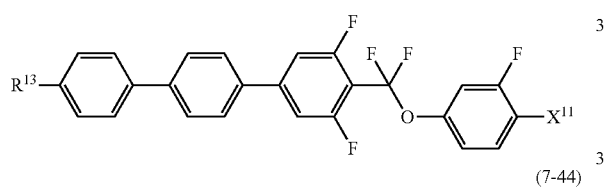
(7-44)
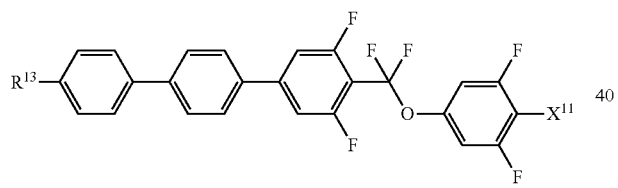
(7-45)
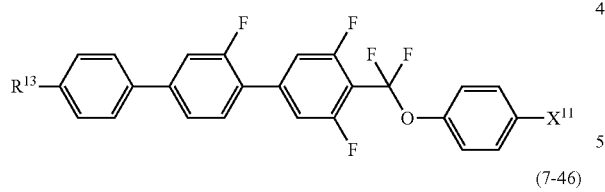
(7-46)
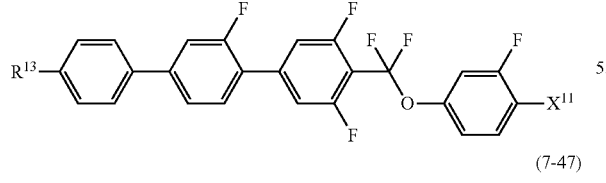
(7-47)
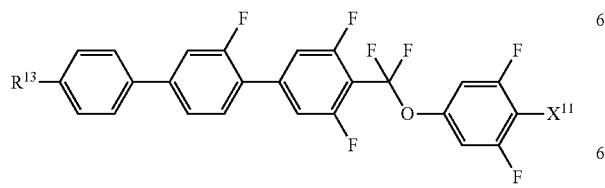
(7-48)
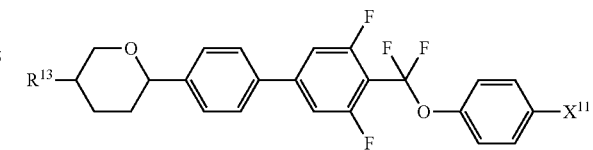
(7-49)
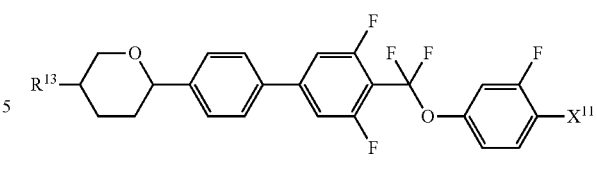
(7-50)
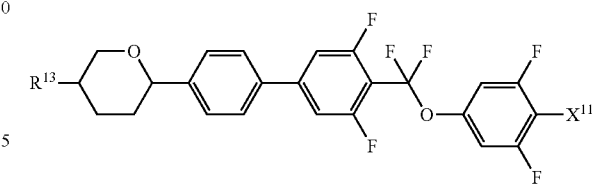
(7-51)
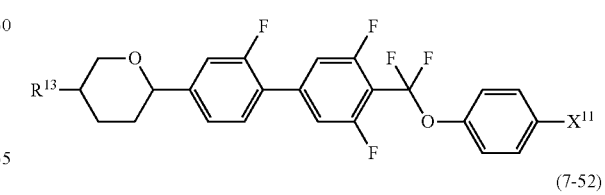
(7-52)
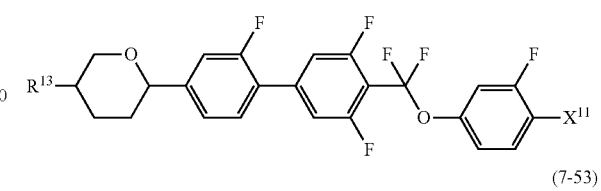
(7-53)
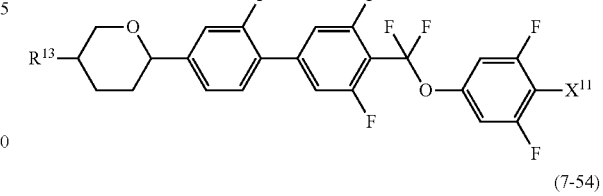
(7-54)
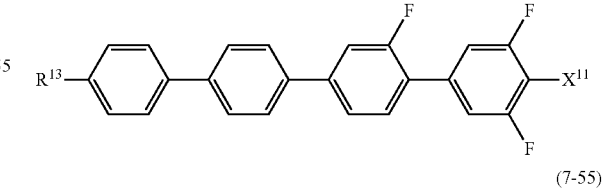
(7-55)
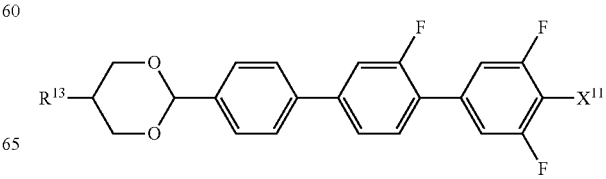

(7-56)
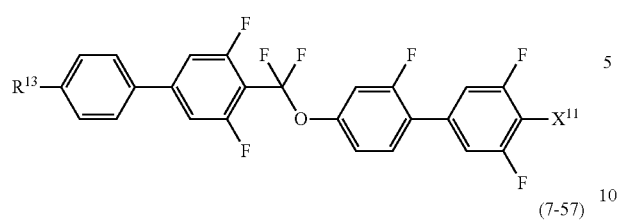

(7-57)
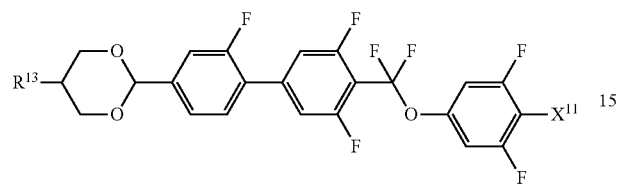

The component C has positive dielectric anisotropy and very excellent stability to heat and light, etc., and can thus be used for preparing the composition for use in modes such as IPS, FFS, and OCB, etc. The content of the component C is suitably 1 to 99 wt %, preferably 10 to 97 wt %, and more preferably 40 to 95 wt %, based on the weight of the liquid crystal composition. When the component C is added to a composition having negative dielectric anisotropy, the content of the component C is preferably 30 wt % or less. By addition of the component C, the elastic constant of the composition can be adjusted, and a voltage-transmittance curve of the device can be adjusted.

The component D is the compound (8) in which the right terminal group is —C≡N or —C≡C—C≡N. Preferred examples of the component D include compounds (8-1) to (8-64). In the compounds as the component D, $R^{14}$ is alkyl having 1 to 10 carbons or alkenyl having 2 to 10 carbons, wherein at least one —CH$_2$— in the alkyl and alkenyl is optionally replaced with —O—, and at least one hydrogen in the alkyl and alkenyl is optionally replaced with fluorine; and $X^{12}$ is —C≡N or —C≡C—C≡N.

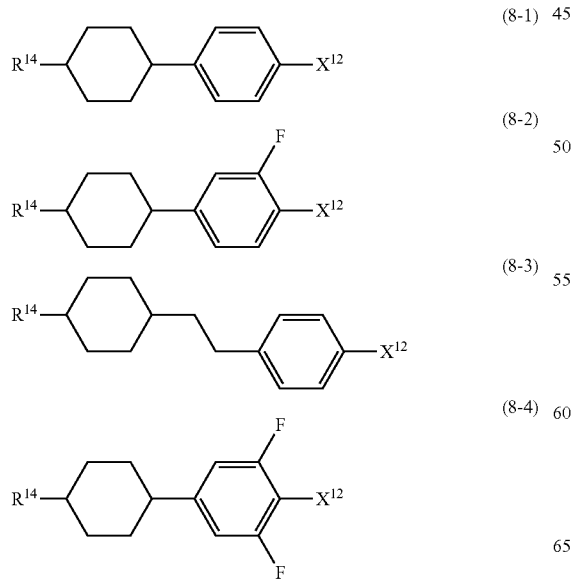

(8-5)
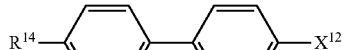

(8-6)
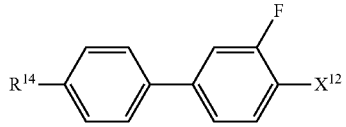

(8-7)
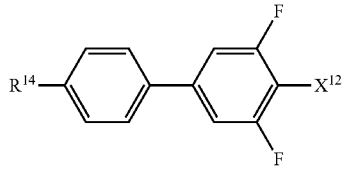

(8-8)
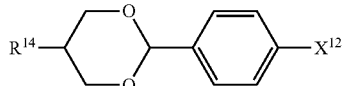

(8-9)
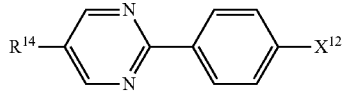

(8-10)
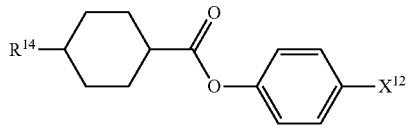

(8-11)
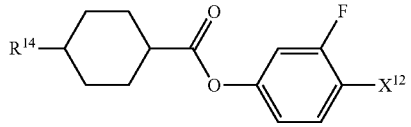

(8-12)
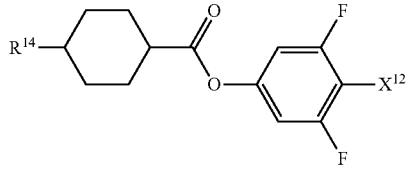

(8-13)
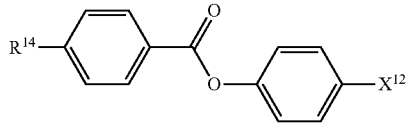

(8-14)
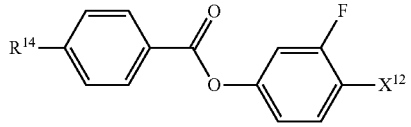

(8-15)
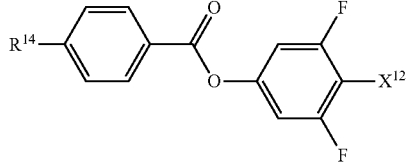

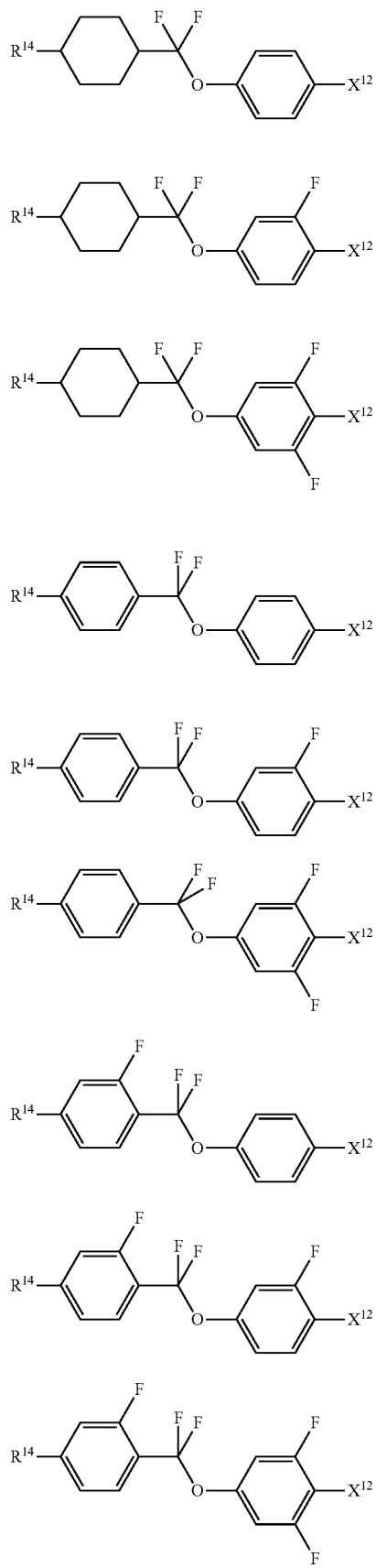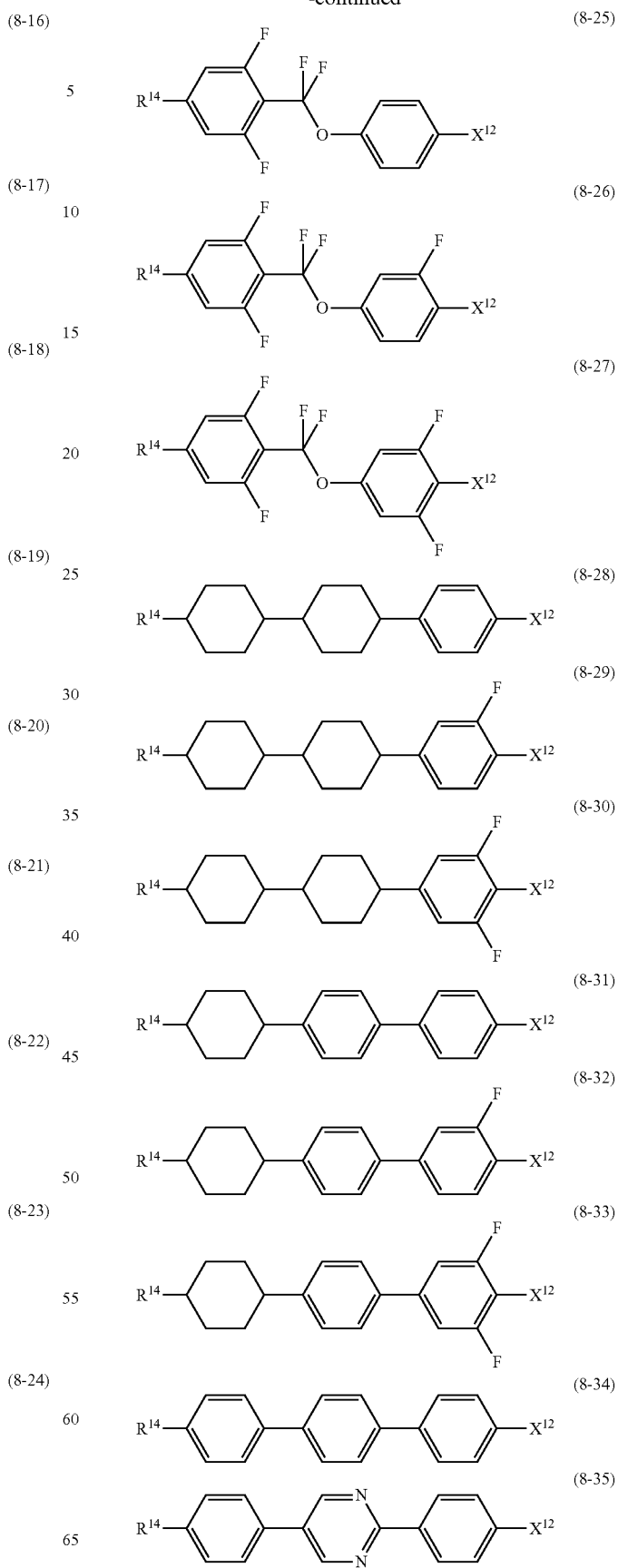

(8-36)
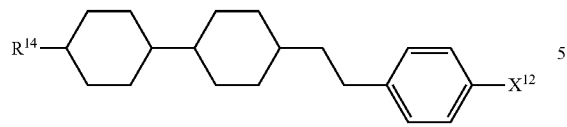
(8-37)
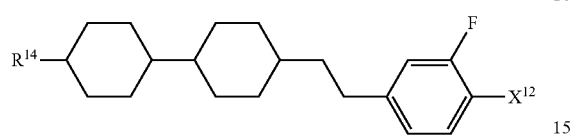
(8-38)
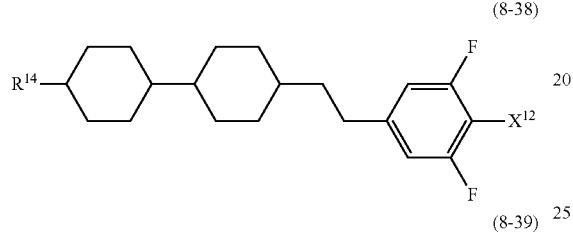
(8-39)
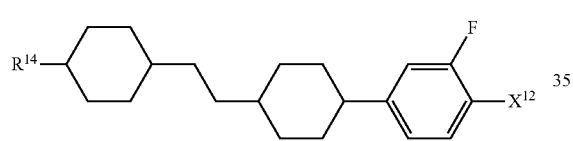
(8-40)
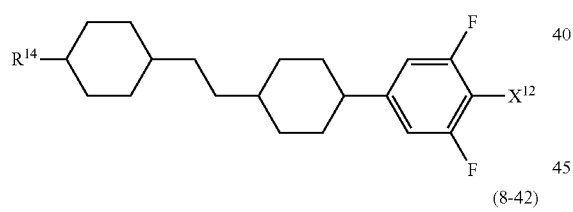
(8-41)
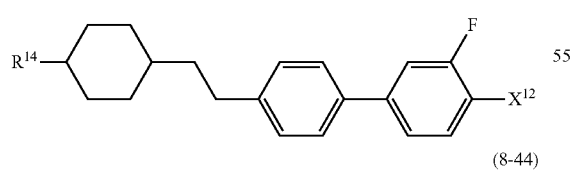
(8-42)
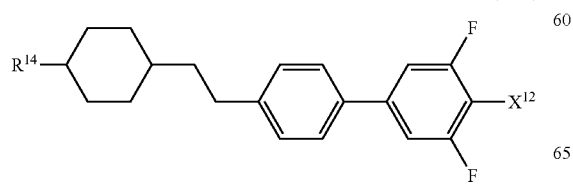
(8-43)
(8-44)
(8-45)
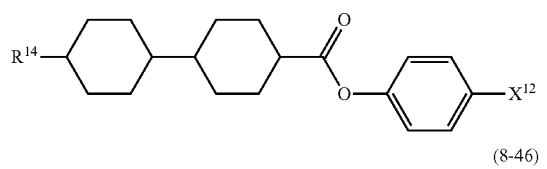
(8-46)
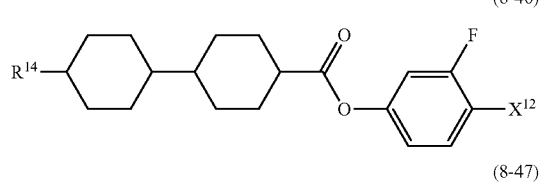
(8-47)
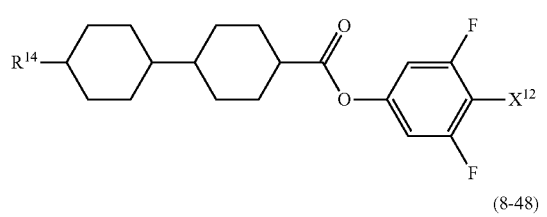
(8-48)
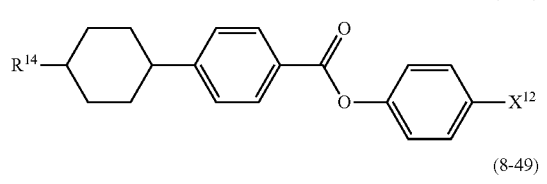
(8-49)
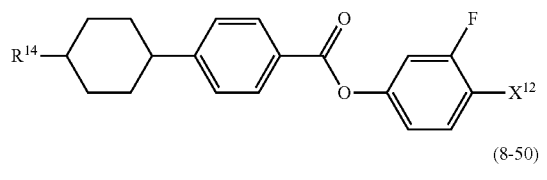
(8-50)
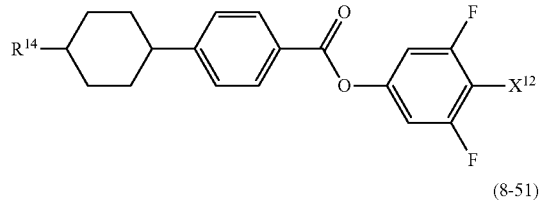
(8-51)
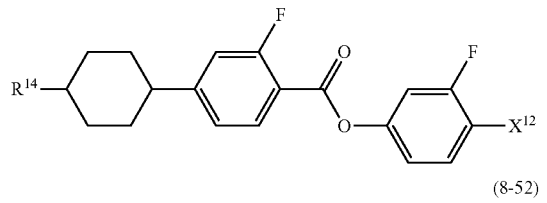
(8-52)
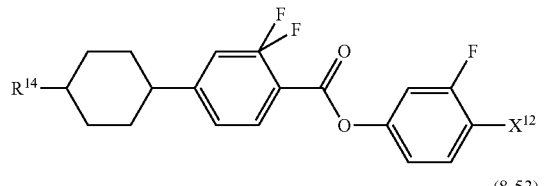
(8-53)
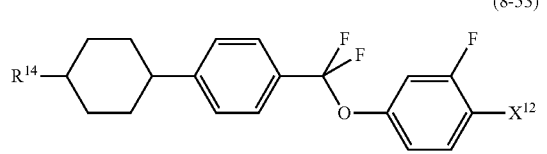

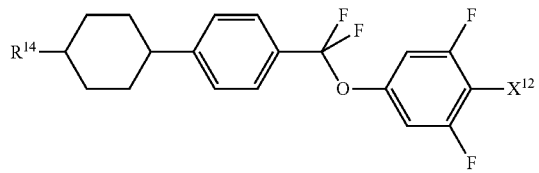
(8-54)

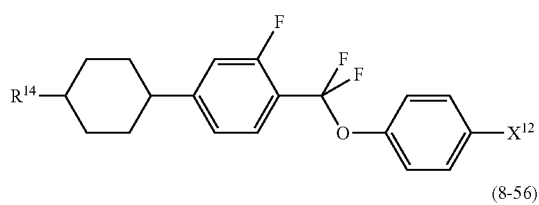
(8-55)

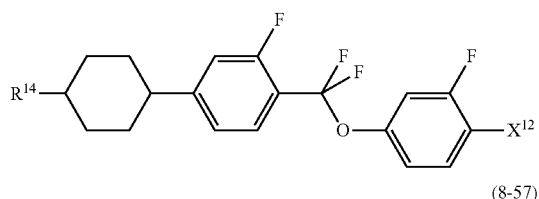
(8-56)

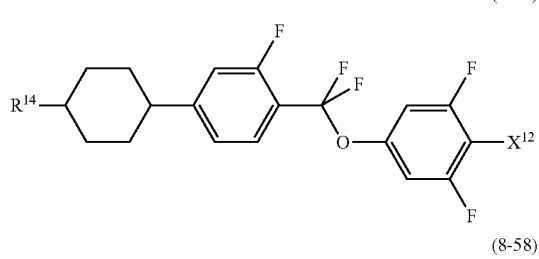
(8-57)

(8-58)

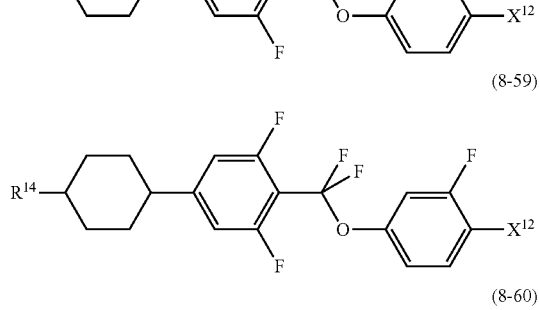
(8-59)

(8-60)

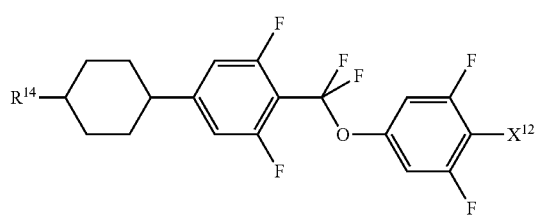
(8-61)

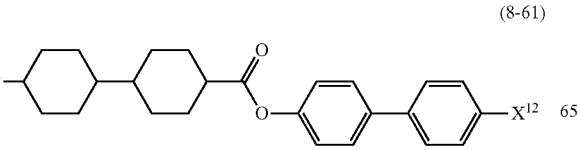

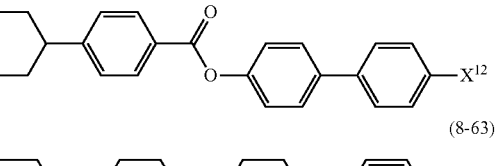
(8-62)

(8-63)

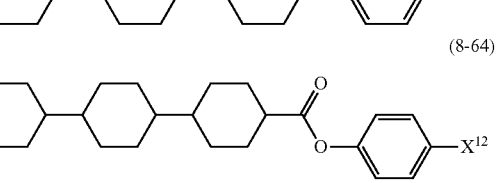
(8-64)

The component D has large positive dielectric anisotropy, and can thus be primarily used for preparing the composition for use in modes such as TN or the like. By addition of the component D, the dielectric anisotropy of the composition can be increased. The component D has an effect of broadening a temperature range of a liquid crystal phase, adjusting viscosity, or adjusting optical anisotropy. The component D is also useful for adjusting the voltage-transmittance curve of the device.

In preparing the composition for use in modes such as TN or the like, the content of the component D is suitably 1 to 99 wt %, preferably 10 to 97 wt %, and more preferably 40 to 95 wt %, based on the weight of the liquid crystal composition. When the component D is added to a composition having negative dielectric anisotropy, the content of the component D is preferably 30 wt % or less. By addition of the component D, the elastic constant of the composition can be adjusted, and the voltage-transmittance curve of the device can be adjusted.

The component E includes compounds (9) to (15). These compounds have phenylene in which lateral positions are replaced with two halogens, such as 2,3-difluoro-1,4-phenylene. Preferred examples of the component E include compounds (9-1) to (9-8), compounds (10-1) to (10-17), compound (11-1), compounds (12-1) to (12-3), compounds (13-1) to (13-11), compounds (14-1) to (14-3), and compounds (15-1) to (15-3). In the compounds as the component E, $R^{15}$ and $R^{16}$ are independently alkyl having 1 to 10 carbons or alkenyl having 2 to 10 carbons, wherein at least one —CH$_2$— in the alkyl and alkenyl is optionally replaced with —O—, and at least one hydrogen in the alkyl and alkenyl is optionally replaced with fluorine; $R^{17}$ is hydrogen, fluorine, alkyl having 1 to 10 carbons, or alkenyl having 2 to 10 carbons, wherein at least one —CH$_2$— in the alkyl and alkenyl is optionally replaced with —O—, and at least one hydrogen in the alkyl and alkenyl is optionally replaced with fluorine.

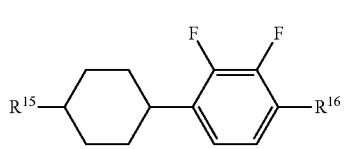
(9-1)

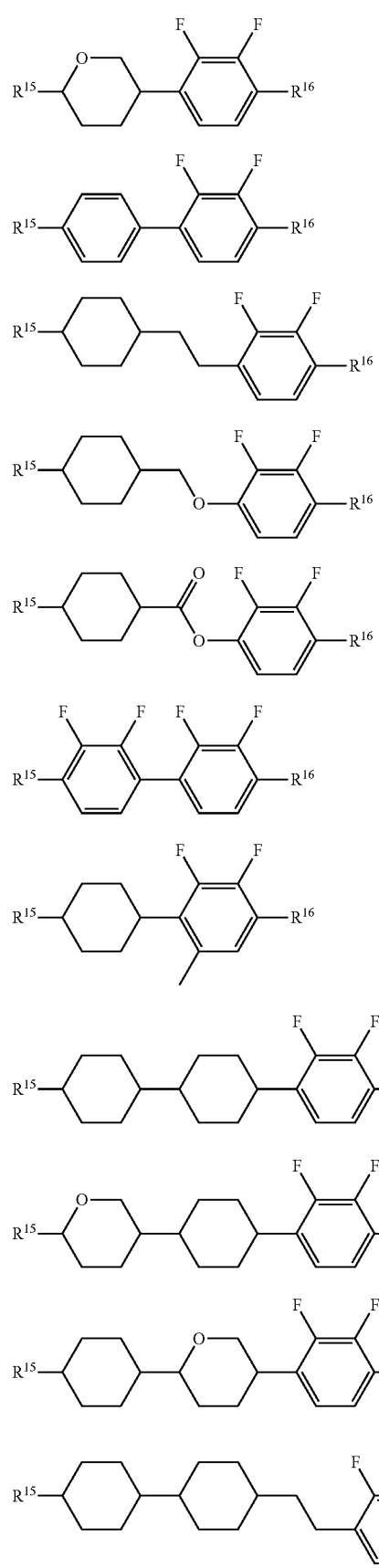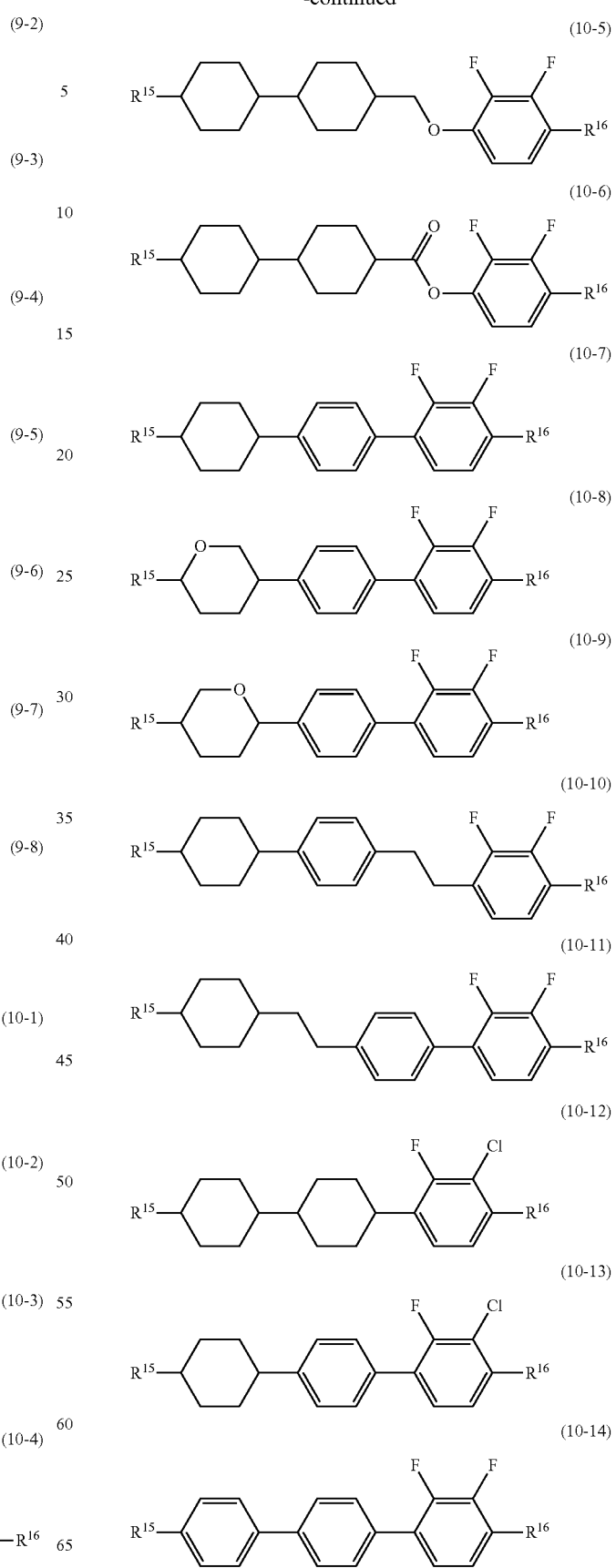

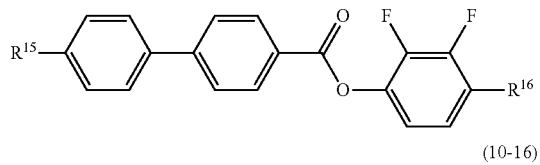
(10-15)
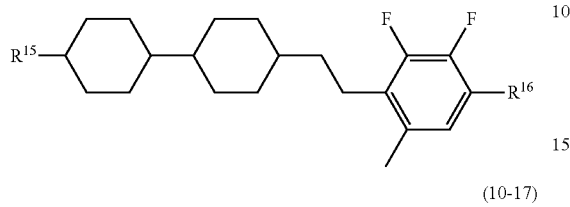
(10-16)
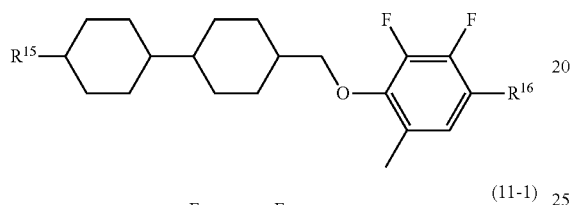
(10-17)
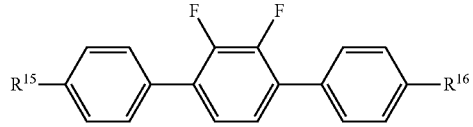
(11-1)
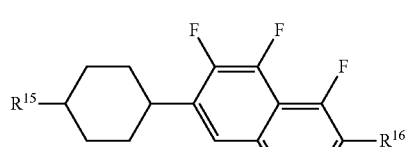
(12-1)
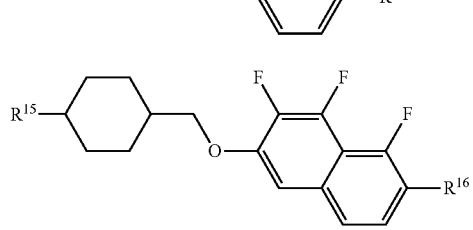
(12-2)
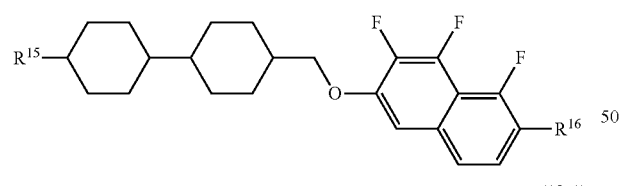
(12-3)
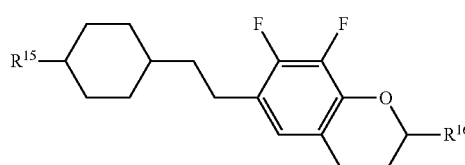
(13-1)
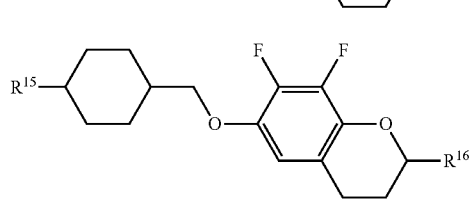
(13-2)
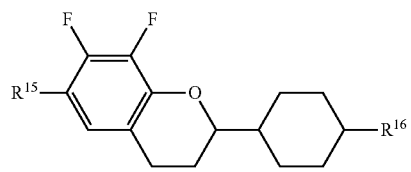
(13-3)
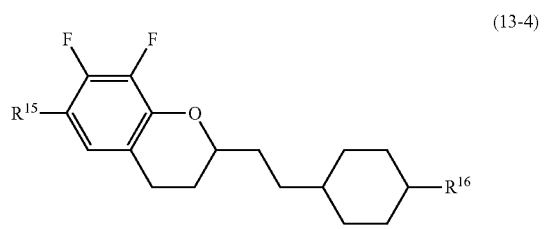
(13-4)
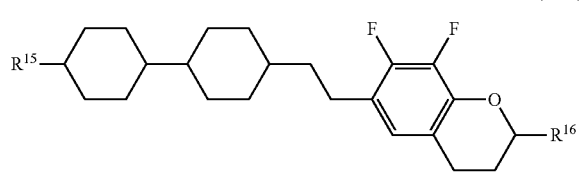
(13-5)
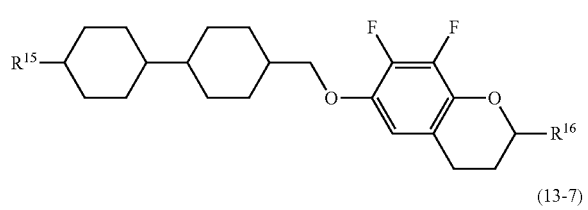
(13-6)
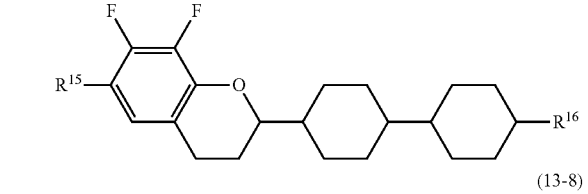
(13-7)
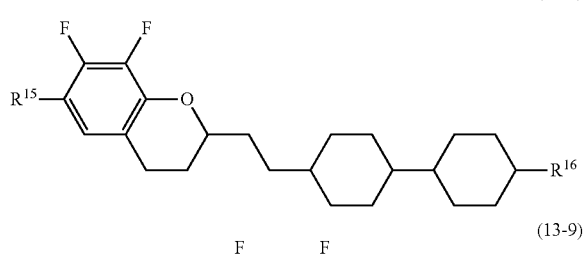
(13-8)
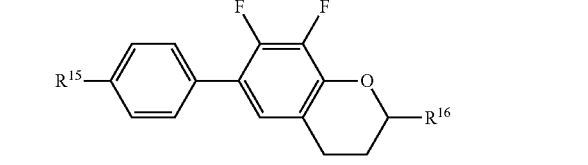
(13-9)
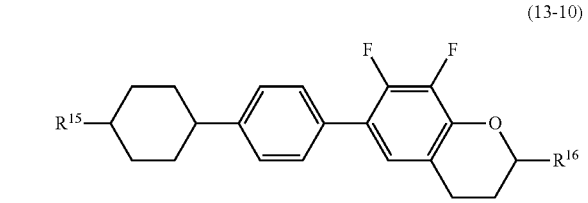
(13-10)

-continued

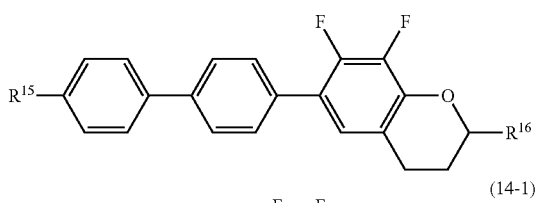
(13-11)

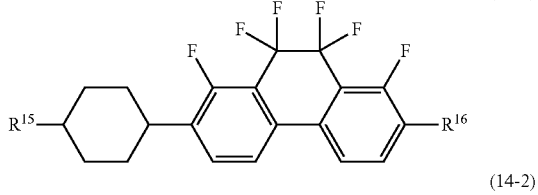
(14-1)

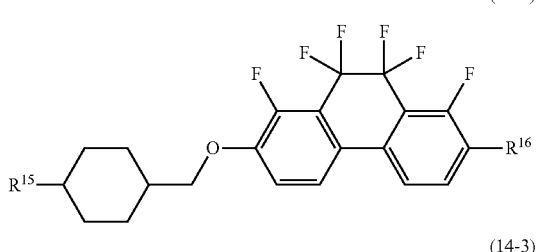
(14-2)

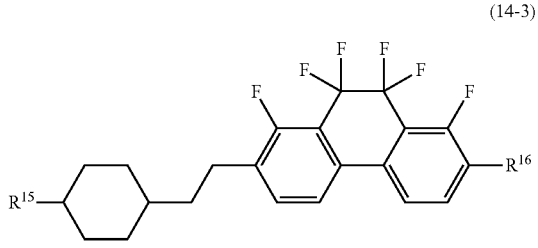
(14-3)

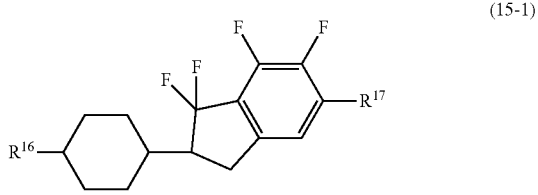
(15-1)

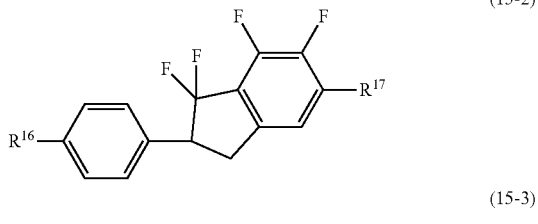
(15-2)

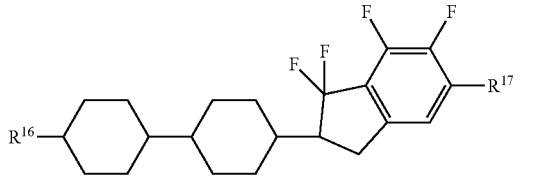
(15-3)

The component E has large negative dielectric anisotropy. The component E can be used for preparing the composition for use in modes such as IPS and VA, etc. As the content of the component E is increased, the dielectric anisotropy of the composition is increased negatively but the viscosity is increased. Therefore, the content is preferably as low as possible as long as a required value of threshold voltage of the device is satisfied. When considering that the dielectric anisotropy is about −5, the content is preferably 40 wt % or more to perform sufficient voltage driving.

In the component E, the compound (9) is a bicyclic compound, and thus mainly has an effect of reducing viscosity, adjusting optical anisotropy or increasing dielectric anisotropy. The compounds (10) and (11) are tricyclic compounds, and thus mainly have an effect of increasing the maximum temperature, increasing optical anisotropy or increasing dielectric anisotropy. The compounds (12) to (15) have an effect of increasing dielectric anisotropy.

In preparing the composition for use in modes such as IPS and VA, etc., the content of the component E is preferably 40 wt % or more, more preferably 50 to 95 wt %, based on the weight of the liquid crystal composition. When the component E is added to a composition having positive dielectric anisotropy, the content of the component E is preferably 30 wt % or less. By addition of the component E, the elastic constant of the composition can be adjusted, and the voltage-transmittance curve of the device can be adjusted.

By a suitable combination of the aforementioned components B, C, D and E, a liquid crystal composition that satisfies at least one of characteristics such as high maximum temperature, low minimum temperature, small viscosity, suitable (large or small) optical anisotropy, large positive or negative dielectric anisotropy, large specific resistance, high stability to ultraviolet light or heat, and a suitable (large or small) elastic constant, etc. can be prepared. A liquid crystal compound different from the components B, C, D and E may also be added if necessary. Since the compound (1) as the component A is added to the composition, this composition is stable to light.

3-2. Additives

The liquid crystal composition is prepared by a well-known method. For example, the component compounds are mixed together and dissolve in each other by heating. An additive may further be added to the composition according to the use. Examples of the additive include a polymerizable compound, a polymerization initiator, a polymerization inhibitor, an optically active compound, an antioxidant, an ultraviolet absorbent, other light stabilizers, a heat stabilizer, and a defoamer, etc. Such additives are well-known to persons skilled in the art and have been described in literatures.

In a PSA-type device, the polymerizable compound is added for producing a polymer in the liquid crystal composition. The polymer is produced in the liquid crystal composition by irradiation with ultraviolet light to polymerize the polymerizable compound in a state in which a voltage has been applied between electrodes. By this method, a suitable pretilt can be obtained, and a liquid crystal display device having shortened response time and improved image burn-in can thus be obtained. Preferred examples of the polymerizable compound include an acrylate, a methacrylate, a vinyl compound, a vinyloxy compound, propenyl ether, an epoxy compound (oxirane, oxetane), and vinyl ketone. More preferred examples include a compound having at least one acryloyloxy and a compound having at least one methacryloyloxy. More preferred examples also include a compound having both acryloyloxy and methacryloyloxy.

More preferred examples include compounds (M-1) to (M-17). In these compounds, $R^{25}$ to $R^{31}$ are independently hydrogen or methyl; s, v and x are independently 0 or 1; t and u are independently an integer of 1 to 10; $L^{21}$ to $L^{26}$ are independently hydrogen or fluorine, and $L^{27}$ and $L^{28}$ are independently hydrogen, fluorine, or methyl.

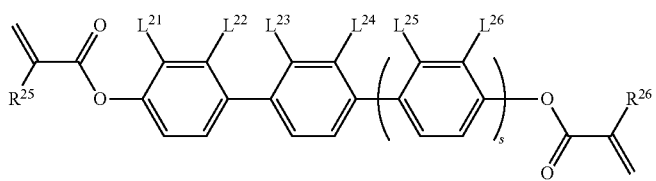
(M-1)
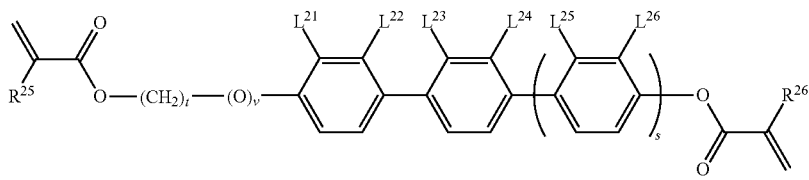
(M-2)
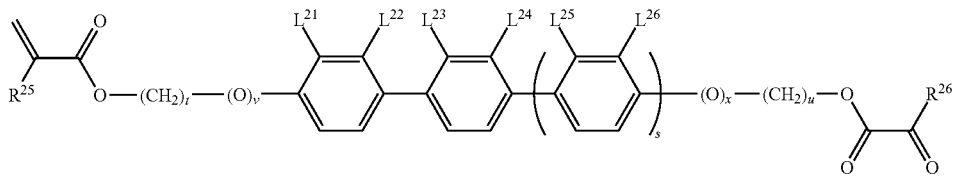
(M-3)
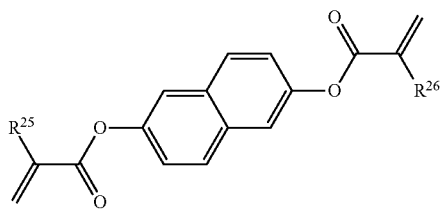
(M-4)
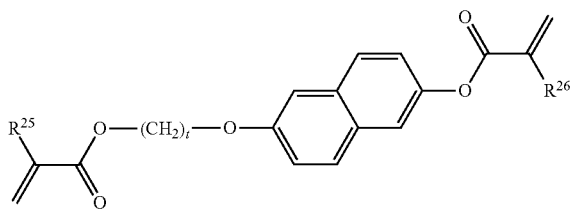
(M-5)
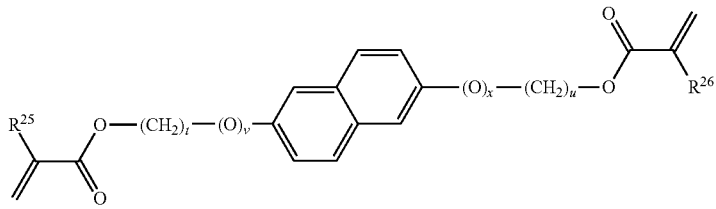
(M-6)
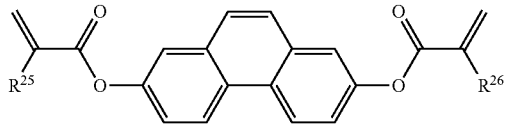
(M-7)
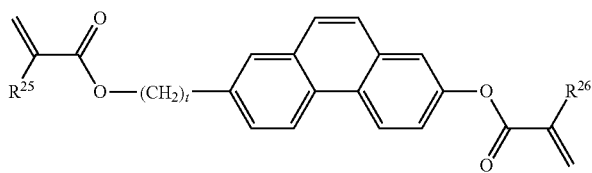
(M-8)

(M-9)
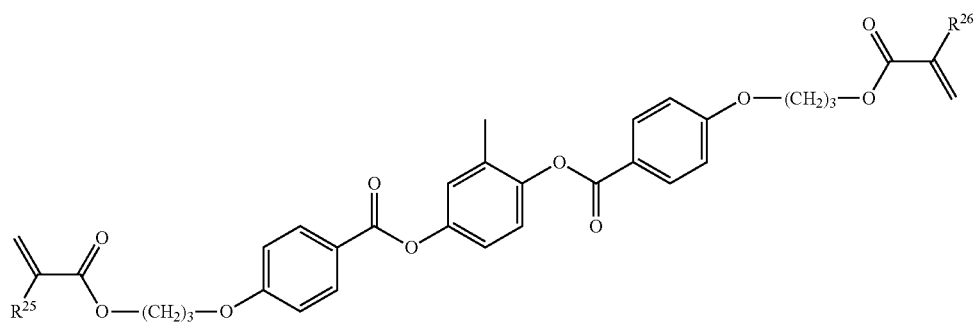
(M-10)
(M-11)
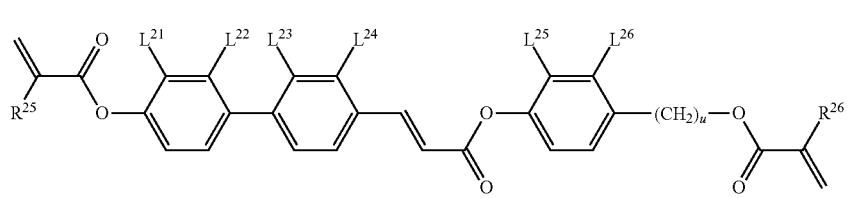
(M-12)
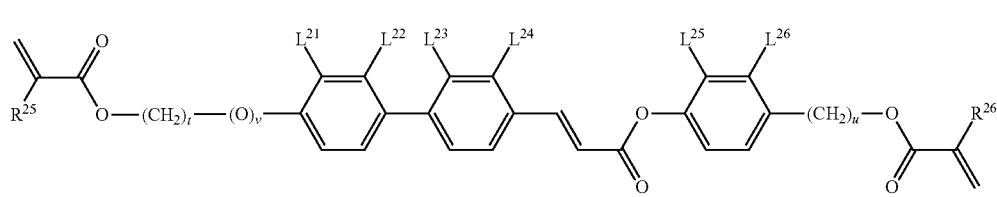
(M-13)
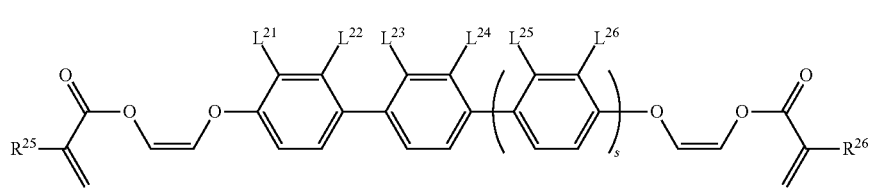
(M-14)
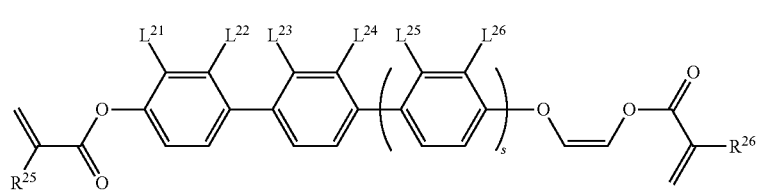

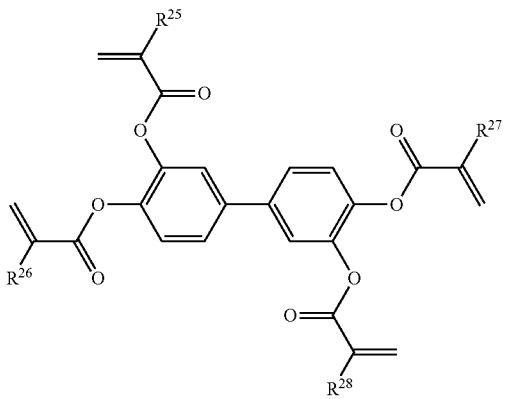

(M-15)

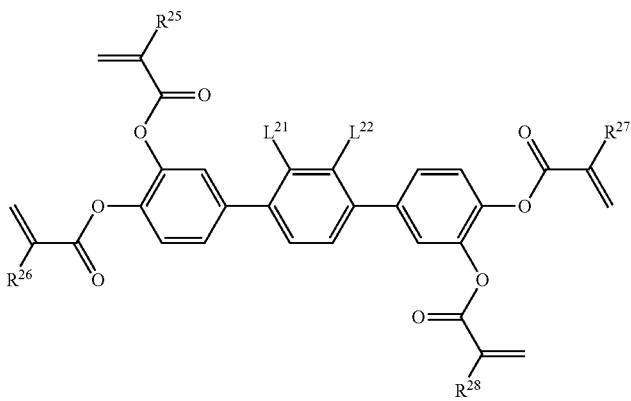

(M-16)

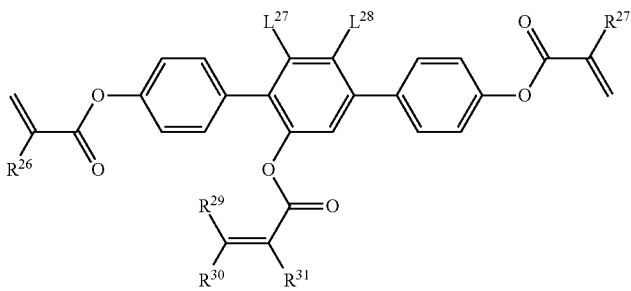

(M-17)

The polymerizable compound can be promptly polymerized by addition of a polymerization initiator. By optimization of a reaction temperature, the amount of remaining polymerizable compound can be reduced. Examples of a photo-radical polymerization initiator include TPO, 1173 and 4265 from Darocur series, and 184, 369, 500, 651, 784, 819, 907, 1300, 1700, 1800, 1850, and 2959 from Irgacure series, all made by BASF.

Additional examples of the photo-radical polymerization initiator include 4-methoxyphenyl-2,4-bis(trichloromethyl)triazine, 2-(4-butoxystyryl)-5-trichloromethyl-1,3,4-oxadiazole, 9-phenylacridine, 9,10-benzphenazine, a benzophenone/Michler's ketone mixture, a hexaarylbiimidazole/mercaptobenzimidazole mixture, 1-(4-isopropylphenyl)-2-hydroxy-2-methylpropane-1-one, benzyl dimethyl ketal, 2-methyl-1-[4-(methylthio)phenyl]-2-morpholinopropane-1-one, a 2,4-diethylxanthone/methyl p-dimethylaminobenzoate mixture, and a benzophenone/methyltriethanolamine mixture.

After the photo-radical polymerization initiator is added to the liquid crystal composition, polymerization can be carried out by irradiation with ultraviolet light in a state in which an electric field has been applied. However, an unreacted polymerization initiator or a decomposition product of the polymerization initiator might cause display defects of the device, such as image burn-in. In order to prevent this, the photopolymerization may also be carried out with no addition of the polymerization initiator. The irradiated light has a wavelength of preferably 150 to 500 nm, more preferably 250 to 450 nm, and most preferably 300 to 400 nm.

During storage of the polymerizable compound, a polymerization inhibitor may be added in order to prevent polymerization. The polymerizable compound is usually added to the composition without removing the polymerization inhibitor. Examples of the polymerization inhibitor include hydroquinone, a hydroquinone derivative such as methylhydroquinone, 4-t-butylcatechol, 4-methoxyphenol, and phenothiazine, etc.

The optically active compound has an effect of inducing a helical structure in liquid crystal molecules to give a necessary torsion angle so as to prevent reverse torsion. By addition of the optically active compound, a helical pitch can be adjusted. Two or more optically active compounds may be added for adjusting temperature dependence of the helical pitch. Preferred examples of the optically active compound include the following compounds (Op-1) to (Op-18). In the compound (Op-18), ring J is 1,4-cyclohexylene or 1,4-phenylene, and $R^{28}$ is alkyl having 1 to 10 carbons.

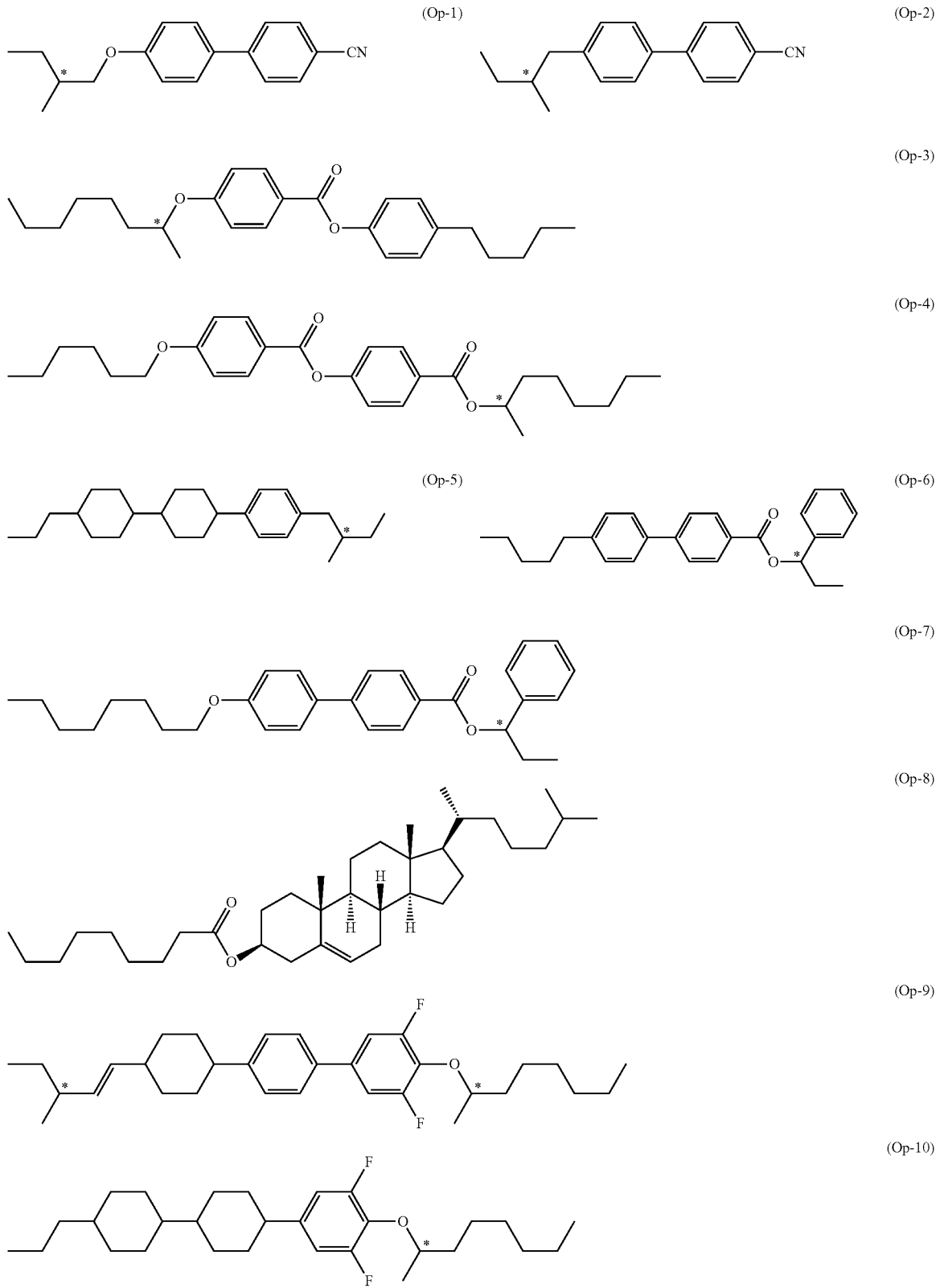

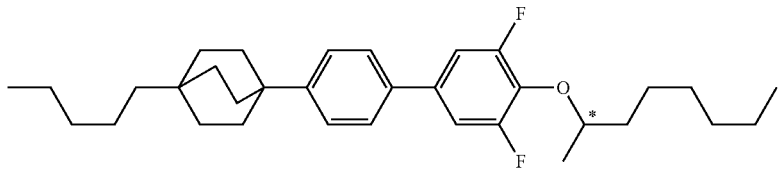
(Op-11)
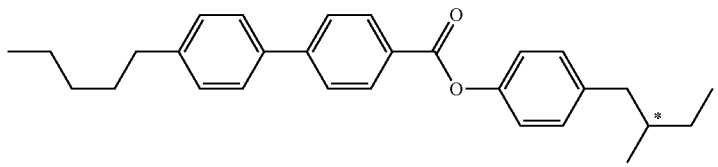
(Op-12)
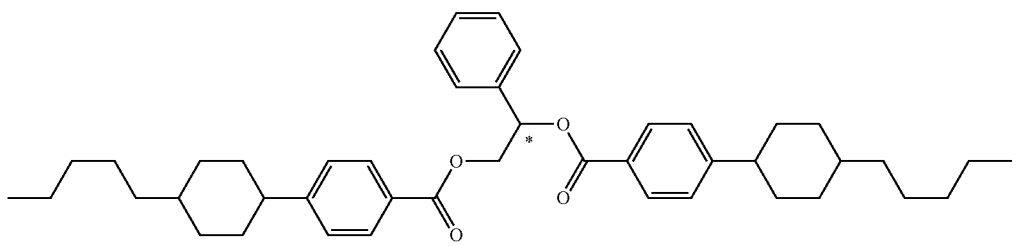
(Op-13)
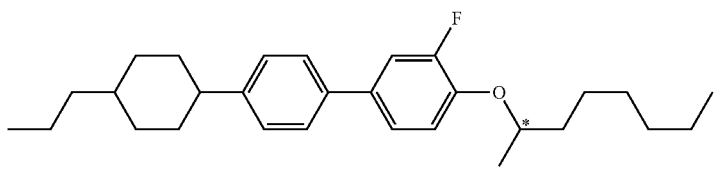
(Op-14)
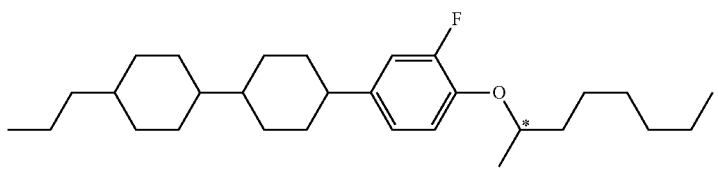
(Op-15)
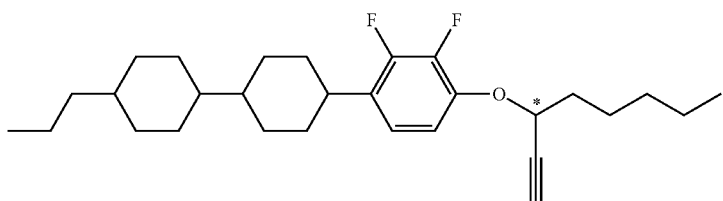
(Op-16)
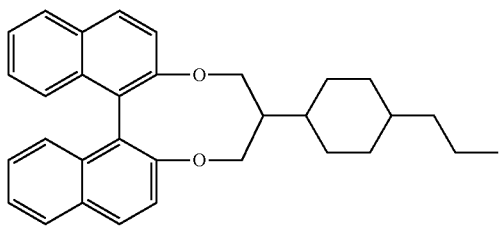
(Op-17)

(Op-18)

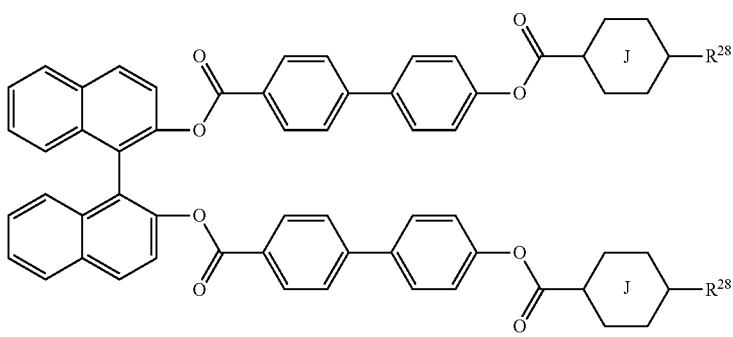

The antioxidant is effective for maintaining a large voltage holding ratio. Preferred examples of the antioxidant include the following compounds (AO-1) and (AO-2), IRGANOX 415, IRGANOX 565, IRGANOX 1010, IRGANOX 1035, IRGANOX 3114, and IRGANOX 1098 (trade names, made by BASF). The ultraviolet absorbent is effective for preventing reduction in the maximum temperature. Preferred examples of the ultraviolet absorbent include a benzophenone derivative, a benzoate derivative, and a triazole derivative, etc. Specific examples thereof include the following compounds (AO-3) and (AO-4), TINUVIN 329, TINUVIN P, TINUVIN 326, TINUVIN 234, TINUVIN 213, TINUVIN 400, TINUVIN 328, and TINUVIN 99-2 (trade names, made by BASF), and 1,4-diazabicyclo[2.2.2]octane (DABCO).

The light stabilizer such as an amine having steric hindrance is preferred for maintaining a large voltage holding ratio. Preferred examples of the light stabilizer include the following compounds (AO-5) and (AO-6), TINUVIN 144, TINUVIN 765 and TINUVIN 770DF (trade names, made by BASF). The heat stabilizer is also effective for maintaining a large voltage holding ratio, and preferred examples thereof include IRGAFOS 168 (trade name, made by BASF). The defoamer is effective for preventing foaming. Preferred examples of the defoamer include dimethyl silicone oil and methyl phenyl silicone oil, etc.

(AO-1)

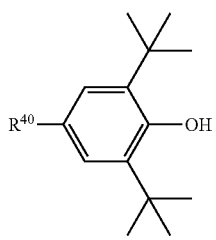

(AO-2)

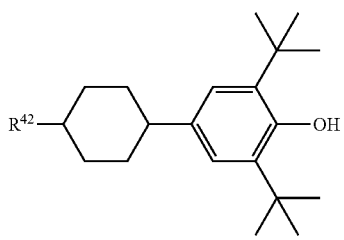

(AO-3)

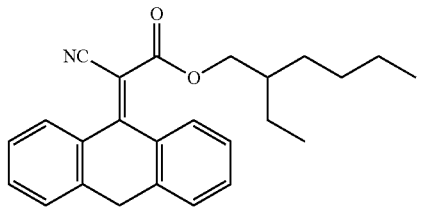

(AO-4)

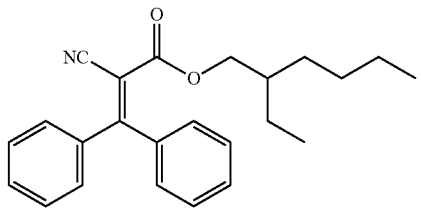

(AO-5)

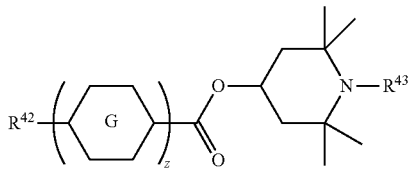

(AO-6)

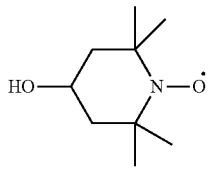

In the compound (AO-1), $R^{40}$ is alkyl having 1 to 20 carbons, alkoxy having 1 to 20 carbons, $-COOR^{41}$ or $-CH_2CH_2COOR^{41}$, wherein $R^{41}$ is alkyl having 1 to 20 carbons. In the compounds (AO-2) and (AO-5), $R^{42}$ is alkyl having 1 to 20 carbons. In the compound (AO-5), $R^{43}$ is hydrogen, methyl, or —O. (oxygen radical); ring G is 1,4-cyclohexylene or 1,4-phenylene; and z is 1, 2, or 3.

4. Liquid Crystal Display Device

The liquid crystal composition can be used in a liquid crystal display device having an operating mode such as PC, TN, STN, or OCB, etc. and driven by an active matrix (AM) method. This composition can also be used in a liquid crystal display device having an operating mode such as PC, TN, STN, OCB, VA, or IPS, etc. and driven by a passive matrix (PM) method. The device in these methods may be of any of a reflective type, a transmissive type and a transflective type.

This composition can also be used in a nematic curvilinear aligned phase (NCAP) device produced by microencapsulating a nematic liquid crystal, a polymer dispersed liquid crystal display device (PDLCD) produced by forming a three-dimensional network polymer in a liquid crystal, and a polymer network liquid crystal display device (PNLCD). When the polymerizable compound is added in an amount of about 10 wt % or less based on the weight of the liquid crystal composition, a PSA-type liquid crystal display device is produced. A preferred ratio is about 0.1 to 2 wt %, and a more preferred ratio is about 0.2 to 1.0 wt %. The PSA-type liquid crystal display device can be driven by methods such as an active matrix (AM) method and a passive matrix (PM) method. Such a device may be of any of a reflective type, a transmissive type and a transflective type. By increasing the amount of the polymerizable compound added, a device in the polymer dispersed mode can also be produced.

EXAMPLES

The invention is further described in details according to examples (including synthesis examples and use examples). The invention is not limited to these examples. The invention includes a mixture of a composition of Use Example 1 and a composition of Use Example 2. The invention also includes a composition prepared by mixing at least two compositions of the use examples.

1. Examples of Compound (1)

The compound (1) was synthesized by procedures shown in the examples. Unless otherwise specified, the reactions were performed under a nitrogen atmosphere. The compound (1) was synthesized by procedures shown in Example 1 and so on. The synthesized compound was identified by methods such as NMR analysis, etc. Characteristics of the compound were measured by methods described below.

NMR analysis: DRX-500 made by Bruker BioSpin K.K. was used for the measurement. In the measurement of $^1$H-NMR, a sample was dissolved in a deuterated solvent such as $CDCl_3$, and measured at 500 MHz at room temperature in 16 times of accumulation. Tetramethylsilane was used as the internal standard. The measurement of $^{19}$F-NMR was carried out using $CFCl_3$ as the internal standard in 24 times of accumulation. In the description of the nuclear magnetic resonance spectrum, "s" denotes singlet, "d" denotes doublet, "t" denotes triplet, "q" denotes quartet, "quin" denotes quintet, "sex" denotes sextet, "m" denotes multiplet, and "br" denotes broad.

Gas chromatography (GC) analysis: GC-2010 Gas Chromatograph made by Shimadzu Corporation was used for the measurement. The capillary column DB-1 (length=60 m, inner diameter=0.25 mm, film thickness=0.25 μm) made by Agilent Technologies Inc. was used as the column. Helium (1 ml/min) was used as the carrier gas. The sample evaporation chamber was set at 300° C., and the detector (flame ionization detector, FID) was set at 300° C. The sample was dissolved in acetone so as to prepare a solution of 1 wt %, and then 1 μl of the obtained solution was poured into the sample evaporation chamber. The GCsolution system made by Shimadzu Corporation or the like was used as the recorder.

HPLC analysis: Prominence (LC-20AD; SPD-20A) made by Shimadzu Corporation was used for the measurement. YMC-Pack ODS-A (length-150 mm, inner diameter-4.6 mm, particle diameter=5 μm) made by YMC Co., Ltd. was used as the column. A mixture obtained by properly mixing acetonitrile and water was used as the eluent. A UV detector, an RI detector, or a Corona detector or the like was properly used as the detector. When the UV detector was used, the detection wavelength was 254 nm. The sample was dissolved in acetonitrile so as to prepare a solution of 0.1 wt %, and 1 μL of the solution was introduced to the sample chamber. C-R7Aplus made by Shimadzu Corporation was used as the recorder.

Ultraviolet-visible spectroscopic analysis: PharmaSpec UV-1700 made by Shimadzu Corporation was used for the measurement. The detection wavelength was 190 nm to 700 nm. The sample was dissolved in acetonitrile so as to prepare a 0.01 mmol/L solution, and the solution was placed in a quartz cell (optical path length=1 cm) and then measured.

Measurement sample: the compound itself was used as a sample in measuring the phase structure and the transition temperature (clearing point, melting point, polymerization start temperature, etc.). A mixture of a compound and a mother liquid crystal was used as a sample in measuring the characteristics such as the maximum temperature of a nematic phase, viscosity, optical anisotropy, and dielectric anisotropy, etc.

Measurement method: the characteristics were measured by the following methods. Most of these methods were those described in the JEITA Standards (JEITA•ED-2521B) deliberated and established by the Japan Electronics and Information Technology Industries Association (JEITA), or modifications of the same. No thin-film transistor (TFT) was attached to a TN device used for the measurement.

(1) Phase Structure (1) The sample was placed on a hot plate (FP52 Hot Stage made by Mettler Toledo International Inc.) of a melting point apparatus equipped with a polarizing microscope, and a state of phase and a change thereof were observed with the polarizing microscope while the sample was heated at a rate of 3° C./min, and a phase type was specified.

(2) Transition Temperature (° C.)

A scanning calorimeter, Diamond DSC System made by PerkinElmer, Inc., or a high sensitivity differential scanning calorimeter, X-DSC7000 made by SII NanoTechnology Inc., was used for the measurement. The sample was heated and then cooled at a rate of 3° C./min. A starting point of an endothermic peak or an exothermic peak caused by a phase change of the sample was calculated by extrapolation, and the transition temperature was determined. The melting point and the polymerization start temperature of a compound were also measured using this apparatus. The temperature at which the compound changes from solid to a liquid crystal phase such as smectic phase or nematic phase is sometimes simply referred to as "minimum temperature of a liquid crystal phase." The temperature at which the compound changes from a liquid crystal phase to liquid is sometimes simply referred to as "clearing point."

Crystals were expressed as C. When types of the crystals were distinguishable, the crystals were expressed as $C_1$ or $C_2$. The smectic phase was expressed as S and the nematic phase as N. When a smectic A phase, a smectic B phase, a smectic C phase or a smectic F phase was distinguishable in the smectic phases, it was expressed as $S_A$, $S_B$, $S_C$ or $S_F$. A liquid (isotropic) was expressed as I. The transition temperature was expressed as, e.g., "C 50.0 N 100.0 I." This means that the transition temperature from crystal to a nematic phase is 50.0° C., and the transition temperature from a nematic phase to liquid is 100.0° C.

(3) Maximum Temperature of Nematic Phase ($T_N$, or NI; ° C.)

The sample was placed on a hot plate of a melting point apparatus equipped with a polarizing microscope and was heated at a rate of 1° C./min. The temperature at which a part of the sample changed from a nematic phase to an isotropic liquid was measured. When the sample was a mixture of the compound (1) and a mother liquid crystal, the maximum temperature was represented by the symbol $T_{NI}$. When the sample was a mixture of the compound (1) and a compound such as the component B, C or D, the maximum temperature was represented by the symbol NI. The maximum temperature of a nematic phase is sometimes simply referred to as "maximum temperature."

(4) Minimum Temperature of Nematic Phase ($T_C$; ° C.)

The sample having a nematic phase was stored in a freezer at 0° C., −10° C., −20° C., −30° C., and −40° C. for 10 days, and then observed for the liquid crystal phase. For example, when the sample maintained a nematic phase at −20° C. and changed to crystal or a smectic phase at −30° C., the $T_c$ was recorded as "≤−20° C." The minimum temperature of a nematic phase is sometimes simply referred to as "minimum temperature."

(5) Viscosity (Bulk Viscosity; η; Measured at 20° C.; mPa·s)

An E-type rotational viscometer made by Tokyo Keiki Inc. was used for the measurement.

(6) Optical Anisotropy (Refractive Index Anisotropy; Measured at 25° C.; Δn)

The measurement was carried out using light of 589 nm with an Abbe refractometer having a polarizing plate mounted on an ocular lens. The surface of the main prism was rubbed in a direction, and then the sample was dripped onto the main prism. The refractive index (n∥) was measured when the direction of polarized light was parallel to that of the rubbing, and the refractive index (n⊥) was measured when the direction of polarized light was perpendicular to that of the rubbing. The value of optical anisotropy (Δn) was calculated from an equation of "Δn=n∥−n⊥."

(7) Specific Resistance (ρ; Measured at 25° C.; Ωcm)

1.0 mL of the sample was poured into a vessel equipped with electrodes. DC voltage (10 V) was applied to the vessel, and the DC current after 10 seconds was measured. The specific resistance was calculated from the following equation: (specific resistance)=[(voltage)×(electric capacity of vessel)]/[(DC current)×(dielectric constant in vacuum)].

(8) Voltage Holding Ratio (VHR-1; Measured at 25° C.; %)

The TN device used for the measurement had a polyimide alignment film, and had a distance (cell gap) of 5 μm between two glass substrates. The sample was placed into the device, and then the device was sealed with an adhesive curable on irradiation with ultraviolet light. The device was charged by applying a pulse voltage (60 microseconds at 5 V). A decaying voltage was measured for 16.7 milliseconds with a high-speed voltmeter, and an area A between a voltage curve and a horizontal axis per unit cycle was calculated. An area B was an area without decay. A voltage holding ratio was expressed by a percentage of the area A relative to the area B.

(9) Voltage Holding Ratio (VHR-2; Measured at 80° C.; %)

A voltage holding ratio was measured by the same procedure as above except that the measurement was carried out at 80° C. instead of 25° C. The results obtained were represented by the symbol VHR-2.

(10) Voltage Holding Ratio (VHR-3; Measured at 25° C.; %)

A voltage holding ratio was measured after irradiation with ultraviolet light, and stability to ultraviolet light was evaluated. The TN device used for the measurement has a polyimide alignment film, and has a cell gap of 5 μm. The sample was poured into the device, and the device was irradiated with light for 20 minutes. The light source is an extra-high pressure mercury lamp, USH-500D (made by Ushio Inc.), and a distance between the device and the light source is 20 cm. In the measurement of VHR-3, a decaying voltage was measured for 16.7 milliseconds. A composition having a large VHR-3 has great stability to ultraviolet light. The VHR-3 is preferably 90% or more, more preferably 95% or more.

(11) Voltage Holding Ratio (VHR-4; Measured at 25° C.; %)

A TN device into which the sample was poured was heated in a constant-temperature bath at 80° C. for 500 hours, and then stability to heat was evaluated by measuring a voltage holding ratio. In the measurement of VHR-4, a decaying voltage was measured for 16.7 milliseconds. A composition having a large VHR-4 has great stability to heat.

Methods for measuring the characteristics may differ for a sample having positive dielectric anisotropy and a sample having negative dielectric anisotropy. The measurement methods for the case with positive dielectric anisotropy are described in measurements (12a) to (16a). The case with negative dielectric anisotropy is described in the measurements (12b) to (16b).

(12a) Viscosity (Rotational Viscosity; γ1; Measured at 25° C.; mPa·s)

Positive dielectric anisotropy: the measurement was carried out following the method described in M. Imai et al., Molecular Crystals and Liquid Crystals, Vol. 259, 37 (1995). The sample was placed into a TN device with a twist angle of 0 degree and a distance (cell gap) of 5 μm between two glass substrates. The device was applied with a voltage in a range of 16 to 19.5 V, stepwise by 0.5 V. After a period of 0.2 second with no voltage application, application was repeated under the conditions of only one rectangular wave (rectangular pulse; 0.2 second) and no application (2 seconds). The peak current and the peak time of a transient current resulting from this application were measured. The value of rotational viscosity was obtained according to these measured values and Equation (8) on page 40 of the paper of M. Imai et al. The value of dielectric anisotropy required for this calculation was obtained by the method described below using the device by which the rotational viscosity was measured.

(12b) Viscosity (Rotational Viscosity; γ1; Measured at 25° C.; mPa·s)

Negative dielectric anisotropy: the measurement was carried out following the method described in M. Imai et al., Molecular Crystals and Liquid Crystals, Vol. 259, 37 (1995). The sample was placed into a VA device with a distance (cell gap) of 20 μm between two glass substrates. The device was applied with a voltage in a range of 39 to 50 V, stepwise by 1 V. After a period of 0.2 second with no voltage application, application was repeated under the conditions of only one rectangular wave (rectangular pulse; 0.2 second) and no application (2 seconds). The peak current and the peak time of a transient current resulting from this application were measured. The value of rotational viscosity was obtained according to these measured values and Equation (8) on page 40 of the paper of M. Imai et al. The dielectric anisotropy value required for this calculation was measured as described in the following section of "Dielectric anisotropy."

(13a) Dielectric Anisotropy (Δ∈; Measured at 25° C.)

Positive dielectric anisotropy: the sample was placed into a TN device with a distance (cell gap) of 9 μm between two glass substrates and a twist angle of 80 degrees. The device was applied with a sine wave (10 V, 1 kHz), and the dielectric constant (∈∥) in the major-axis direction of the liquid crystal molecule was measured after 2 seconds. The device was applied with a sine wave (0.5 V, 1 kHz), and the dielectric constant (∈⊥) in the minor-axis direction of the liquid crystal molecule was measured after 2 seconds. The value of dielectric anisotropy was calculated from an equation of "Δ∈=∈∥−∈⊥."

(13b) Dielectric Anisotropy (Δ∈; Measured at 25° C.)

Negative dielectric anisotropy: the value of dielectric anisotropy was calculated from the equation of "Δ∈=∈∥−∈⊥." The dielectric constants (∈∥ and ∈⊥) were measured as follows.

1) Measurement of dielectric constant (∈∥): an ethanol (20 mL) solution of octadecyltriethoxysilane (0.16 mL) was coated on a sufficiently washed glass substrate. The glass substrate was rotated by a spinner, and then heated at 150° C. for 1 hour. The sample was placed into a VA device with a distance (cell gap) of 4 μm between two glass substrates, and the device was sealed with an adhesive curable on irradiation with ultraviolet light. The device was applied with a sine wave (0.5 V, 1 kHz), and the dielectric constant (c) in the major-axis direction of the liquid crystal molecule was measured after 2 seconds.

2) Measurement of dielectric constant (∈⊥): a polyimide solution was coated on a sufficiently washed glass substrate. The glass substrate was burned, and then the resulting alignment film was subjected to rubbing. The sample was placed into a TN device with a distance (cell gap) of 9 μm between two glass substrates and a twist angle of 80 degrees. The device was applied with a sine wave (0.5 V, 1 kHz), and the dielectric constant (∈⊥) in the minor-axis direction of the liquid crystal molecule was measured after 2 seconds.

(14a) Elastic Constant (K; Measured at 25° C.; pN)

Positive dielectric anisotropy: an LCR meter, HP 4284A made by Yokogawa-Hewlett-Packard, Ltd., was used for the measurement. The sample was placed into a horizontal alignment device with a distance (cell gap) of 20 μm between two glass substrates. The device was applied with an electric charge of 0 to 20 V, and electrostatic capacity and applied voltage were measured. The measured values of electrostatic capacity (C) and applied voltage (V) were fitted to Equation (2.98) and Equation (2.101) on page 75 of the "Liquid Crystal Device Handbook" (Nikkan Kogyo Shimbun, Ltd.), and values of $K_{11}$ and $K_{33}$ were obtained from Equation (2.99). Next, $K_{22}$ was calculated from Equation (3.18) on page 171 using the previously obtained values of $K_{11}$ and $K_{33}$. The elastic constant K was an average value of $K_{11}$, $K_{22}$ and $K_{33}$ thus obtained.

(14b) Elastic Constant ($K_{11}$ and $K_{33}$; Measured at 25° C.; pN)

Negative dielectric anisotropy: an elastic constant measurement system, Model EC-1 made by Toyo Corporation, was used for the measurement. The sample was placed into a vertical alignment device with a distance (cell gap) of 20 μM between two glass substrates. The device was applied with an electric charge of 20 to 0 V, and electrostatic capacity and applied voltage were measured. The values of electrostatic capacity (C) and applied voltage (V) were fitted to Equation (2.98) and Equation (2.101) on page 75 of the "Liquid Crystal Device Handbook" (Nikkan Kogyo Shimbun, Ltd.), and the value of elastic constant was obtained from Equation (2.100).

(15a) Threshold Voltage (Vth; Measured at 25° C.; V)

Positive dielectric anisotropy: a luminance meter, Model LCD5100 made by Otsuka Electronics Co., Ltd., was used for the measurement. The light source was a halogen lamp. The sample was placed into a TN device in a normally white mode with a distance (cell gap) of 0.45/Δn (μm) between two glass substrates and a twist angle of 80 degrees. A voltage (32 Hz, rectangular wave) applied to the device was increased stepwise from 0 V to 10 V at an increment of 0.02 V. On this occasion, the device was irradiated with light in the vertical direction, and the amount of light passing through the device was measured. A voltage-transmittance curve was plotted in a manner that the transmittance was 100% when the amount of light became the maximum and the transmittance was 0% when the amount of light was the minimum. The threshold voltage was the voltage corresponding to the transmittance of 90%.

(15b) Threshold Voltage (Vth; Measured at 25° C.; V)

Negative dielectric anisotropy: a luminance meter, Model LCD5100 made by Otsuka Electronics Co., Ltd., was used for the measurement. The light source was a halogen lamp. The sample was placed into a VA device in a normally black mode with a distance (cell gap) of 4 μm between two glass substrates and an antiparallel rubbing direction, and the device was sealed with an adhesive curable on irradiation with ultraviolet light. A voltage (60 Hz, rectangular wave) applied to the device was increased stepwise from 0 V to 20 V at an increment of 0.02 V. On this occasion, the device was irradiated with light in the vertical direction, and the amount of light passing through the device was measured. A voltage-transmittance curve was plotted in a manner that the transmittance was 100% when the amount of light became the maximum and the transmittance was 0% when the amount of light was the minimum. The threshold voltage was the voltage corresponding to the transmittance of 10%.

(16a) Response Time (τ; Measured at 25° C.; ms)

Positive dielectric anisotropy: a luminance meter, Model LCD5100 made by Otsuka Electronics Co., Ltd., was used for the measurement. The light source was a halogen lamp. The low-pass filter was set at 5 kHz. The sample was placed into a TN device in a normally white mode with a distance (cell gap) of 5.0 μm between two glass substrates and a twist angle of 80 degrees. A rectangular wave (60 Hz, 5 V, 0.5 second) was applied to the device. On this occasion, the device was irradiated with light in the vertical direction, and the amount of light passing through the device was measured. The transmittance was regarded as 100% when the amount of light became the maximum and the transmittance was regarded as 0% when the amount of light was the minimum. Rise time (τr; millisecond) was the time required for a change in transmittance from 90% to 10%. Fall time (τf; millisecond) was the time required for a change in transmittance from 10% to 90%. The response time was the sum of the rise time and the fall time thus obtained.

(16b) Response Time (τ; Measured at 25° C.; ms)

Negative dielectric anisotropy: a luminance meter, Model LCD5100 made by Otsuka Electronics Co., Ltd., was used for the measurement. The light source was a halogen lamp. The low-pass filter was set at 5 kHz. The sample was placed into a PVA device in a normally black mode with a distance (cell gap) of 3.2 μm between two glass substrates and an antiparallel rubbing direction. The device was sealed with an adhesive curable on irradiation with ultraviolet light. A voltage that was about a little higher than the threshold voltage was applied to the device for 1 minute, and then, the device was irradiated with ultraviolet light of 23.5 mW/cm² for 8 minutes while a voltage of 5.6 V was applied. A rectangular wave (60 Hz, 10 V, 0.5 second) was applied to the device. On this occasion, the device was irradiated with light in the vertical direction, and the amount of light passing through the device was measured. The transmittance was regarded as 100% when the amount of light became the maximum and the transmittance was regarded as 0% when the amount of light was the minimum. The response time was the time required for a change in transmittance from 90% to 10% (fall time; millisecond).

Example 1

Synthesis of Compound (No. 60)

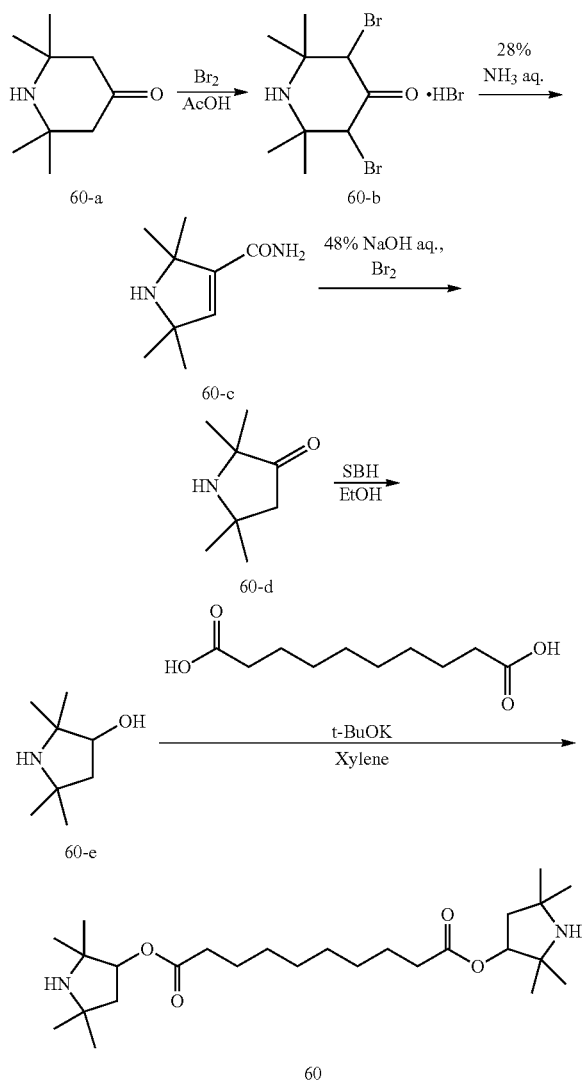

First Process:

2,2,6,6-tetramethylpiperidone (25.0 g, 0.16 mmol) and acetic acid (100 ml) were placed into a 500 ml four-necked flask under an argon gas stream, and the resultant was cooled by an ice bath. After it was confirmed that the internal temperature became 10° C. or lower, an acetic acid (70 ml) solution of bromine (18 ml, 56.1 g, 0.56 mol) was dripped in for 2 hours so that the internal temperature did not exceed 20° C. The reaction mixture was returned to room temperature, and was further stirred for 22 hours. The precipitated solid was filtered, washed with acetic acid (50 ml), water (50 ml) and ether (50 ml*2) in sequence, and dried, thereby obtaining a bromide (60-b) (57.5 g, 0.146 mol) at a yield of 91%.

Second Process:

28% ammonia water (150 ml, 2.22 mol) was placed into a 500 ml four-necked flask equipped with a mechanical stirrer, and the bromide (57.5 g, 0.146 mol) was put therein little by little under ice cooling. The resultant was gradually heated to room temperature, and was then stirred continuously for 6 hours. 10%-NaOH aqueous solution (10 g) was placed into the reaction mixture, and the product was extracted with ethyl acetate (100 ml*3). The water layer was concentrated and dissolved in 1N—NaOH aqueous solution (20 g), followed by further extraction with ethyl acetate (100 ml*3). The combined organic layers were dried with anhydrous magnesium sulfate, and were concentrated. Crude pyrrolinecarboxamide (60-c) (20.6 g, 0.122 mol) was obtained at a yield of 84%.

Third Process:

48%-NaOH aqueous solution (61.5 g, 0.738 mol) and water (68 ml) were placed into a 500 ml four-necked flask equipped with a mechanical stirrer, and the resultant was cooled by an ice bath. After it was confirmed that the solution became nearly 0° C., bromine (7.7 ml, 24.0 g, 0.150 mol) was dripped in. Next, an aqueous (200 ml) solution of crude pyrrolinecarboxamide (20.6 g, 0.122 mol) was added, and the resultant was heated under reflux for 6 hours. After cooling, extraction was performed with ethyl acetate (100 ml*3). The combined organic layers were dried with anhydrous magnesium sulfate, and were concentrated. The residue was column purified (Kieselgel 60/n-heptane: ethyl acetate), and pyrrolidinone (60-d) (2.1 g, 14.9 mmol) was obtained at a yield of 12%.

Fourth Process:

Pyrrolidinone (2.1 g, 14.9 mmol) and ethanol (10 ml) were placed into a 200 ml eggplant flask, and sodium borohydride (SBH; 0.57 g, 15 mmol) was added under ice cooling. After the resultant was stirred for 1 hour, acetone (4 ml) was added. Saturated saline solution (20 g) was put therein, followed by extraction with ethyl acetate (100 ml*3). The combined organic layers were dried with anhydrous magnesium sulfate and were concentrated. The residue was column purified (Kieselgel 60/CHCl₃:MeOH), and pyrrolidinol (60-e) (1.5 g, 10.5 mmol) was obtained at a yield of 70%.

Fifth Process:

Pyrrolidinol (1.5 g, 10.5 mmol), dimethylsebacate (1.21 g, 5.2 mmol) and xylene (20 ml) were placed into a 100 ml three-necked flask equipped with a Dean-Stark trap. t-BuOK (0.12 g, 1.05 mmol) was added, and then the resultant was heated. The resultant was continuously heated under reflux for 13 hours while distilling off low boiling point fractions. The reaction mixture was stood to cool, and saturated saline solution (20 g) was added, followed by extraction with ethyl acetate (50 ml*2). The combined organic layers were concentrated, the residue was column purified (Kieselgel 60/CHCl₃: MeOH), and sebacate (60) (0.99 g, yield=42%) was obtained.

¹H-NMR (CDCl₃; δ ppm): 4.99 (dd, J=5.7, 4.0 Hz, 1H×2), 2.32 (t, J=7.5 Hz, 2H×2), 2.19 (dd, J=14.0, 5.7 Hz, 1H×2) 2.0 (bs, 1H×2), 1.80 (dd, J=14.0, 4.0 Hz, 1H×2), 1.63 (m, 4H), 1.31 (m, 8H), 1.26 (s, 3H×2), 1.25 (s, 3H×2), 1.19 (s, 3H×2), 1.14 (s, 3H×2).

Example 2

Synthesis of Compound (No. 61)

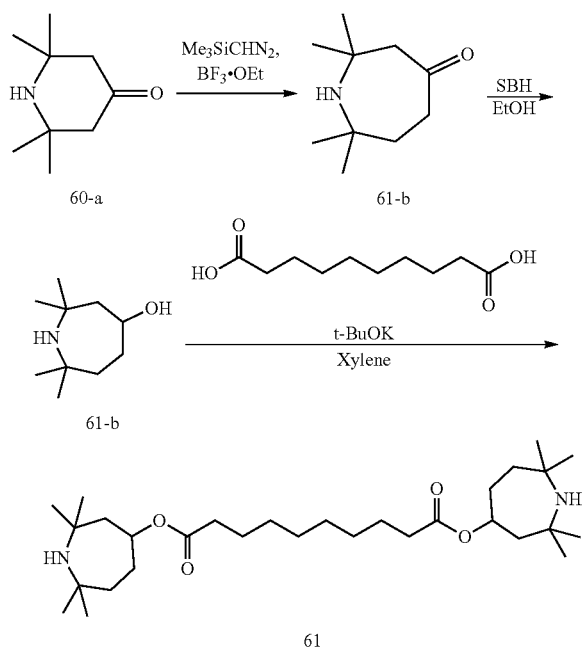

First Process:

2,2,6,6-tetramethylpiperidone (1.55 g, 10 mmol) and dried methylene chloride (15 ml) were added in a 200 ml four-necked flask under an argon gas stream, and the resultant was cooled by a dry-ice/acetone bath. After it was confirmed that the internal temperature became −70° C., BF$_3$.OEt (3.3 ml, 3.73 g, 26.2 mmol) was added. After that, hexane solution (25 ml, 0.6 mol) of trimethylsilyldiazomethane was dripped in for 30 minutes. After the resultant was stirred at the same temperature for 1 hour, acetic acid (1 ml) was added. 10 minutes later, saturated NaHCO$_3$ aqueous solution (30 g) was added, and the resultant was gradually heated to room temperature. The product was extracted with isopropyl ether (30 ml*2), and the extract was washed with saturated saline solution (20 ml*2). The water layer was concentrated and dissolved in 1N—NaOH aqueous solution (20 g), followed by extraction with ethyl acetate (30 ml*3). The combined ethyl acetate solution was concentrated, the residue was column purified (Kieselgel 60/CHCl$_3$:MeOH), and the intended tetramethyl azepanone (61-b) (3.1 g, 18.3 mmol, purity=97%) was obtained at a yield of 46%.

Second Process:

The tetramethyl azepanone (3.1 g, 18.3 mmol) and ethanol (18 ml) were placed into a 100 ml four-necked flask, and sodium borohydride (SBH; 0.5 g, 13.2 mmol) was added under ice cooling. 1.5 hours later, sodium borohydride (0.3 g, 7.9 mmol) was further additionally added. After the resultant was stirred for 2 hours, acetone (5 ml) was added. Saturated saline solution (30 g) was poured therein, followed by extraction with ethyl acetate (50 ml*3). The extract was concentrated, the residue was column purified (Kieselgel 60/CHCl$_3$:MeOH), and azepanol (61-c) (2.0 g, 11.7 mmol, purity=99.3%) was obtained at a yield of 64%.

Third Process:

The azepanol (2.0 g, 11.7 mmol), dimethylsebacate (3.5 g, 5.85 mmol) and xylene (20 ml) were placed into a three-necked flask equipped with a Dean-Stark trap. Potassium tert-butoxide (0.131 g, 1.17 mmol) was added, and the resultant was then heated. The resultant was continuously heated under reflux for 13 hours while distilling off low boiling point fractions. The reaction mixture was stood to cool, and saturated saline solution (20 g) was added, followed by extraction with ethyl acetate (50 ml*2). The combined organic layers were concentrated, the residue was column purified (Kieselgel 60/CHCl$_3$: MeOH), and sebacate (61) (0.504 g) was obtained at a yield of 17%.

$^1$H-NMR (CDCl$_3$; δ ppm): 4.97 (tt, J=10.3, 3.4 Hz, 1H×2), 2.25 (t, J=7.6 Hz, 2H×2), 1.87 (m, 4H), 1.72 (m, 6H), 1.58 (m, 6H), 1.30 (m, 8H), 1.22 (s, 3H×2), 1.16 (s, 3H×2), 1.15 (m, 2H), 1.15 (s, 3H×2), 1.11 (s, 3H×2).

Example 3

Comparison of Solubility at Low Temperature

The solubility of the compound of the invention was compared with that of a conventional compound. First of all, the following mother liquid crystal (M) was prepared. The component compounds were represented by symbols in accordance with the definitions in the later-described Table 2.

| | | |
|---|---|---|
| 3-HH-V | (2-1) | 29% |
| 1-BB-3 | (2-8) | 10% |
| 3-BB(2F,3F)-O2 | (9-3) | 13% |
| 2-HH1OB(2F,3F)-O2 | (10-5) | 20% |
| 3-HH1OB(2F,3F)-O2 | (10-5) | 14% |
| 3-HHB-1 | (3-1) | 8% |
| 2-BBB(2F)-5 | (3-8) | 6% |

Characteristics of the mother liquid crystal (M) were as follows. NI=74.5° C.; Δn=0.106; and Δ∈=−3.0.

Next, a low temperature storage test was carried out. The compound (No. 60) of the invention was added to the mother liquid crystal (M) in a ratio of 1000 ppm, so as to obtain a composition (X-1). 0.5 ml of the composition (X-1) and a glass capillary tube were placed into a 10 ml vial, and the vial was capped under a nitrogen gas stream. The cap portion was sealed using parafilm, and the resultant was then stored in a freezer at −20° C. The compound (No. 61) of the invention was also added to the mother liquid crystal (M) in a ratio of 1000 ppm, so as to prepare a composition (X-2). This composition was sealed in a vial by the same procedure, and was stored in a freezer at −20° C. 30 days later, upon observation of the two compositions, neither appearance of a smectic phase nor precipitation of crystals was confirmed, and the nematic phase was maintained.

(No. 60)

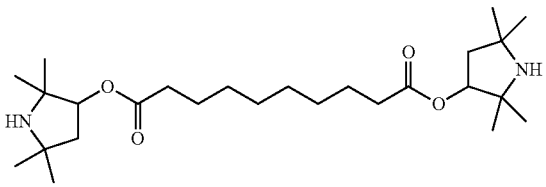

(No. 61)

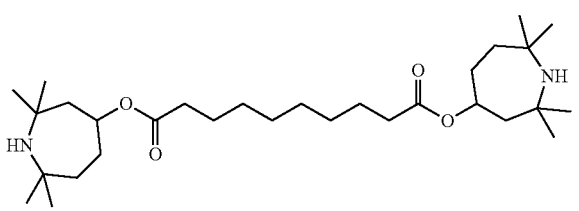

(LA-77)

As a comparative compound, a compound (LA-77) made by ADEKA Corporation was selected. This compound is a commercially available hindered amine light stabilizer. The compound (LA-77) was added to the mother liquid crystal (M) in a ratio of 1000 ppm, so as to prepare a composition (X-3). One day after the composition (X-3) was stored in a freezer at −20° C. by the same procedure as above, appearance of a smectic phase was confirmed.

The above results indicate that a liquid crystal composition to which the compound (No. 37) or (No. 38) was added maintained the nematic phase even at low temperature. It can be concluded that the compound of the invention has high solubility in the liquid crystal composition and is therefore very useful.

In accordance with the synthesis methods described in Examples 1 and 2, the following compounds (No. 1) to (No. 369) and so on can be synthesized.

| No. | |
|---|---|
| 1 | 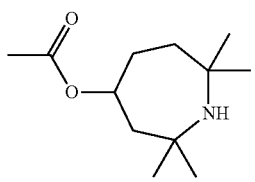 |
| 2 | 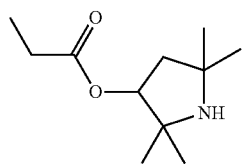 |
| 3 | 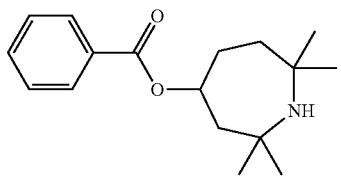 [SMILES: CC1(C)CCC(OC(=O)c2ccccc2)CC(C)(C)N1] |
| 4 | 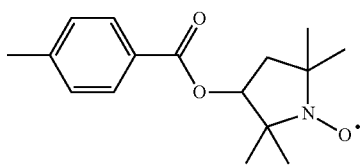 [SMILES: Cc1ccc(C(=O)OC2CC(C)(C)N(O)C2(C)C)cc1] |
| 5 | 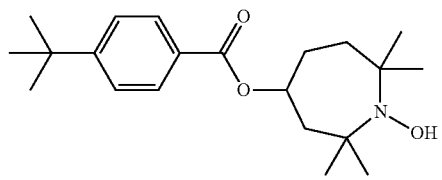 [SMILES: CC(C)(C)c1ccc(C(=O)OC2CCC(C)(C)N(O)C(C)(C)C2)cc1] |

| No. | |
|---|---|
| 6 | 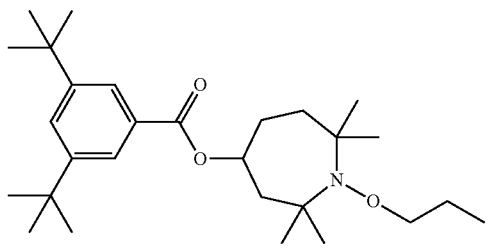 [SMILES: CCCON1C(C)(C)CCC(OC(=O)c2cc(C(C)(C)C)cc(C(C)(C)C)c2)CC1(C)C] |
| 7 | 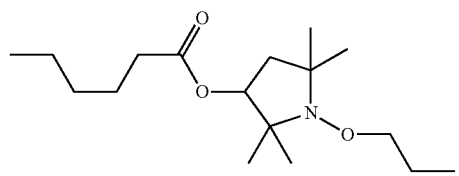 [SMILES: CCCCCC(=O)OC1CC(C)(C)N(OCCC)C1(C)C] |
| 8 | 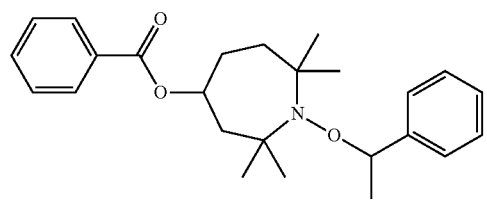 [SMILES: CC(ON1C(C)(C)CCC(OC(=O)c2ccccc2)CC1(C)C)c1ccccc1] |
| 9 | 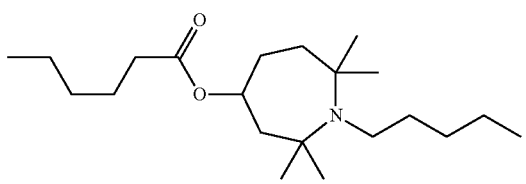 [SMILES: CCCCCC(=O)OC1CCC(C)(C)N(CCCCC)C(C)(C)C1] |
| 10 | 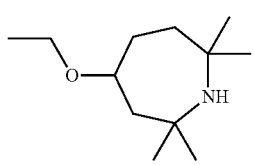 |
| 11 | 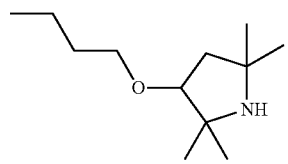 |
| 12 | 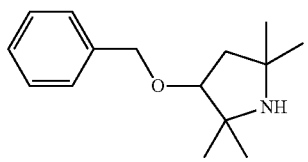 [SMILES: CC1(C)CC(OCc2ccccc2)C(C)(C)N1] |
| 13 | 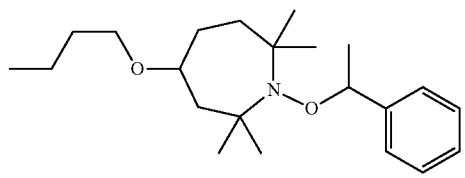 [SMILES: CCCCOC1CCC(C)(C)N(OC(C)c2ccccc2)C(C)(C)C1] |

| No. | |
|---|---|
| 14 | 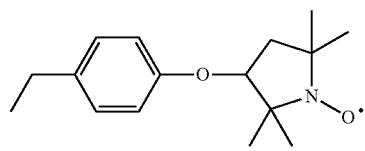 [SMILES: CCc1ccc(OC2CC(C)(C)N(O)C2(C)C)cc1] |
| 15 | 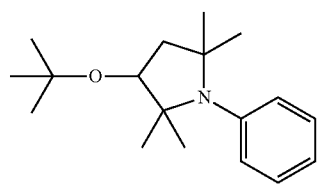 [SMILES: CC(C)(C)OC1CC(C)(C)N(c2ccccc2)C1(C)C] |
| 16 | 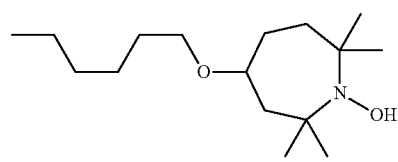 [SMILES: CCCCCCOC1CCC(C)(C)N(O)C(C)(C)C1] |
| 17 | 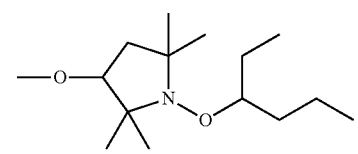 [SMILES: CCCC(CC)ON1C(C)(C)CC(OC)C1(C)C] |
| 18 | 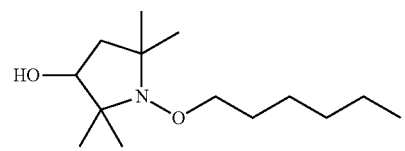 [SMILES: CCCCCCON1C(C)(C)CC(O)C1(C)C] |
| 19 | 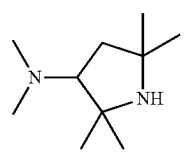 |
| 20 | 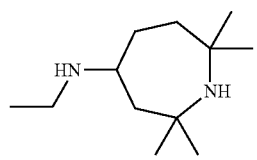 |
| 21 | 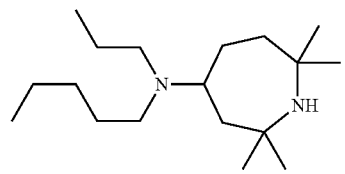 [SMILES: CCCCCN(CCC)C1CCC(C)(C)NC(C)(C)C1] |
| 22 | 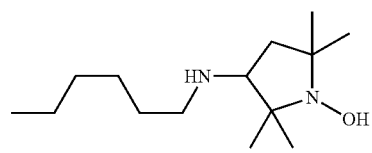 [SMILES: CCCCCCNC1CC(C)(C)N(O)C1(C)C] |

| No. | |
|---|---|
| 23 | 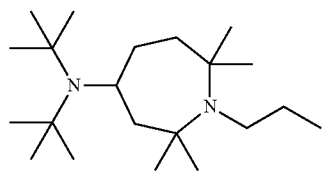 [SMILES: CCCN1C(C)(C)CCC(N(C(C)(C)C)C(C)(C)C)CC1(C)C] |
| 24 | 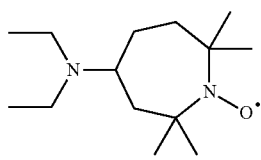 [SMILES: CCN(CC)C1CCC(C)(C)N(O)C(C)(C)C1] |
| 25 | 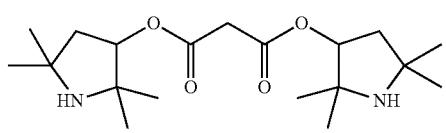 |
| 26 | 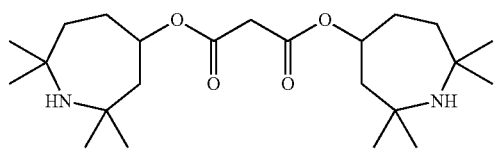 |
| 27 | 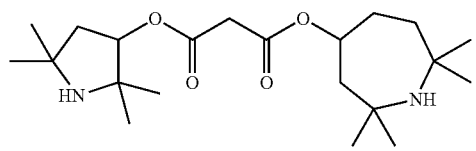 |
| 28 | 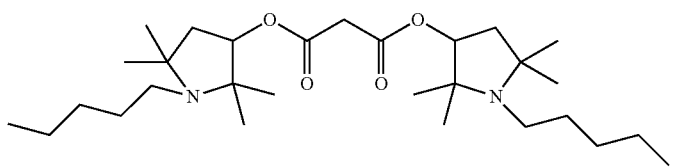 [SMILES: CCCCCN1C(C)(C)CC(OC(=O)CC(=O)OC2CC(C)(C)N(CCCCC)C2(C)C)C1(C)C] |
| 29 | 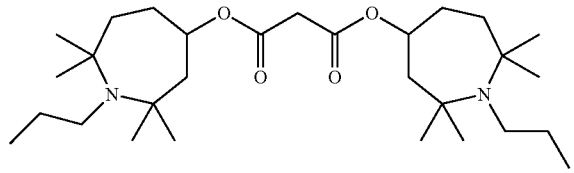 [SMILES: CCCN1C(C)(C)CCC(OC(=O)CC(=O)OC2CCC(C)(C)N(CCC)C(C)(C)C2)CC1(C)C] |
| 30 | 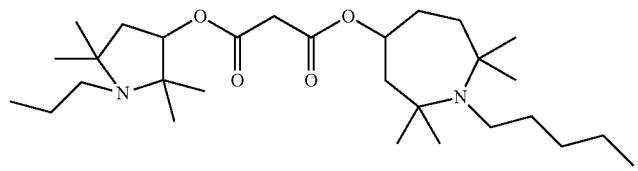 [SMILES: CCCCCN1C(C)(C)CCC(OC(=O)CC(=O)OC2CC(C)(C)N(CCC)C2(C)C)CC1(C)C] |
| 31 | 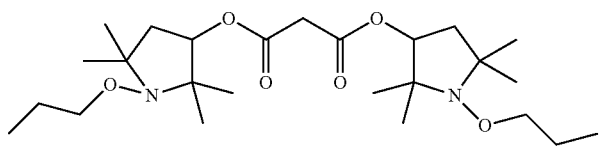 [SMILES: CCCON1C(C)(C)CC(OC(=O)CC(=O)OC2CC(C)(C)N(OCCC)C2(C)C)C1(C)C] |

| No. |  |
|---|---|
| 32 | 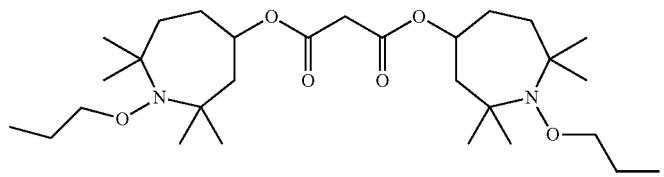 [SMILES: CCCON1C(C)(C)CCC(OC(=O)CC(=O)OC2CCC(C)(C)N(OCCC)C(C)(C)C2)CC1(C)C] |
| 33 | 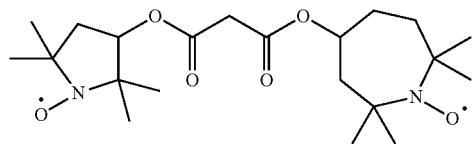 |
| 34 | 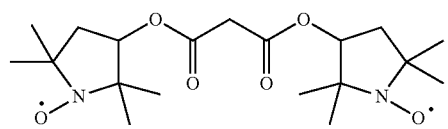 |
| 35 | 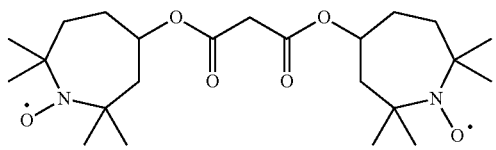 |
| 36 | 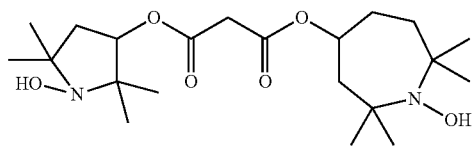 |
| 37 | 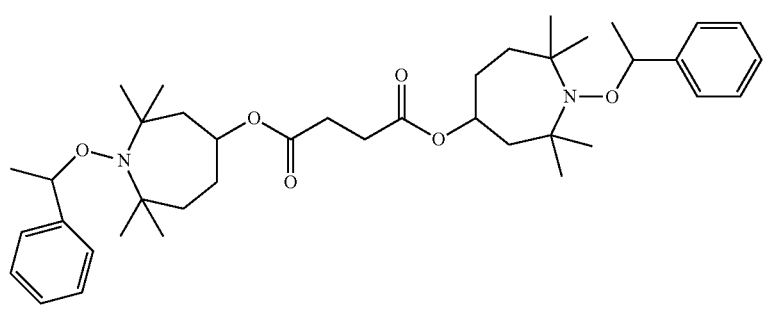 [SMILES: CC(ON1C(C)(C)CCC(OC(=O)CCC(=O)OC2CCC(C)(C)N(OC(C)c3ccccc3)C(C)(C)C2)CC1(C)C)c1ccccc1] |
| 38 | 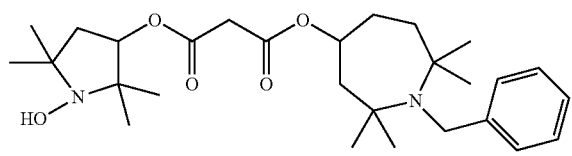 [SMILES: CC1(C)CCC(OC(=O)CC(=O)OC2CC(C)(C)N(O)C2(C)C)CC(C)(C)N1Cc1ccccc1] |
| 39 | 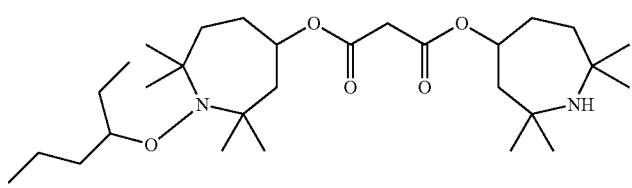 [SMILES: CCCC(CC)ON1C(C)(C)CCC(OC(=O)CC(=O)OC2CCC(C)(C)NC(C)(C)C2)CC1(C)C] |

| No. | |
|---|---|
| 40 | 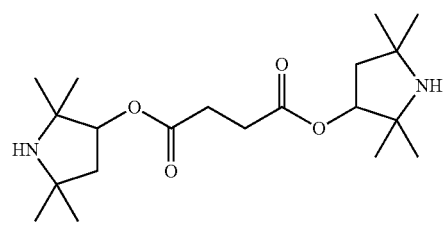 [SMILES: CC1(C)CC(OC(=O)CCC(=O)OC2CC(C)(C)NC2(C)C)C(C)(C)N1] |
| 41 | 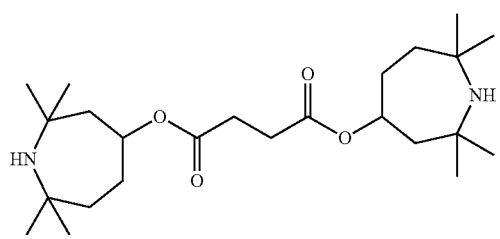 |
| 42 | 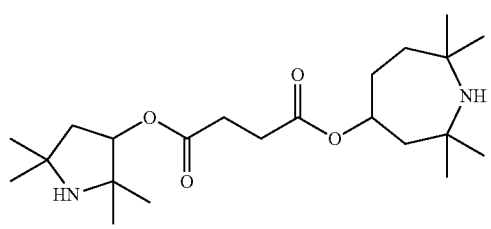 |
| 43 | 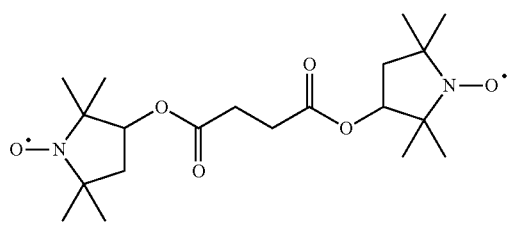 [SMILES: CC1(C)CC(OC(=O)CCC(=O)OC2CC(C)(C)N(O)C2(C)C)C(C)(C)N1O] |
| 44 | 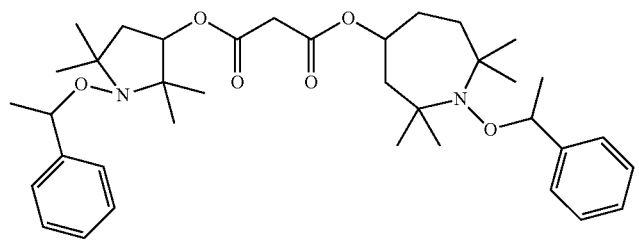 [SMILES: CC(ON1C(C)(C)CCC(OC(=O)CC(=O)OC2CC(C)(C)N(OC(C)c3ccccc3)C2(C)C)CC1(C)C)c1ccccc1] |
| 45 | 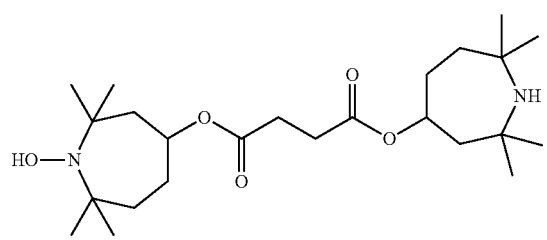 [SMILES: CC1(C)CCC(OC(=O)CCC(=O)OC2CCC(C)(C)N(O)C(C)(C)C2)CC(C)(C)N1] |

| No. |
|---|
| 46 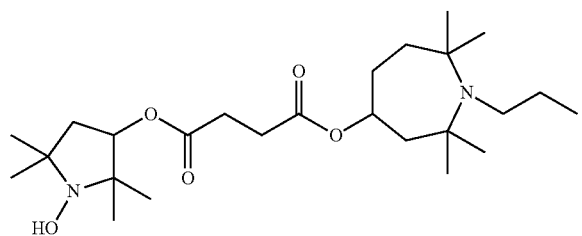 [SMILES: CCCN1C(C)(C)CCC(OC(=O)CCC(=O)OC2CC(C)(C)N(O)C2(C)C)CC1(C)C] |
| 47 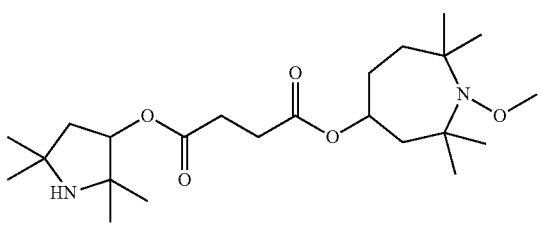 |
| 48 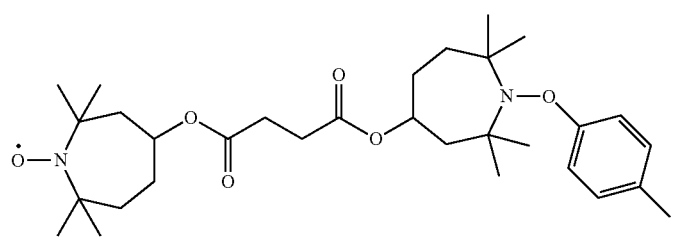 [SMILES: Cc1ccc(ON2C(C)(C)CCC(OC(=O)CCC(=O)OC3CCC(C)(C)N(O)C(C)(C)C3)CC2(C)C)cc1] |
| 49 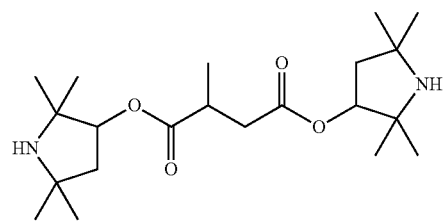 [SMILES: CC(CC(=O)OC1CC(C)(C)NC1(C)C)C(=O)OC1CC(C)(C)NC1(C)C] |
| 50 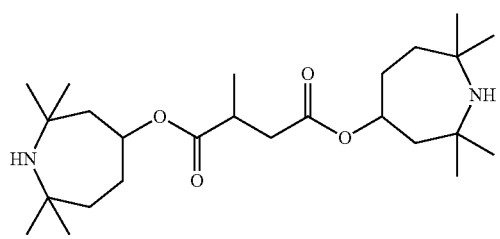 |
| 51 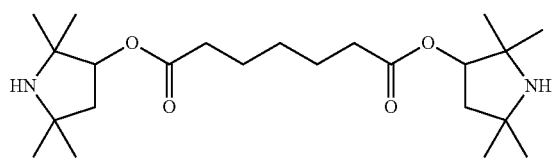 [SMILES: CC1(C)CC(OC(=O)CCCCCC(=O)OC2CC(C)(C)NC2(C)C)C(C)(C)N1] |
| 52 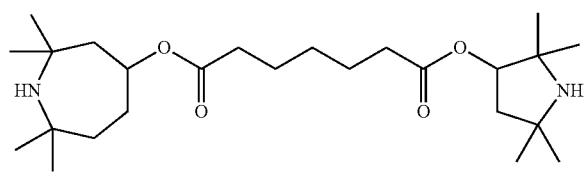 |

| No. | |
|---|---|
| 53 | 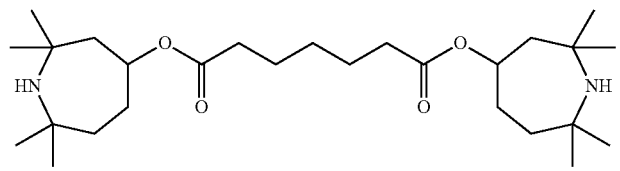 |
| 54 | 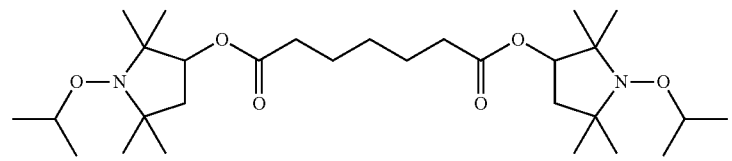 [SMILES: CC(C)ON1C(C)(C)CC(OC(=O)CCCCCC(=O)OC2CC(C)(C)N(OC(C)C)C2(C)C)C1(C)C] |
| 55 | 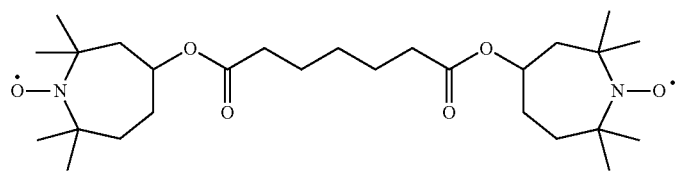 [SMILES: CC1(C)CCC(OC(=O)CCCCCC(=O)OC2CCC(C)(C)N(O)C(C)(C)C2)CC(C)(C)N1O] |
| 56 | 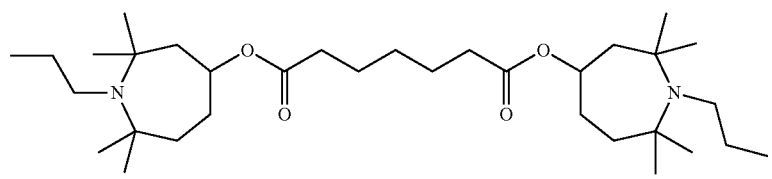 [SMILES: CCCN1C(C)(C)CCC(OC(=O)CCCCCC(=O)OC2CCC(C)(C)N(CCC)C(C)(C)C2)CC1(C)C] |
| 57 | 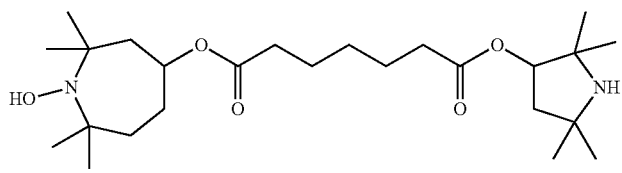 [SMILES: CC1(C)CC(OC(=O)CCCCCC(=O)OC2CCC(C)(C)N(O)C(C)(C)C2)C(C)(C)N1] |
| 58 | 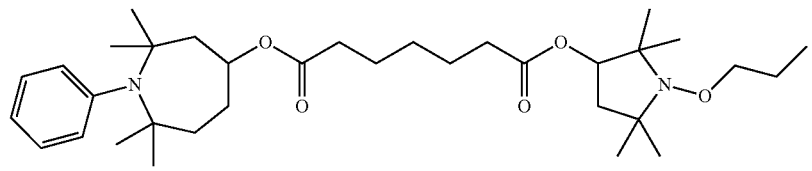 [SMILES: CCCON1C(C)(C)CC(OC(=O)CCCCCC(=O)OC2CCC(C)(C)N(c3ccccc3)C(C)(C)C2)C1(C)C] |
| 59 | 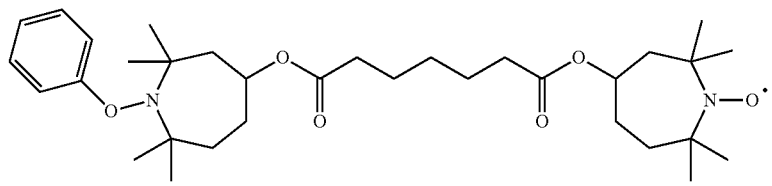 [SMILES: CC1(C)CCC(OC(=O)CCCCCC(=O)OC2CCC(C)(C)N(Oc3ccccc3)C(C)(C)C2)CC(C)(C)N1O] |
| 60 | 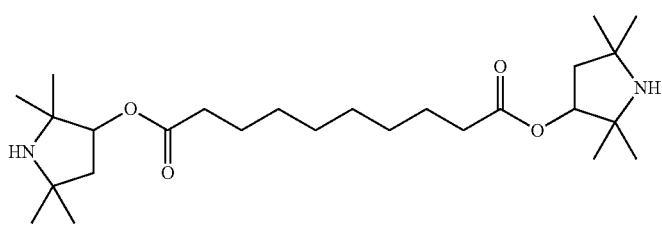 [SMILES: CC1(C)CC(OC(=O)CCCCCCCCC(=O)OC2CC(C)(C)NC2(C)C)C(C)(C)N1] |

-continued
| No. | |
|---|---|
| 61 | 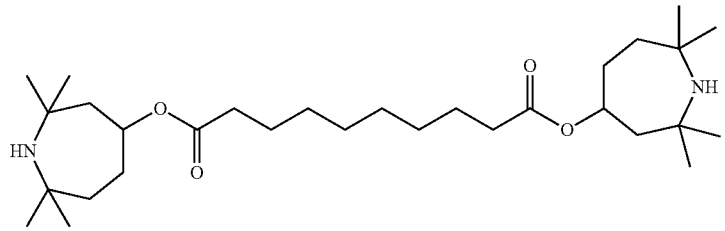 |
| 62 | 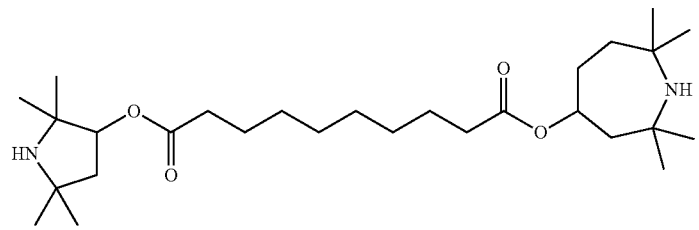 |
| 63 | 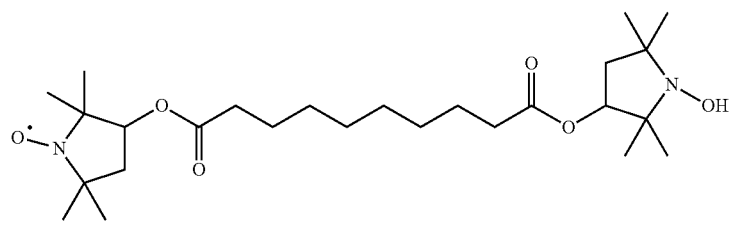 [SMILES: CC1(C)CC(OC(=O)CCCCCCCCC(=O)OC2CC(C)(C)N(O)C2(C)C)C(C)(C)N1O] |
| 64 | 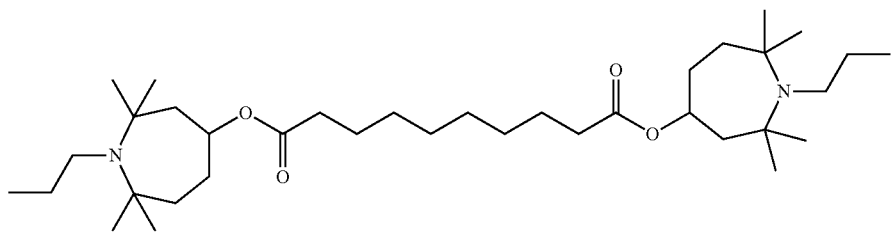 [SMILES: CCCN1C(C)(C)CCC(OC(=O)CCCCCCCCC(=O)OC2CCC(C)(C)N(CCC)C(C)(C)C2)CC1(C)C] |
| 65 | 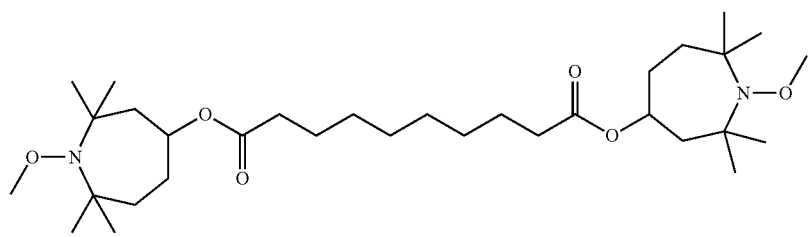 |
| 66 | 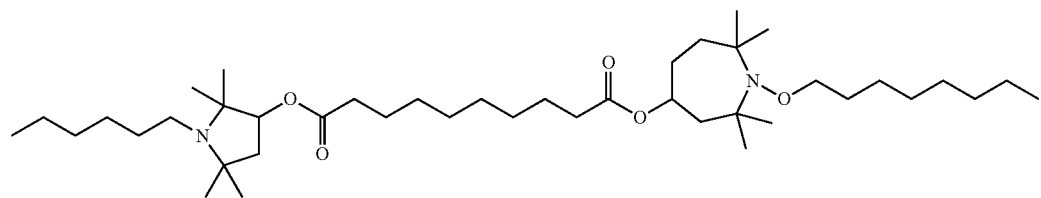 [SMILES: CCCCCCCCON1C(C)(C)CCC(OC(=O)CCCCCCCCC(=O)OC2CC(C)(C)N(CCCCCC)C2(C)C)CC1(C)C] |

-continued
| No. |
|---|
| 67 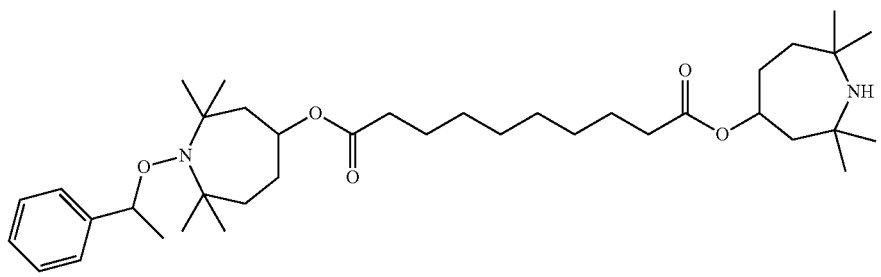 [SMILES: CC(ON1C(C)(C)CCC(OC(=O)CCCCCCCCC(=O)OC2CCC(C)(C)NC(C)(C)C2)CC1(C)C)c1ccccc1] |
| 68 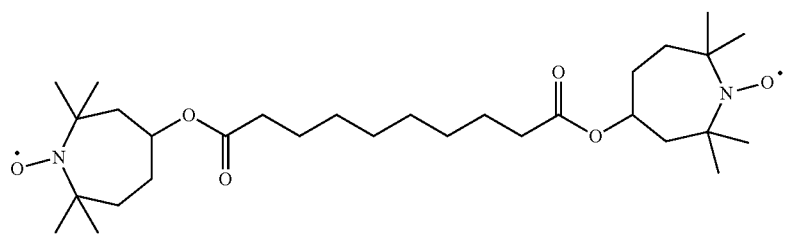 [SMILES: CC1(C)CCC(OC(=O)CCCCCCCCC(=O)OC2CCC(C)(C)N(O)C(C)(C)C2)CC(C)(C)N1O] |
| 69 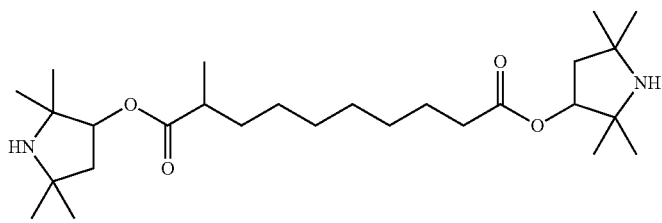 [SMILES: CC(CCCCCCCC(=O)OC1CC(C)(C)NC1(C)C)C(=O)OC1CC(C)(C)NC1(C)C] |
| 70 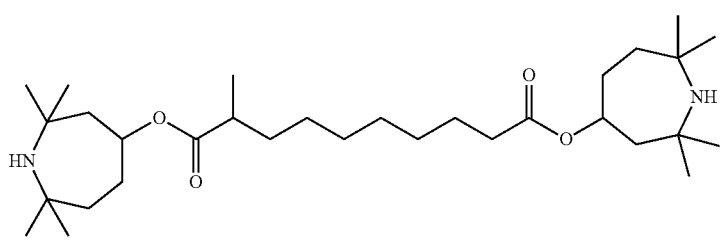 |
| 71 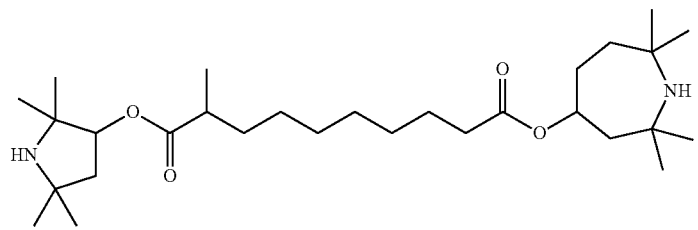 |
| 72 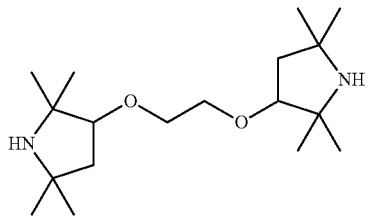 [SMILES: CC1(C)CC(OCCOC2CC(C)(C)NC2(C)C)C(C)(C)N1] |

| No. | |
|---|---|
| 73 | 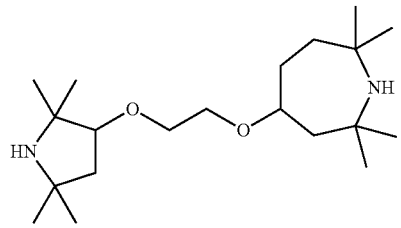 [SMILES: CC1(C)CCC(OCCOC2CC(C)(C)NC2(C)C)CC(C)(C)N1] |
| 74 | 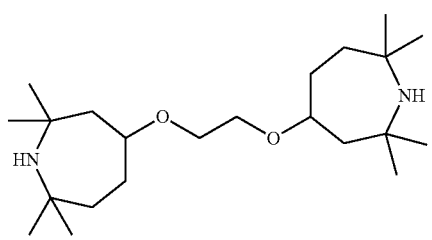 |
| 75 | 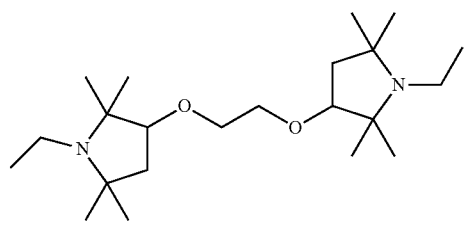 [SMILES: CCN1C(C)(C)CC(OCCOC2CC(C)(C)N(CC)C2(C)C)C1(C)C] |
| 76 | 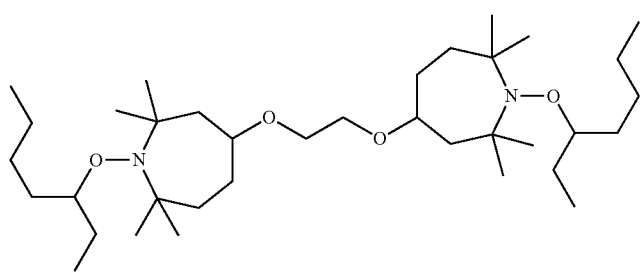 [SMILES: CCCCC(CC)ON1C(C)(C)CCC(OCCOC2CCC(C)(C)N(OC(CC)CCCC)C(C)(C)C2)CC1(C)C] |
| 77 | 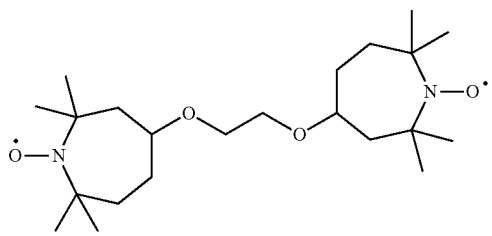 [SMILES: CC1(C)CCC(OCCOC2CCC(C)(C)N(O)C(C)(C)C2)CC(C)(C)N1O] |
| 78 | 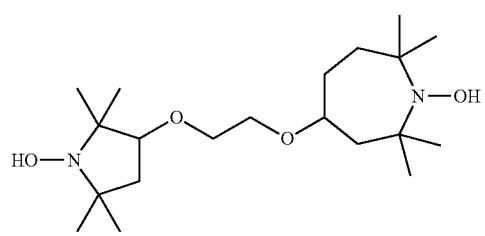 [SMILES: CC1(C)CCC(OCCOC2CC(C)(C)N(O)C2(C)C)CC(C)(C)N1O] |

-continued
| No. |
|---|
| 79 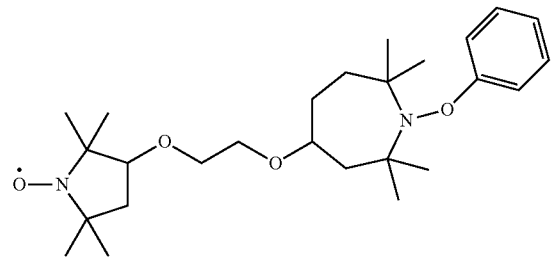 [SMILES: CC1(C)CCC(OCCOC2CC(C)(C)N(O)C2(C)C)CC(C)(C)N1Oc1ccccc1] |
| 80 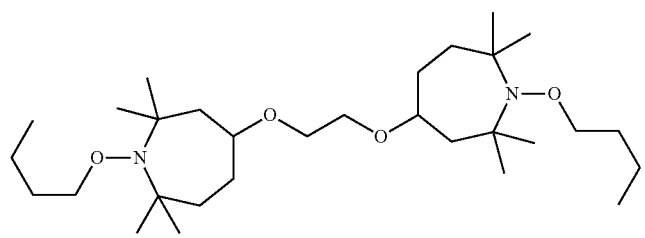 [SMILES: CCCCON1C(C)(C)CCC(OCCOC2CCC(C)(C)N(OCCCC)C(C)(C)C2)CC1(C)C] |
| 81 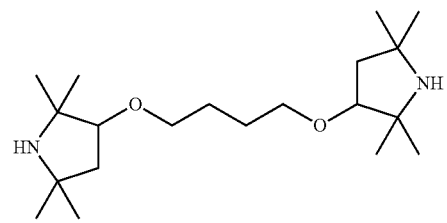 [SMILES: CC1(C)CC(OCCCCOC2CC(C)(C)NC2(C)C)C(C)(C)N1] |
| 82 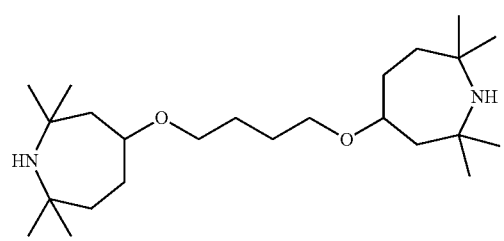 |
| 83 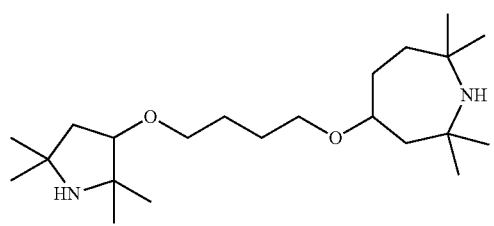 |
| 84 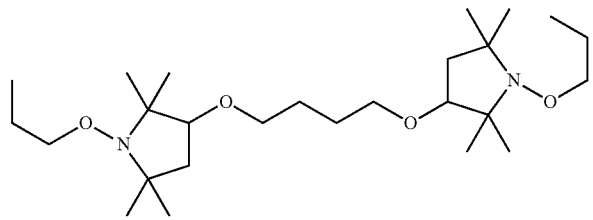 [SMILES: CCCON1C(C)(C)CC(OCCCCOC2CC(C)(C)N(OCCC)C2(C)C)C1(C)C] |

| No. |
|---|
| 85 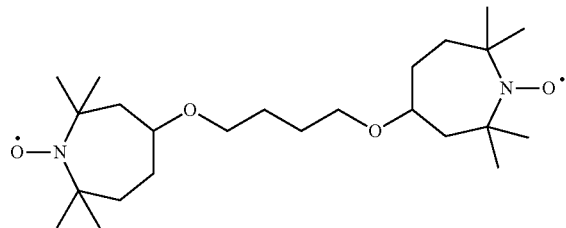 [SMILES: CC1(C)CCC(OCCCCOC2CCC(C)(C)N(O)C(C)(C)C2)CC(C)(C)N1O] |
| 86 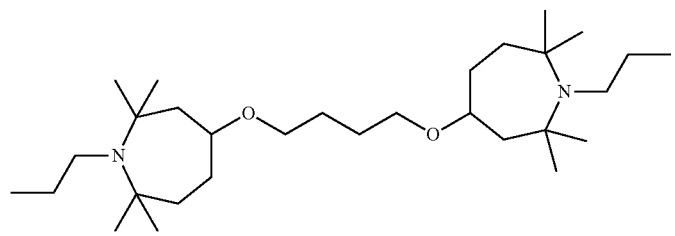 [SMILES: CCCN1C(C)(C)CCC(OCCCCOC2CCC(C)(C)N(CCC)C(C)(C)C2)CC1(C)C] |
| 87 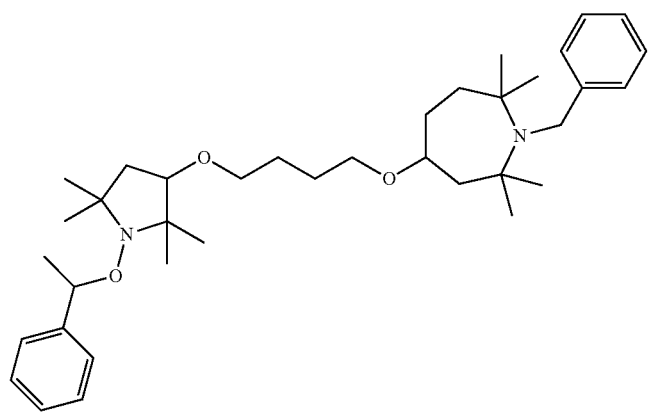 [SMILES: CC(ON1C(C)(C)CC(OCCCCOC2CCC(C)(C)N(Cc3ccccc3)C(C)(C)C2)C1(C)C)c1ccccc1] |
| 88 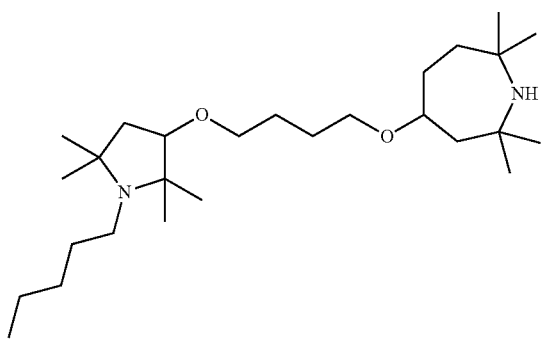 [SMILES: CCCCCN1C(C)(C)CC(OCCCCOC2CCC(C)(C)NC(C)(C)C2)C1(C)C] |
| 89 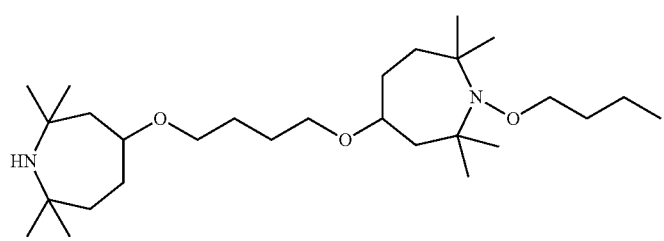 [SMILES: CCCCON1C(C)(C)CCC(OCCCCOC2CCC(C)(C)NC(C)(C)C2)CC1(C)C] |

| No. | |
|---|---|
| 90 | 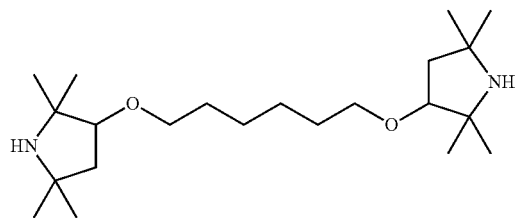 [SMILES: CC1(C)CC(OCCCCCCOC2CC(C)(C)NC2(C)C)C(C)(C)N1] |
| 91 | 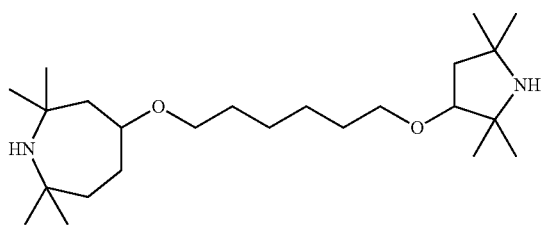 [SMILES: CC1(C)CCC(OCCCCCCOC2CC(C)(C)NC2(C)C)CC(C)(C)N1] |
| 92 | 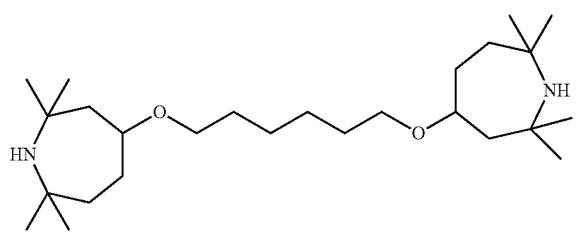 |
| 93 | 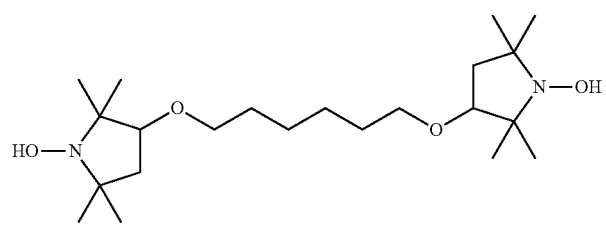 [SMILES: CC1(C)CC(OCCCCCCOC2CC(C)(C)N(O)C2(C)C)C(C)(C)N1O] |
| 94 | 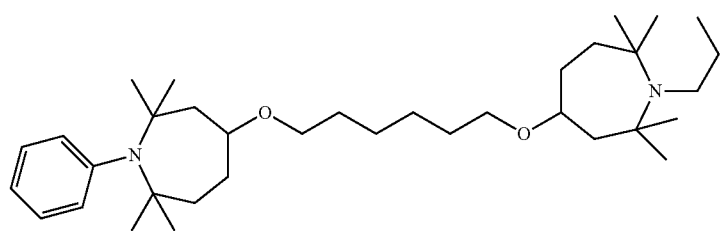 [SMILES: CCCN1C(C)(C)CCC(OCCCCCCOC2CCC(C)(C)N(c3ccccc3)C(C)(C)C2)CC1(C)C] |
| 95 | 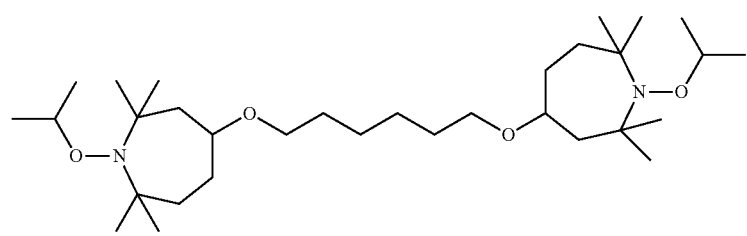 [SMILES: CC(C)ON1C(C)(C)CCC(OCCCCCCOC2CCC(C)(C)N(OC(C)C)C(C)(C)C2)CC1(C)C] |

| No. | |
|---|---|
| 96 | 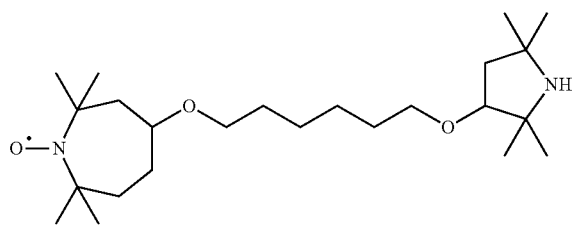 [SMILES: CC1(C)CC(OCCCCCCOC2CCC(C)(C)N(O)C(C)(C)C2)C(C)(C)N1] |
| 97 | 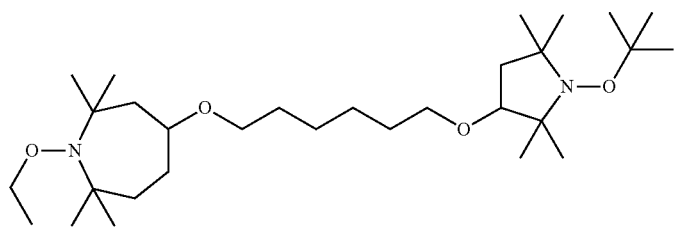 [SMILES: CCON1C(C)(C)CCC(OCCCCCCOC2CC(C)(C)N(OC(C)(C)C)C2(C)C)CC1(C)C] |
| 98 | 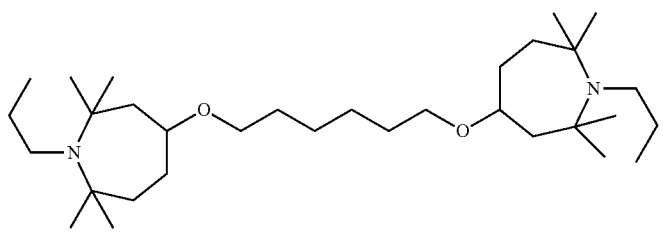 [SMILES: CCCN1C(C)(C)CCC(OCCCCCCOC2CCC(C)(C)N(CCC)C(C)(C)C2)CC1(C)C] |
| 99 | 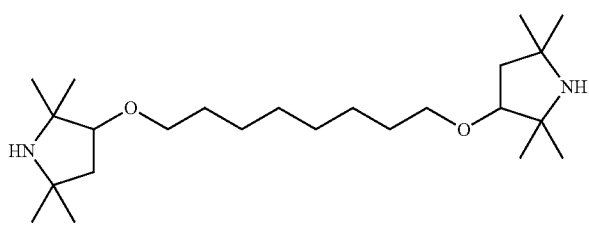 [SMILES: CC1(C)CC(OCCCCCCCCOC2CC(C)(C)NC2(C)C)C(C)(C)N1] |
| 100 | 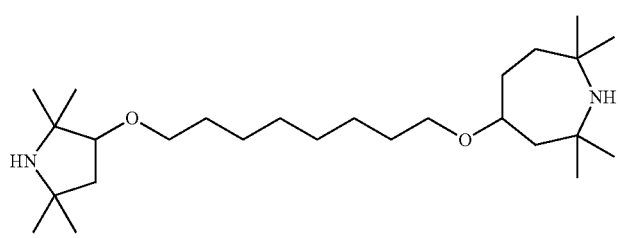 [SMILES: CC1(C)CCC(OCCCCCCCCOC2CC(C)(C)NC2(C)C)CC(C)(C)N1] |
| 101 | 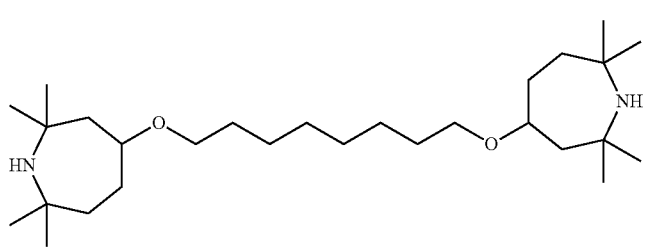 |
| 102 | 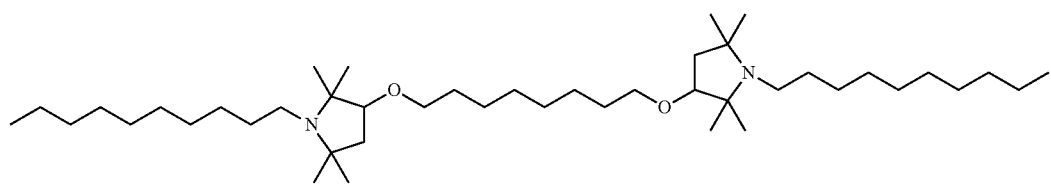 [SMILES: CCCCCCCCCCN1C(C)(C)CC(OCCCCCCCCOC2CC(C)(C)N(CCCCCCCCCC)C2(C)C)C1(C)C] |

| No. |
|---|
| 103 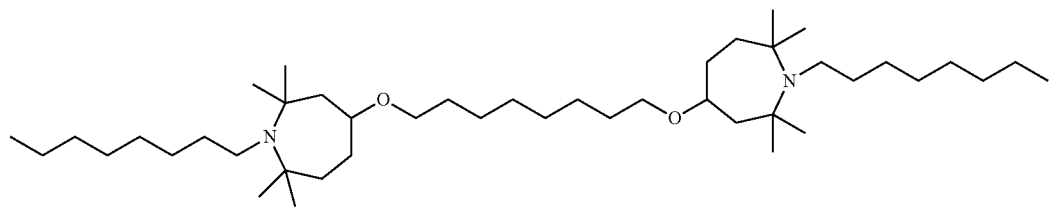 [SMILES: CCCCCCCCN1C(C)(C)CCC(OCCCCCCCCOC2CCC(C)(C)N(CCCCCCCC)C(C)(C)C2)CC1(C)C] |
| 104 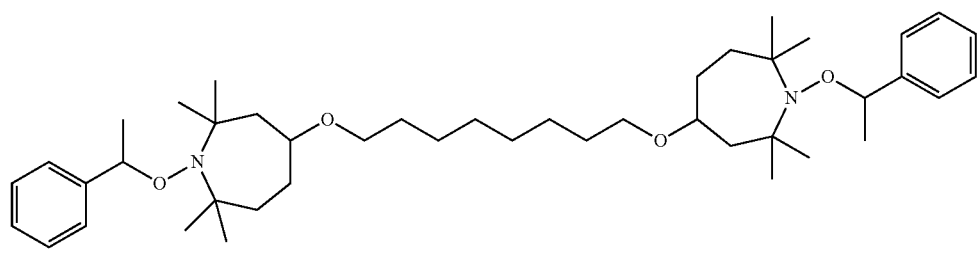 [SMILES: CC(ON1C(C)(C)CCC(OCCCCCCCCOC2CCC(C)(C)N(OC(C)c3ccccc3)C(C)(C)C2)CC1(C)C)c1ccccc1] |
| 105 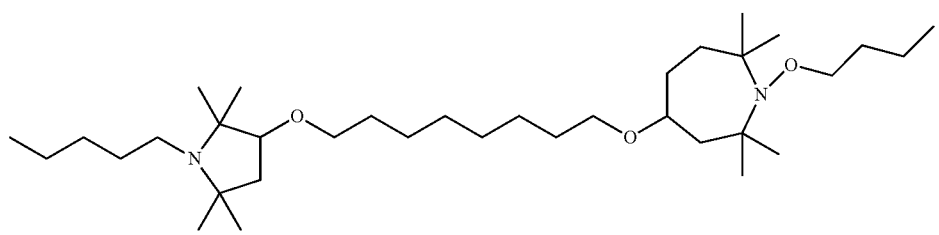 [SMILES: CCCCCN1C(C)(C)CC(OCCCCCCCCOC2CCC(C)(C)N(OCCCC)C(C)(C)C2)C1(C)C] |
| 106 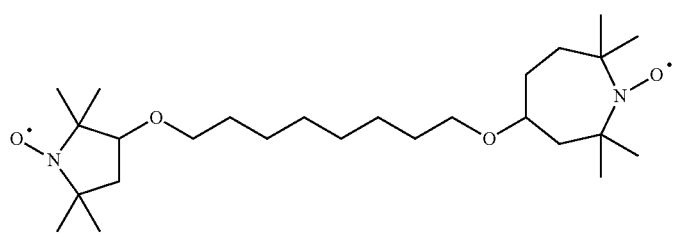 [SMILES: CC1(C)CCC(OCCCCCCCCOC2CC(C)(C)N(O)C2(C)C)CC(C)(C)N1O] |
| 107 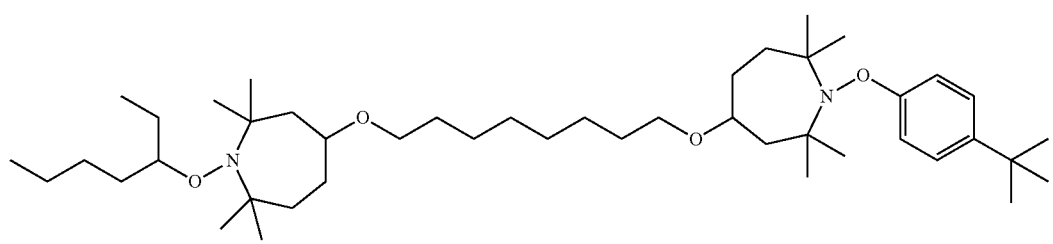 [SMILES: CCCCC(CC)ON1C(C)(C)CCC(OCCCCCCCCOC2CCC(C)(C)N(Oc3ccc(C(C)(C)C)cc3)C(C)(C)C2)CC1(C)C] |
| 108 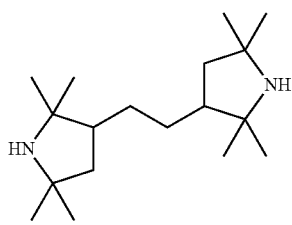 [SMILES: CC1(C)CC(CCC2CC(C)(C)NC2(C)C)C(C)(C)N1] |

-continued
| No. | |
|---|---|
| 109 | 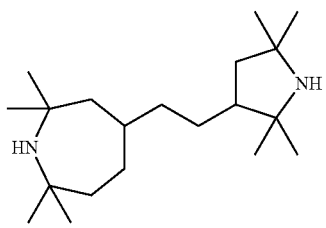 [SMILES: CC1(C)CCC(CCC2CC(C)(C)NC2(C)C)CC(C)(C)N1] |
| 110 | 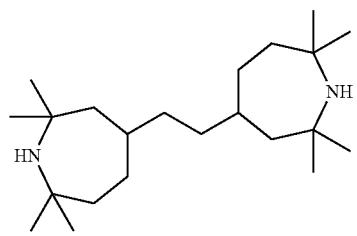 |
| 111 | 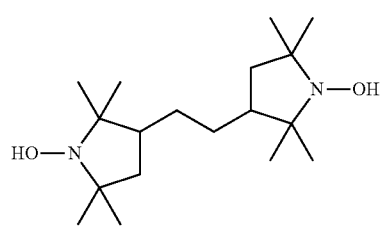 [SMILES: CC1(C)CC(CCC2CC(C)(C)N(O)C2(C)C)C(C)(C)N1O] |
| 112 | 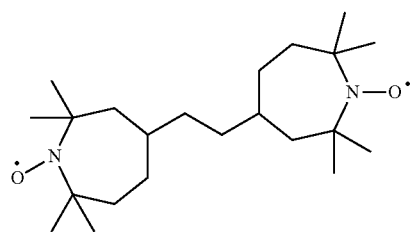 [SMILES: CC1(C)CCC(CCC2CCC(C)(C)N(O)C(C)(C)C2)CC(C)(C)N1O] |
| 113 | 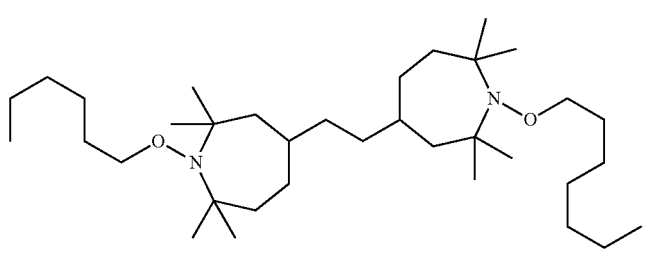 [SMILES: CCCCCCCON1C(C)(C)CCC(CCC2CCC(C)(C)N(OCCCCCC)C(C)(C)C2)CC1(C)C] |
| 114 | 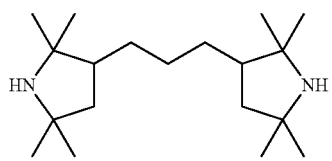 [SMILES: CC1(C)CC(CCCC2CC(C)(C)NC2(C)C)C(C)(C)N1] |
| 115 | 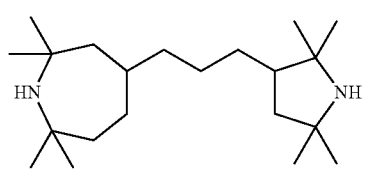 [SMILES: CC1(C)CCC(CCCC2CC(C)(C)NC2(C)C)CC(C)(C)N1] |

| No. | |
|---|---|
| 116 | 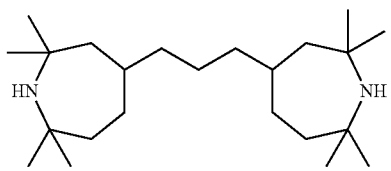 |
| 117 | 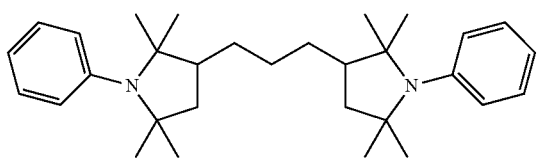 [SMILES: CC1(C)CC(CCCC2CC(C)(C)N(c3ccccc3)C2(C)C)C(C)(C)N1c1ccccc1] |
| 118 | 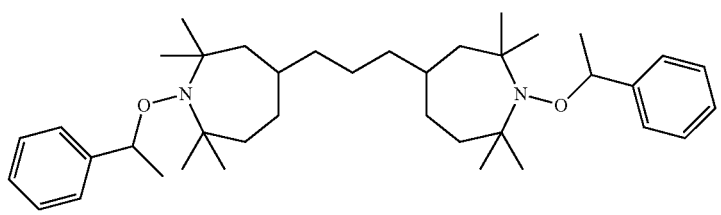 [SMILES: CC(ON1C(C)(C)CCC(CCCC2CCC(C)(C)N(OC(C)c3ccccc3)C(C)(C)C2)CC1(C)C)c1ccccc1] |
| 119 | 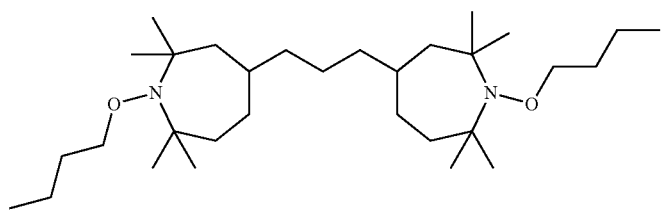 [SMILES: CCCCON1C(C)(C)CCC(CCCC2CCC(C)(C)N(OCCCC)C(C)(C)C2)CC1(C)C] |
| 120 | 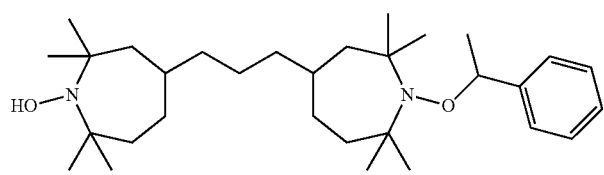 [SMILES: CC(ON1C(C)(C)CCC(CCCC2CCC(C)(C)N(O)C(C)(C)C2)CC1(C)C)c1ccccc1] |
| 121 | 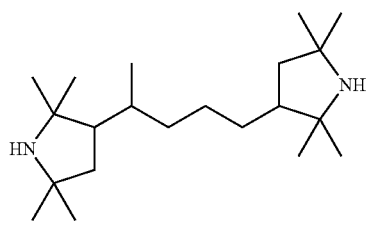 [SMILES: CC(CCCC1CC(C)(C)NC1(C)C)C1CC(C)(C)NC1(C)C] |
| 122 | 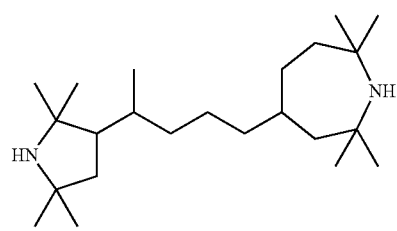 [SMILES: CC(CCCC1CCC(C)(C)NC(C)(C)C1)C1CC(C)(C)NC1(C)C] |

-continued
| No. | |
|---|---|
| 123 | 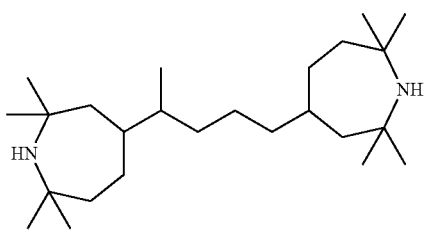 |
| 124 | 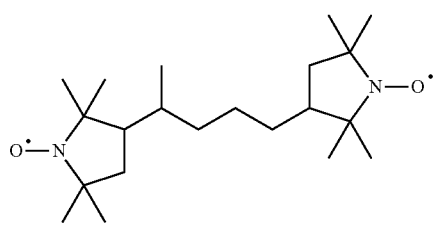 [SMILES: CC(CCCC1CC(C)(C)N(O)C1(C)C)C1CC(C)(C)N(O)C1(C)C] |
| 125 | 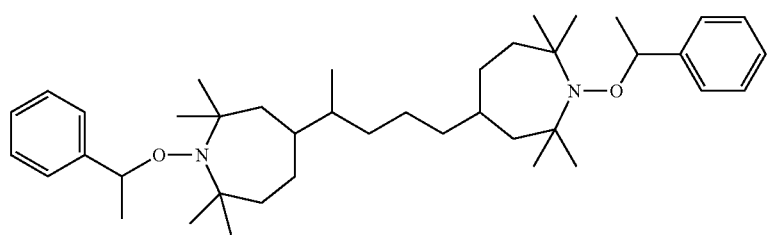 [SMILES: CC(ON1C(C)(C)CCC(CCCC(C)C2CCC(C)(C)N(OC(C)c3ccccc3)C(C)(C)C2)CC1(C)C)c1ccccc1] |
| 126 | 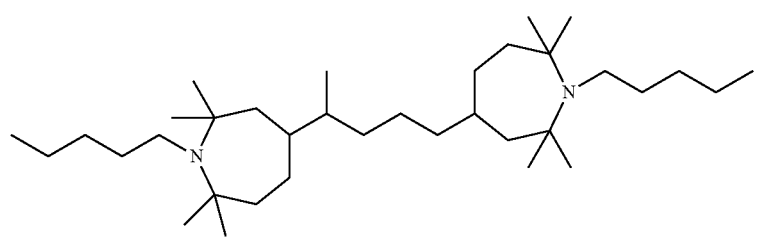 [SMILES: CCCCCN1C(C)(C)CCC(CCCC(C)C2CCC(C)(C)N(CCCCC)C(C)(C)C2)CC1(C)C] |
| 127 | 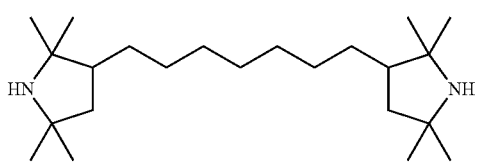 [SMILES: CC1(C)CC(CCCCCCCC2CC(C)(C)NC2(C)C)C(C)(C)N1] |
| 128 | 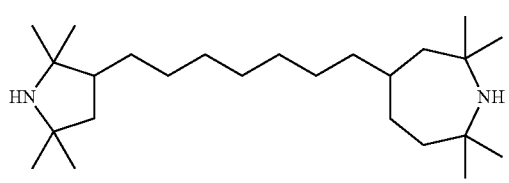 [SMILES: CC1(C)CCC(CCCCCCCC2CC(C)(C)NC2(C)C)CC(C)(C)N1] |
| 129 | 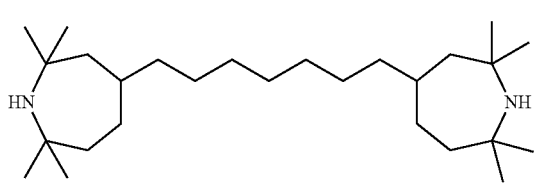 |

| No. | |
|---|---|
| 130 | 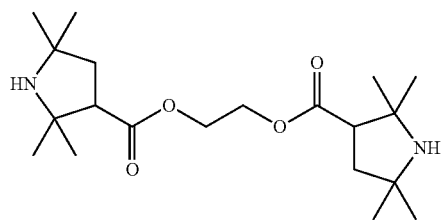 [SMILES: CC1(C)CC(C(=O)OCCOC(=O)C2CC(C)(C)NC2(C)C)C(C)(C)N1] |
| 131 | 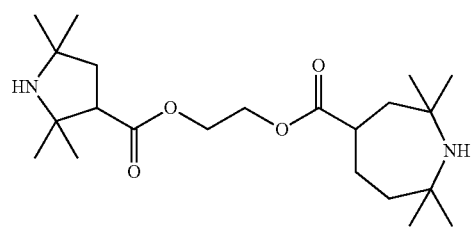 [SMILES: CC1(C)CCC(C(=O)OCCOC(=O)C2CC(C)(C)NC2(C)C)CC(C)(C)N1] |
| 132 | 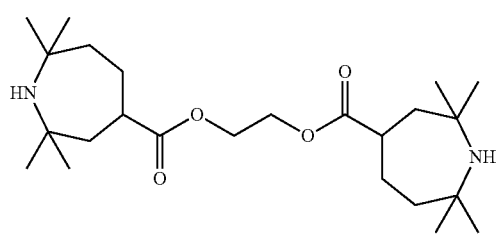 |
| 133 | 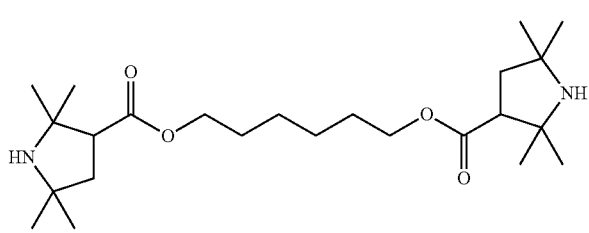 [SMILES: CC1(C)CC(C(=O)OCCCCCCOC(=O)C2CC(C)(C)NC2(C)C)C(C)(C)N1] |
| 134 | 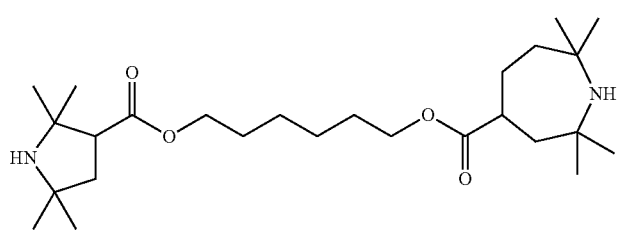 [SMILES: CC1(C)CCC(C(=O)OCCCCCCOC(=O)C2CC(C)(C)NC2(C)C)CC(C)(C)N1] |
| 135 | 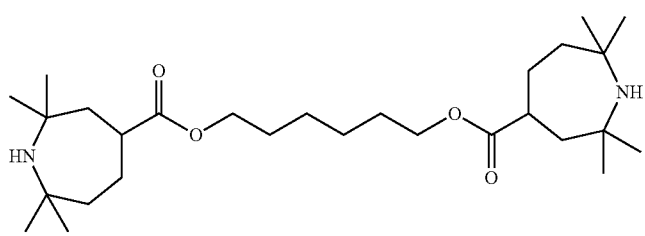 |
| 136 | 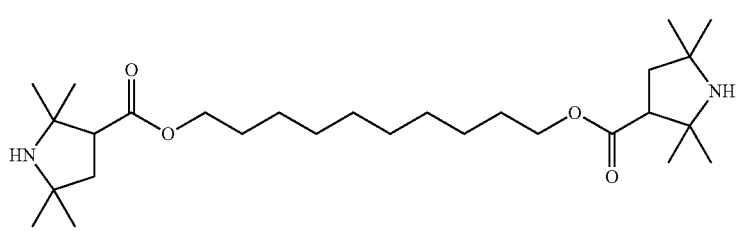 [SMILES: CC1(C)CC(C(=O)OCCCCCCCCCCOC(=O)C2CC(C)(C)NC2(C)C)C(C)(C)N1] |

-continued
| No. | |
|---|---|
| 137 | 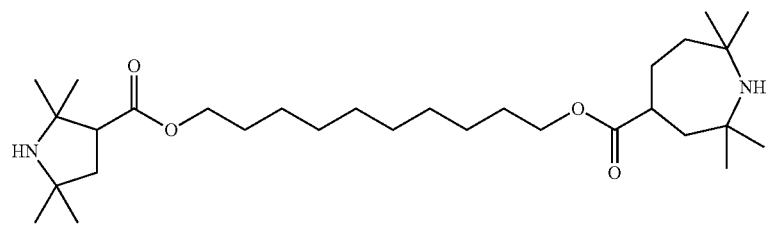 [SMILES: CC1(C)CCC(C(=O)OCCCCCCCCCCOC(=O)C2CC(C)(C)NC2(C)C)CC(C)(C)N1] |
| 138 | 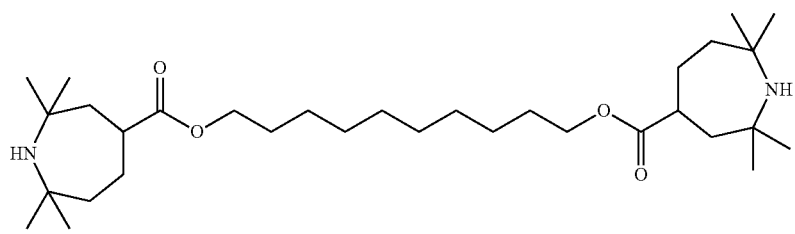 |
| 139 | 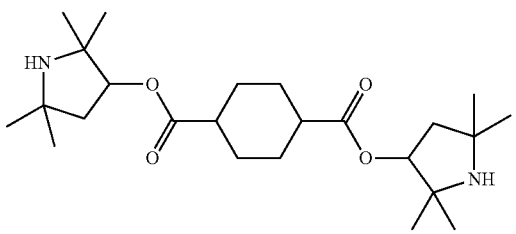 |
| 140 | 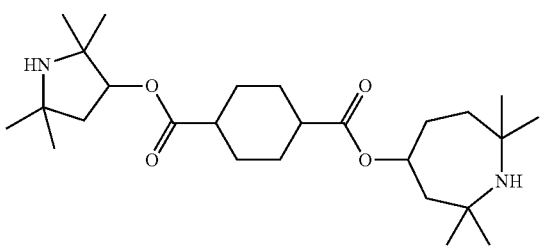 |
| 141 | 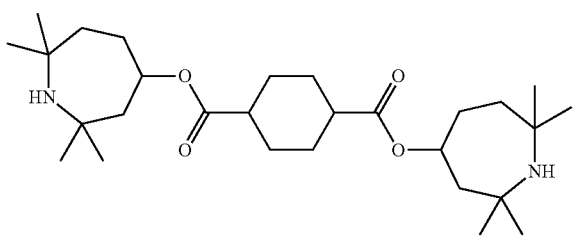 |
| 142 | 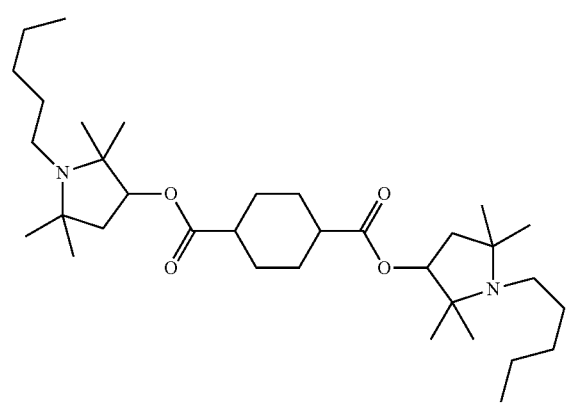 [SMILES: CCCCCN1C(C)(C)CC(OC(=O)C2CCC(C(=O)OC3CC(C)(C)N(CCCCC)C3(C)C)CC2)C1(C)C] |

| No. |
|---|
| 143 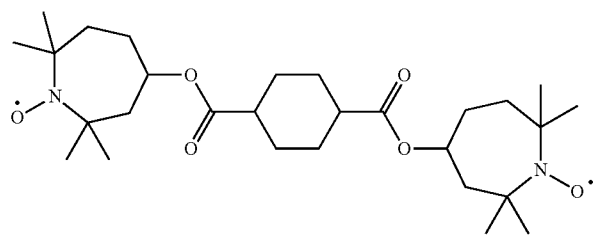 [SMILES: CC1(C)CCC(OC(=O)C2CCC(C(=O)OC3CCC(C)(C)N(O)C(C)(C)C3)CC2)CC(C)(C)N1O] |
| 144 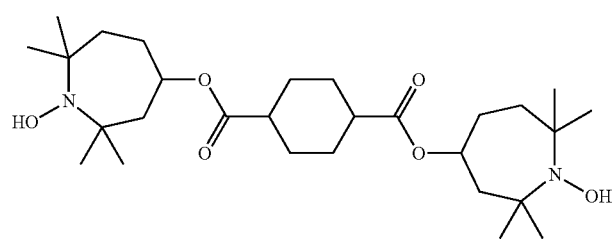 [SMILES: CC1(C)CCC(OC(=O)C2CCC(C(=O)OC3CCC(C)(C)N(O)C(C)(C)C3)CC2)CC(C)(C)N1O] |
| 145 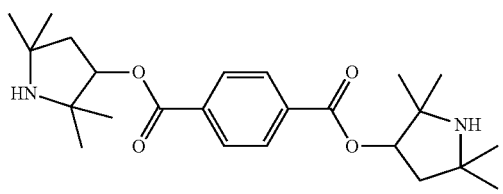 |
| 146 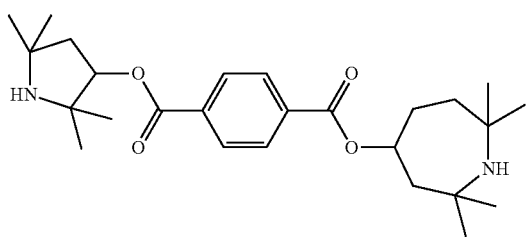 |
| 147 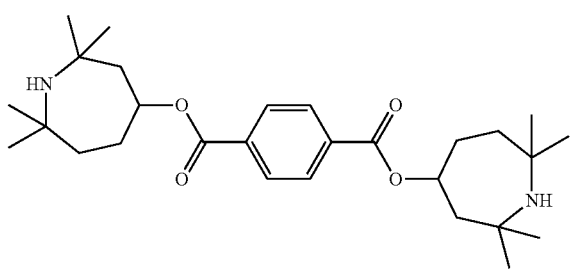 |
| 148 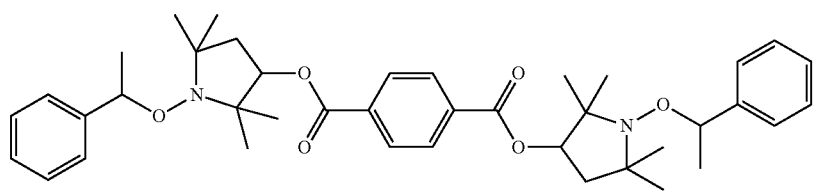 [SMILES: CC(ON1C(C)(C)CC(OC(=O)c2ccc(C(=O)OC3CC(C)(C)N(OC(C)c4ccccc4)C3(C)C)cc2)C1(C)C)c1ccccc1] |

| No. |
|---|
| 149 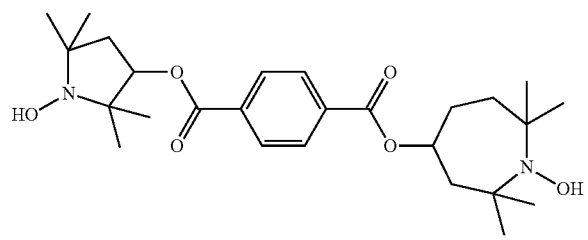 [SMILES: CC1(C)CCC(OC(=O)c2ccc(C(=O)OC3CC(C)(C)N(O)C3(C)C)cc2)CC(C)(C)N1O] |
| 150 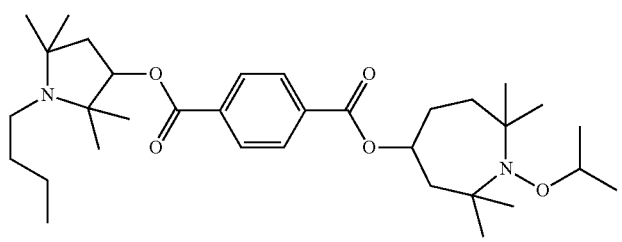 [SMILES: CCCCN1C(C)(C)CC(OC(=O)c2ccc(C(=O)OC3CCC(C)(C)N(OC(C)C)C(C)(C)C3)cc2)C1(C)C] |
| 151 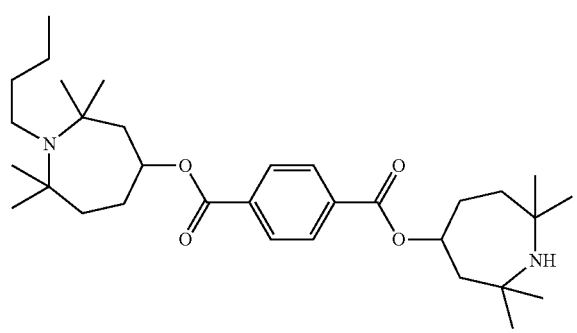 [SMILES: CCCCN1C(C)(C)CCC(OC(=O)c2ccc(C(=O)OC3CCC(C)(C)NC(C)(C)C3)cc2)CC1(C)C] |
| 152 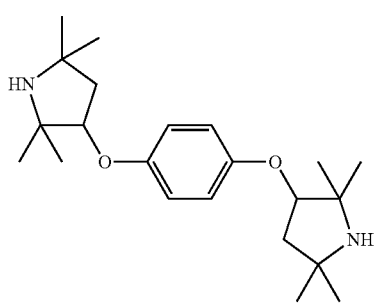 |
| 153 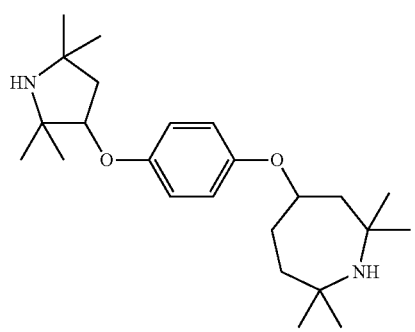 |

| No. |
|---|
| 154 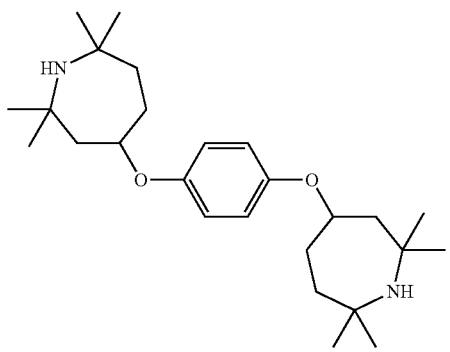 |
| 155 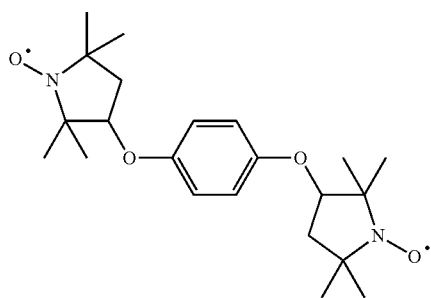 [SMILES: CC1(C)CC(Oc2ccc(OC3CC(C)(C)N(O)C3(C)C)cc2)C(C)(C)N1O] |
| 156 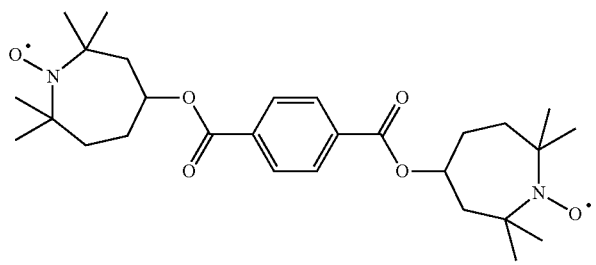 [SMILES: CC1(C)CCC(OC(=O)c2ccc(C(=O)OC3CCC(C)(C)N(O)C(C)(C)C3)cc2)CC(C)(C)N1O] |
| 157 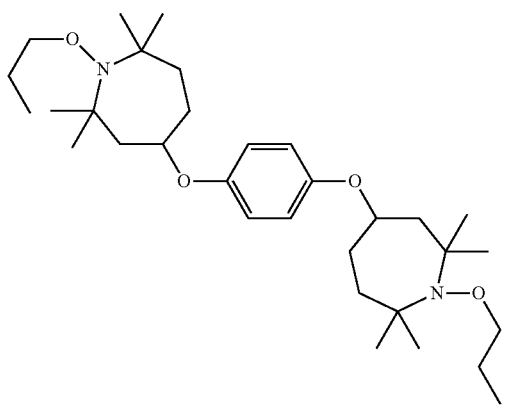 [SMILES: CCCON1C(C)(C)CCC(Oc2ccc(OC3CCC(C)(C)N(OCCC)C(C)(C)C3)cc2)CC1(C)C] |

| No. | |
|---|---|
| 158 | 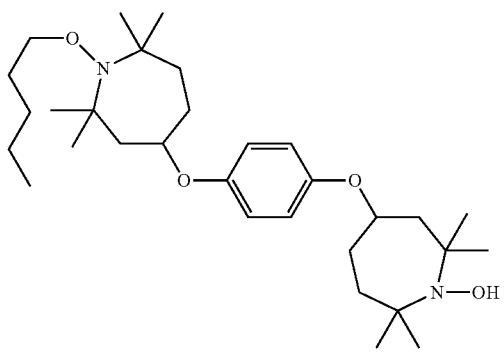 [SMILES: CCCCCON1C(C)(C)CCC(Oc2ccc(OC3CCC(C)(C)N(O)C(C)(C)C3)cc2)CC1(C)C] |
| 159 | 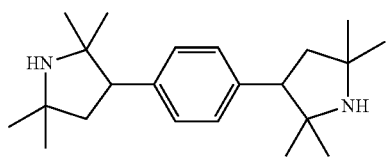 |
| 160 | 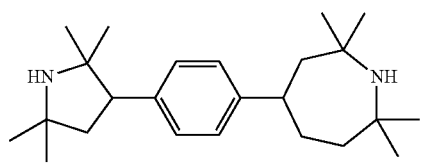 |
| 161 | 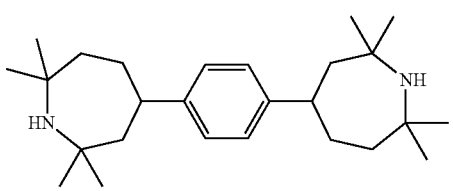 |
| 162 | 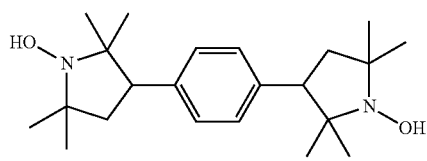 [SMILES: CC1(C)CC(c2ccc(C3CC(C)(C)N(O)C3(C)C)cc2)C(C)(C)N1O] |
| 163 | 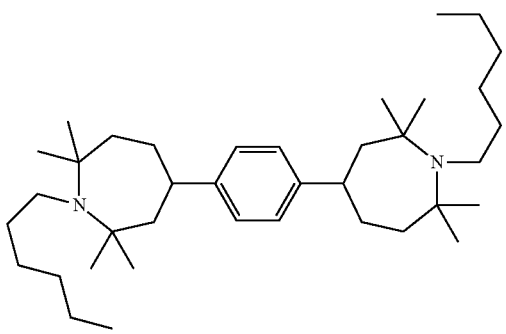 [SMILES: CCCCCCN1C(C)(C)CCC(c2ccc(C3CCC(C)(C)N(CCCCCC)C(C)(C)C3)cc2)CC1(C)C] |

| No. |
|---|
| 164 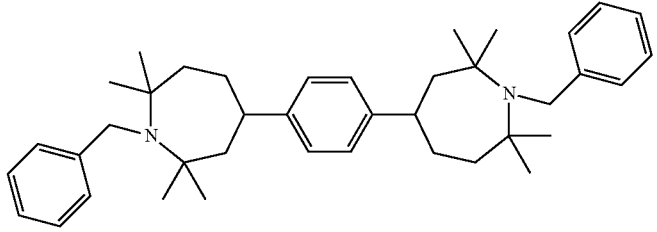 [SMILES: CC1(C)CCC(c2ccc(C3CCC(C)(C)N(Cc4ccccc4)C(C)(C)C3)cc2)CC(C)(C)N1Cc1ccccc1] |
| 165 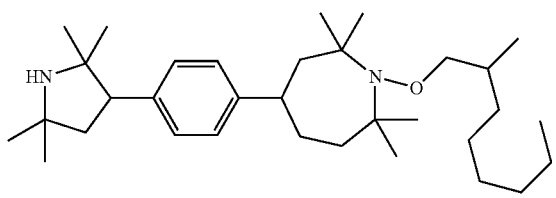 [SMILES: CCCCCCC(C)CON1C(C)(C)CCC(c2ccc(C3CC(C)(C)NC3(C)C)cc2)CC1(C)C] |
| 166 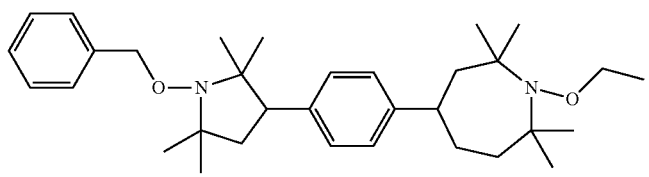 |
| 167 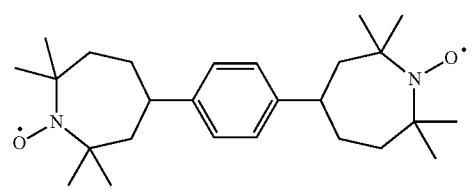 |
| 168 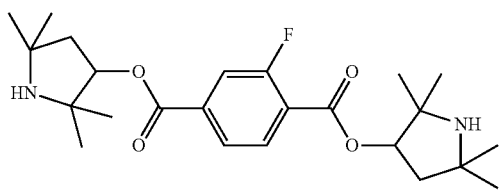 |
| 169 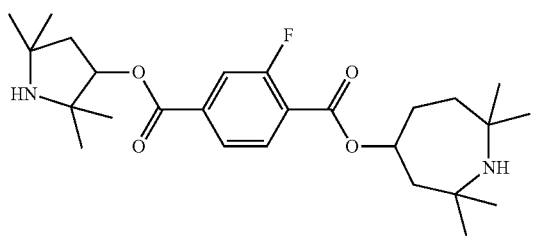 |
| 170 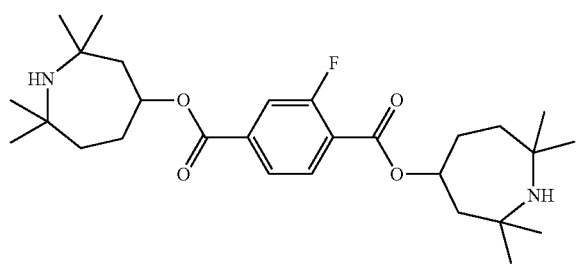 |

| No. | |
|---|---|
| 171 | 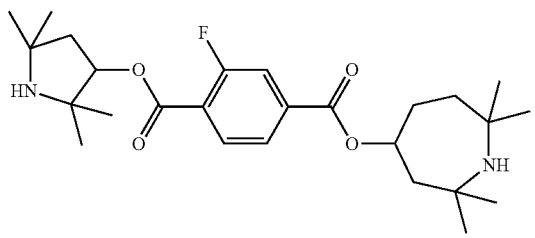 |
| 172 | 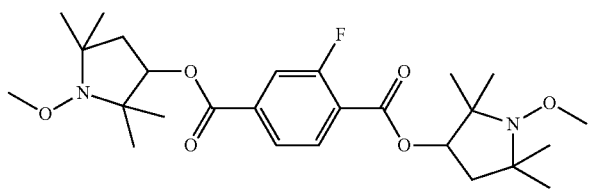 |
| 173 | 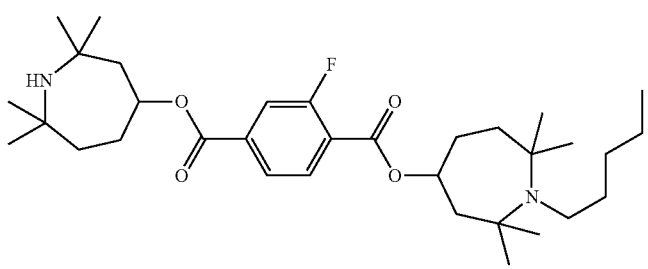 [SMILES: CCCCCN1C(C)(C)CCC(OC(=O)c2ccc(C(=O)OC3CCC(C)(C)NC(C)(C)C3)cc2F)CC1(C)C] |
| 174 | 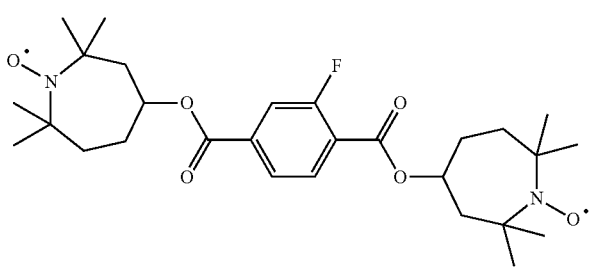 |
| 175 | 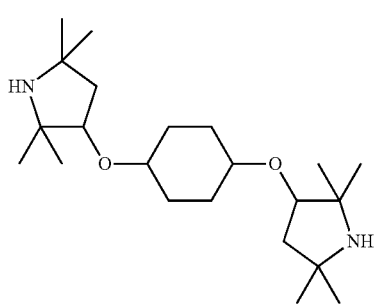 |
| 176 | 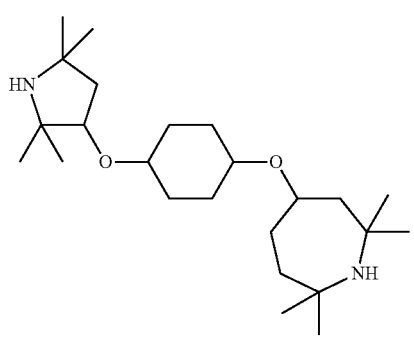 |

| No. | |
|---|---|
| 177 | 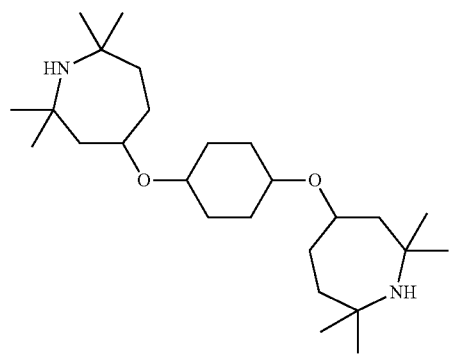 |
| 178 | 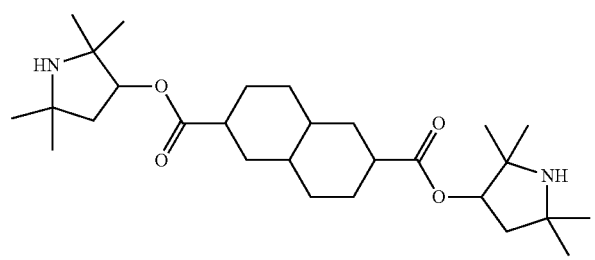 |
| 179 | 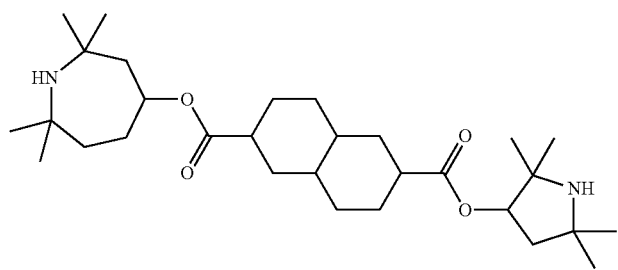 |
| 180 | 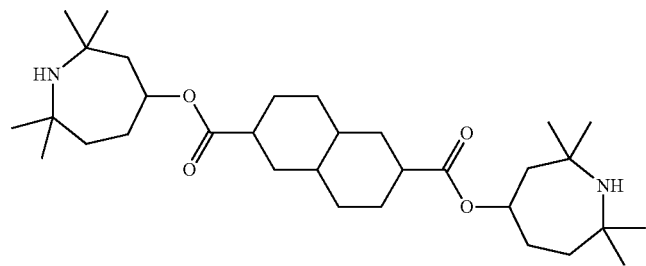 |
| 181 | 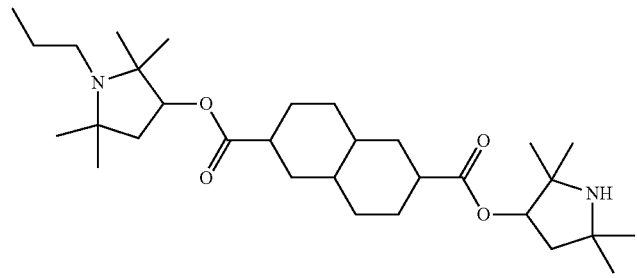 [SMILES: CCCN1C(C)(C)CC(OC(=O)C2CCC3CC(C(=O)OC4CC(C)(C)NC4(C)C)CCC3C2)C1(C)C] |

| No. | |
|---|---|
| 182 | 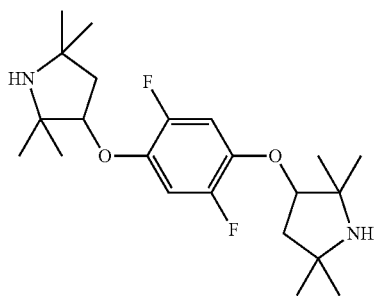 |
| 183 | 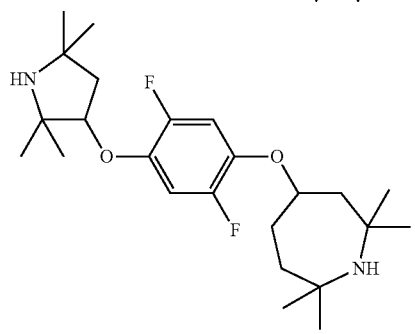 |
| 184 | 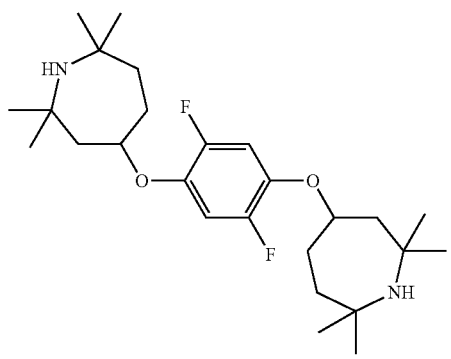 |
| 185 | 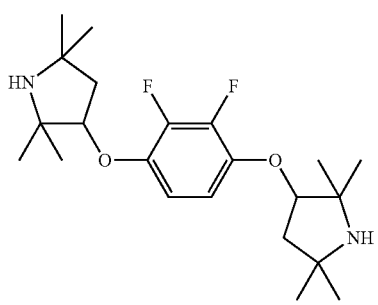 |
| 186 | 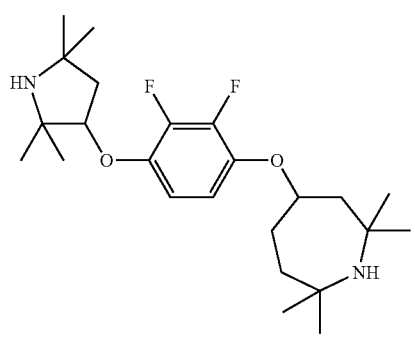 |

-continued
| No. | |
|---|---|
| 187 | 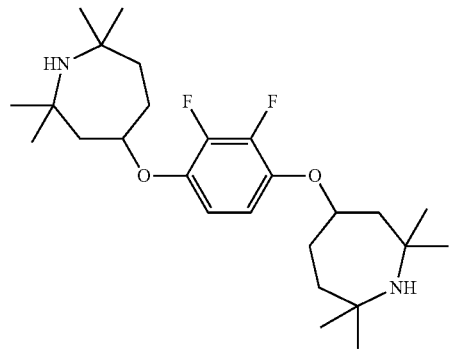 |
| 188 | 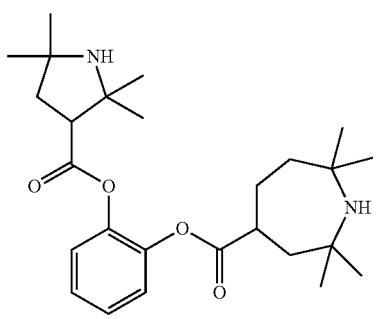 |
| 189 | 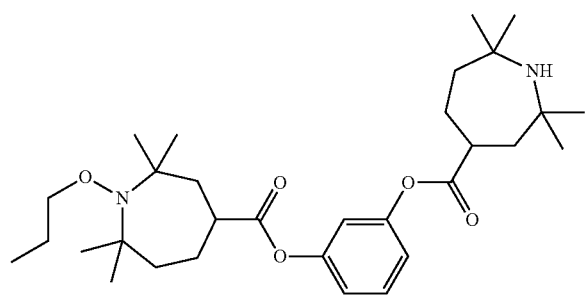 [SMILES: CCCON1C(C)(C)CCC(C(=O)Oc2cccc(OC(=O)C3CCC(C)(C)NC(C)(C)C3)c2)CC1(C)C] |
| 190 | 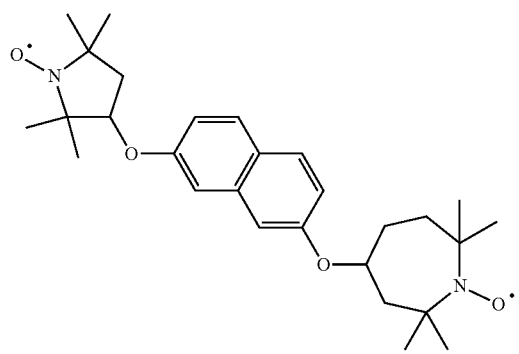 [SMILES: CC1(C)CCC(Oc2ccc3ccc(OC4CC(C)(C)N(O)C4(C)C)cc3c2)CC(C)(C)N1O] |
| 200 | 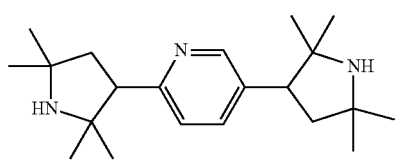 |

-continued
| No. | |
|---|---|
| 201 | 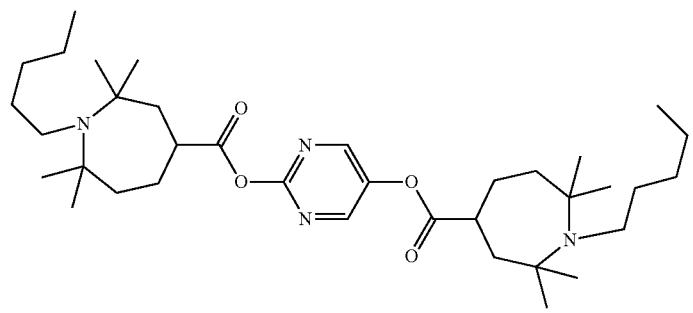 [SMILES: CCCCCN1C(C)(C)CCC(C(=O)Oc2cnc(OC(=O)C3CCC(C)(C)N(CCCCC)C(C)(C)C3)nc2)CC1(C)C] |
| 202 | 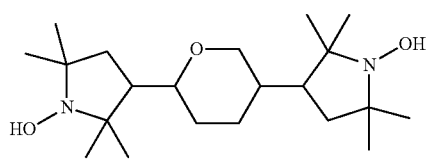 |
| 203 | 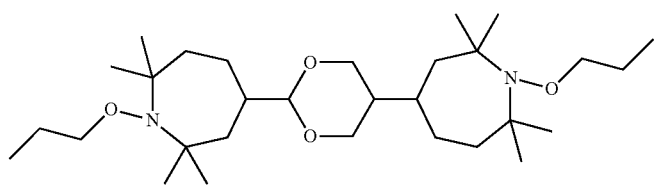 [SMILES: CCCON1C(C)(C)CCC(C2COC(C3CCC(C)(C)N(OCCC)C(C)(C)C3)OC2)CC1(C)C] |
| 204 | 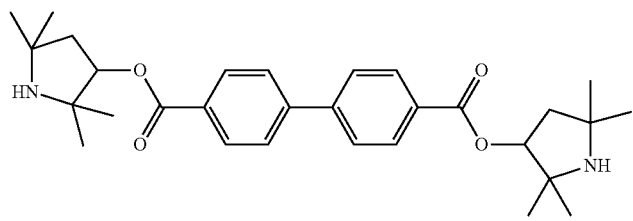 |
| 205 | 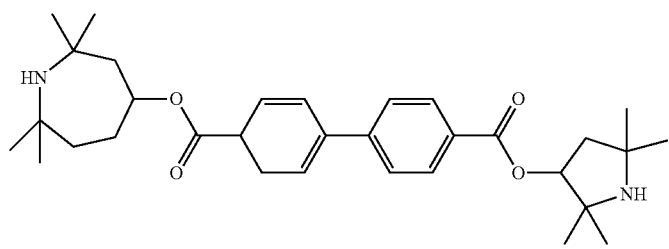 |
| 206 | 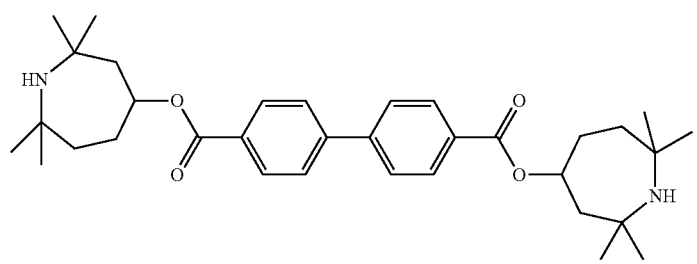 |

| No. | |
|---|---|
| 207 | 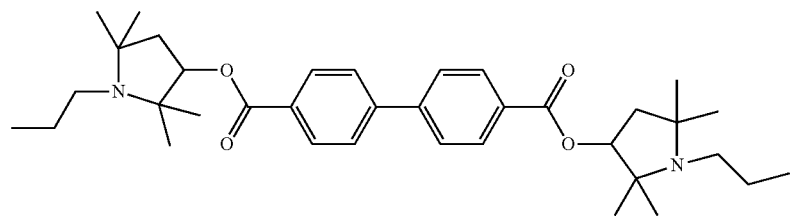 [SMILES: CCCN1C(C)(C)CC(OC(=O)c2ccc(-c3ccc(C(=O)OC4CC(C)(C)N(CCC)C4(C)C)cc3)cc2)C1(C)C] |
| 208 | 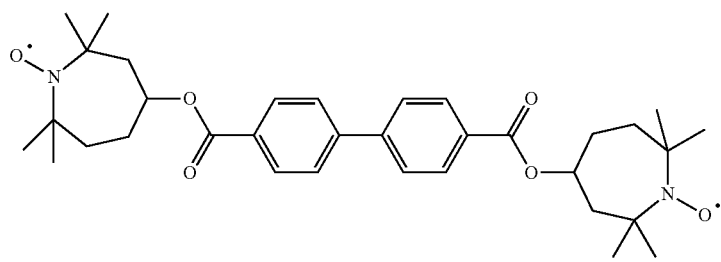 [SMILES: CC1(C)CCC(OC(=O)c2ccc(-c3ccc(C(=O)OC4CCC(C)(C)N(O)C(C)(C)C4)cc3)cc2)CC(C)(C)N1O] |
| 209 | 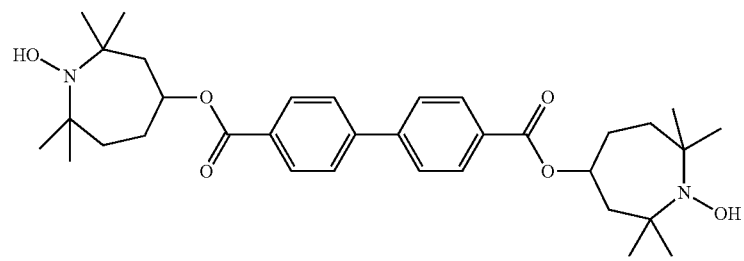 [SMILES: CC1(C)CCC(OC(=O)c2ccc(-c3ccc(C(=O)OC4CCC(C)(C)N(O)C(C)(C)C4)cc3)cc2)CC(C)(C)N1O] |
| 210 | 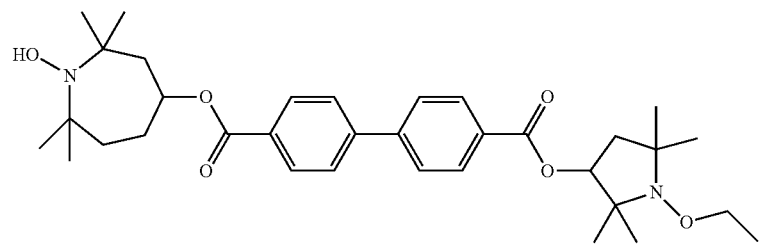 [SMILES: CCON1C(C)(C)CC(OC(=O)c2ccc(-c3ccc(C(=O)OC4CCC(C)(C)N(O)C(C)(C)C4)cc3)cc2)C1(C)C] |
| 211 | 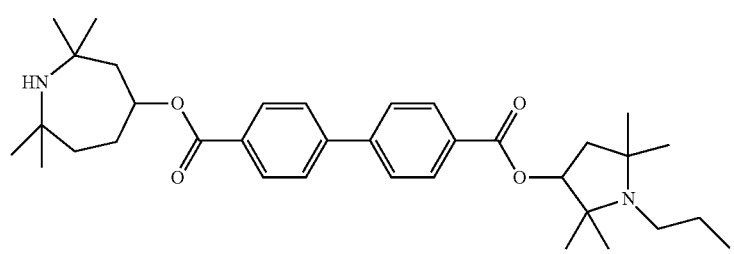 [SMILES: CCCN1C(C)(C)CC(OC(=O)c2ccc(-c3ccc(C(=O)OC4CCC(C)(C)NC(C)(C)C4)cc3)cc2)C1(C)C] |
| 212 | 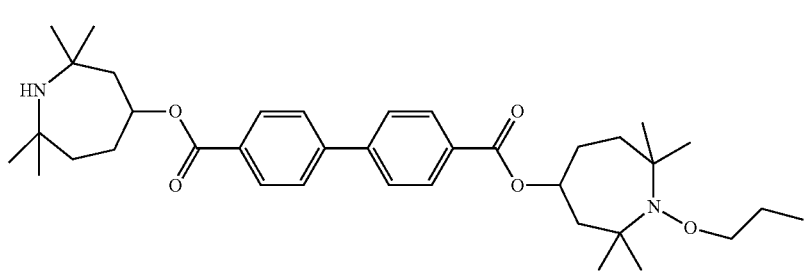 [SMILES: CCCON1C(C)(C)CCC(OC(=O)c2ccc(-c3ccc(C(=O)OC4CCC(C)(C)NC(C)(C)C4)cc3)cc2)CC1(C)C] |

| No. | |
|---|---|
| 213 | 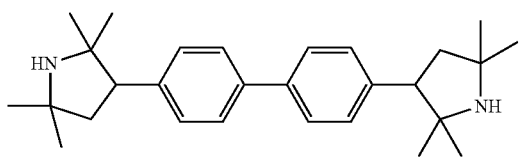 |
| 214 | 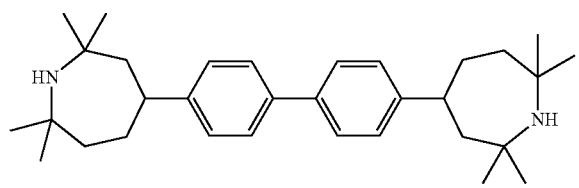 |
| 215 | 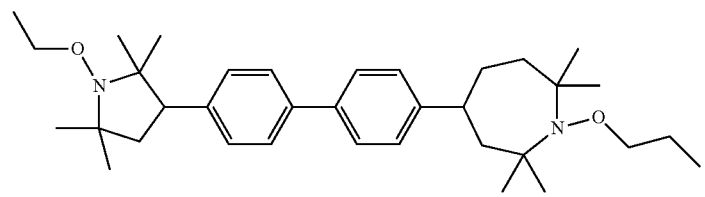 [SMILES: CCCON1C(C)(C)CCC(c2ccc(-c3ccc(C4CC(C)(C)N(OCC)C4(C)C)cc3)cc2)CC1(C)C] |
| 216 | 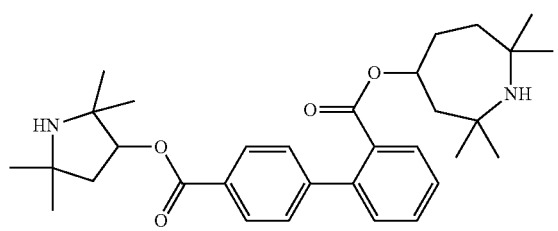 |
| 217 | 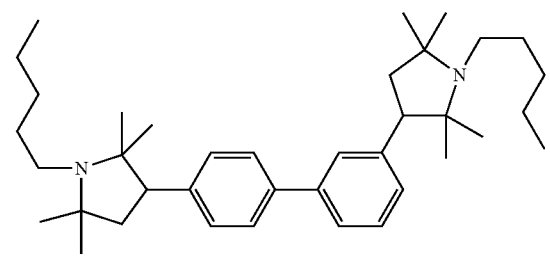 [SMILES: CCCCCN1C(C)(C)CC(c2ccc(-c3cccc(C4CC(C)(C)N(CCCCC)C4(C)C)c3)cc2)C1(C)C] |
| 218 | 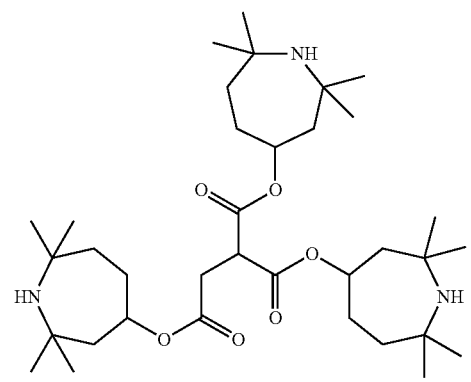 |

| No. | |
|---|---|
| 219 | 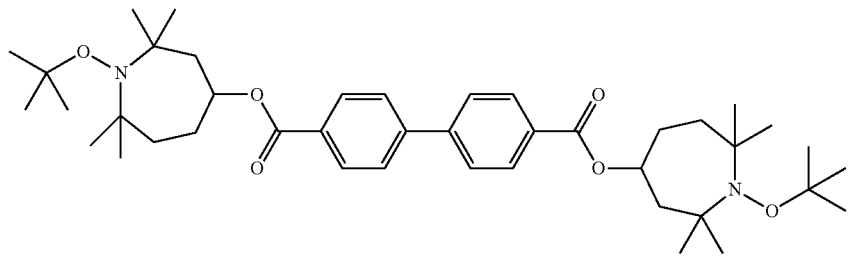 [SMILES: CC(C)(C)ON1C(C)(C)CCC(OC(=O)c2ccc(-c3ccc(C(=O)OC4CCC(C)(C)N(OC(C)(C)C)C(C)(C)C4)cc3)cc2)CC1(C)C] |
| 220 | 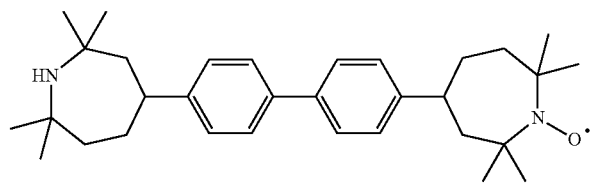 |
| 221 | 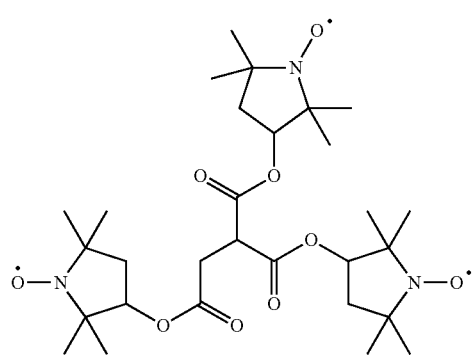 [SMILES: CC1(C)CC(OC(=O)CC(C(=O)OC2CC(C)(C)N(O)C2(C)C)C(=O)OC2CC(C)(C)N(O)C2(C)C)C(C)(C)N1O] |
| 222 | 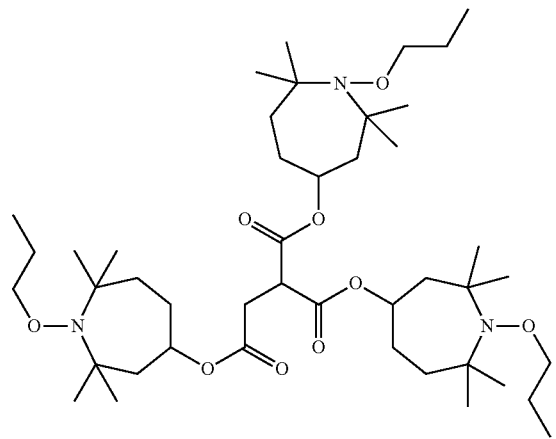 [SMILES: CCCON1C(C)(C)CCC(OC(=O)CC(C(=O)OC2CCC(C)(C)N(OCCC)C(C)(C)C2)C(=O)OC2CCC(C)(C)N(OCCC)C(C)(C)C2)CC1(C)C] |

| No. |
| --- |
| 223 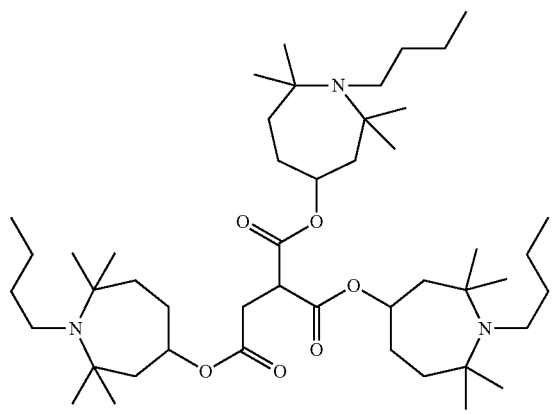 [SMILES: CCCCN1C(C)(C)CCC(OC(=O)CC(C(=O)OC2CCC(C)(C)N(CCCC)C(C)(C)C2)C(=O)OC2CCC(C)(C)N(CCCC)C(C)(C)C2)CC1(C)C] |
| 224 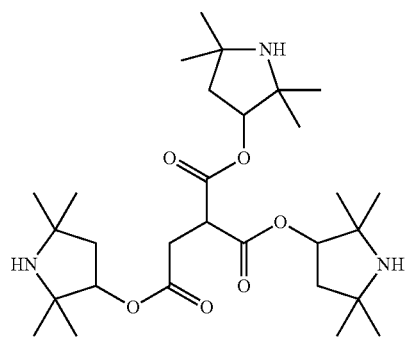 [SMILES: CC1(C)CC(OC(=O)CC(C(=O)OC2CC(C)(C)NC2(C)C)C(=O)OC2CC(C)(C)NC2(C)C)C(C)(C)N1] |
| 225 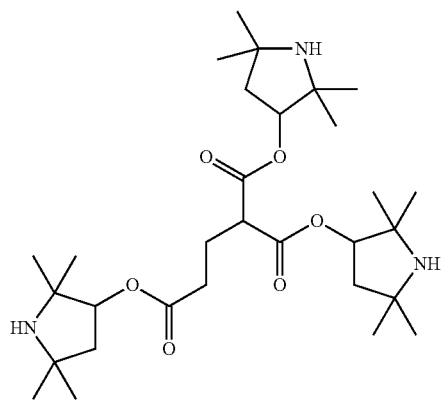 [SMILES: CC1(C)CC(OC(=O)CCC(C(=O)OC2CC(C)(C)NC2(C)C)C(=O)OC2CC(C)(C)NC2(C)C)C(C)(C)N1] |
| 226 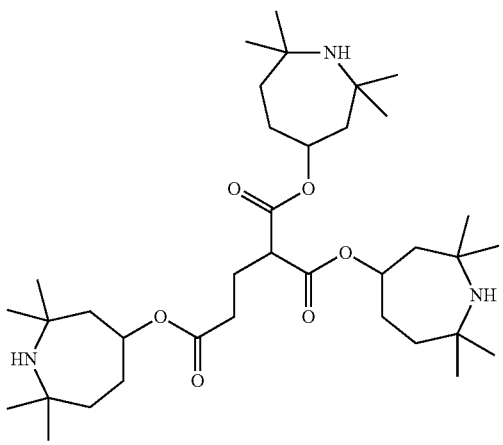 |

US 9,676,686 B2
167                                                    168
-continued
| No. |
|---|
| 227 | 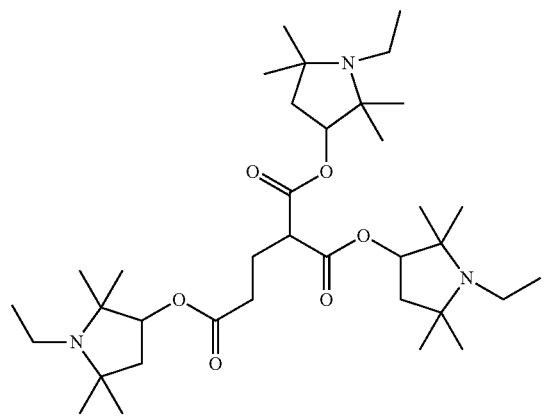 [SMILES: CCN1C(C)(C)CC(OC(=O)CCC(C(=O)OC2CC(C)(C)N(CC)C2(C)C)C(=O)OC2CC(C)(C)N(CC)C2(C)C)C1(C)C] |
| 228 | 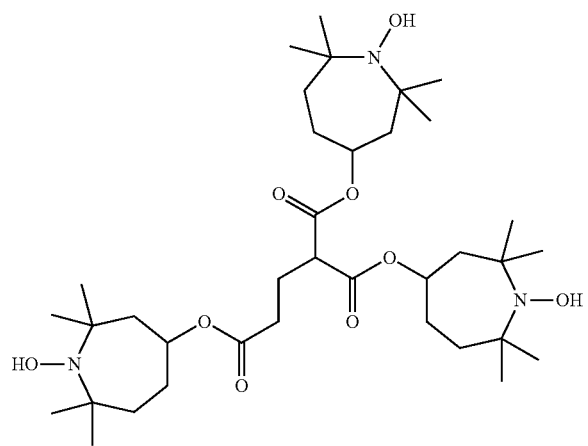 [SMILES: CC1(C)CCC(OC(=O)CCC(C(=O)OC2CCC(C)(C)N(O)C(C)(C)C2)C(=O)OC2CCC(C)(C)N(O)C(C)(C)C2)CC(C)(C)N1O] |
| 229 | 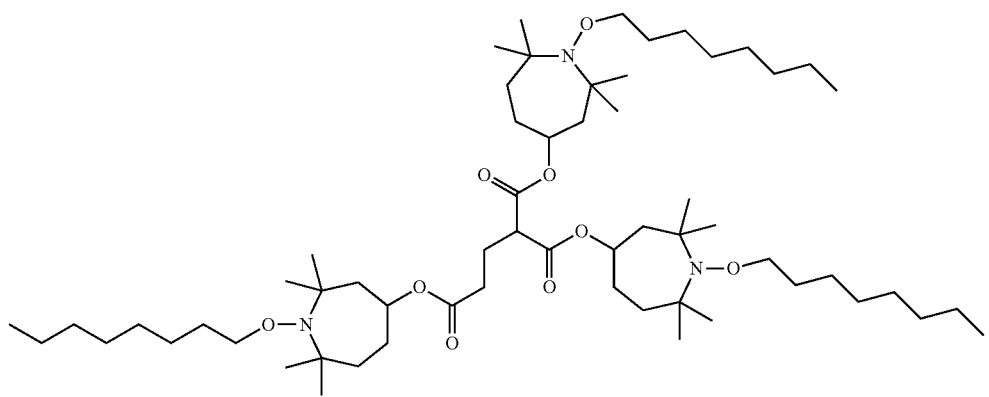 [SMILES: CCCCCCCCON1C(C)(C)CCC(OC(=O)CCC(C(=O)OC2CCC(C)(C)N(OCCCCCCCC)C(C)(C)C2)C(=O)OC2CCC(C)(C)N(OCCCCCCCC)C(C)(C)C2)CC1(C)C] |
| 230 | 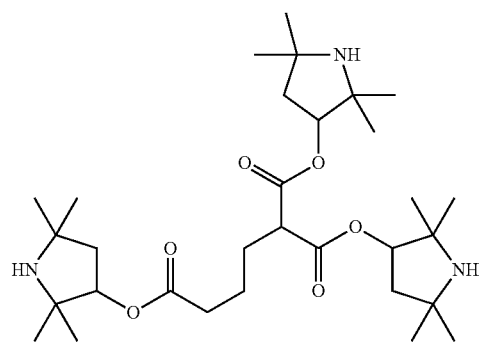 [SMILES: CC1(C)CC(OC(=O)CCCC(C(=O)OC2CC(C)(C)NC2(C)C)C(=O)OC2CC(C)(C)NC2(C)C)C(C)(C)N1] |

| No. | |
|---|---|
| 231 | 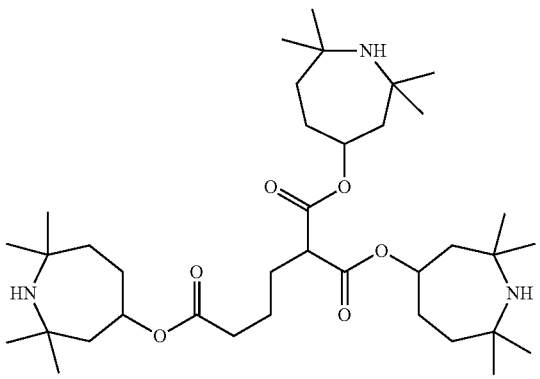 |
| 232 | 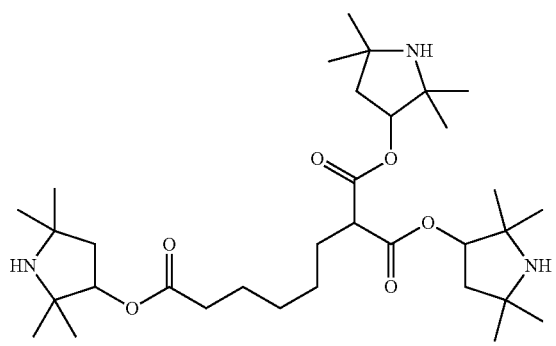 |
| 233 | 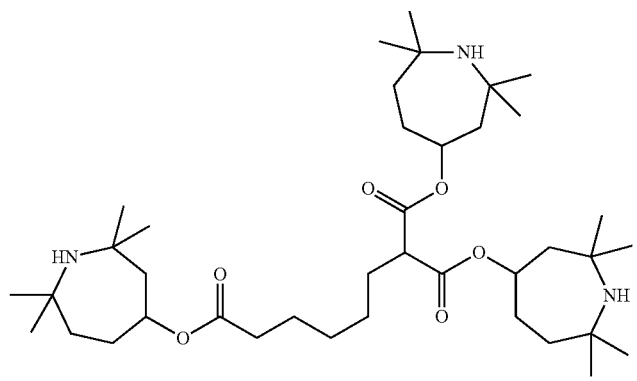 |
| 234 | 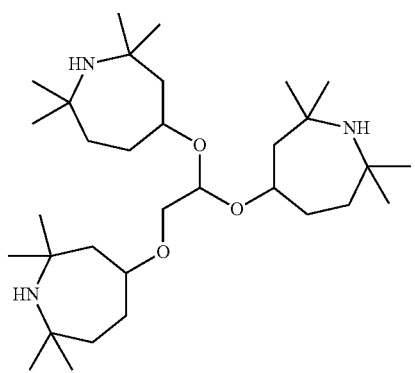 |

| No. |
|---|
| 235 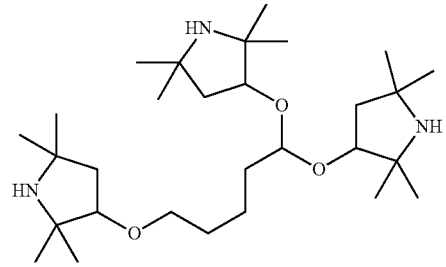 |
| 236 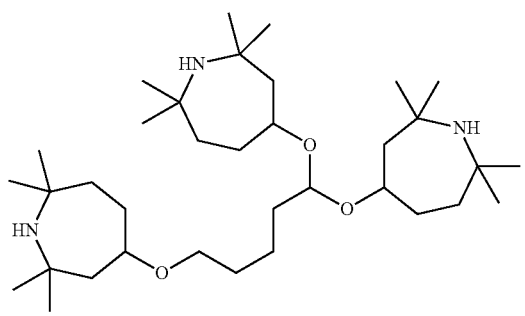 |
| 237 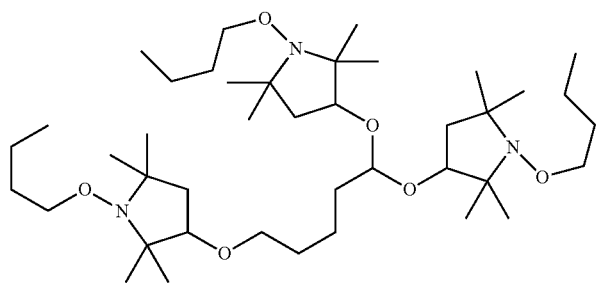 [SMILES: CCCCON1C(C)(C)CC(OCCCCC(OC2CC(C)(C)N(OCCCC)C2(C)C)OC2CC(C)(C)N(OCCCC)C2(C)C)C1(C)C] |
| 238 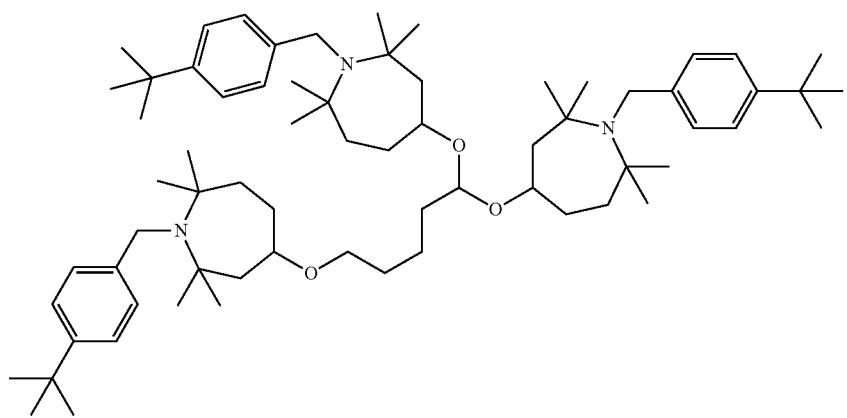 [SMILES: CC(C)(C)c1ccc(CN2C(C)(C)CCC(OCCCCC(OC3CCC(C)(C)N(Cc4ccc(C(C)(C)C)cc4)C(C)(C)C3)OC3CCC(C)(C)N(Cc4ccc(C(C)(C)C)cc4)C(C)(C)C3)CC2(C)C)cc1] |

| No. | |
|---|---|
| 239 | 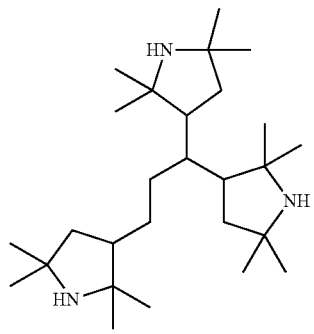 |
| 240 | 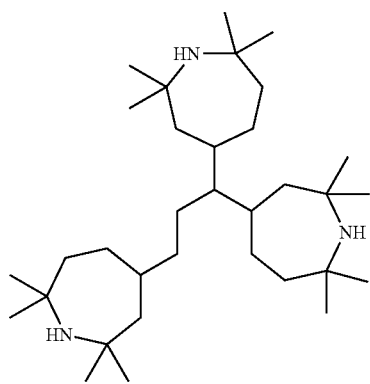 |
| 241 | 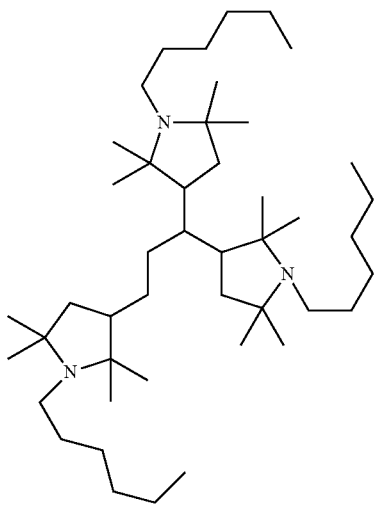 [SMILES: CCCCCCN1C(C)(C)CC(CCC(C2CC(C)(C)N(CCCCCC)C2(C)C)C2CC(C)(C)N(CCCCCC)C2(C)C)C1(C)C] |
| 242 | 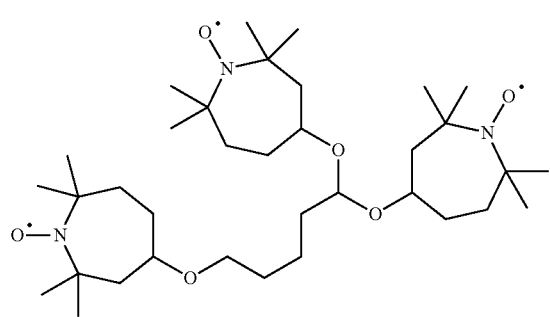 [SMILES: CC1(C)CCC(OCCCCC(OC2CCC(C)(C)N(O)C(C)(C)C2)OC2CCC(C)(C)N(O)C(C)(C)C2)CC(C)(C)N1O] |

US 9,676,686 B2
-continued
| No. | |
|---|---|
| 243 | 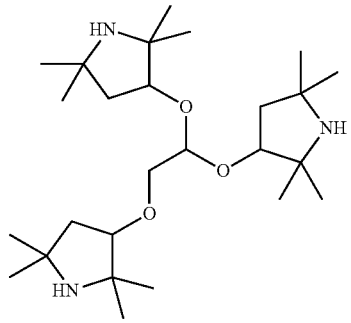 |
| 244 | 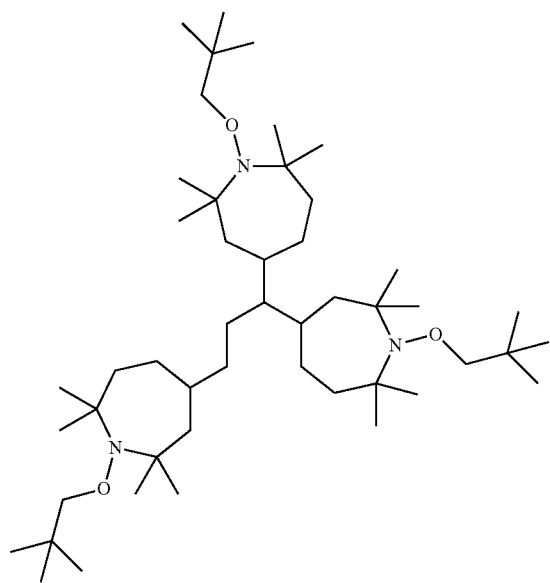 [SMILES: CC(C)(C)CON1C(C)(C)CCC(CCC(C2CCC(C)(C)N(OCC(C)(C)C)C(C)(C)C2)C2CCC(C)(C)N(OCC(C)(C)C)C(C)(C)C2)CC1(C)C] |
| 245 | 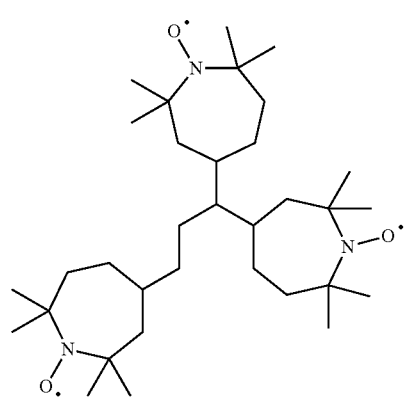 [SMILES: CC1(C)CCC(CCC(C2CCC(C)(C)N(O)C(C)(C)C2)C2CCC(C)(C)N(O)C(C)(C)C2)CC(C)(C)N1O] |
| 246 | 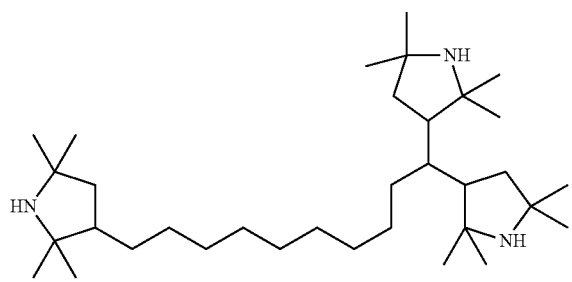 [SMILES: CC1(C)CC(CCCCCCCCCC(C2CC(C)(C)NC2(C)C)C2CC(C)(C)NC2(C)C)C(C)(C)N1] |

| No. |
|---|
| 247 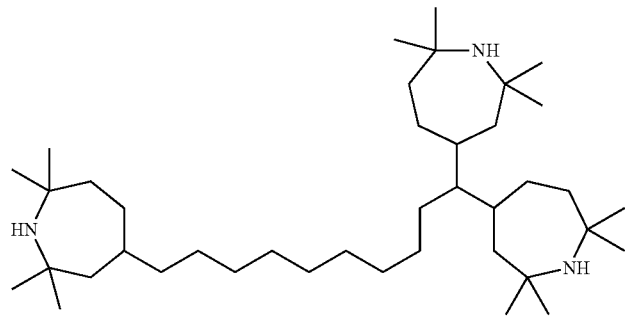 |
| 248 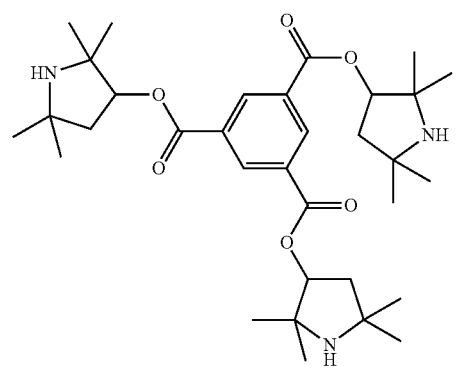 |
| 249 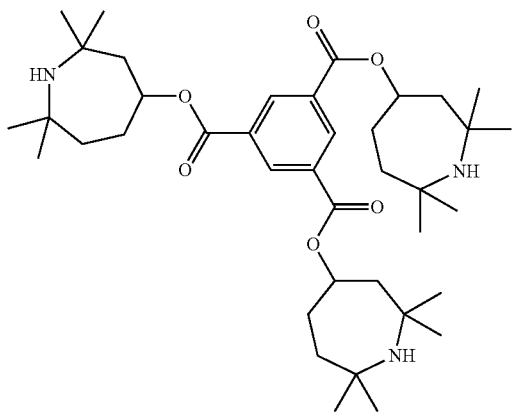 |
| 250 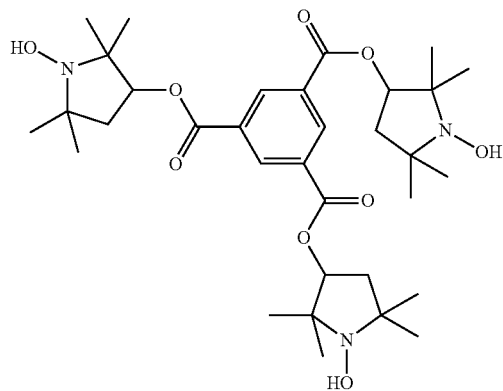 [SMILES: CC1(C)CC(OC(=O)c2cc(C(=O)OC3CC(C)(C)N(O)C3(C)C)cc(C(=O)OC3CC(C)(C)N(O)C3(C)C)c2)C(C)(C)N1O] |

| No. |
|---|
| 251 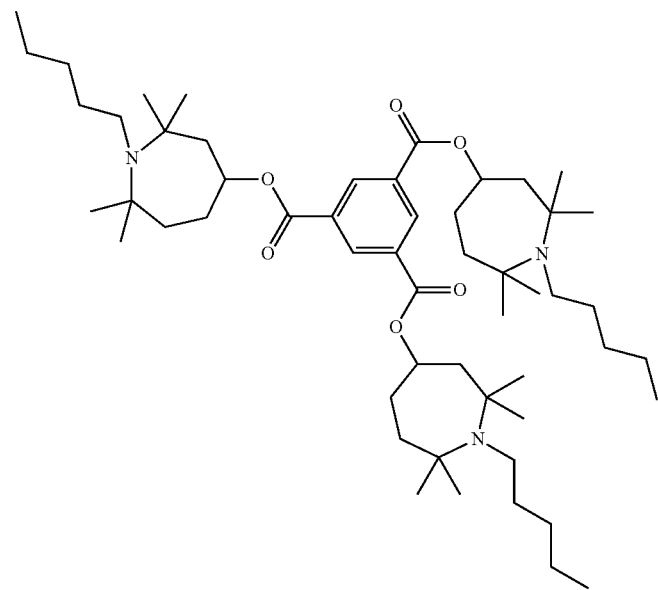 [SMILES: CCCCCN1C(C)(C)CCC(OC(=O)c2cc(C(=O)OC3CCC(C)(C)N(CCCCC)C(C)(C)C3)cc(C(=O)OC3CCC(C)(C)N(CCCCC)C(C)(C)C3)c2)CC1(C)C] |
| 252 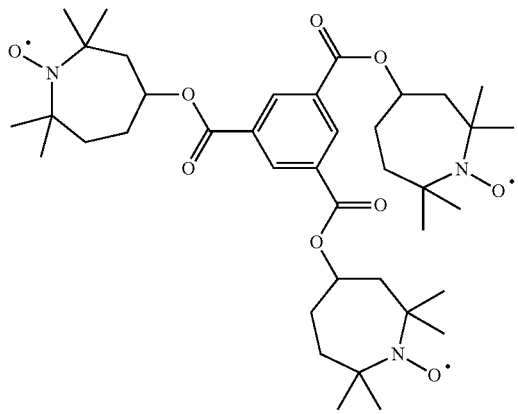 |
| 253 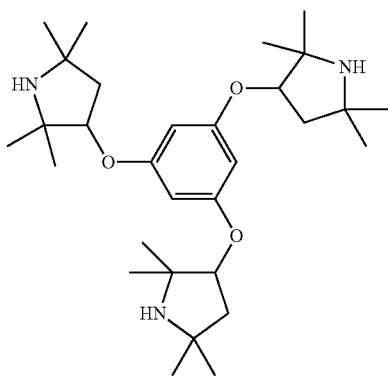 |

| No. | |
|---|---|
| 254 | 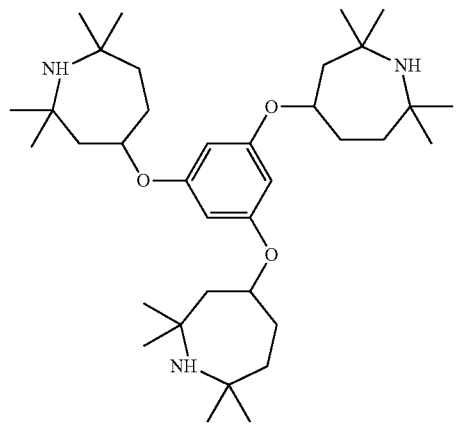 |
| 256 | 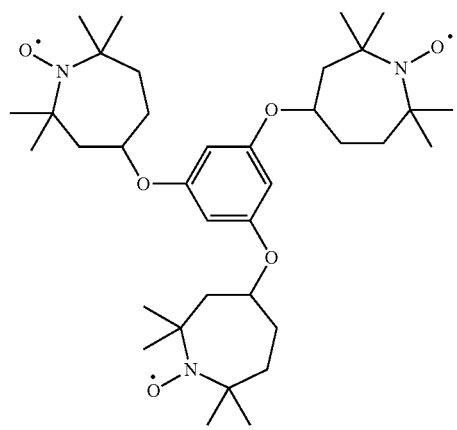 |
| 257 | 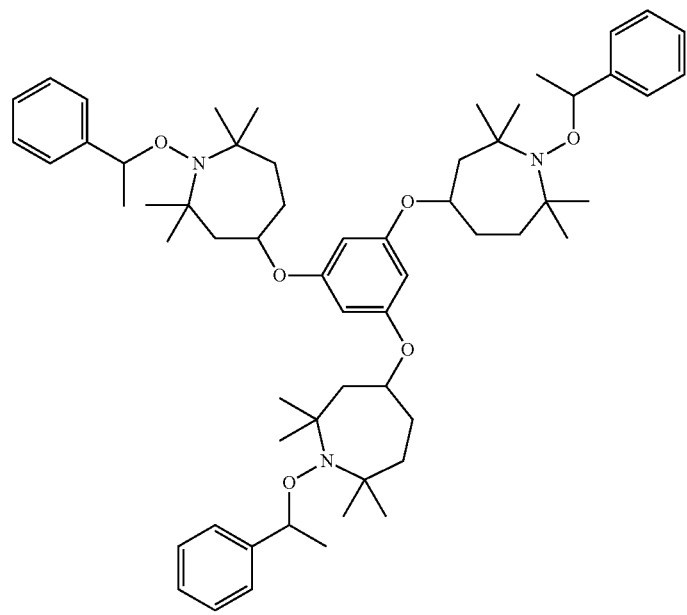 [SMILES: CC(ON1C(C)(C)CCC(Oc2cc(OC3CCC(C)(C)N(OC(C)c4ccccc4)C(C)(C)C3)cc(OC3CCC(C)(C)N(OC(C)c4ccccc4)C(C)(C)C3)c2)CC1(C)C)c1ccccc1] |

| No. |
|---|
| 258 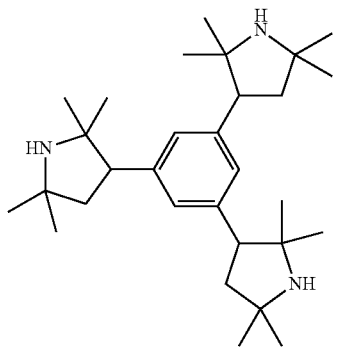 |
| 259 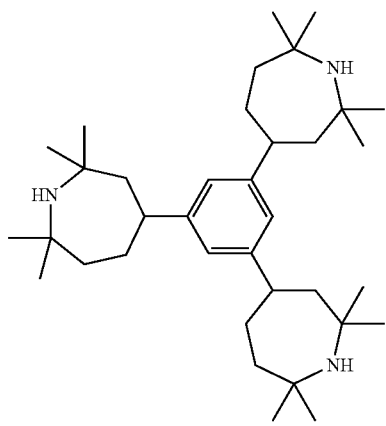 |
| 260 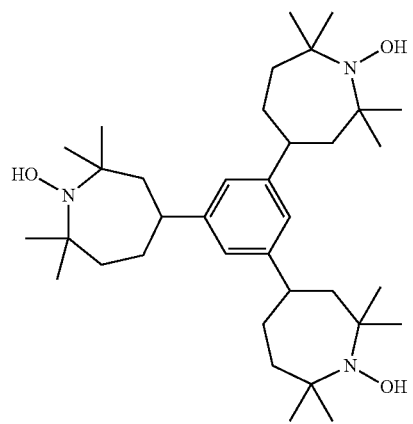 |

| No. | |
|---|---|
| 261 | 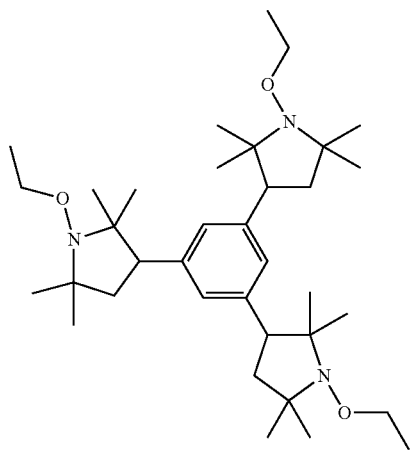 [SMILES: CCON1C(C)(C)CC(c2cc(C3CC(C)(C)N(OCC)C3(C)C)cc(C3CC(C)(C)N(OCC)C3(C)C)c2)C1(C)C] |
| 262 | 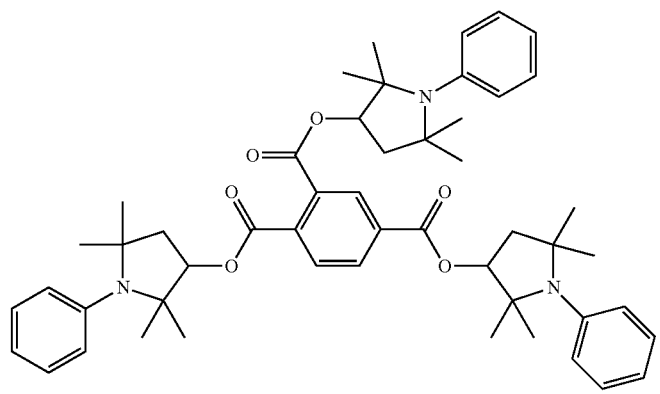 [SMILES: CC1(C)CC(OC(=O)c2ccc(C(=O)OC3CC(C)(C)N(c4ccccc4)C3(C)C)c(C(=O)OC3CC(C)(C)N(c4ccccc4)C3(C)C)c2)C(C)(C)N1c1ccccc1] |
| 263 | 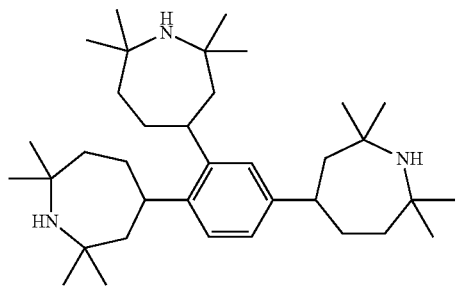 |
| 264 | 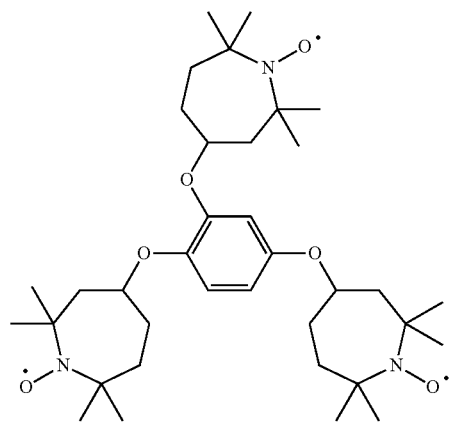 |

| No. | |
|---|---|
| 265 | 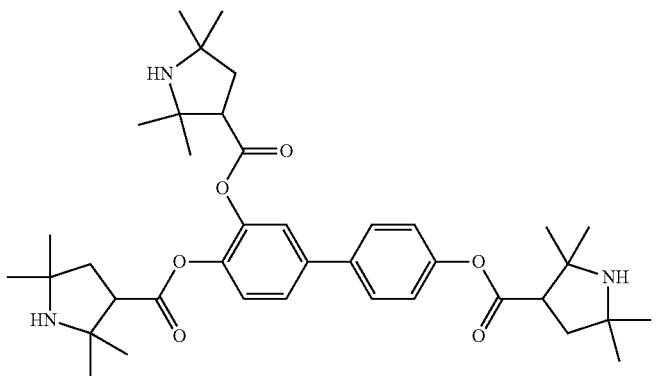 |
| 266 | 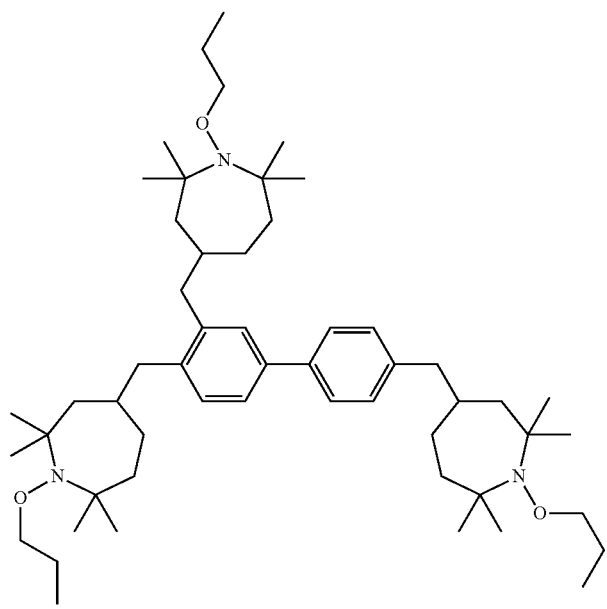 [SMILES: CCCON1C(C)(C)CCC(Cc2ccc(-c3ccc(CC4CCC(C)(C)N(OCCC)C(C)(C)C4)c(CC4CCC(C)(C)N(OCCC)C(C)(C)C4)c3)cc2)CC1(C)C] |
| 267 | 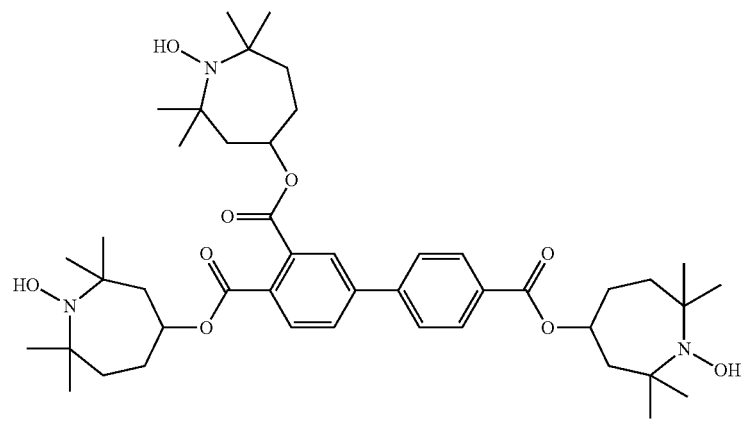 [SMILES: CC1(C)CCC(OC(=O)c2ccc(-c3ccc(C(=O)OC4CCC(C)(C)N(O)C(C)(C)C4)c(C(=O)OC4CCC(C)(C)N(O)C(C)(C)C4)c3)cc2)CC(C)(C)N1O] |

| No. | |
|---|---|
| 268 | 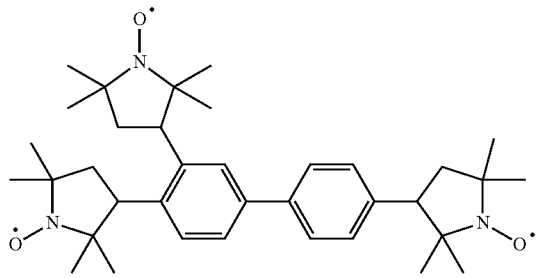 |
| 269 | 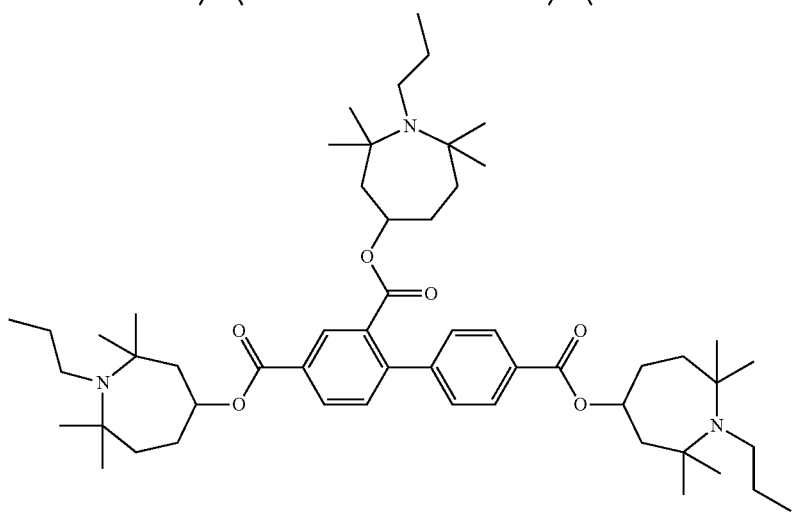 |
| 270 | 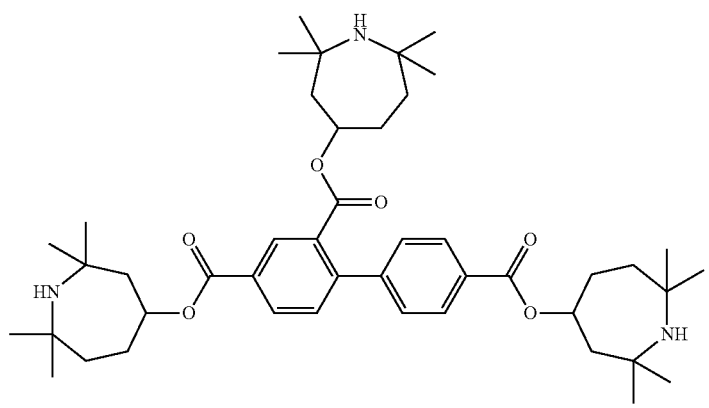 |
| 271 | 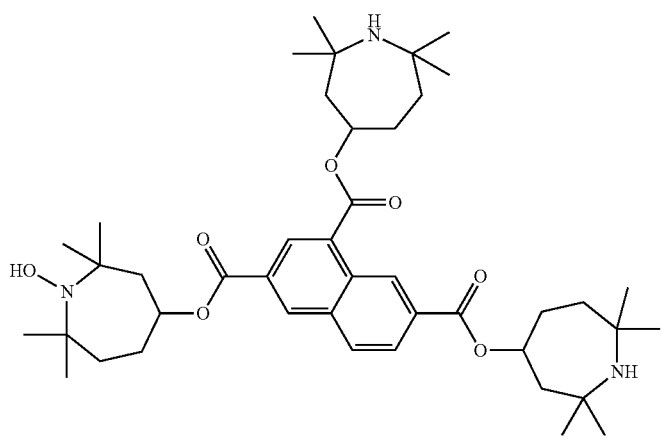 |

| No. |
|---|
| 272 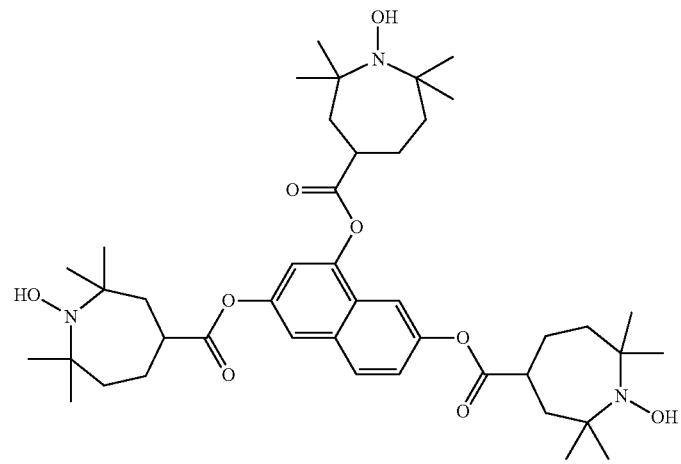 |
| 273 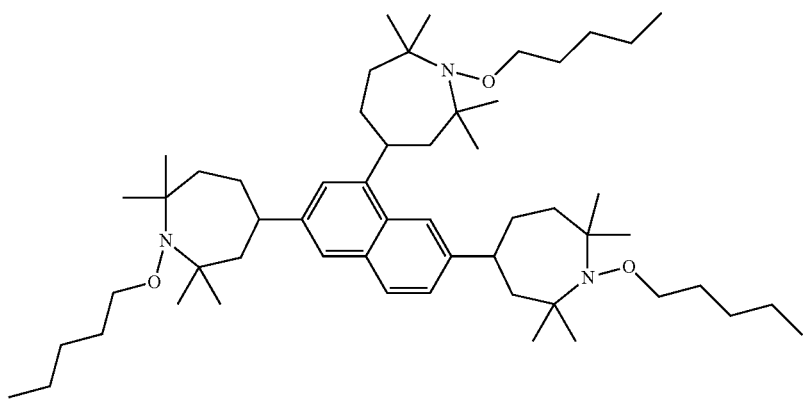 [SMILES: CCCCCON1C(C)(C)CCC(c2cc(C3CCC(C)(C)N(OCCCCC)C(C)(C)C3)c3cc(C4CCC(C)(C)N(OCCCCC)C(C)(C)C4)ccc3c2)CC1(C)C] |
| 274 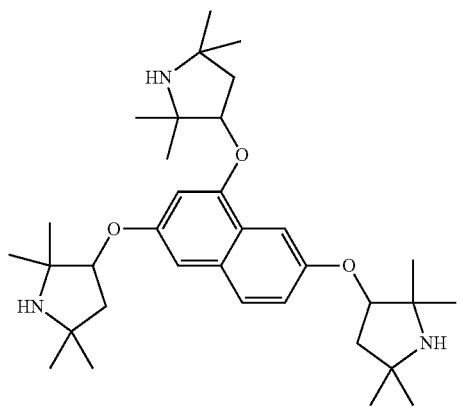 |

| No. |
|---|
| 275 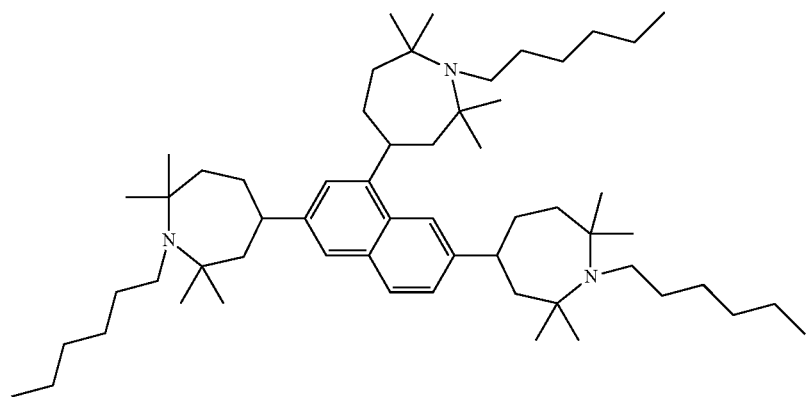 [SMILES: CCCCCCN1C(C)(C)CCC(c2cc(C3CCC(C)(C)N(CCCCCC)C(C)(C)C3)c3cc(C4CCC(C)(C)N(CCCCCC)C(C)(C)C4)ccc3c2)CC1(C)C] |
| 276 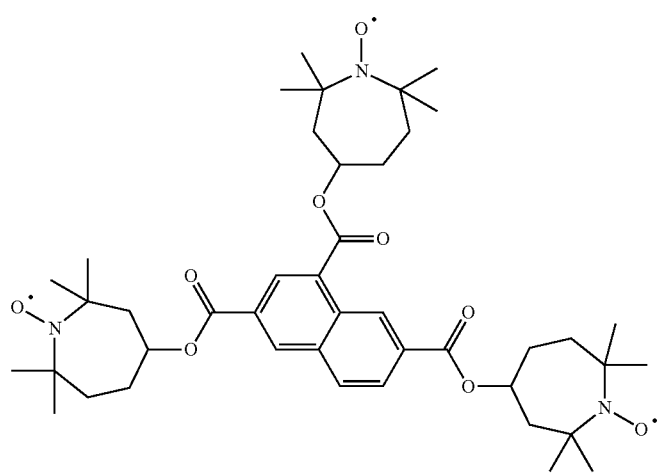 |
| 277 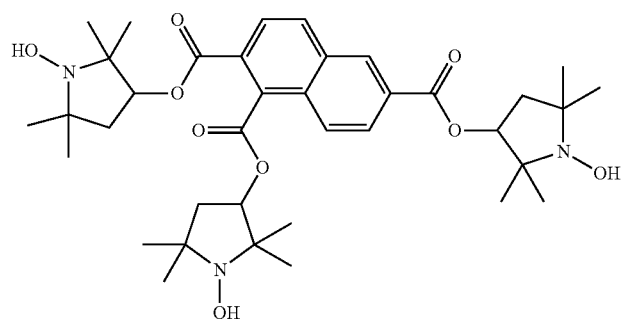 [SMILES: CC1(C)CC(OC(=O)c2ccc3c(C(=O)OC4CC(C)(C)N(O)C4(C)C)c(C(=O)OC4CC(C)(C)N(O)C4(C)C)ccc3c2)C(C)(C)N1O] |
| 278 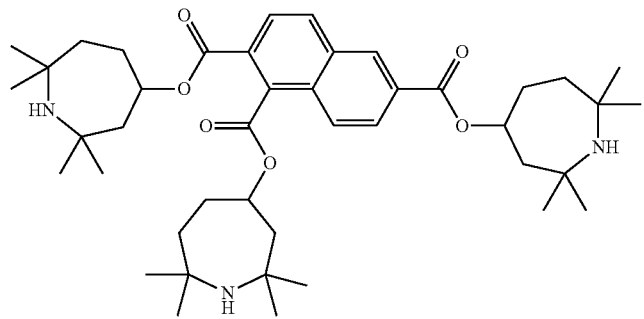 |

| No. |
|---|
| 279 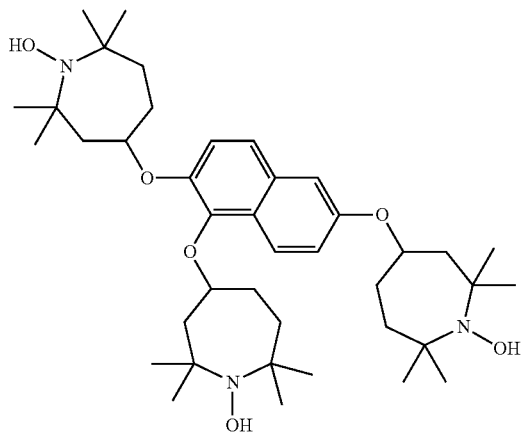 |
| 280 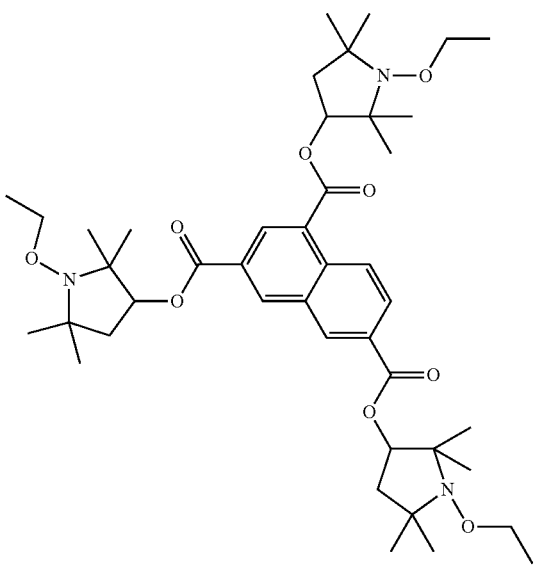 [SMILES: CCON1C(C)(C)CC(OC(=O)c2ccc3c(C(=O)OC4CC(C)(C)N(OCC)C4(C)C)cc(C(=O)OC4CC(C)(C)N(OCC)C4(C)C)cc3c2)C1(C)C] |
| 281 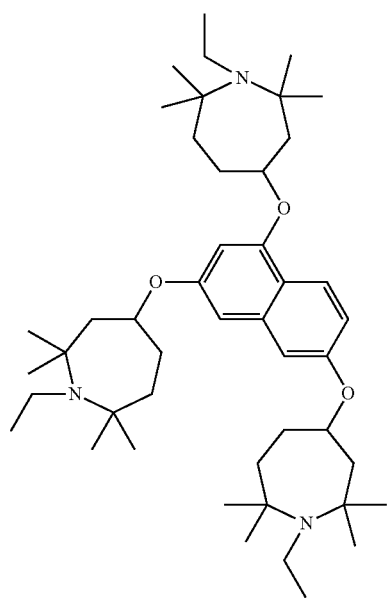 [SMILES: CCN1C(C)(C)CCC(Oc2ccc3c(OC4CCC(C)(C)N(CC)C(C)(C)C4)cc(OC4CCC(C)(C)N(CC)C(C)(C)C4)cc3c2)CC1(C)C] |

| No. |
|---|
| 282 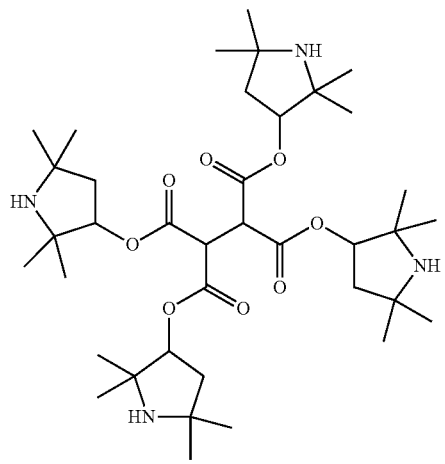 |
| 283 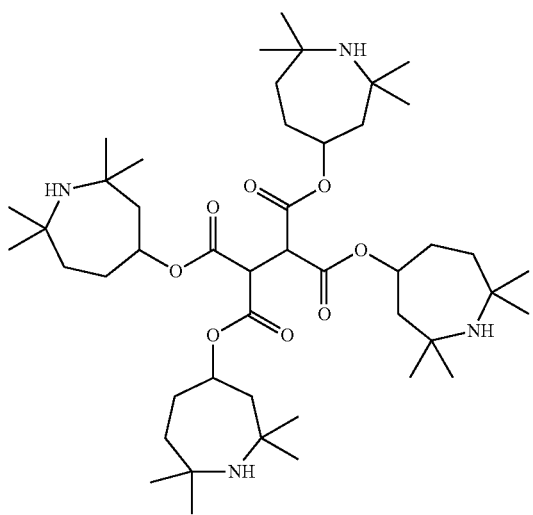 |
| 284 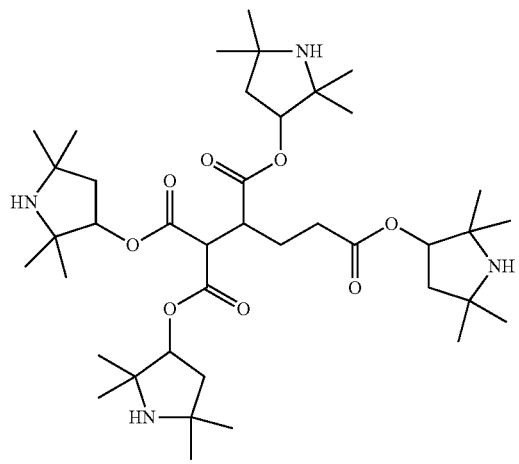 |

| No. |
|---|
| 285 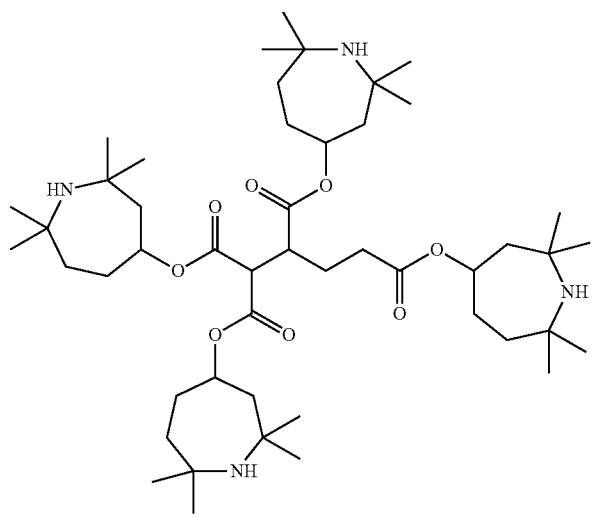 |
| 286 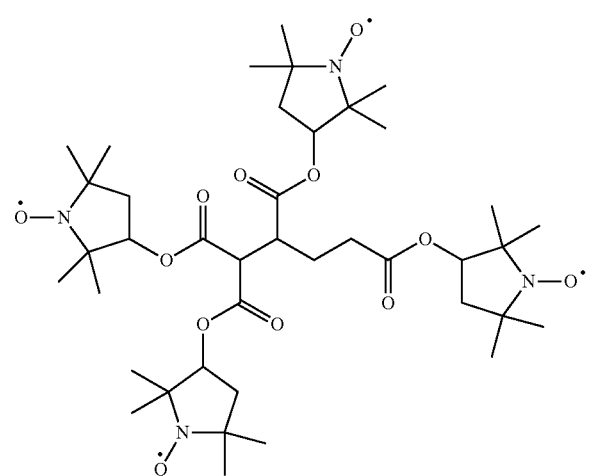 [SMILES: CC1(C)CC(OC(=O)CCC(C(=O)OC2CC(C)(C)N(O)C2(C)C)C(C(=O)OC2CC(C)(C)N(O)C2(C)C)C(=O)OC2CC(C)(C)N(O)C2(C)C)C(C)(C)N1O] |
| 287 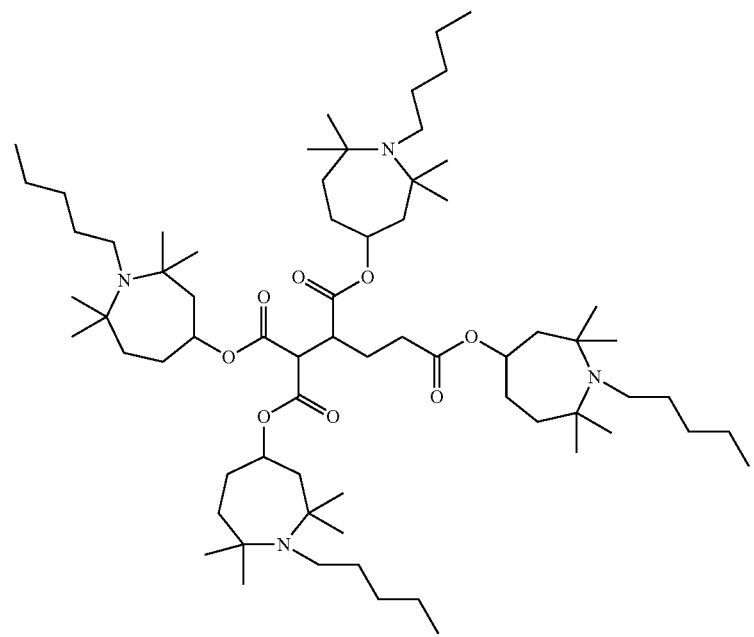 [SMILES: CCCCCN1C(C)(C)CCC(OC(=O)CCC(C(=O)OC2CCC(C)(C)N(CCCCC)C(C)(C)C2)C(C(=O)OC2CCC(C)(C)N(CCCCC)C(C)(C)C2)C(=O)OC2CCC(C)(C)N(CCCCC)C(C)(C)C2)CC1(C)C] |

| No. |
|---|
| 288 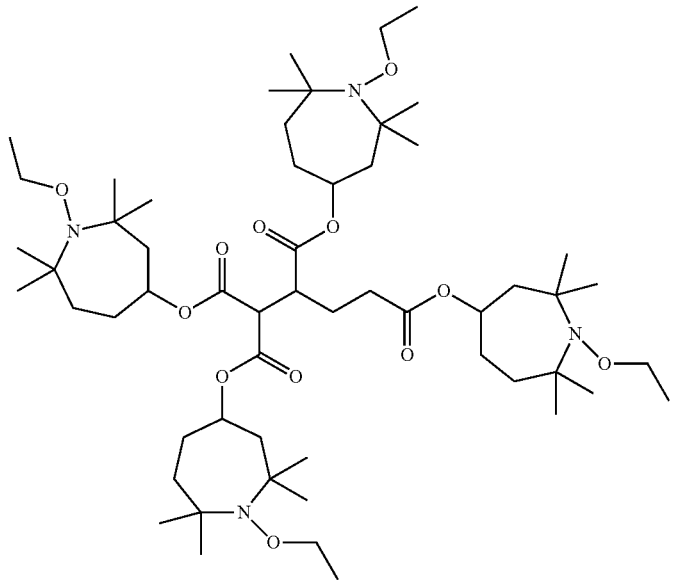 [SMILES: CCON1C(C)(C)CCC(OC(=O)CCC(C(=O)OC2CCC(C)(C)N(OCC)C(C)(C)C2)C(C(=O)OC2CCC(C)(C)N(OCC)C(C)(C)C2)C(=O)OC2CCC(C)(C)N(OCC)C(C)(C)C2)CC1(C)C] |
| 289 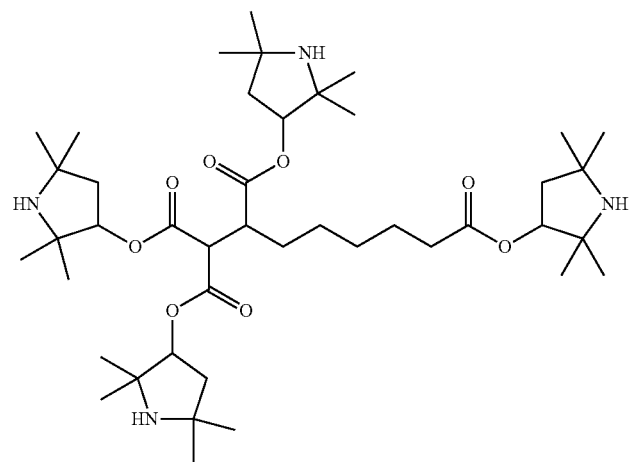 [SMILES: CC1(C)CC(OC(=O)CCCCCC(C(=O)OC2CC(C)(C)NC2(C)C)C(C(=O)OC2CC(C)(C)NC2(C)C)C(=O)OC2CC(C)(C)NC2(C)C)C(C)(C)N1] |
| 290 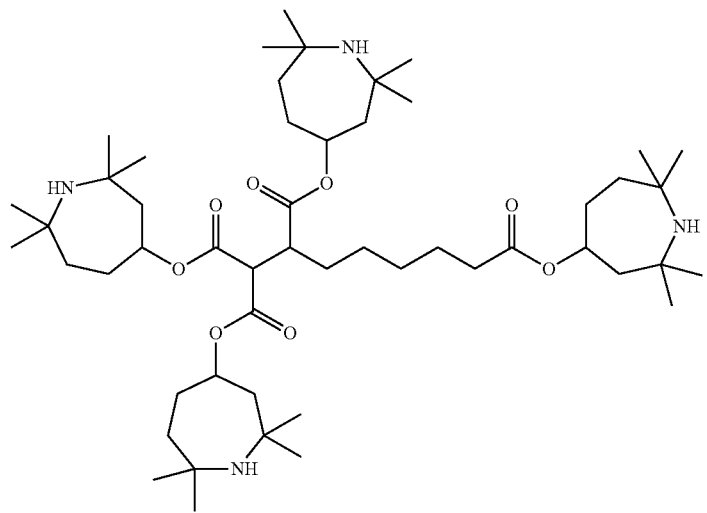 |

| No. |  |
|---|---|
| 291 | 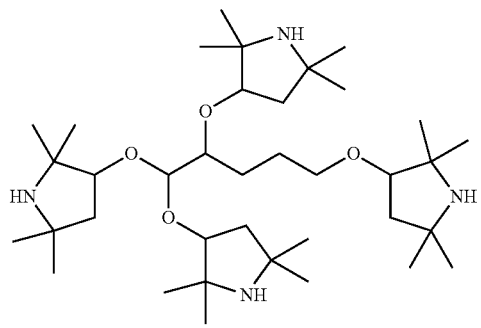 |
| 292 | 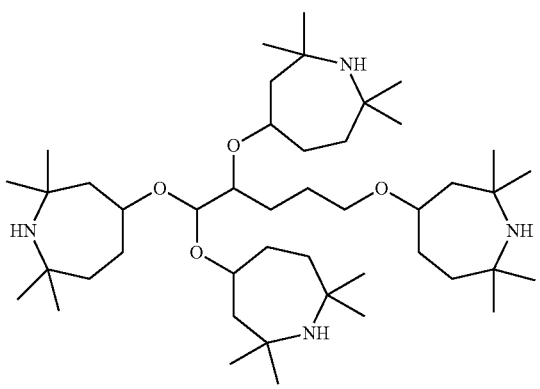 |
| 293 | 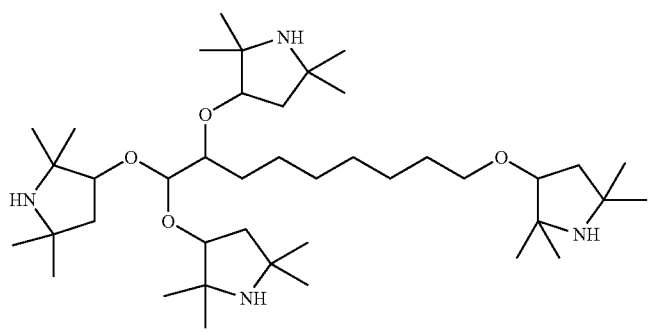 |
| 294 | 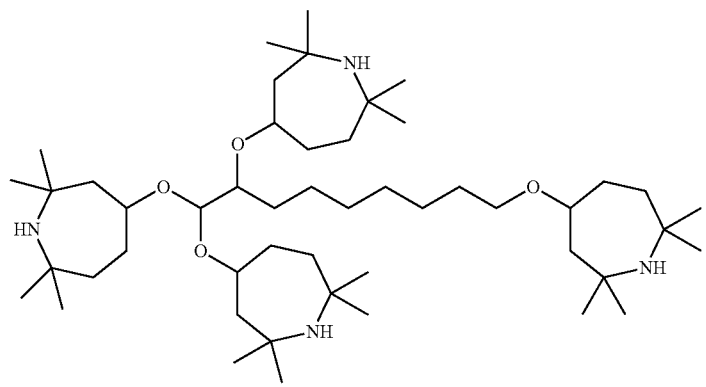 |

| No. |
|---|
| 295 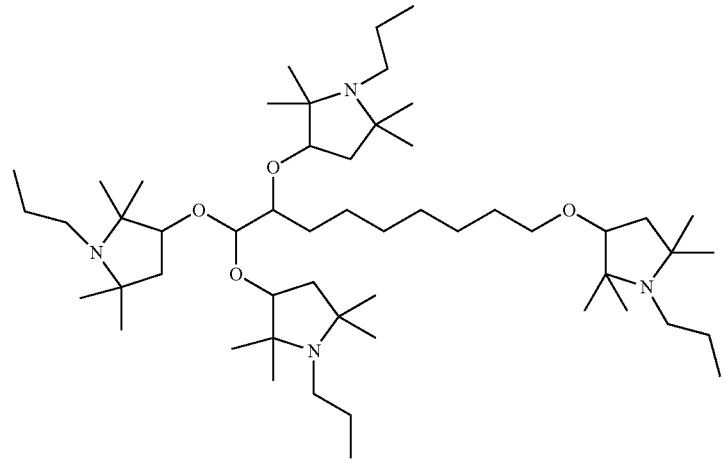 [SMILES: CCCN1C(C)(C)CC(OCCCCCCCC(OC2CC(C)(C)N(CCC)C2(C)C)C(OC2CC(C)(C)N(CCC)C2(C)C)OC2CC(C)(C)N(CCC)C2(C)C)C1(C)C] |
| 296 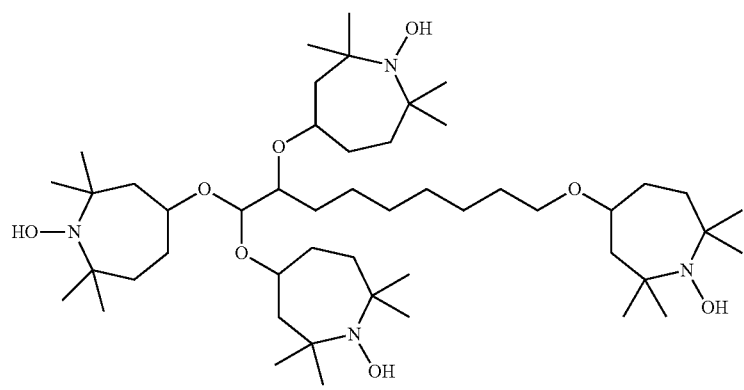 [SMILES: CC1(C)CCC(OCCCCCCCC(OC2CCC(C)(C)N(O)C(C)(C)C2)C(OC2CCC(C)(C)N(O)C(C)(C)C2)OC2CCC(C)(C)N(O)C(C)(C)C2)CC(C)(C)N1O] |
| 297 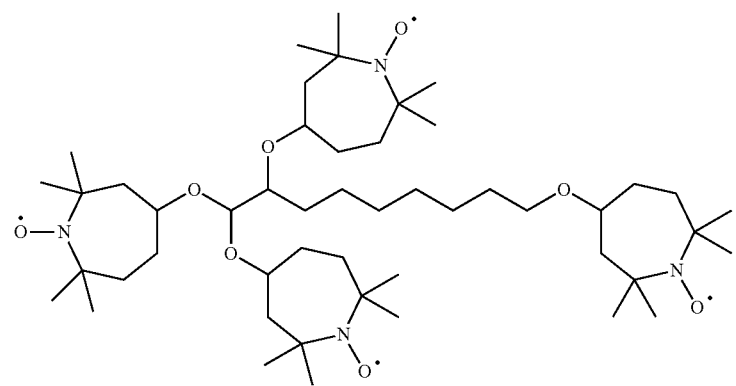 [SMILES: CC1(C)CCC(OCCCCCCCC(OC2CCC(C)(C)N(O)C(C)(C)C2)C(OC2CCC(C)(C)N(O)C(C)(C)C2)OC2CCC(C)(C)N(O)C(C)(C)C2)CC(C)(C)N1O] |

| No. | |
|---|---|
| 298 | 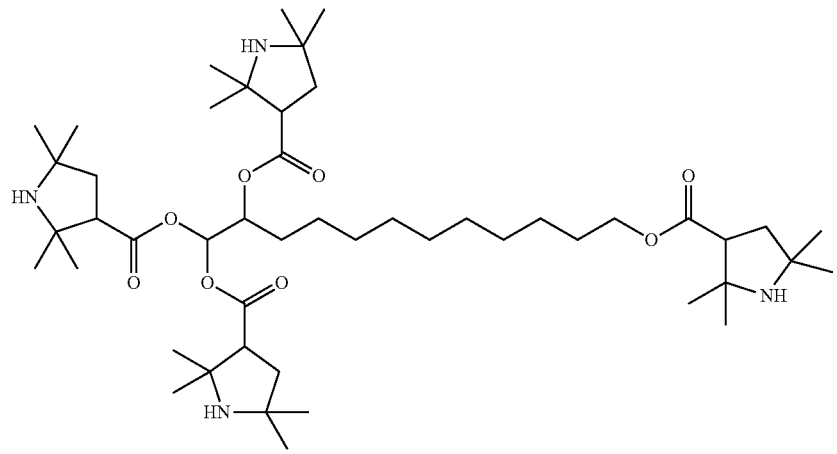 [SMILES: CC1(C)CC(C(=O)OCCCCCCCCCCC(OC(=O)C2CC(C)(C)NC2(C)C)C(OC(=O)C2CC(C)(C)NC2(C)C)OC(=O)C2CC(C)(C)NC2(C)C)C(C)(C)N1] |
| 299 | 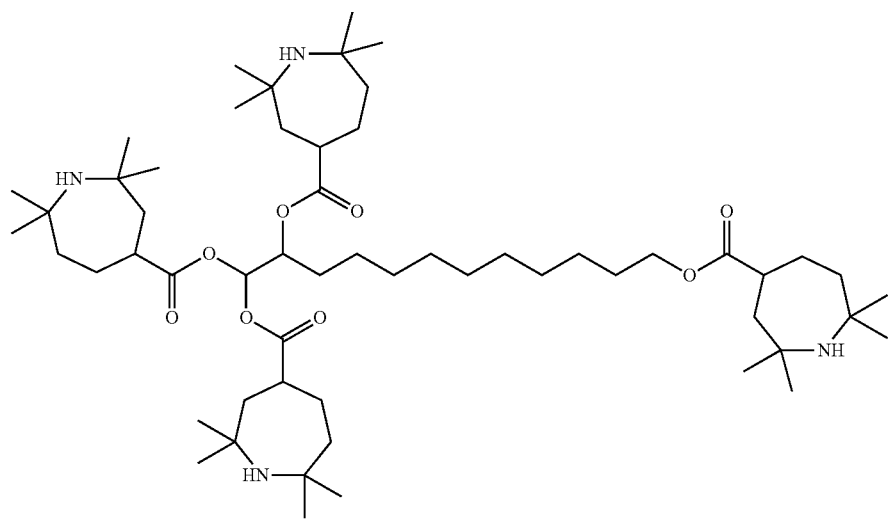 |
| 300 | 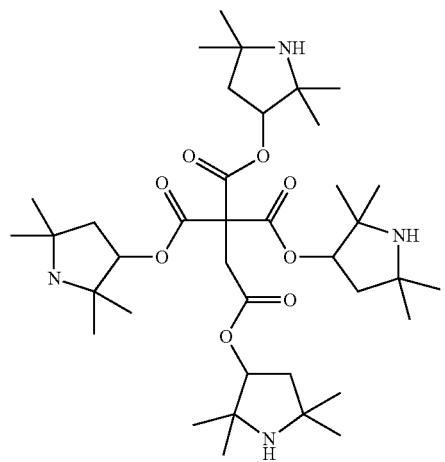 |

| No. | |
|---|---|
| 301 | 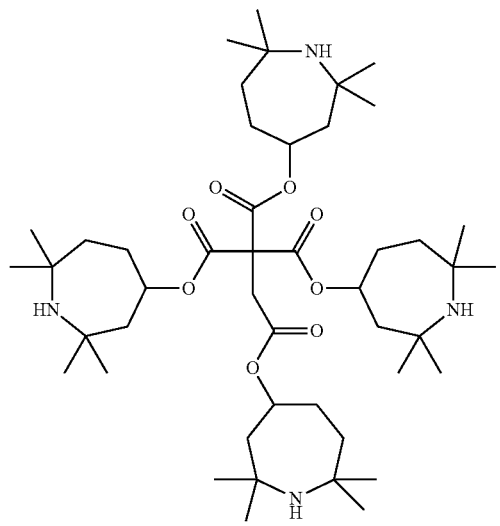 |
| 302 | 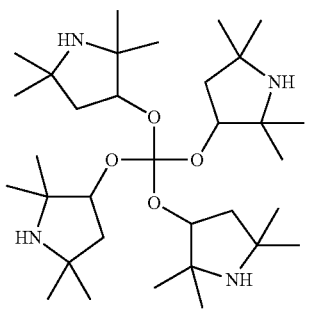 |
| 303 | 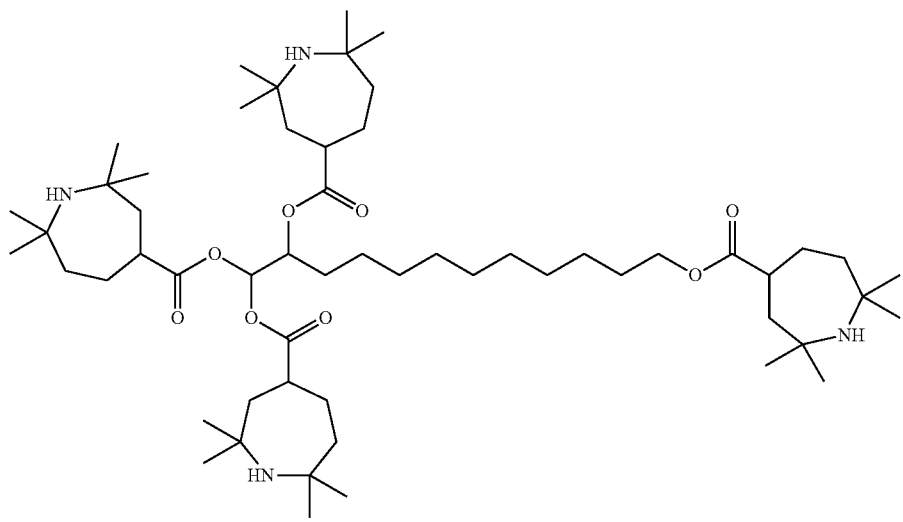 |

| No. |
|---|
| 304 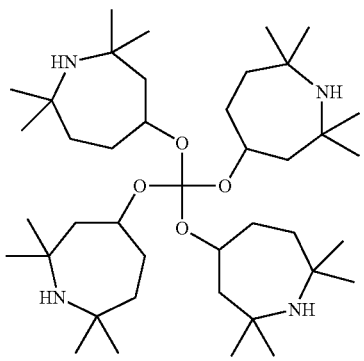 |
| 305 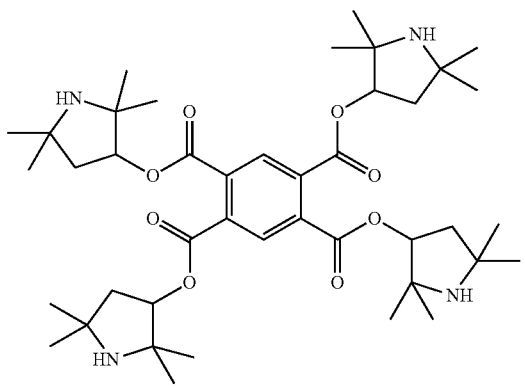 |
| 306 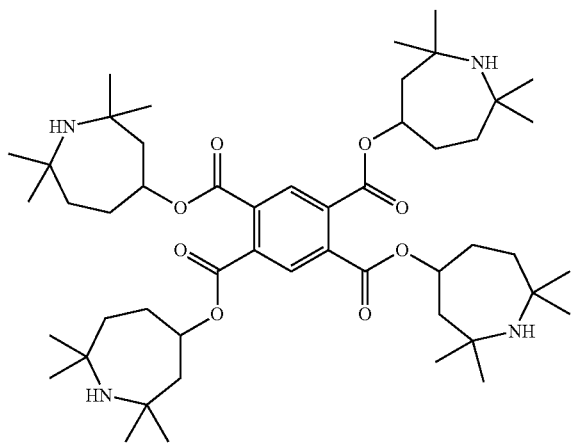 |
| 307 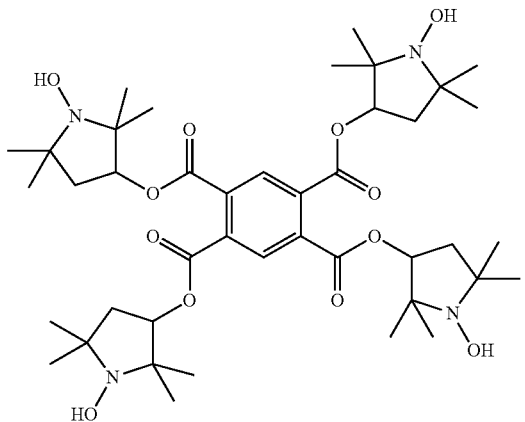 |

-continued
| No. |
|---|
308
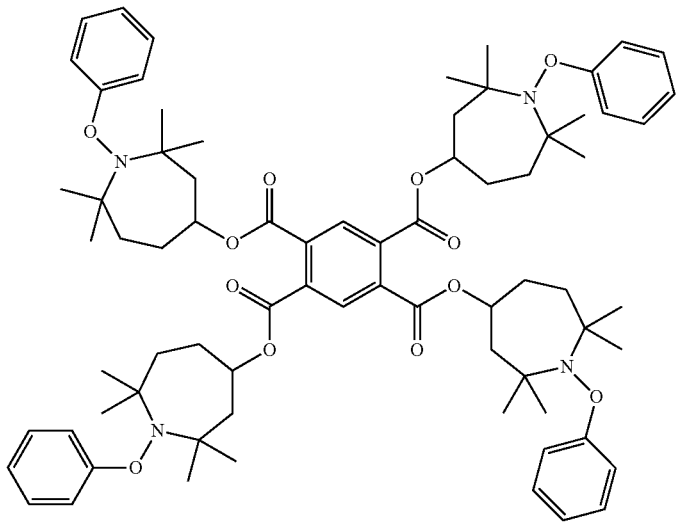 [SMILES: CC1(C)CCC(OC(=O)c2cc(C(=O)OC3CCC(C)(C)N(Oc4ccccc4)C(C)(C)C3)c(C(=O)OC3CCC(C)(C)N(Oc4ccccc4)C(C)(C)C3)cc2C(=O)OC2CCC(C)(C)N(Oc3ccccc3)C(C)(C)C2)CC(C)(C)N1Oc1ccccc1]
309
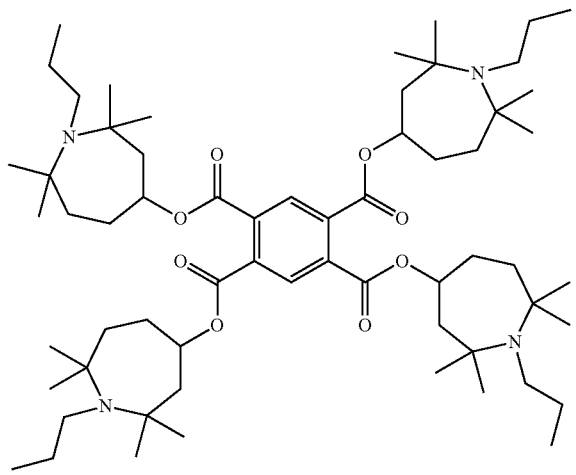 [SMILES: CCCN1C(C)(C)CCC(OC(=O)c2cc(C(=O)OC3CCC(C)(C)N(CCC)C(C)(C)C3)c(C(=O)OC3CCC(C)(C)N(CCC)C(C)(C)C3)cc2C(=O)OC2CCC(C)(C)N(CCC)C(C)(C)C2)CC1(C)C]
310
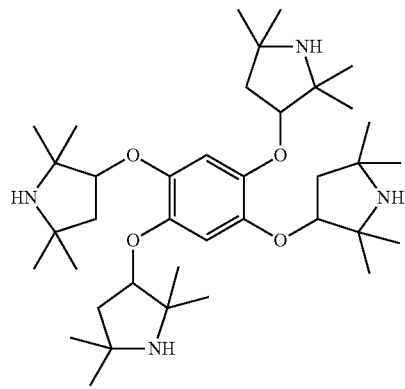 [SMILES: CC1(C)CC(Oc2cc(OC3CC(C)(C)NC3(C)C)c(OC3CC(C)(C)NC3(C)C)cc2OC2CC(C)(C)NC2(C)C)C(C)(C)N1]

-continued
| No. |
|---|
| 311 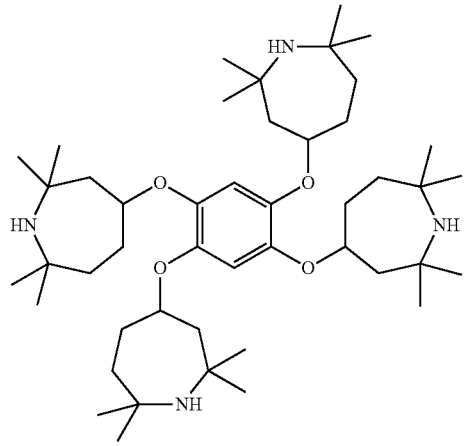 |
| 312 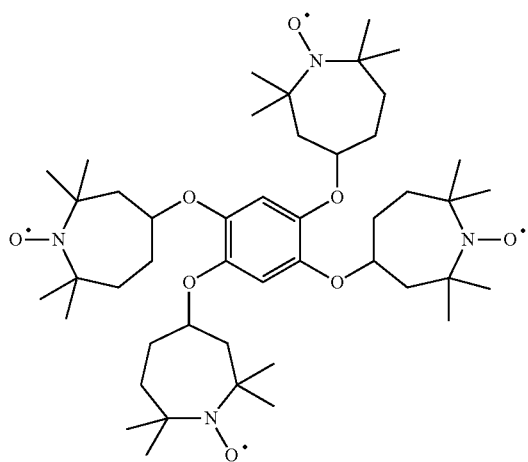 [SMILES: CC1(C)CCC(Oc2cc(OC3CCC(C)(C)N(O)C(C)(C)C3)c(OC3CCC(C)(C)N(O)C(C)(C)C3)cc2OC2CCC(C)(C)N(O)C(C)(C)C2)CC(C)(C)N1O] |
| 313 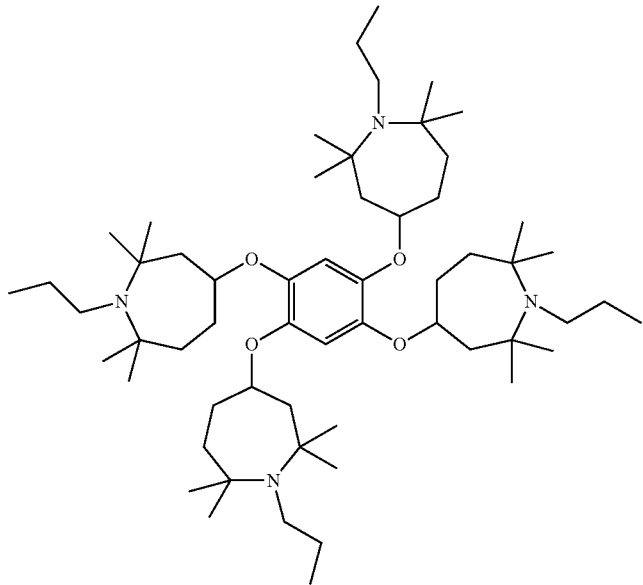 [SMILES: CCCN1C(C)(C)CCC(Oc2cc(OC3CCC(C)(C)N(CCC)C(C)(C)C3)c(OC3CCC(C)(C)N(CCC)C(C)(C)C3)cc2OC2CCC(C)(C)N(CCC)C(C)(C)C2)CC1(C)C] |

| No. |
|---|
| 314 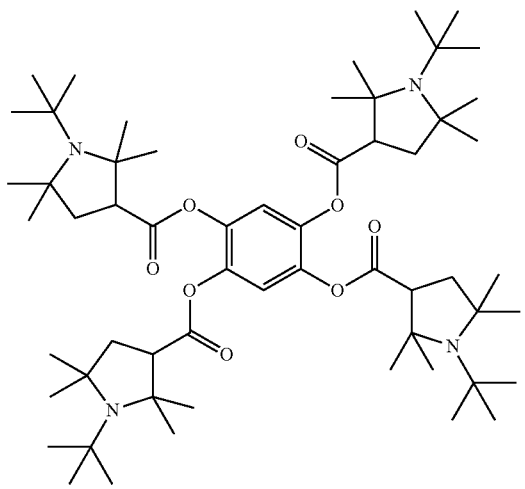 |
| 315 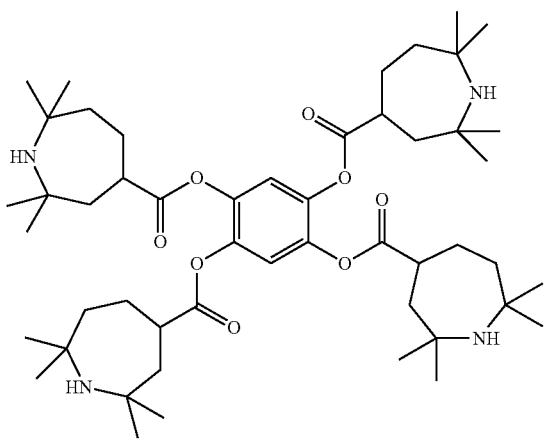 |
| 316 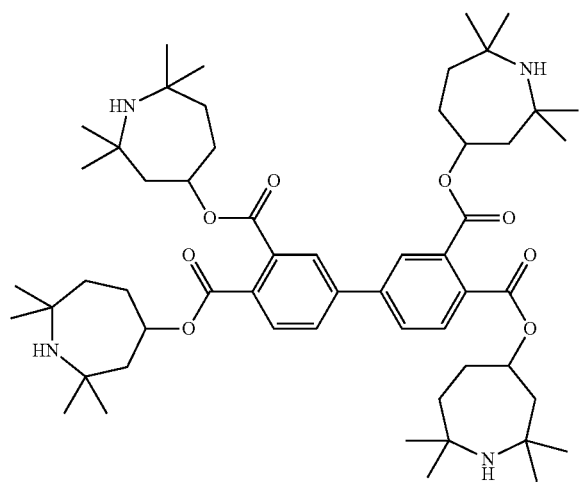 |

-continued
| No. |
|---|
| 317 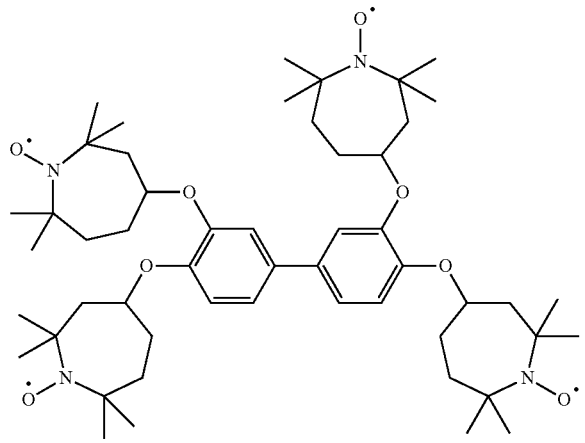 |
| 318 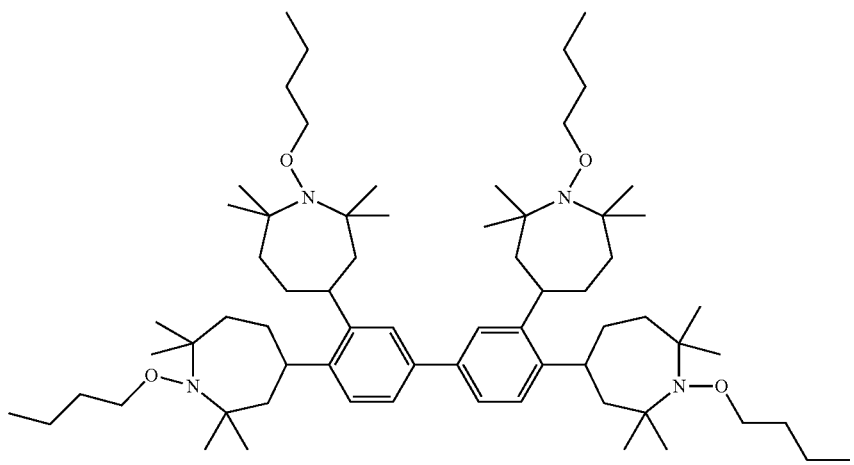 [SMILES: CCCCON1C(C)(C)CCC(c2ccc(-c3ccc(C4CCC(C)(C)N(OCCCC)C(C)(C)C4)c(C4CCC(C)(C)N(OCCCC)C(C)(C)C4)c3)cc2C2CCC(C)(C)N(OCCCC)C(C)(C)C2)CC1(C)C] |
| 319 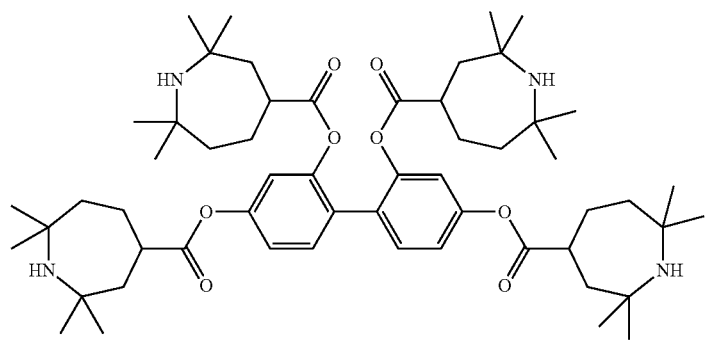 |

| No. | |
|---|---|
| 320 | 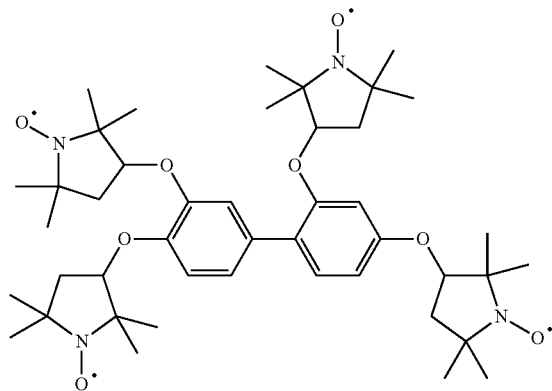 [SMILES: CC1(C)CC(Oc2ccc(-c3ccc(OC4CC(C)(C)N(O)C4(C)C)c(OC4CC(C)(C)N(O)C4(C)C)c3)c(OC3CC(C)(C)N(O)C3(C)C)c2)C(C)(C)N1O] |
| 321 | 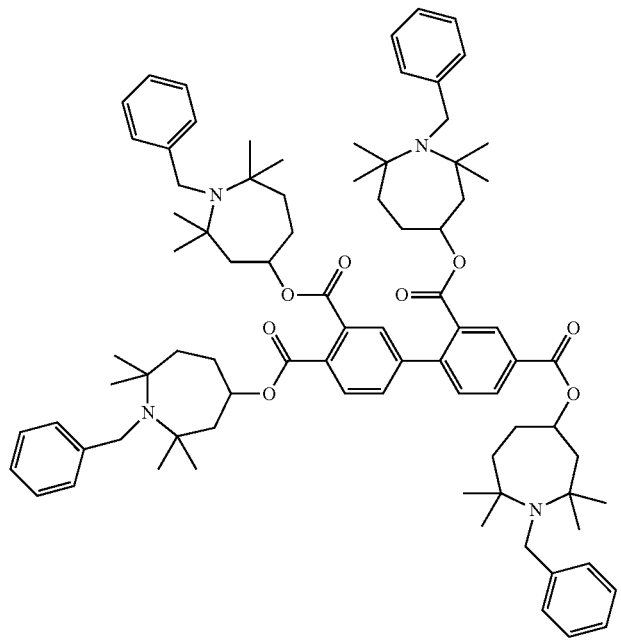 [SMILES: CC1(C)CCC(OC(=O)c2ccc(-c3ccc(C(=O)OC4CCC(C)(C)N(Cc5ccccc5)C(C)(C)C4)c(C(=O)OC4CCC(C)(C)N(Cc5ccccc5)C(C)(C)C4)c3)c(C(=O)OC3CCC(C)(C)N(Cc4ccccc4)C(C)(C)C3)c2)CC(C)(C)N1Cc1ccccc1] |
| 322 | 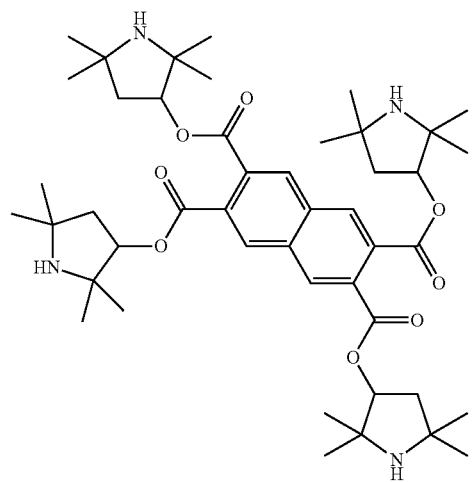 |

US 9,676,686 B2
223 224
-continued
| No. |
|---|
| 323 | 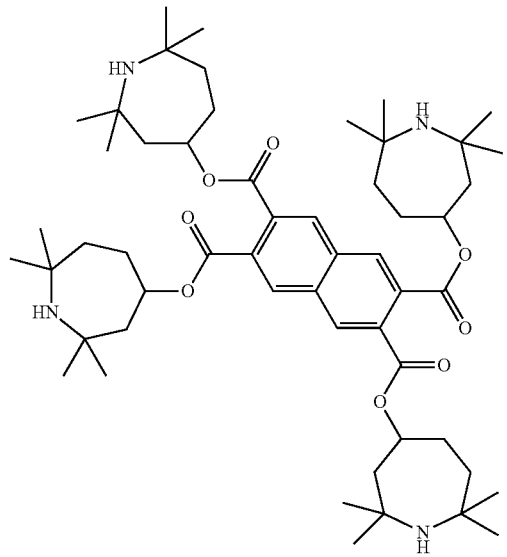 |
| 324 | 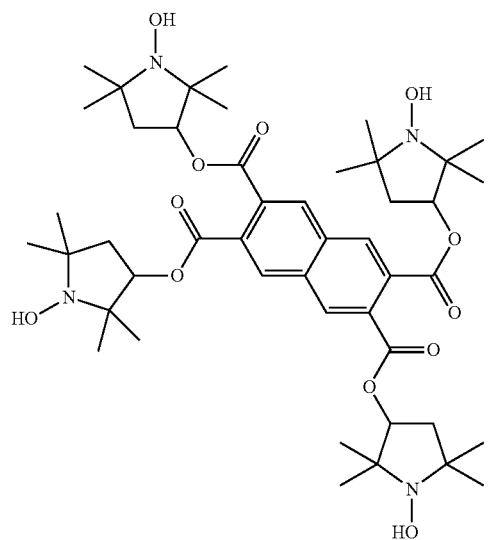 |

-continued
| No. |
|---|
| 325 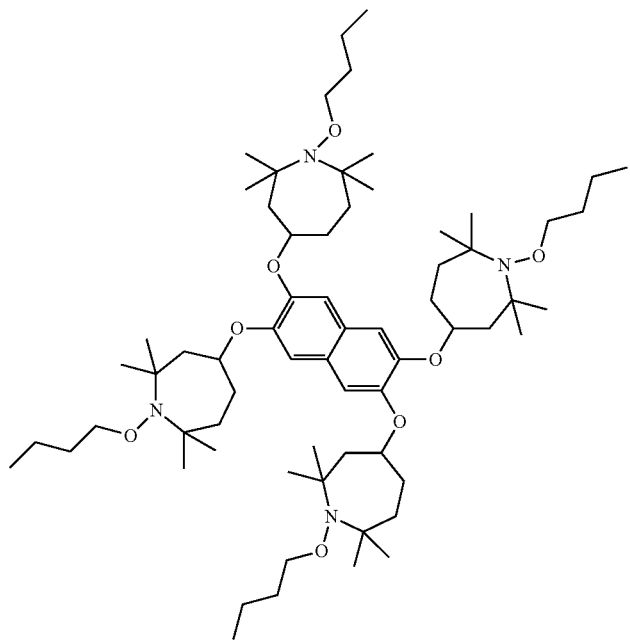 [SMILES: CCCCON1C(C)(C)CCC(Oc2cc3cc(OC4CCC(C)(C)N(OCCCC)C(C)(C)C4)c(OC4CCC(C)(C)N(OCCCC)C(C)(C)C4)cc3cc2OC2CCC(C)(C)N(OCCCC)C(C)(C)C2)CC1(C)C] |
| 326 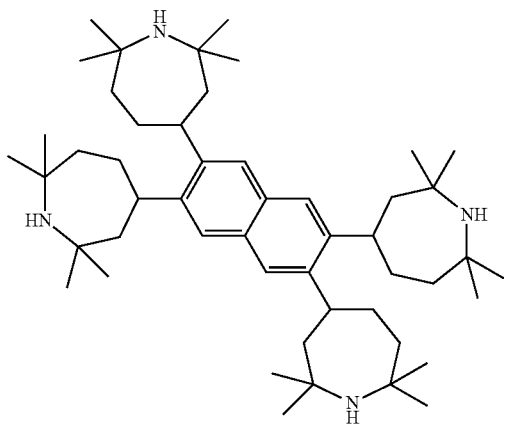 |
| 327 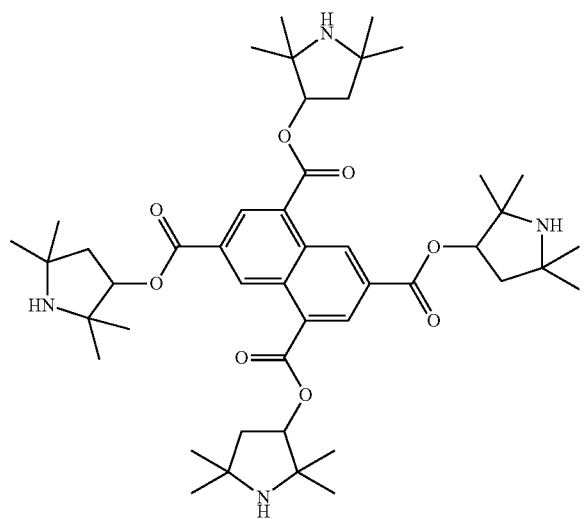 |

| No. |
|---|
| 328 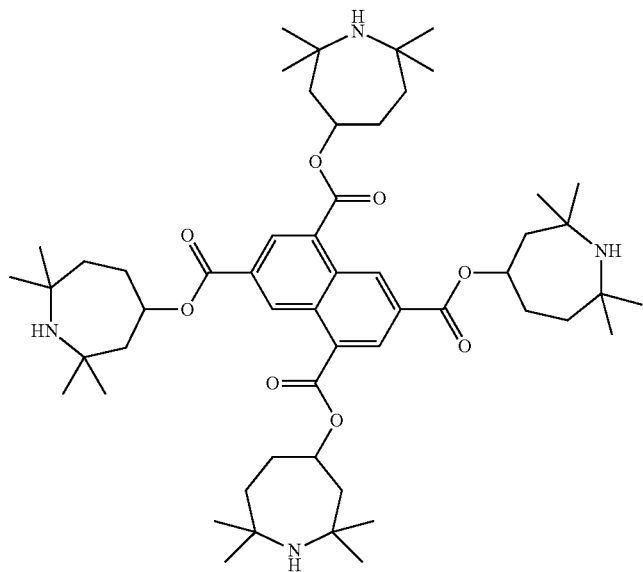 |
| 329 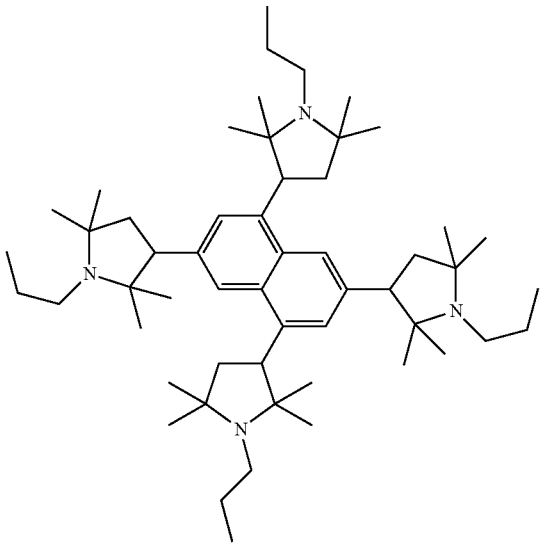 [SMILES: CCCN1C(C)(C)CC(c2cc(C3CC(C)(C)N(CCC)C3(C)C)c3cc(C4CC(C)(C)N(CCC)C4(C)C)cc(C4CC(C)(C)N(CCC)C4(C)C)c3c2)C1(C)C] |

| No. | |
|---|---|
| 330 | 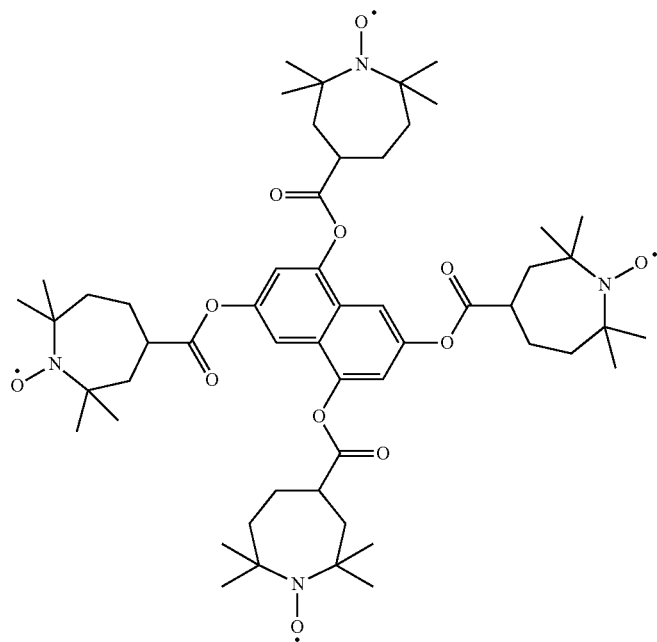 |
| 331 | 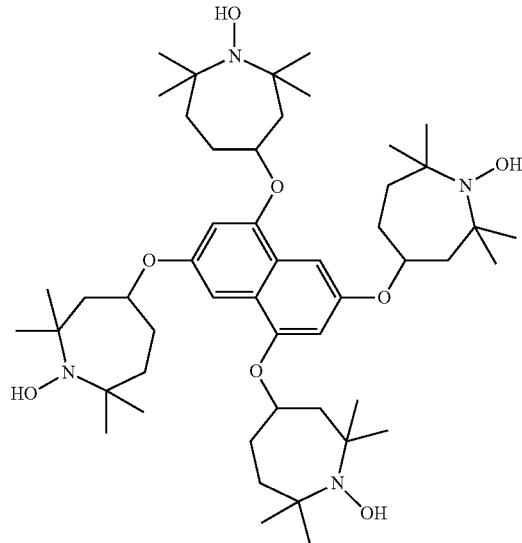 |

| No. |
|---|
| 332 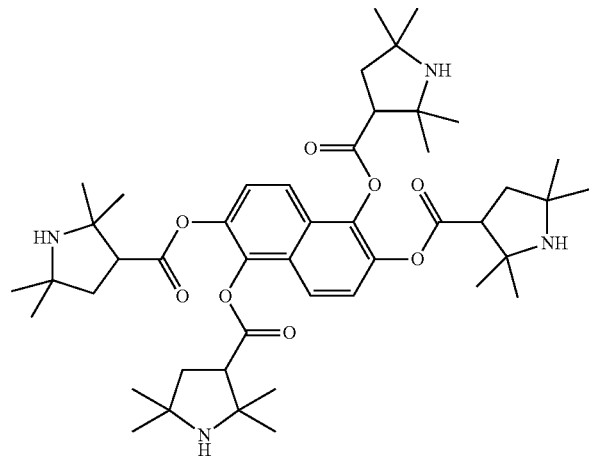 |
| 333 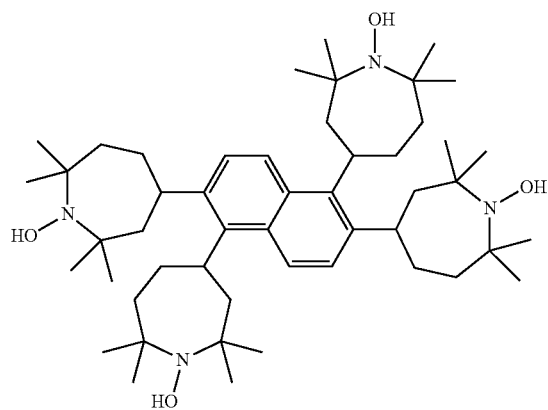 |
| 334 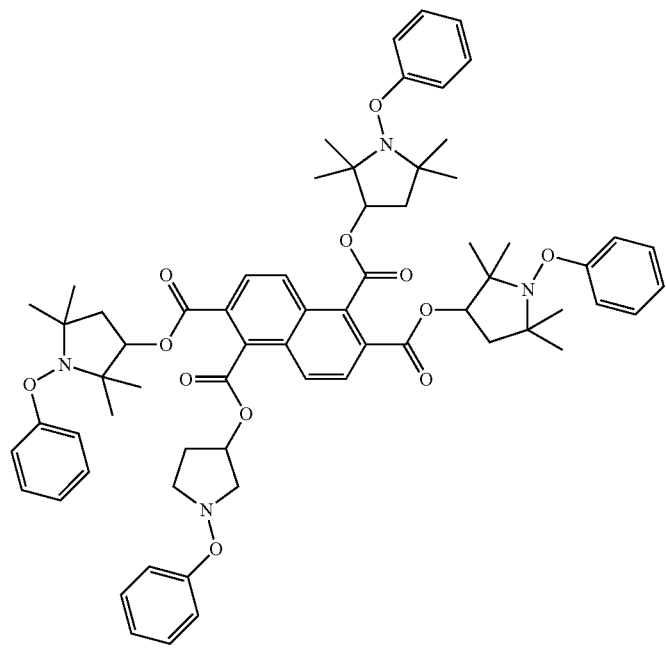 [SMILES: CC1(C)CC(OC(=O)c2ccc3c(C(=O)OC4CC(C)(C)N(Oc5ccccc5)C4(C)C)c(C(=O)OC4CC(C)(C)N(Oc5ccccc5)C4(C)C)ccc3c2C(=O)OC2CCN(Oc3ccccc3)C2)C(C)(C)N1Oc1ccccc1] |

| No. |
|---|
| 335 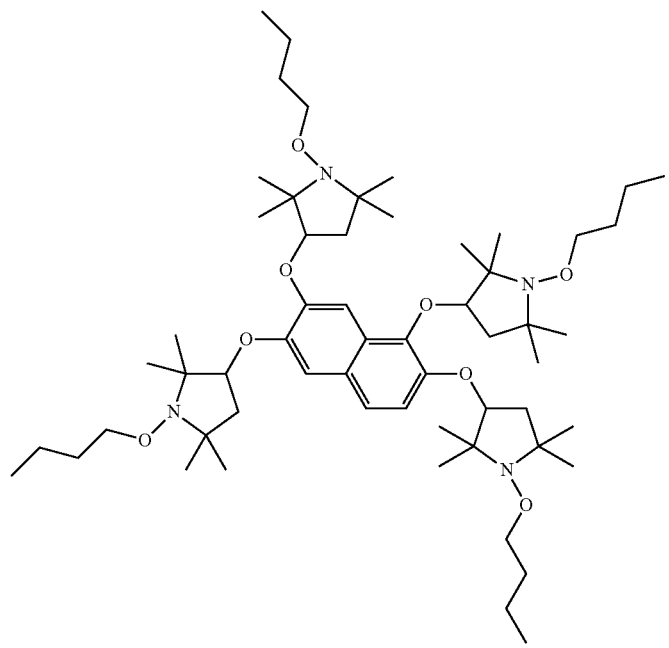 [SMILES: CCCCON1C(C)(C)CC(Oc2cc3ccc(OC4CC(C)(C)N(OCCCC)C4(C)C)c(OC4CC(C)(C)N(OCCCC)C4(C)C)c3cc2OC2CC(C)(C)N(OCCCC)C2(C)C)C1(C)C] |
| 336 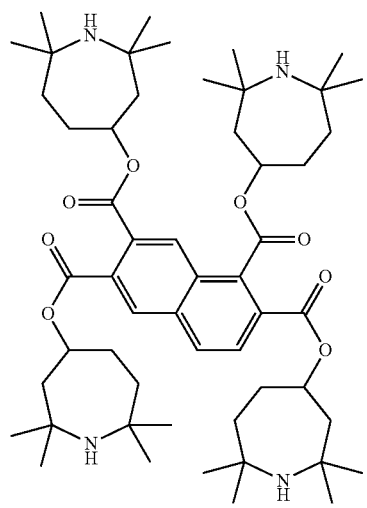 |
| 337 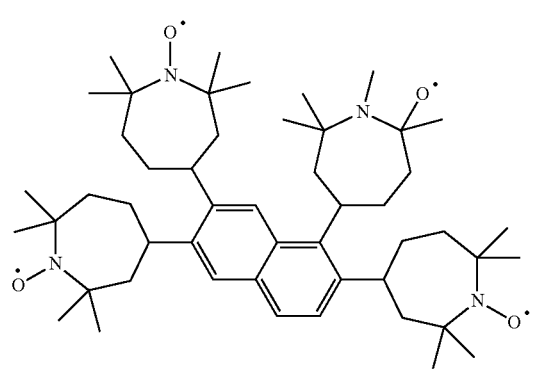 |

-continued
| No. | |
|---|---|
| 338 | 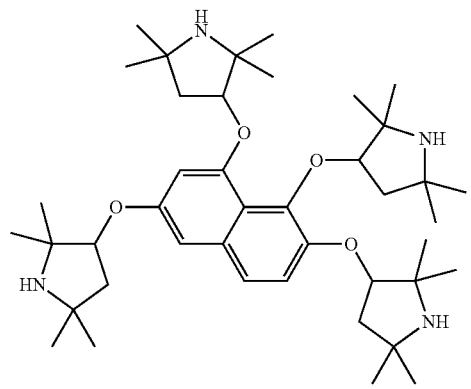 |
| 339 | 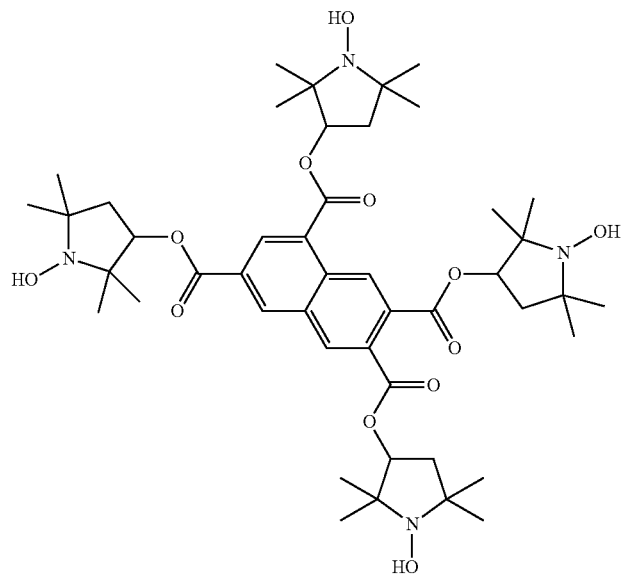 |
| 340 | 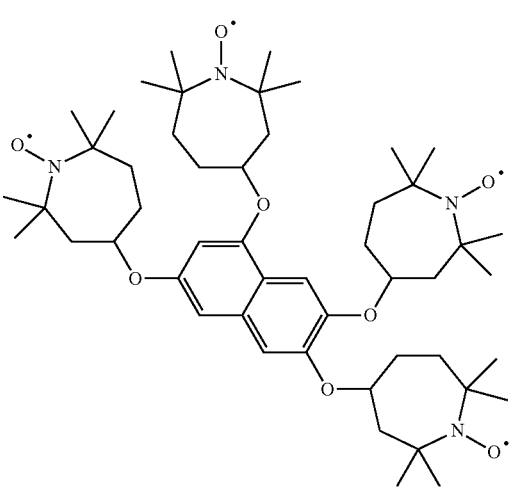 |

| No. | |
|---|---|
| 341 | 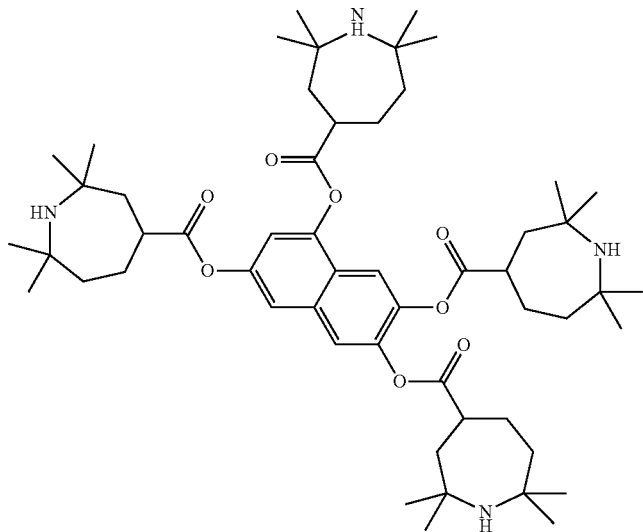 |
| 342 | 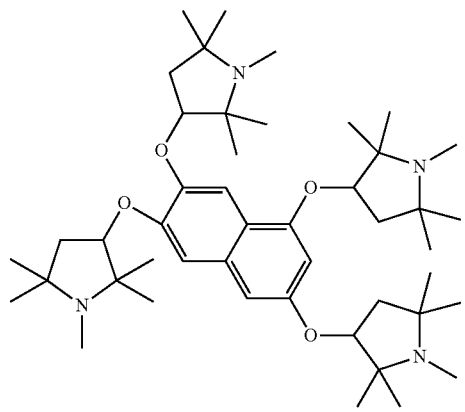 |
| 343 | 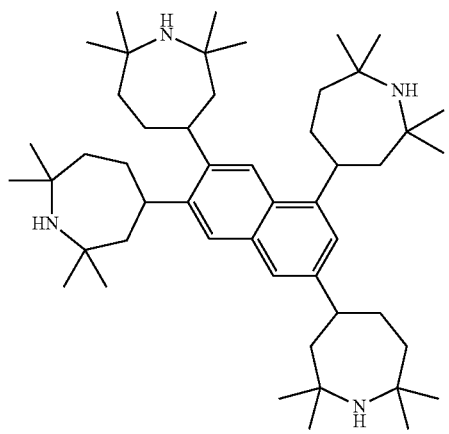 |

| No. | |
|---|---|
| 344 | 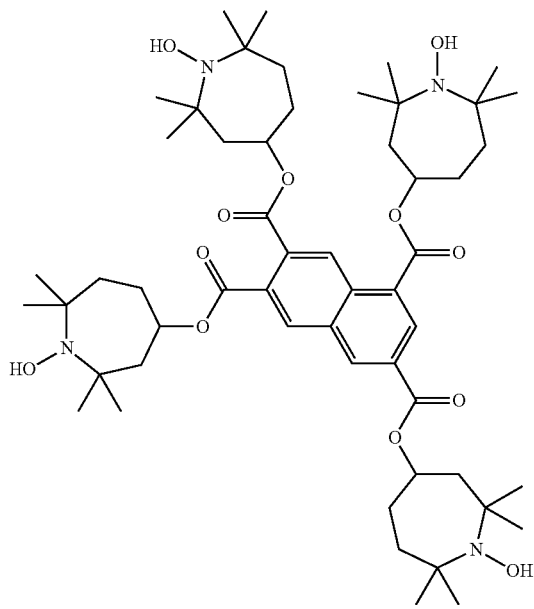 |
| 345 | 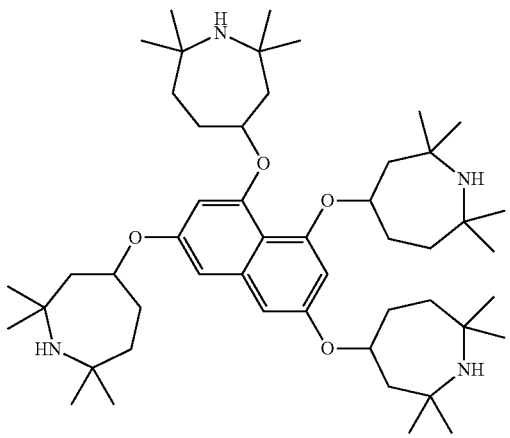 |
| 346 | 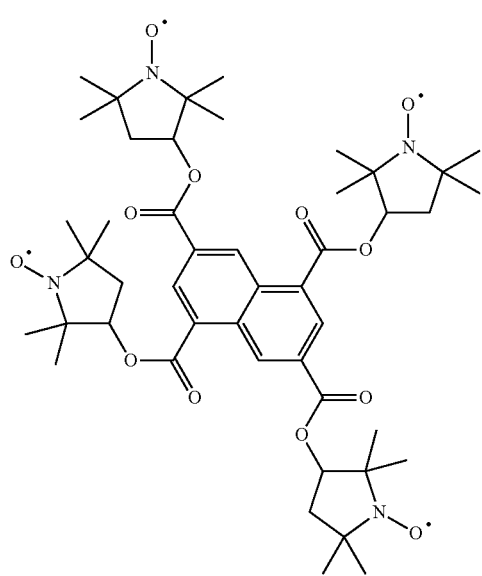 [SMILES: CC1(C)CC(OC(=O)c2cc(C(=O)OC3CC(C)(C)N(O)C3(C)C)c3cc(C(=O)OC4CC(C)(C)N(O)C4(C)C)cc(C(=O)OC4CC(C)(C)N(O)C4(C)C)c3c2)C(C)(C)N1O] |

| No. |
|---|
| 347 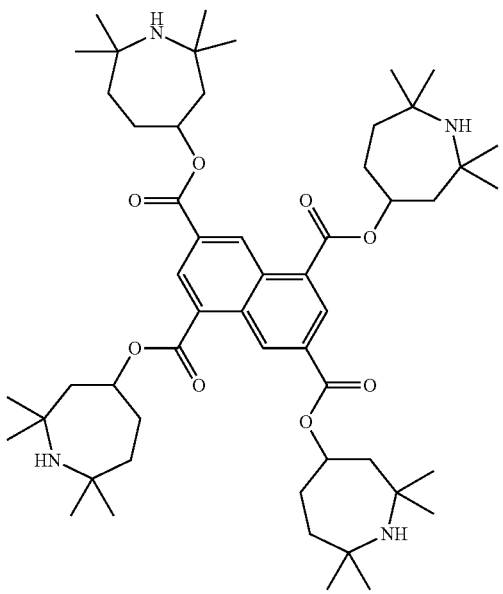 |
| 348 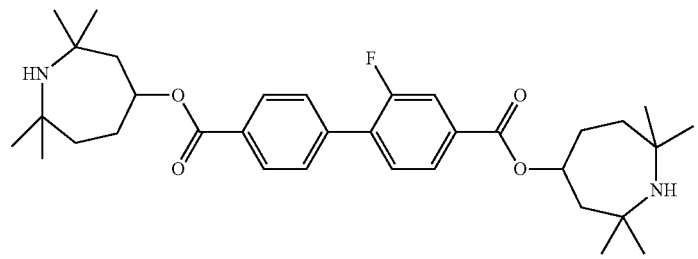 |
| 348 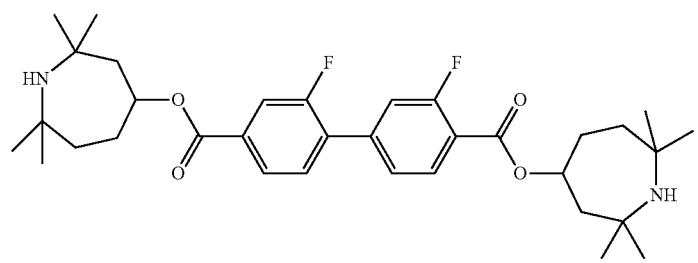 |
| 349 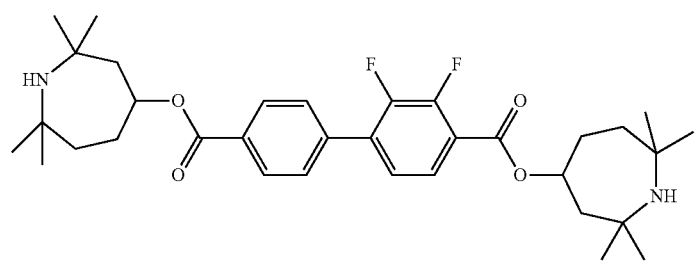 |

| No. | |
|---|---|
| 350 | 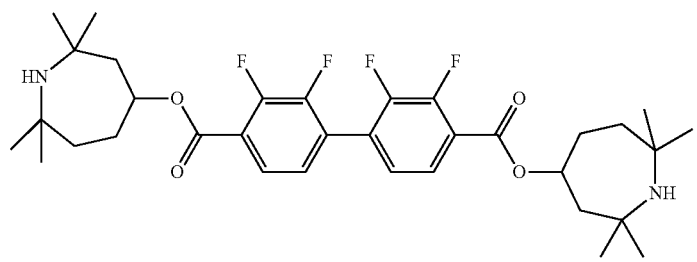 |
| 351 | 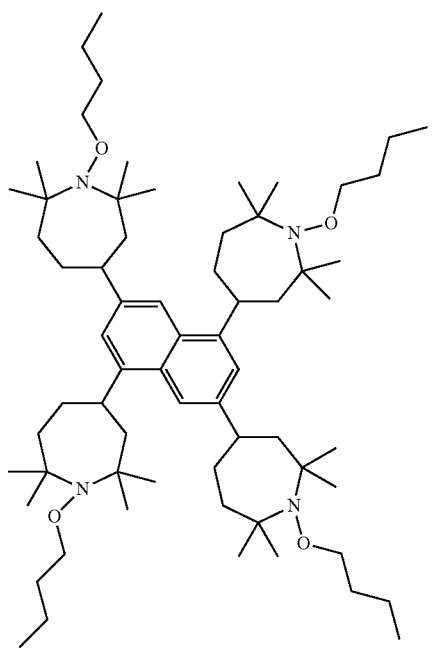 [SMILES: CCCCON1C(C)(C)CCC(c2cc(C3CCC(C)(C)N(OCCCC)C(C)(C)C3)c3cc(C4CCC(C)(C)N(OCCCC)C(C)(C)C4)cc(C4CCC(C)(C)N(OCCCC)C(C)(C)C4)c3c2)CC1(C)C] |
| 352 | 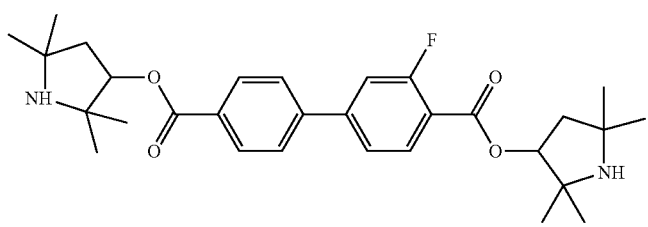 |
| 353 | 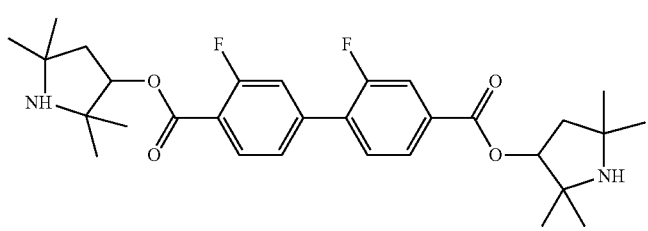 |
| 354 | 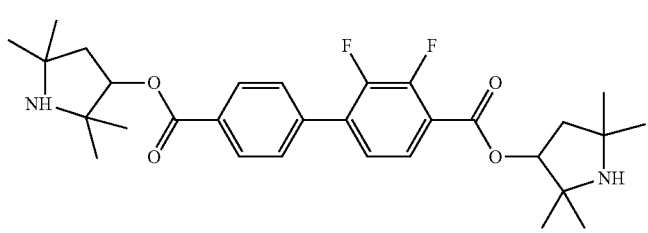 |

| No. | |
|---|---|
| 355 | 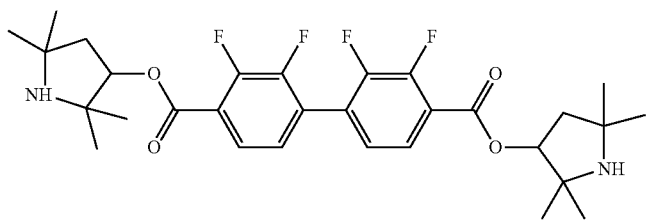 |
| 356 | 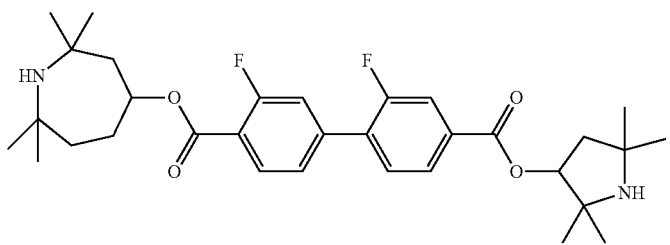 |
| 357 | 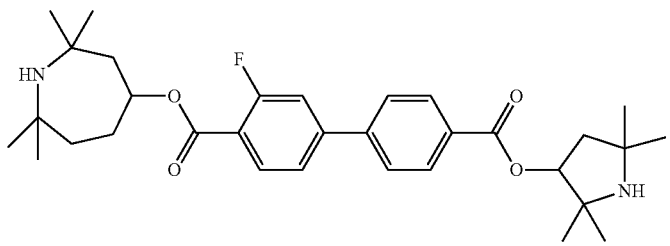 |
| 358 | 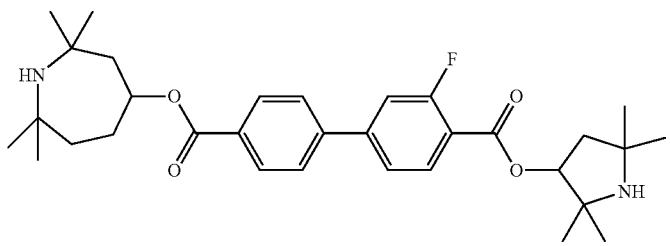 |
| 359 | 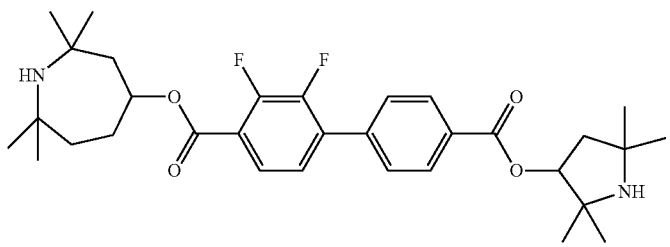 |
| 360 | 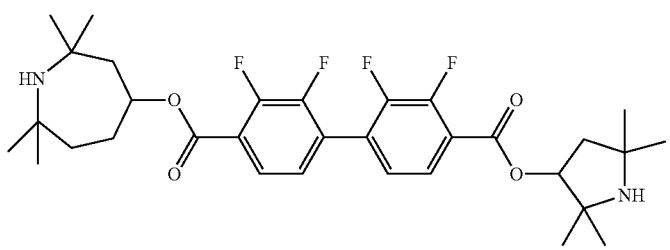 |

| No. | |
|---|---|
| 361 | 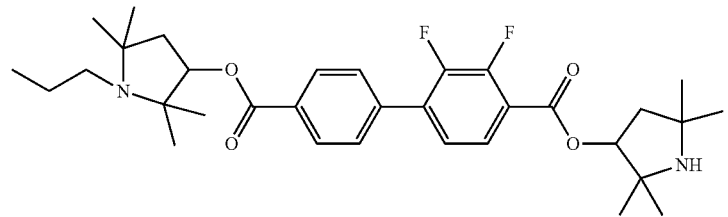 [SMILES: CCCN1C(C)(C)CC(OC(=O)c2ccc(-c3ccc(C(=O)OC4CC(C)(C)NC4(C)C)c(F)c3F)cc2)C1(C)C] |
| 362 | 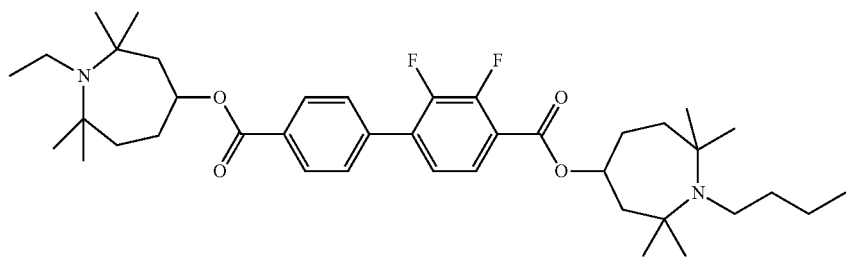 [SMILES: CCCCN1C(C)(C)CCC(OC(=O)c2ccc(-c3ccc(C(=O)OC4CCC(C)(C)N(CC)C(C)(C)C4)cc3)c(F)c2F)CC1(C)C] |
| 363 | 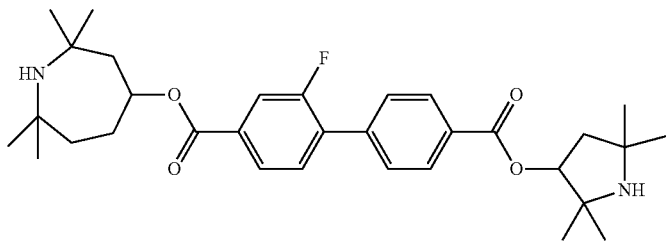 |
| 364 | 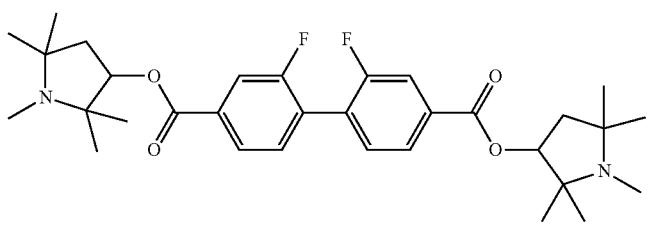 |
| 365 | 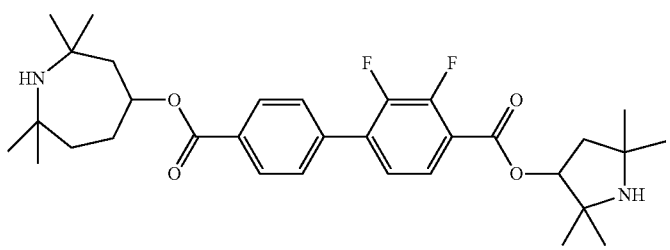 |
| 366 | 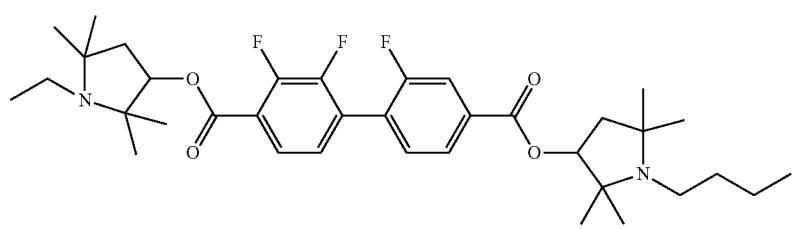 [SMILES: CCCCN1C(C)(C)CC(OC(=O)c2ccc(-c3ccc(C(=O)OC4CC(C)(C)N(CC)C4(C)C)c(F)c3F)c(F)c2)C1(C)C] |

| No. | |
|---|---|
| 367 | 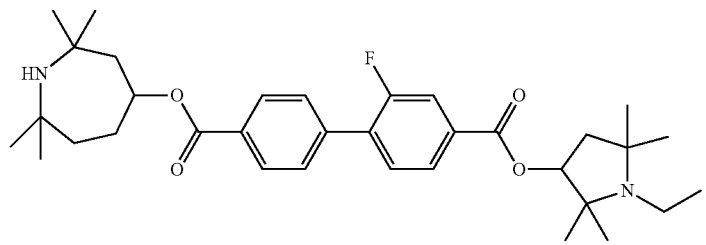 [SMILES: CCN1C(C)(C)CC(OC(=O)c2ccc(-c3ccc(C(=O)OC4CCC(C)(C)NC(C)(C)C4)cc3)c(F)c2)C1(C)C] |
| 368 | 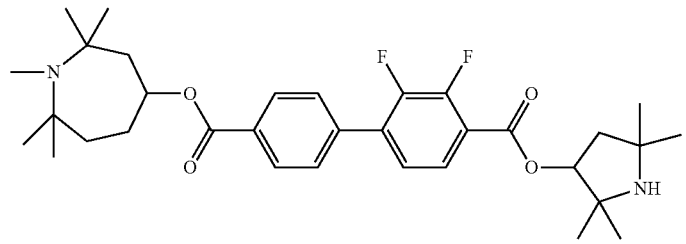 |
| 369 | 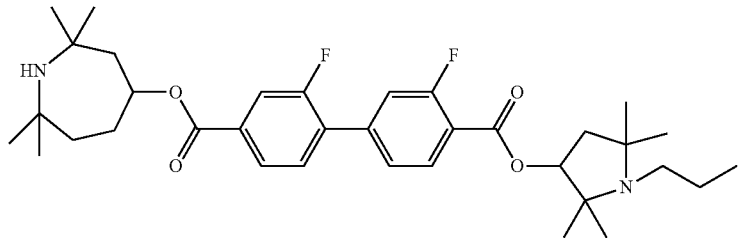 [SMILES: CCCN1C(C)(C)CC(OC(=O)c2ccc(-c3ccc(C(=O)OC4CCC(C)(C)NC(C)(C)C4)cc3F)cc2F)C1(C)C] |

2. Examples of Liquid Crystal Composition

The compounds in the examples (including use examples) were represented by symbols based on the definitions in the following Table 2. In Table 2, the stereo configuration of 1,4-cyclohexylene is trans. In the examples, the number in the parentheses following the symbol corresponds to the number of the compound. The symbol (-) means other liquid crystal compounds. The content (percentage) of a liquid crystal compound is a weight percentage (wt %) based on the weight of a liquid crystal composition. Finally, characteristic values of the liquid crystal composition were summarized. The characteristics were measured according to the methods described previously, and the measured values themselves were recorded without change (without extrapolation).

TABLE 2

| Method of Description of Compound Using Symbols R—($A_1$)—$Z_1$— . . . —$Z_n$—($A_n$)—R' | |
|---|---|
| 1) Left terminal group R— | Symbol |
| $C_nH_{2n+1}$— | n- |
| $C_nH_{2n+1}O$— | nO— |
| $C_mH_{2m+1}OC_nH_{2n}$— | mOn— |
| $CH_2=CH$— | V— |
| $C_nH_{2n+1}$—CH=CH— | nV— |
| $CH_2=CH$—$C_nH_{2n}$— | Vn— |
| $C_mH_{2m+1}$—CH=CH—$C_nH_{2n}$— | mVn— |
| $CF_2=CH$— | VFF— |
| $CF_2=CH$—$C_nH_{2n}$— | VFFn— |

TABLE 2-continued

| Method of Description of Compound Using Symbols R—($A_1$)—$Z_1$— . . . —$Z_n$—($A_n$)—R' | |
|---|---|
| 2) Right terminal group —R' | Symbol |
| —$C_nH_{2n+1}$ | -n |
| —$OC_nH_{2n+1}$ | —On |
| —$COOCH_3$ | —EMe |
| —CH=$CH_2$ | —V |
| —CH=CH—$C_nH_{2n+1}$ | —Vn |
| —$C_nH_{2n}$—CH=$CH_2$ | —nV |
| —$C_mH_{2m}$—CH=CH—$C_nH_{2n+1}$ | —mVn |
| —CH=$CF_2$ | —VFF |
| —F | —F |
| —Cl | —CL |
| —$OCF_3$ | —OCF3 |
| —$OCF_2H$ | —OCF2H |
| —$CF_3$ | —CF3 |
| —OCH=CH—$CF_3$ | —OVCF3 |
| —C≡N | —C |
| 3) Linking group —$Z_n$— | Symbol |
| —$C_nH_{2n}$— | n |
| —COO— | E |
| —CH=CH— | V |
| —$CH_2O$— | 1O |
| —$OCH_2$— | O1 |
| —$CF_2O$— | X |
| —C≡C— | T |
| 4) Ring structure —$A_n$— | Symbol |
| cyclohexylene | H |

TABLE 2-continued

Method of Description of Compound Using Symbols
R—(A$_1$)—Z$_1$— . . . —Z$_n$—(A$_n$)—R'

| Structure | Symbol |
|---|---|
| (phenyl) | B |
| (fluorophenyl) | B(F) |
| (2-fluorophenyl) | B(2F) |
| (difluorophenyl) | B(F,F) |
| (2,5-difluorophenyl) | B(2F,5F) |
| (2,3-difluorophenyl) | B(2F,3F) |
| (pyrimidine) | Py |
| (1,3-dioxane) | G |
| (tetrahydropyran) | Dh |
| (chromane with F,F) | Cro |
| (2F,3Cl-phenyl) | B(2F,3CL) |

TABLE 2-continued

Method of Description of Compound Using Symbols
R—(A$_1$)—Z$_1$— . . . —Z$_n$—(A$_n$)—R'

5) Examples of description

Example 1: 3-HH—V

Example 2: 3-BB(F,F)XB(F,F)—F

Example 3: 3-HH-4

Example 4: 3-HBB(2F,3F)—O2

Use Example 1

| Compound | Code | % |
|---|---|---|
| 3-GB(F)B(F,F)XB(F,F)-F | (7-53) | 5% |
| 3-BB(F)B(F,F)XB(F,F)-F | (7-47) | 3% |
| 4-BB(F)B(F,F)XB(F,F)-F | (7-47) | 5% |
| 5-BB(F)B(F,F)XB(F,F)-F | (7-47) | 4% |
| 3-HH-V | (2-1) | 41% |
| 3-HH-V1 | (2-1) | 6% |
| 3-HHEH-5 | (3-13) | 4% |
| 3-HHB-1 | (3-1) | 4% |
| V-HHB-1 | (3-1) | 5% |
| V2-BB(F)B-1 | (3-6) | 5% |
| 1 V2-BB-F | (2-8) | 3% |
| 3-BB(F,F)XB(F,F)-F | (6-97) | 6% |
| 3-GB(F,F)XB(F,F)-F | (6-113) | 5% |
| 3-HHBB(F,F)-F | (7-6) | 4% |

The following compound (A1) was added to the above composition in a ratio of 0.03 wt %.

(A1)

NI=83.2° C.; Δn=0.103; Δ∈=7.2; and η=13.4 mPa·s.

Use Example 2

| | | |
|---|---|---|
| 5-HB(F)B(F,F)XB(F,F)-F | (7-41) | 5% |
| 3-BB(F)B(F,F)XB(F,F)-F | (7-47) | 3% |
| 4-BB(F)B(F,F)XB(F,F)-F | (7-47) | 7% |
| 5-BB(F)B(F,F)XB(F,F)-F | (7-47) | 3% |
| 3-HH-V | (2-1) | 44% |
| 3-HH-V1 | (2-1) | 7% |
| 3-HHEH-5 | (3-13) | 3% |
| V-HHB-1 | (3-1) | 6% |
| V2-BB(F)B-1 | (3-6) | 5% |
| 1V2-BB-F | (2-8) | 3% |
| 3-BB(F,F)XB(F,F)-F | (6-97) | 11% |
| 3-HHBB(F,F)-F | (7-6) | 3% |

The following compound (A2) was added to the above composition in a ratio of 0.05 wt %.

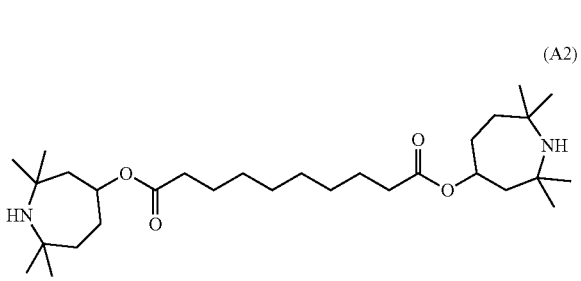

(A2)

NI=78.4° C.; Δn=0.103; Δ∈=6.2; and η=10.6 mPa·s.

Use Example 3

| | | |
|---|---|---|
| 1 V2-BEB(F,F)-C | (8-15) | 10% |
| 3-HB-C | (8-1) | 16% |
| 2-BTB-1 | (2-10) | 10% |
| 5-HH-VFF | (2-1) | 28% |
| 3-HHB-1 | (3-1) | 5% |
| VFF-HHB-1 | (3-1) | 8% |
| VFF2-HHB-1 | (3-1) | 11% |
| 3-H2BTB-2 | (3-17) | 4% |
| 3-H2BTB-3 | (3-17) | 4% |
| 3-H2BTB-4 | (3-17) | 4% |

The following compound (A1) was added to the above composition in a ratio of 0.01 wt %.

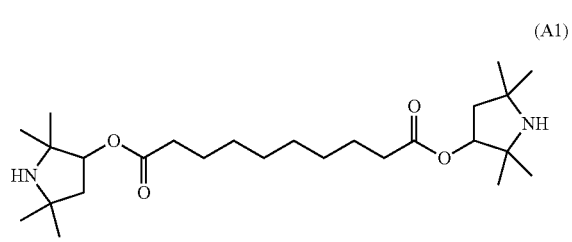

(A1)

NI=79.7° C.; Δn=0.131; Δ∈=9.1; and η=13.8 mPa·s.

Use Example 4

| | | |
|---|---|---|
| 2-HH-3 | (2-1) | 6% |
| 3-HH-V1 | (2-1) | 10% |
| 1 V2-HH-1 | (2-1) | 8% |
| 1 V2-HH-3 | (2-1) | 7% |
| 3-BB(2F,3F)-O2 | (8-7) | 8% |
| 5-BB(2F,3F)-O2 | (8-7) | 4% |
| 3-H1OB(2F,3F)-O2 | (9-5) | 7% |
| 2-HH1OB(2F,3F)-O2 | (10-5) | 8% |
| 3-HH1OB(2F,3F)-O2 | (10-5) | 19% |
| 3-HDhB(2F,3F)-O2 | (10-3) | 7% |
| 2-HBB(2F,3F)-O2 | (10-7) | 5% |
| 3-HBB(2F,3F)-O2 | (10-7) | 4% |
| 3-HHB-1 | (3-1) | 3% |
| 3-HHB-3 | (3-1) | 4% |

The following compound (A2) was added to the above composition in a ratio of 0.03 wt %.

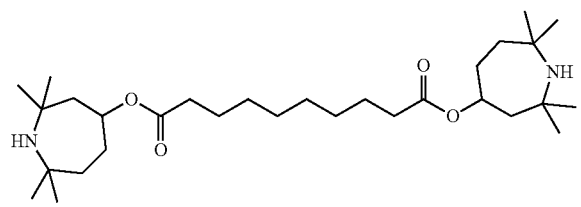

(A2)

NI=90.4° C.; Δn=0.101; Δ∈=−4.7; and η=21.7 mPa·s.

Use Example 5

| | | |
|---|---|---|
| 1-BB-3 | (2-8) | 5% |
| 3-HH-V | (2-1) | 29% |
| 3-HB-O2 | (2-5) | 5% |
| 3-BB(2F,3F)-O2 | (9-3) | 8% |
| 5-BB(2F,3F)-O2 | (9-3) | 6% |
| 2-HH1OB(2F,3F)-O2 | (10-5) | 15% |
| 3-HH1OB(2F,3F)-O2 | (10-5) | 13% |
| 3-HHB-1 | (3-1) | 8% |
| 3-HHB-3 | (3-1) | 5% |
| 5-B(F)BB-2 | (3-1) | 6% |

The following compound (A1) was added to the above composition in a ratio of 0.03 wt %.

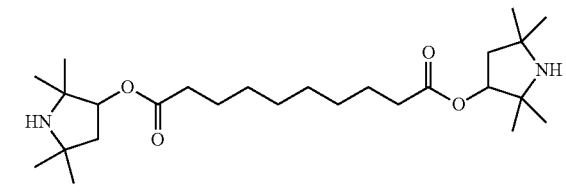

(A1)

NI=77.2° C.; Δn=0.102; Δ∈=−2.6; and η=13.2 mPa·s.

Use Example 6

| | | |
|---|---|---|
| 2-HH-3 | (2-1) | 16% |
| 7-HB-1 | (2-5) | 10% |
| 5-HB-O2 | (2-5) | 8% |
| 3-HB(2F,3F)-O2 | (9-1) | 15% |

-continued

| | | |
|---|---|---|
| 5-HB(2F,3F)-O2 | (9-1) | 13% |
| 3-HHB(2F,3CL)-O2 | (10-12) | 3% |
| 4-HHB(2F,3CL)-O2 | (10-12) | 3% |
| 5-HHB(2F,3CL)-O2 | (10-12) | 5% |
| 3-HH1OCro(7F,8F)-5 | (13-6) | 7% |
| 5-HBB(F)B-2 | (4-8) | 10% |
| 5-HBB(F)B-3 | (4-8) | 10% |

The following compound (A2) was added to the above composition in a ratio of 0.02 wt %.

-continued

| | | |
|---|---|---|
| 2-HBB(2F,3F)-O2 | (10-7) | 3% |
| 3-HBB(2F,3F)-O2 | (10-7) | 9% |
| 5-HBB(2F,3F)-O2 | (10-7) | 9% |
| 3-HBB(2F,3CL)-O2 | (10-13) | 3% |
| 3-HHB-1 | (3-1) | 3% |
| 3-HHB-3 | (3-1) | 4% |

The following compound (A2) was added to the above composition in a ratio of 0.06 wt %.

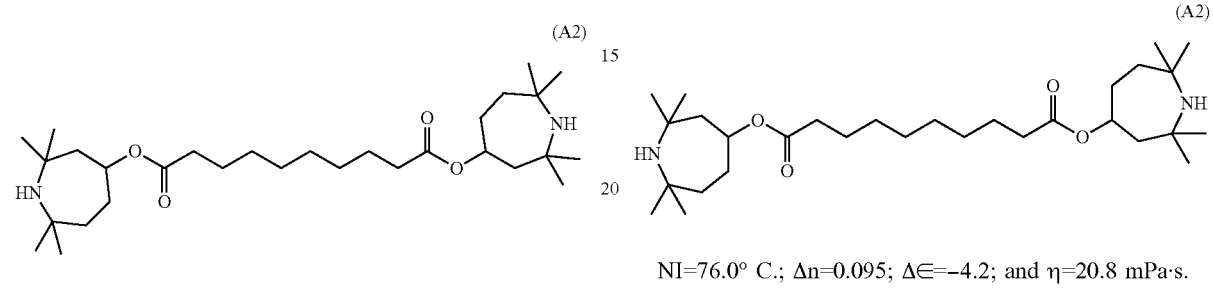

NI=82.7° C.; Δn=0.105; Δ∈=−2.6; and η=25.7 mPa·s.

Use Example 7

| | | |
|---|---|---|
| 2-HH-3 | (2-1) | 18% |
| 3-HH-4 | (2-1) | 9% |
| 1-BB-3 | (2-8) | 9% |
| 3-HB-O2 | (2-5) | 2% |
| 3-BB(2F,3F)-O2 | (9-3) | 9% |
| 5-BB(2F,3F)-O2 | (9-3) | 6% |
| 2-HH1OB(2F,3F)-O2 | (10-5) | 11% |
| 3-HH1OB(2F,3F)-O2 | (10-5) | 18% |
| 5-HBB(2F,3F)-O2 | (10-7) | 9% |
| 3-HHB-1 | (3-1) | 3% |
| 3-HHB-O1 | (3-1) | 3% |
| 5-B(F)BB-2 | (3-8) | 3% |

The following compound (A1) was added to the above composition in a ratio of 0.05 wt %.

NI=76.0° C.; Δn=0.095; Δ∈=−4.2; and η=20.8 mPa·s.

Use Example 9

| | | |
|---|---|---|
| 3-HH-4 | (2-1) | 5% |
| 3-HH-V | (2-1) | 10% |
| 3-HB-O2 | (2-5) | 5% |
| 3-HB(2F,3F)-O2 | (9-1) | 12% |
| 5-HB(2F,3F)-O2 | (9-1) | 12% |
| 2-HHB(2F,3F)-1 | (10-1) | 12% |
| 3-HHB(2F,3F)-1 | (10-1) | 12% |
| 3-HHB(2F,3F)-O2 | (10-1) | 13% |
| 5-HHB(2F,3F)-O2 | (10-1) | 13% |
| 3-HHB-1 | (3-1) | 6% |

The following compound (A1) was added to the above composition in a ratio of 0.01 wt %.

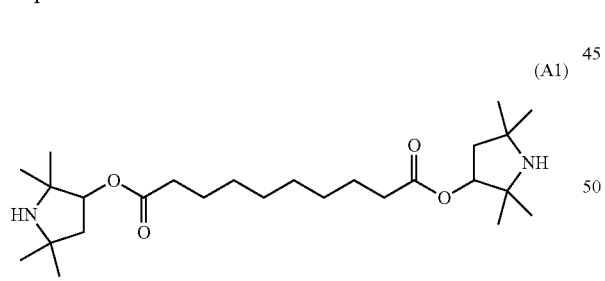

NI=79.1° C.; Δn=0.107; Δ∈=−3.4; and η=17.5 mPa·s.

Use Example 8

| | | |
|---|---|---|
| 3-HH-4 | (2-1) | 15% |
| 3-HH-5 | (2-1) | 7% |
| 3-HB-O2 | (2-5) | 7% |
| 5-HB-O2 | (2-5) | 5% |
| 3-H2B(2F,3F)-O2 | (9-4) | 15% |
| 5-H2B(2F,3F)-O2 | (9-4) | 15% |
| 3-HHB(2F,3CL)-O2 | (10-12) | 5% |

NI=91.2° C.; Δn=0.083; Δ∈=−3.3; and η=35.6 mPa·s.

Use Example 10

| | | |
|---|---|---|
| 5-HB-CL | (5-1) | 5% |
| 7-HB(F)-F | (5-3) | 8% |
| 3-HH-4 | (2-1) | 10% |
| 3-HH-EMe | (2-2) | 21% |
| 3-HHEB-F | (6-10) | 8% |
| 5-HHEB-F | (6-10) | 7% |
| 3-HHEB(F,F)-F | (6-12) | 10% |
| 4-HHEB(F,F)-F | (6-12) | 4% |
| 4-HGB(F,F)-F | (6-103) | 5% |
| 5-HGB(F,F)-F | (6-103) | 5% |
| 2-H2GB(F,F)-F | (6-106) | 4% |

-continued

| | | |
|---|---|---|
| 3-H2GB(F,F)-F | (6-106) | 6% |
| 5-GHB(F,F)-F | (6-109) | 7% |

The following compound (A2) was added to the above composition in a ratio of 0.02 wt %.

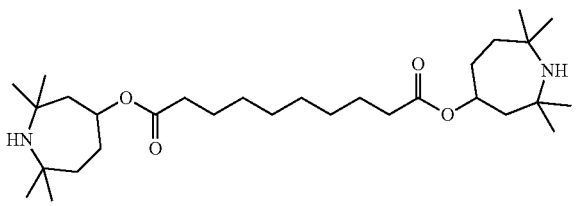

(A2)

NI=75.4° C.; Δn=0.063; Δ∈=5.7; and η=18.7 mPa·s.

Use Example 11

| | | |
|---|---|---|
| 5-HB-CL | (5-1) | 13% |
| 7-HB(F,F)-F | (5-4) | 3% |
| 3-HH-4 | (2-1) | 10% |
| 3-HH-5 | (2-1) | 6% |
| 3-HB-O2 | (2-5) | 15% |
| 3-HHB-1 | (3-1) | 9% |
| 3-HHB-O1 | (3-1) | 5% |
| 2-HHB(F)-F | (6-2) | 7% |
| 3-HHB(F)-F | (6-2) | 9% |
| 5-HHB(F)-F | (6-2) | 7% |
| 3-HHB(F,F)-F | (6-3) | 6% |
| 3-H2HB(F,F)-F | (6-12) | 5% |
| 4-H2HB(F,F)-F | (6-12) | 5% |

The following compound (A1) was added to the above composition in a ratio of 0.04 wt %.

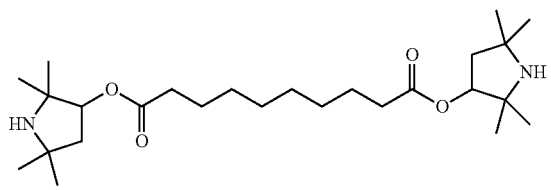

(A1)

NI=75.5° C.; Δn=0.075; Δ∈2.7; and η=14.4 mPa·s.

Use Example 12

| | | |
|---|---|---|
| 3-HB-CL | (5-2) | 4% |
| 5-HB-CL | (5-2) | 6% |
| 3-HHB-OCF3 | (6-1) | 5% |
| 3-H2HB-OCF3 | (6-13) | 5% |
| 5-H4HB-OCF3 | (6-19) | 15% |
| V-HHB(F)-F | (6-2) | 5% |
| 3-HHB(F)-F | (6-2) | 7% |
| 5-HHB(F)-F | (6-2) | 5% |
| 3-H4HB(F,F)-CF3 | (6-21) | 8% |
| 5-H4HB(F,F)-CF3 | (6-21) | 10% |
| 5-H2HB(F,F)-F | (6-15) | 5% |
| 5-H4HB(F,F)-F | (6-21) | 7% |
| 2-H2BB(F)-F | (6-26) | 5% |
| 3-H2BB(F)-F | (6-26) | 8% |
| 3-HBEB(F,F)-F | (6-39) | 5% |

The following compound (A2) was added to the above composition in a ratio of 0.05 wt %.

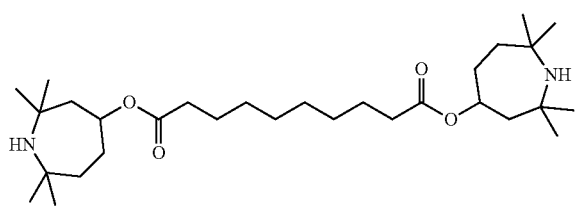

(A2)

NI=70.6° C.; Δn=0.096; Δ∈8.3; and η=25.4 mPa·s.

Use Example 13

| | | |
|---|---|---|
| 5-HB-CL | (5-2) | 11% |
| 3-HH-4 | (2-1) | 7% |
| 3-HHB-1 | (3-1) | 6% |
| 3-HHB(F,F)-F | (6-3) | 8% |
| 3-HBB(F,F)-F | (6-24) | 20% |
| 5-HBB(F,F)-F | (6-24) | 15% |
| 3-HHEB(F,F)-F | (6-12) | 10% |
| 4-HHEB(F,F)-F | (6-12) | 6% |
| 2-HBEB(F,F)-F | (6-39) | 3% |
| 3-HBEB(F,F)-F | (6-39) | 5% |
| 5-HBEB(F,F)-F | (6-39) | 3% |
| 3-HHBB(F,F)-F | (7-6) | 6% |

The following compound (A1) was added to the above composition in a ratio of 0.05 wt %.

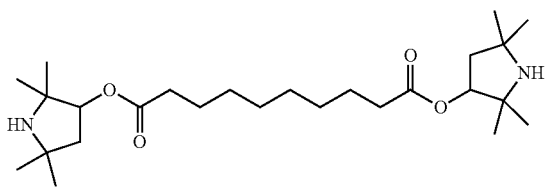

(A1)

NI=80.9° C.; Δn=0.104; Δ∈=8.6; and η=22.7 mPa·s.

Use Example 14

| | | |
|---|---|---|
| 5-HB-F | (5-2) | 12% |
| 6-HB-F | (5-2) | 9% |
| 7-HB-F | (5-2) | 7% |
| 2-HHB-OCF3 | (6-1) | 6% |
| 3-HHB-OCF3 | (6-1) | 8% |
| 4-HHB-OCF3 | (6-1) | 7% |
| 5-HHB-OCF3 | (6-1) | 6% |
| 3-HH2B-OCF3 | (6-4) | 5% |
| 5-HH2B-OCF3 | (6-4) | 4% |
| 3-HHB(F,F)-OCF2H | (6-3) | 3% |

| | | |
|---|---|---|
| 3-HHB(F,F)-OCF3 | (6-3) | 5% |
| 3-HH2B(F)-F | (6-5) | 3% |
| 3-HBB(F)-F | (6-23) | 8% |
| 5-HBB(F)-F | (6-23) | 11% |
| 5-HBBH-3 | (4-4) | 3% |
| 3-HB(F)BH-3 | (4-2) | 3% |

The following compound (A2) was added to the above composition in a ratio of 0.03 wt %.

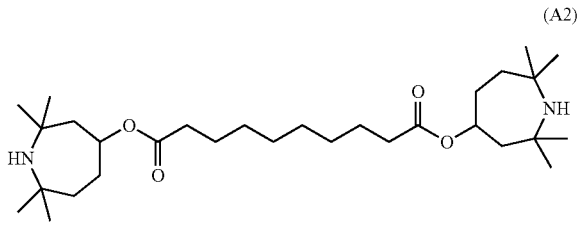

(A2)

NI=86.3° C.; Δn=0.092; Δ∈=4.4; and η=14.4 mPa·s.

Use Example 15

| | | |
|---|---|---|
| 3-HHB(F,F)-F | (6-3) | 8% |
| 3-H2HB(F,F)-F | (6-15) | 10% |
| 4-H2HB(F,F)-F | (6-15) | 8% |
| 5-H2HB(F,F)-F | (6-15) | 8% |
| 3-HBB(F,F)-F | (6-24) | 20% |
| 5-HBB(F,F)-F | (6-24) | 19% |
| 3-H2BB(F,F)-F | (6-23) | 11% |
| 5-HHBB(F,F)-F | (7-6) | 3% |
| 5-HHEBB-F | (7-17) | 2% |
| 3-HH2BB(F,F)-F | (7-15) | 4% |
| 1O1-HBBH-4 | (4-1) | 4% |
| 1O1-HBBH-5 | (4-1) | 3% |

The following compound (A1) was added to the above composition in a ratio of 0.02 wt %.

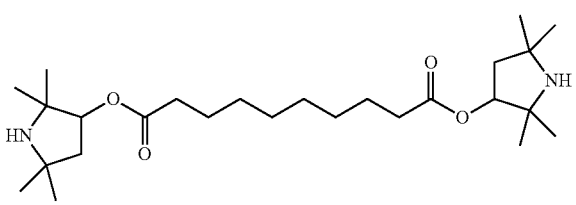

(A1)

NI=97.1° C.; Δn=0.115; Δ∈=9.0; and η=35.0 mPa·s.

Use Example 16

| | | |
|---|---|---|
| 5-HB-CL | (5-2) | 14% |
| 3-HH-4 | (2-1) | 14% |
| 3-HH-5 | (2-1) | 5% |
| 3-HHB-F | (6-1) | 5% |
| 3-HHB-CL | (6-1) | 3% |
| 4-HHB-CL | (6-1) | 4% |
| 3-HHB(F)-F | (6-2) | 8% |
| 4-HHB(F)-F | (6-2) | 9% |
| 5-HHB(F)-F | (6-2) | 9% |
| 7-HHB(F)-F | (6-2) | 8% |
| 5-HBB(F)-F | (6-23) | 4% |
| 1O1-HBBH-5 | (4-1) | 3% |
| 3-HHBB(F,F)-F | (7-6) | 2% |
| 4-HHBB(F,F)-F | (7-6) | 3% |
| 5-HHBB(F,F)-F | (7-6) | 3% |
| 3-HH2BB(F,F)-F | (7-15) | 3% |
| 4-HH2BB(F,F)-F | (7-15) | 3% |

The following compound (A2) was added to the above composition in a ratio of 0.01 wt %.

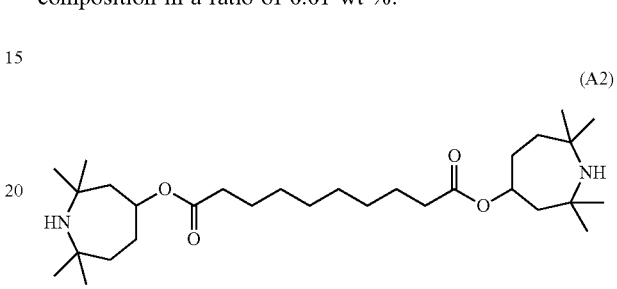

(A2)

NI=116.3° C.; Δn=0.090; Δ∈=3.6; and η=18.8 mPa·s.

Use Example 17

| | | |
|---|---|---|
| 7-HB(F,F)-F | (5-4) | 7% |
| 3-HB-O2 | (2-5) | 3% |
| 2-HHB(F)-F | (6-2) | 9% |
| 3-HHB(F)-F | (6-2) | 12% |
| 5-HHB(F)-F | (6-2) | 9% |
| 2-HBB(F)-F | (6-2) | 9% |
| 3-HBB(F)-F | (6-2) | 9% |
| 5-HBB(F)-F | (6-2) | 16% |
| 2-HBB-F | (6-1) | 3% |
| 3-HBB-F | (6-1) | 4% |
| 5-HBB-F | (6-1) | 4% |
| 3-HBB(F,F)-F | (6-24) | 5% |
| 5-HBB(F,F)-F | (6-24) | 10% |

The following compound (A1) was added to the above composition in a ratio of 0.03 wt %.

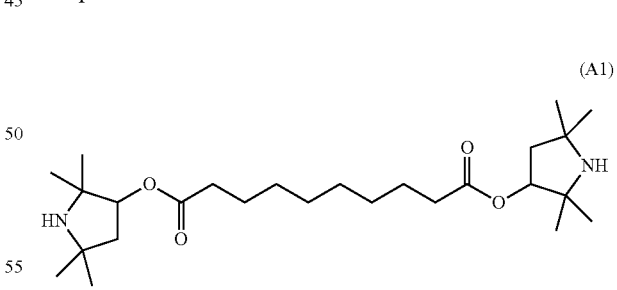

(A1)

NI=82.1° C.; Δn=0.112; Δ∈=5.5; and η=25.8 mPa·s.

Use Example 18

| | | |
|---|---|---|
| 2-HB-C | (8-1) | 8% |
| 3-HB-C | (8-1) | 9% |
| 3-HB-O2 | (2-5) | 15% |
| 2-BTB-1 | (2-10) | 3% |

| | | |
|---|---|---|
| 3-HHB-F | (6-1) | 5% |
| 3-HHB-1 | (3-1) | 7% |
| 3-HHB-O1 | (3-1) | 6% |
| 3-HHB-3 | (3-1) | 13% |
| 3-HHEB-F | (6-10) | 4% |
| 5-HHEB-F | (6-10) | 4% |
| 2-HHB(F)-F | (6-2) | 6% |
| 3-HHB(F)-F | (6-2) | 6% |
| 5-HHB(F)-F | (6-2) | 6% |
| 3-HHB(F,F)-F | (6-3) | 8% |

The following compound (A2) was added to the above composition in a ratio of 0.04 wt %.

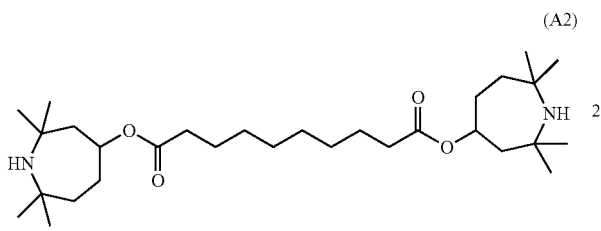

(A2)

NI=98.8° C.; Δn=0.099; Δ∈=4.7; and η=18.1 mPa·s.

Use Example 19

| | | |
|---|---|---|
| 3-HB-O2 | (2-5) | 10% |
| 5-HB-CL | (5-2) | 13% |
| 3-HBB(F,F)-F | (6-24) | 7% |
| 3-PyB(F)-F | (5-15) | 10% |
| 5-PyB(F)-F | (5-15) | 10% |
| 3-PyBB-F | (6-80) | 9% |
| 4-PyBB-F | (6-80) | 9% |
| 5-PyBB-F | (6-80) | 10% |
| 5-HBB(F)B-2 | (4-5) | 11% |
| 5-HBB(F)B-3 | (4-5) | 11% |

The following compound (A1) was added to the above composition in a ratio of 0.02 wt %.

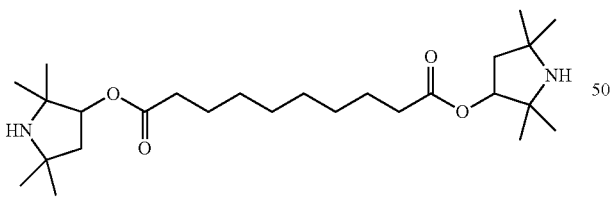

(A1)

NI=101.1° C.; Δn=0.191; Δ∈=7.7; and η=39.8 mPa·s.

INDUSTRIAL APPLICABILITY

The compound (1) has an effect of preventing photolysis of a liquid crystal composition and has high solubility in the liquid crystal composition. The liquid crystal composition containing this compound satisfies at least one of characteristics such as high maximum temperature, low minimum temperature, small viscosity, suitable optical anisotropy, large positive or negative dielectric anisotropy, large specific resistance, high stability to ultraviolet light or heat, and a suitable elastic constant, etc. This composition is stable to light. The liquid crystal display device containing this composition has short response time, a large voltage holding ratio, a large contrast ratio, and long service life, etc., and can thus be used in liquid crystal projectors and liquid crystal TVs, etc.

What is claimed is:

1. A liquid crystal composition, containing at least one compound selected from the group consisting of compounds represented by formulae (1-1) to (1-4) and at least one compound selected from the group consisting of compounds represented by formulae (2) to (4),

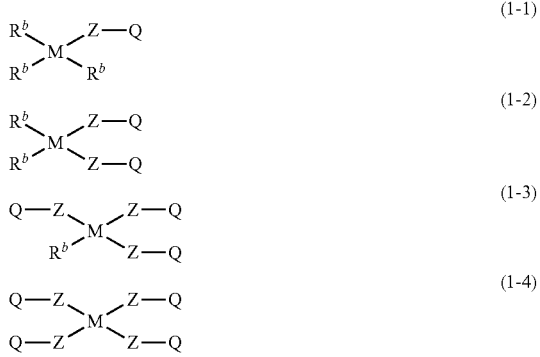

wherein in formulae (1-1) to (1-4),

M is a tetravalent aliphatic hydrocarbon group having 1 to 20 carbons or a tetravalent aromatic hydrocarbon group having 1 to 20 carbons, wherein at least one —$CH_2$— in these groups is optionally replaced with —O— or —S—, one or two —CH=CH— in these groups are optionally replaced with —CH=N—, and at least one hydrogen in these groups is optionally replaced with fluorine or chlorine;

Z is a single bond, —O—, —COO—, or —OCO—;

Q is a monovalent group represented by formula (Q-1) or (Q-2), wherein $R^a$ is hydrogen, —O., —OH, or —$R^1$;

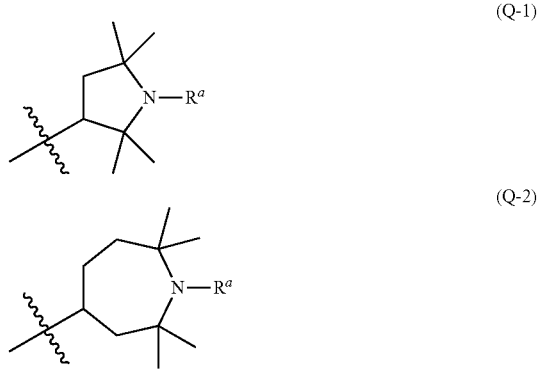

$R^b$ is hydrogen, fluorine, or —$R^2$; and $R^1$ and $R^2$ are independently alkyl having 1 to 20 carbons, arylalkyl having 1 to 20 carbons, or aryl having 1 to 20 carbons, wherein at least one —$CH_2$— in the alkyl is optionally replaced with —O—, —CO—, —COO—, or —OCO—, and —$CH_3$ located at a terminal of the alkyl is optionally replaced with —NHR³ or —NR⁴R⁵, wherein R³, R⁴ and R⁵ are independently alkyl having 1 to 10 carbons;

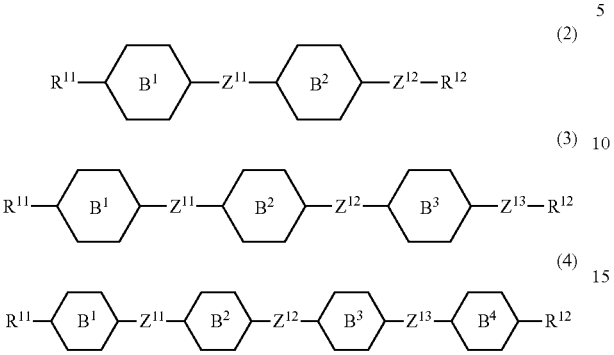

wherein in formulae (2) to (4),
R¹¹ and R¹² are independently alkyl having 1 to 10 carbons or alkenyl having 2 to 10 carbons, wherein at least one —CH₂— in the alkyl or alkenyl is optionally replaced with —O—, and at least one hydrogen in the alkyl or alkenyl is optionally replaced with fluorine;
ring B¹, ring B², ring B³, and ring B⁴ are independently 1,4-cyclohexylene, 1,4-phenylene, 2-fluoro-1,4-phenylene, 2,5-difluoro-1,4-phenylene, or pyrimidine-2,5-diyl; and
Z¹¹, Z¹², and Z¹³ are independently a single bond, —CH₂CH₂—, —CH=CH—, or —COO—.

2. The liquid crystal composition according to claim 1, wherein in formulae (1-1) to (1-4) of claim 1, at least one Q is a monovalent group represented by formula (Q-2),

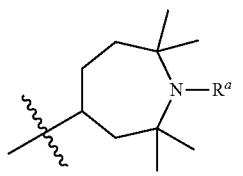

wherein in formula (Q-2), Rᵃ is hydrogen, —O., —OH, or —R¹; and
R¹ is alkyl having 1 to 20 carbons, arylalkyl having 1 to 20 carbons, or aryl having 1 to 20 carbons, wherein at least one —CH₂— in the alkyl is optionally replaced with —O—, —CO—, —COO—, or —OCO—, and —CH₃ located at a terminal of the alkyl is optionally replaced with —NHR³ or —NR⁴R⁵, wherein R³, R⁴ and R⁵ are independently alkyl having 1 to 10 carbons.

3. The liquid crystal composition according to claim 1, wherein the at least one compound selected from the group consisting of compounds represented by formulae (1-1) to (1-4) is a compound represented by any one of formulae (1-1a) to (1-4a),

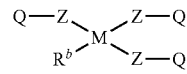

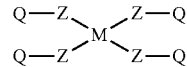

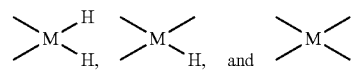

wherein in formulae (1-1a) to (1-4a),

are divalent, trivalent or tetravalent groups, formed by removing hydrogen from alkane having 1 to 15 carbons, alkane having 1 to 15 carbons in which at least one —CH₂— is replaced with —O—, cyclohexane, bicyclohexane, decahydronaphthalene, tetrahydropyran, dioxane, benzene, benzene in which at least one hydrogen is replaced with fluorine, biphenyl, naphthalene, pyridine, or pyrimidine;
Z is a single bond, —O—, —COO—, or —OCO—;
Q is a monovalent group represented by formula (Q-1) or (Q-2), wherein Rᵃ is hydrogen, —O., —OH, or —R¹,

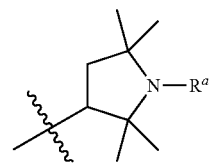

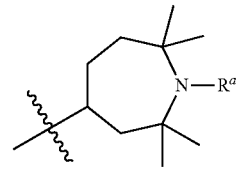

Rᵇ is hydrogen, fluorine, or —R²; and
R¹ and R² are independently alkyl having 1 to 20 carbons, arylalkyl having 1 to 20 carbons, or aryl having 1 to 20 carbons, wherein at least one —CH₂— in the alkyl is optionally replaced with —O—, and —CH₃ located at a terminal of the alkyl is optionally replaced with —NHR³ or —NR⁴R⁵, wherein R³, R⁴ and R⁵ are independently alkyl having 1 to 10 carbons.

4. The liquid crystal composition according to claim 3, wherein in formulae (1-1a) to (1-4a) of claim 3,

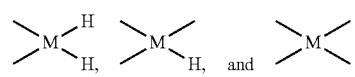

are independently any one of a divalent group represented by formulae (M-1) to (M-7), a trivalent group represented by formulae (M-8) to (M-23), and a tetravalent group represented by formulae (M-24) to (M-42), wherein c is an integer of 0 to 16

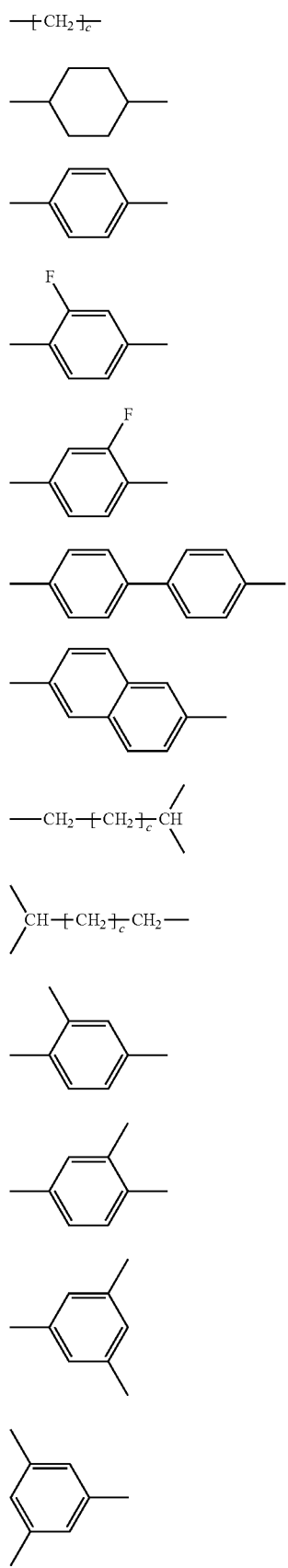
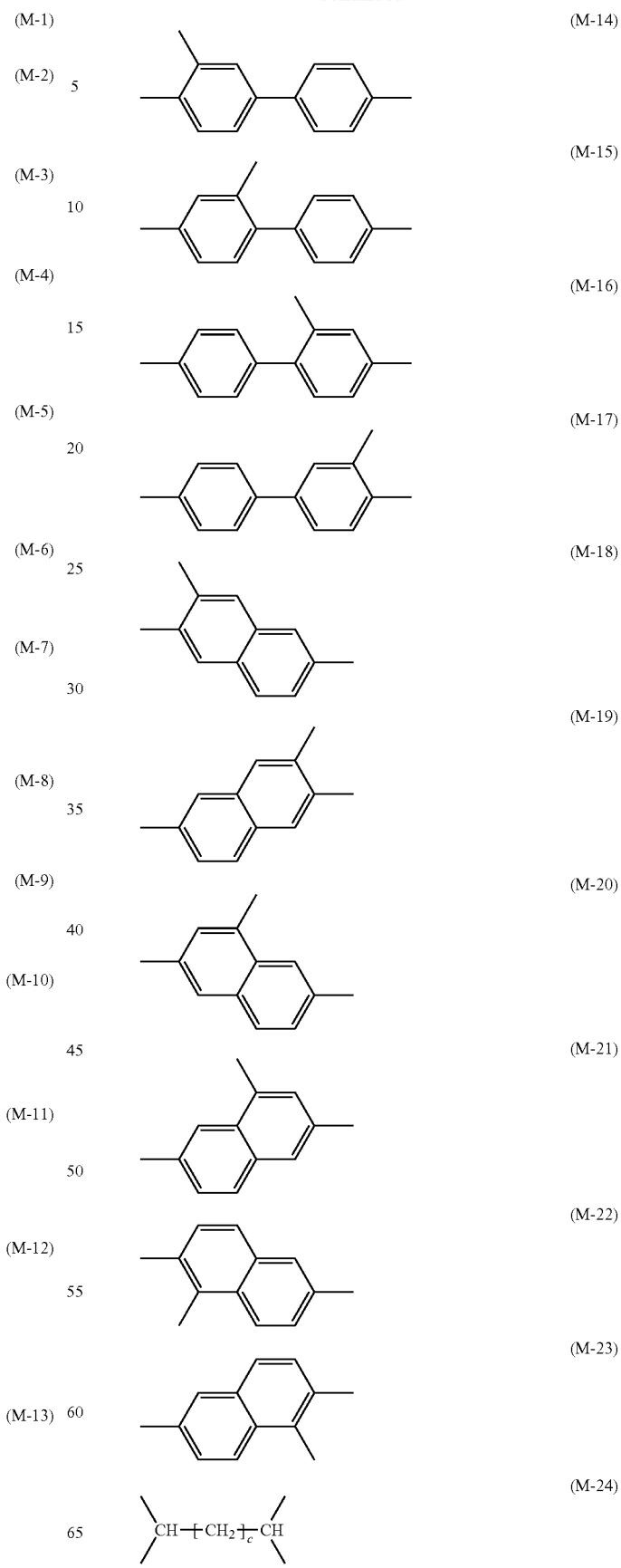

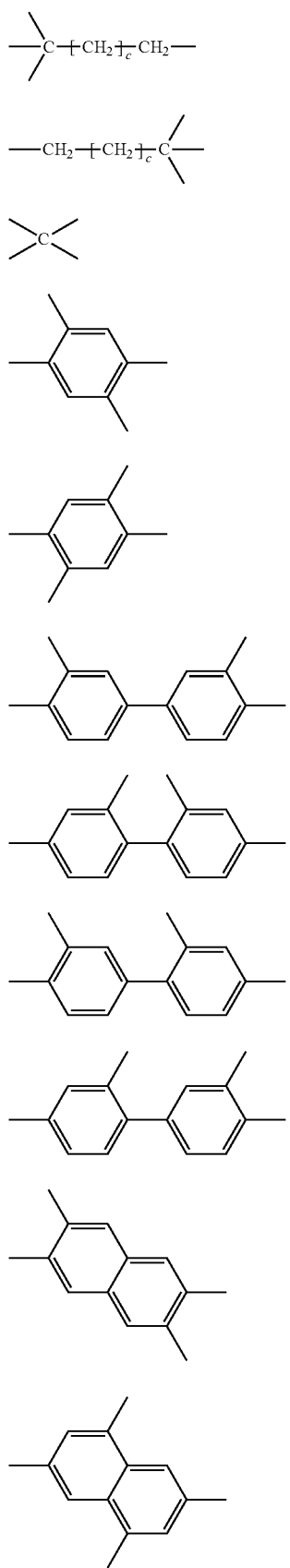
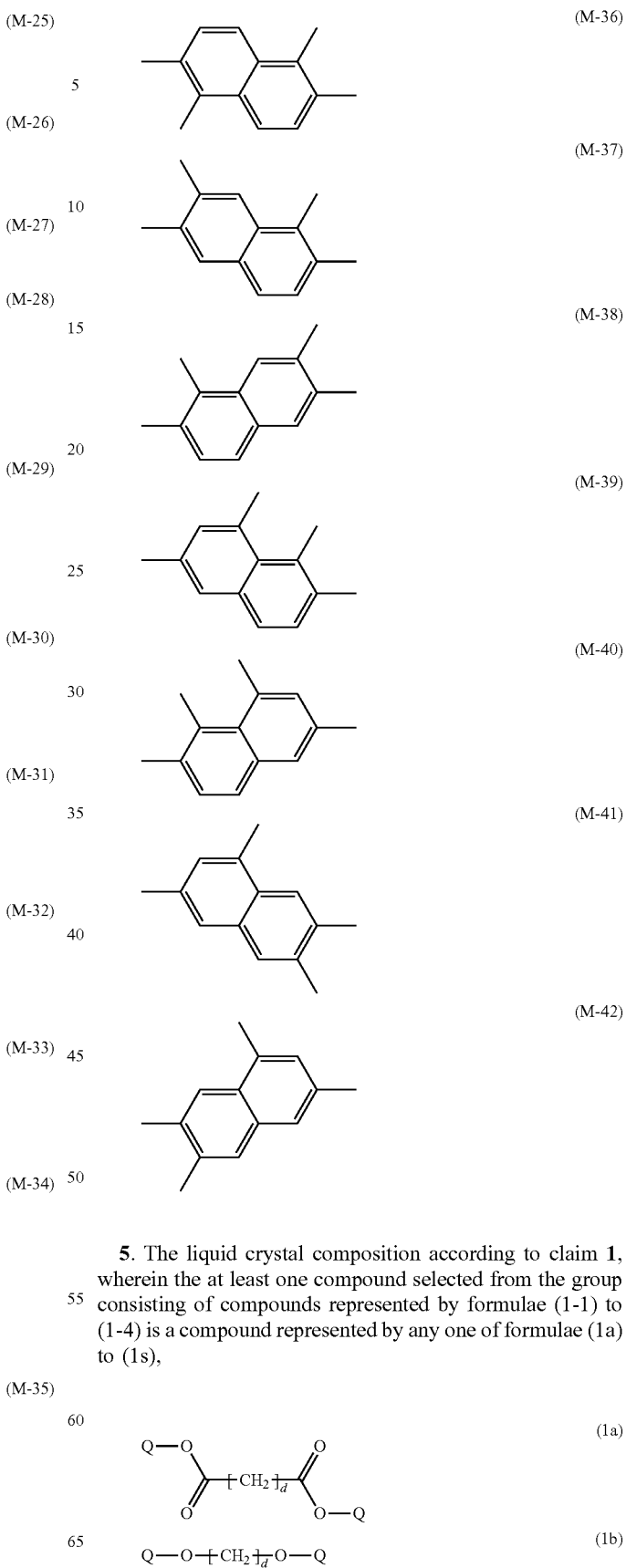
5. The liquid crystal composition according to claim 1, wherein the at least one compound selected from the group consisting of compounds represented by formulae (1-1) to (1-4) is a compound represented by any one of formulae (1a) to (1s),
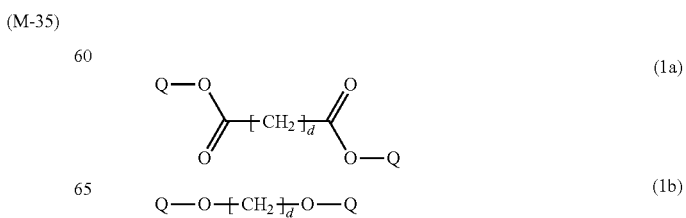

 (1c)
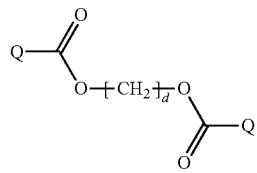 (1d)
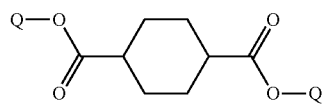 (1e)
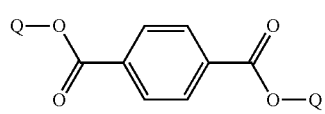 (1f)
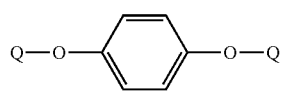 (1g)
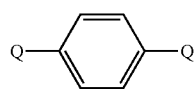 (1h)
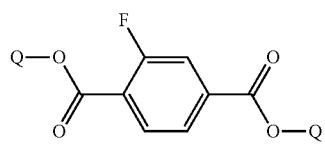 (1i)
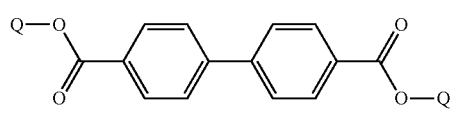 (1j)
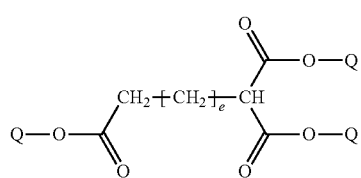 (1k)
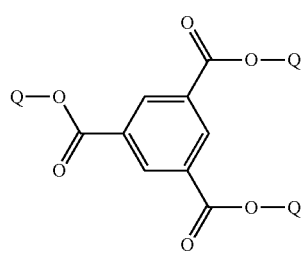 (1l)
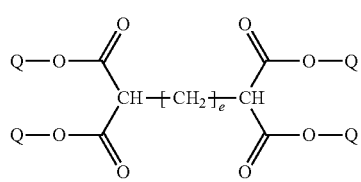 (1m)
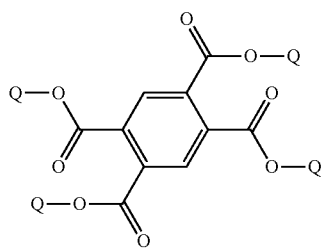 (1n)
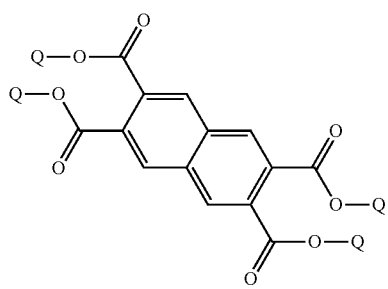 (1o)
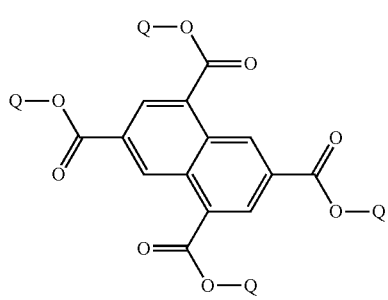 (1p)
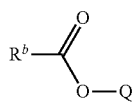 (1q)
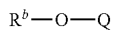 (1r)
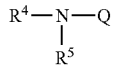 (1s)
wherein in formulae (1a) to (1s),
d is an integer of 1 to 14;
e is an integer of 0 to 13;
Q is a monovalent group represented by formula (Q-1) or (Q-2), wherein $R^a$ is hydrogen, —O., —OH, or —R';
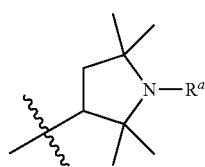 (Q-1)

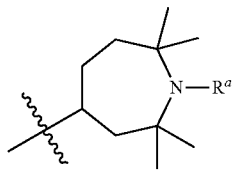
(Q-2)

$R^b$ is hydrogen or $-R^2$;

$R^1$ and $R^2$ are independently alkyl having 1 to 20 carbons, arylalkyl having 1 to 20 carbons, or aryl having 1 to 20 carbons, wherein at least one $-CH_2-$ in the alkyl is optionally replaced with $-O-$; and $R^4$ and $R^5$ are independently alkyl having 1 to 10 carbons.

6. The liquid crystal composition according to claim 5, wherein in formulae (Q-1) and (Q-2) of claim 5, $R^a$ is hydrogen, $-O.$, $-OH$, alkyl having 1 to 10 carbons, or alkoxy having 1 to 10 carbons.

7. The liquid crystal composition according to claim 1, wherein the at least one compound selected from the group consisting of compounds represented by formulae (1-1) to (1-4) is a compound represented by any one of formulae (1a-1), (1f), (1h), and (1n),

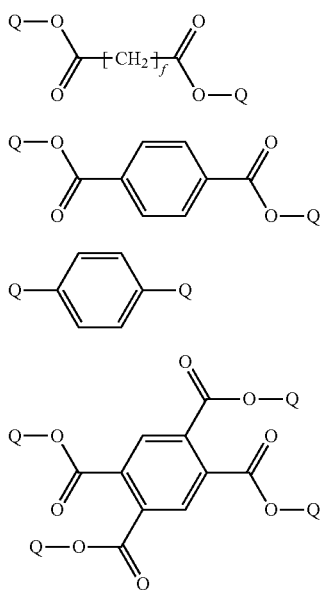

wherein in formulae (1a-1), (1f), (1h), and (1n),
f is an integer of 1 to 12; and
Q is a monovalent group represented by formula (Q-1) or (Q-2), wherein $R^a$ is hydrogen or alkyl having 1 to 15 carbons:

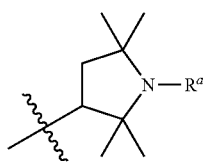
(Q-1)

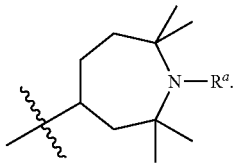
(Q-2)

8. The liquid crystal composition according to claim 1, further containing at least one compound selected from the group consisting of compounds represented by formulae (5) to (7),

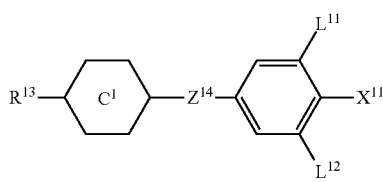
(5)

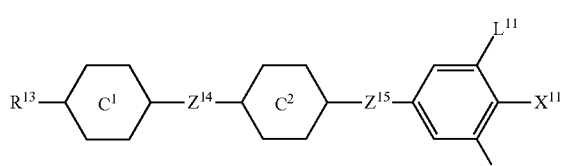
(6)

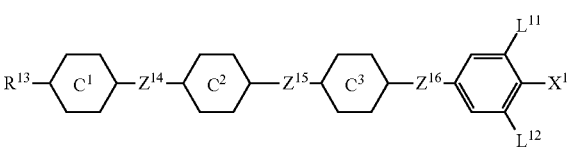
(7)

wherein in formulae (5) to (7),
$R^{13}$ is alkyl having 1 to 10 carbons or alkenyl having 2 to 10 carbons, wherein at least one $-CH_2-$ in the alkyl and alkenyl is optionally replaced with $-O-$, and at least one hydrogen in the alkyl and alkenyl is optionally replaced with fluorine;
$X^{11}$ is fluorine, chlorine, $-OCF_3$, $-OCHF_2$, $-CF_3$, $-CHF_2$, $-CH_2F$, $-OCF_2CHF_2$, or $-OCF_2CHFCF_3$;
ring $C^1$, ring $C^2$ and ring $C^3$ are independently 1,4-cyclohexylene, 1,4-phenylene in which at least one hydrogen is optionally replaced with fluorine, tetrahydropyran-2,5-diyl, 1,3-dioxane-2,5-diyl, or pyrimidine-2,5-diyl;
$Z^{14}$, $Z^{15}$, and $Z^{16}$ are independently a single bond, $-CH_2CH_2-$, $-CH=CH-$, $-COO-$, $-CF_2O-$, $-OCF_2-$, $-CH_2O-$, or $-(CH_2)_4-$; and
$L^{11}$ and $L^{12}$ are independently hydrogen or fluorine.

9. The liquid crystal composition according to claim 1, further containing at least one compound selected from the group consisting of compounds represented by formula (8),

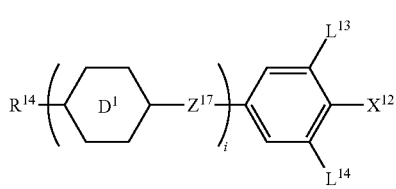
(8)

wherein in formula (8),

R$^{14}$ is alkyl having 1 to 10 carbons or alkenyl having 2 to 10 carbons, wherein at least one —CH$_2$— in the alkyl and alkenyl is optionally replaced with —O—, and at least one hydrogen in the alkyl and alkenyl is optionally replaced with fluorine;

X$^{12}$ is —C≡N or —C≡C—C≡N;

ring D$^1$ is 1,4-cyclohexylene, 1,4-phenylene in which at least one hydrogen is optionally replaced with fluorine, tetrahydropyran-2,5-diyl, 1,3-dioxane-2,5-diyl, or pyrimidine-2,5-diyl;

Z$^{17}$ is a single bond, —CH$_2$CH$_2$—, —COO—, —CF$_2$O—, —OCF$_2$—, or —CH$_2$O—;

L$^{13}$ and L$^{14}$ are independently hydrogen or fluorine; and i is 1, 2, 3, or 4.

10. The liquid crystal composition according to claim 1, further containing at least one compound selected from the group consisting of compounds represented by formulae (9) to (15), wherein in formulae (9) to (15), R$^{15}$ and R$^{16}$ are independently alkyl having 1 to 10 carbons or alkenyl having 2 to 10 carbons, wherein at least one —CH$_2$— in the alkyl and alkenyl is optionally replaced with —O—, and at least one hydrogen in the alkyl and alkenyl is optionally replaced with fluorine;

R$^{17}$ is hydrogen, fluorine, alkyl having 1 to 10 carbons, or alkenyl having 2 to 10 carbons, wherein at least one —CH$_2$— in the alkyl and alkenyl is optionally replaced with —O—, and at least one hydrogen in the alkyl and alkenyl is optionally replaced with fluorine;

ring E$^1$, ring E$^2$, ring E$^3$, and ring E$^4$ are independently 1,4-cyclohexylene, 1,4-cyclohexenylene, 1,4-phenylene in which at least one hydrogen is optionally replaced with fluorine, tetrahydropyran-2,5-diyl, or decahydronaphthalene-2,6-diyl;

ring E$^5$ and ring E$^6$ are independently 1,4-cyclohexylene, 1,4-cyclohexenylene, 1,4-phenylene, tetrahydropyran-2,5-diyl, or decahydronaphthalene-2,6-diyl;

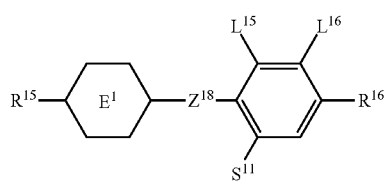

(9)

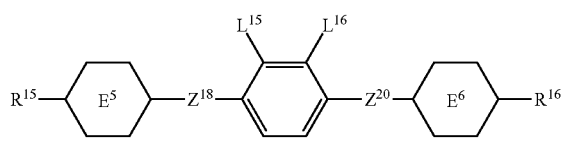

(10)

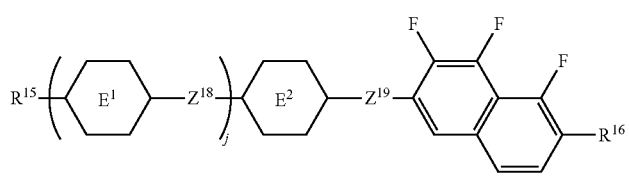

(11)

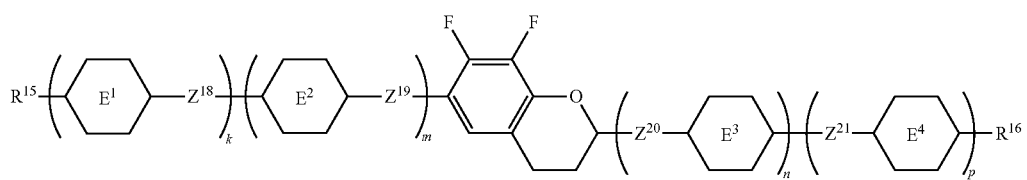

(12)

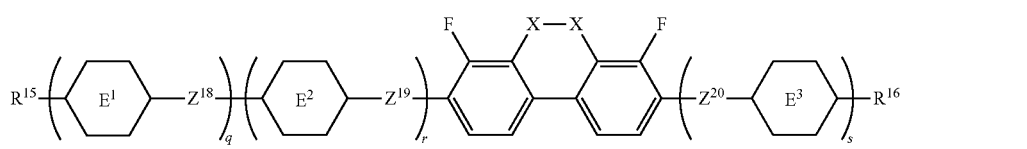

(13)

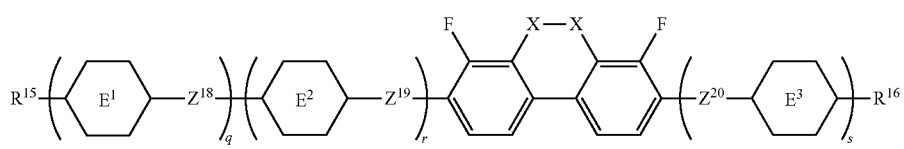

(14)

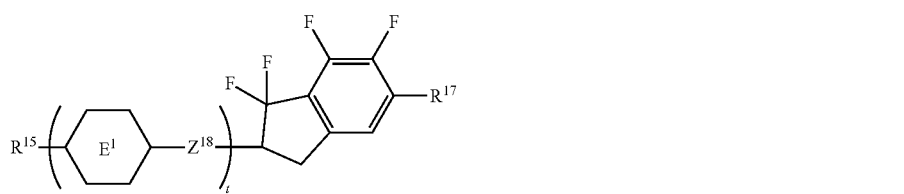

(15)

$Z^{18}$, $Z^{19}$, $Z^{20}$, and $Z^{21}$ are independently a single bond, —CH$_2$CH$_2$—, —COO—, —CH$_2$O—, —OCF$_2$—, or —OCF$_2$CH$_2$CH$_2$—;

$L^{15}$ and $L^{16}$ are independently fluorine or chlorine;

$S^{11}$ is hydrogen or methyl;

X is —CHF— or —CF$_2$—; and j, k, m, n, p, q, r and s are independently 0 or 1, the sum of k, m, n and p is 1 or 2, the sum of q, r and s is 0, 1, 2, or 3, and t is 1, 2, or 3.

11. A compound represented by any one of formulae (1-1) to (1-4),

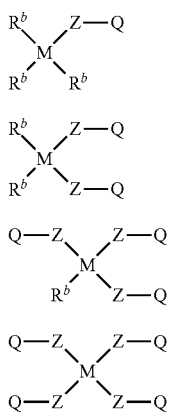

(1-1)

(1-2)

(1-3)

(1-4)

wherein in formulae (1-1) to (1-4),

M is a tetravalent aliphatic hydrocarbon group having 1 to 20 carbons or a tetravalent aromatic hydrocarbon group having 1 to 20 carbons, wherein at least one —CH$_2$— in these groups is optionally replaced with —O— or —S—, one or two —CH=CH— in these groups are optionally replaced with —CH=N—, and at least one hydrogen in these groups is optionally replaced with fluorine or chlorine;

Z is a single bond, —O—, —COO—, or —OCO—;

Q is a monovalent group represented by formula (Q-1) or (Q-2), and at least one Q is a monovalent group represented by formula (Q-2), wherein R$^a$ is hydrogen, —O., —OH, or —R$^1$;

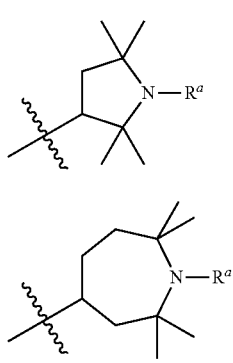

(Q-1)

(Q-2)

R$^b$ is hydrogen, fluorine, or —R$^2$; and

R$^1$ and R$^2$ are independently alkyl having 1 to 20 carbons, arylalkyl having 1 to 20 carbons, or aryl having 1 to 20 carbons, wherein at least one —CH$_2$— in the alkyl is optionally replaced with —O—, —CO—, —COO—, or —OCO—, and —CH$_3$ located at a terminal of the alkyl is optionally replaced with —NHR$^3$ or —NR$^4$R$^5$, wherein R$^3$, R$^4$ and R$^5$ are independently alkyl having 1 to 10 carbons.

12. The compound according to claim 11, represented by any one of formulae (1-1a) to (1-4a),

(1-1a)

(1-2a)

(1-3a)

(1-4a)

wherein in formulae (1-1a) to (1-4a),

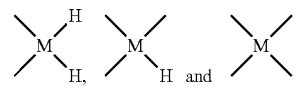

are divalent, trivalent or tetravalent groups, formed by removing hydrogen from alkane having 1 to 15 carbons, alkane having 1 to 15 carbons in which at least one —CH$_2$— is replaced with —O—, cyclohexane, bicyclohexane, decahydronaphthalene, tetrahydropyran, dioxane, benzene, benzene in which at least one hydrogen is replaced with fluorine, biphenyl, naphthalene, pyridine, or pyrimidine;

Z is a single bond, —O—, —COO—, or —OCO—;

Q is a monovalent group represented by formula (Q-1) or (Q-2), and at least one Q is a monovalent group represented by formula (Q-2), wherein R$^a$ is hydrogen, —O., —OH, or —R$^1$;

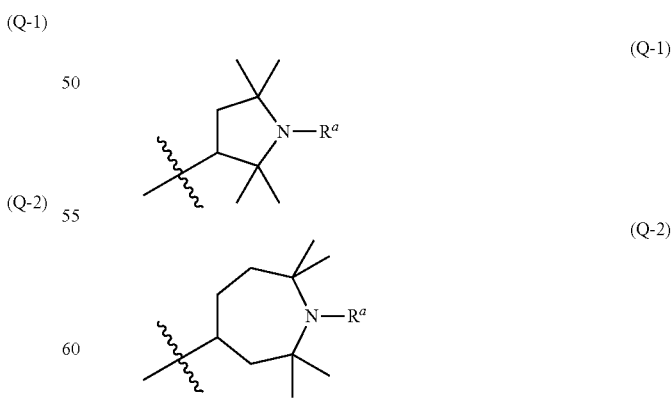

(Q-1)

(Q-2)

R$^b$ is hydrogen, fluorine, or —R$^2$; and

R$^1$ and R$^2$ are independently alkyl having 1 to 20 carbons, arylalkyl having 1 to 20 carbons, or aryl having 1 to 20 carbons, wherein at least one —CH$_2$— in the alkyl is optionally replaced with —O—, and —CH₃ located at a terminal of the alkyl is optionally replaced with —NHR³ or —NR⁴R⁵, wherein R³, R⁴ and R⁵ are independently alkyl having 1 to 10 carbons.

13. The compound according to claim 12, wherein in formulae (1-1a) to (1-4a) of claim 12,

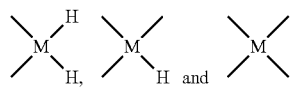

are independently any one of a divalent group represented by formulae (M-1) to (M-7), a trivalent group represented by formulae (M-8) to (M-23), and a tetravalent group represented by formulae (M-24) to (M-42), wherein c is an integer of 0 to 16:

 (M-1)

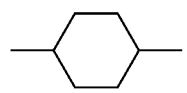 (M-2)

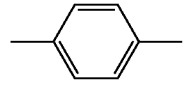 (M-3)

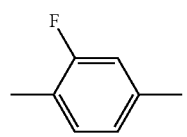 (M-4)

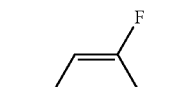 (M-5)

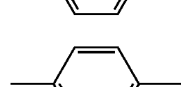 (M-6)

 (M-7)

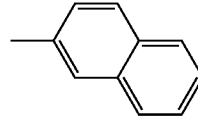 (M-8)

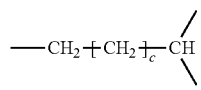 (M-9)

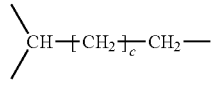 (M-10)

-continued

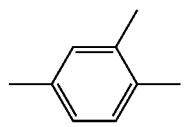 (M-11)

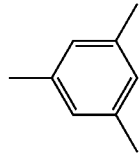 (M-12)

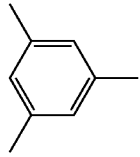 (M-13)

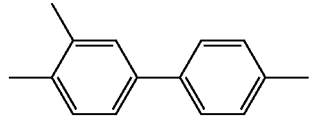 (M-14)

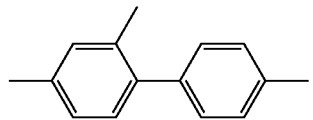 (M-15)

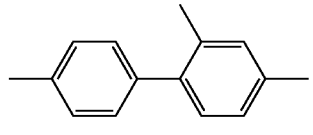 (M-16)

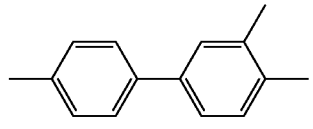 (M-17)

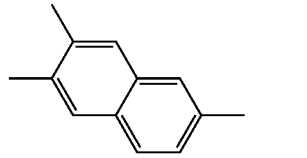 (M-18)

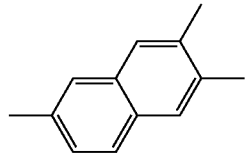 (M-19)

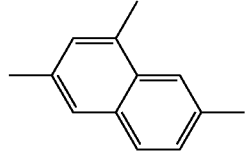 (M-20)

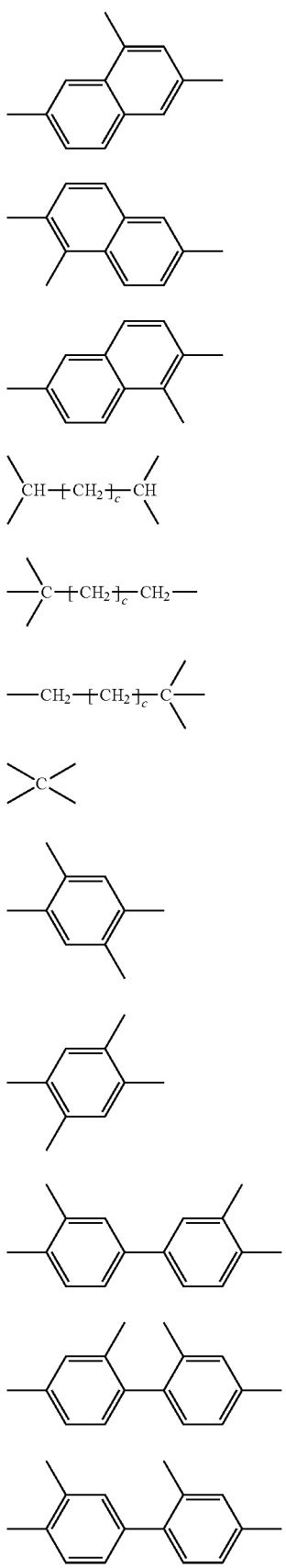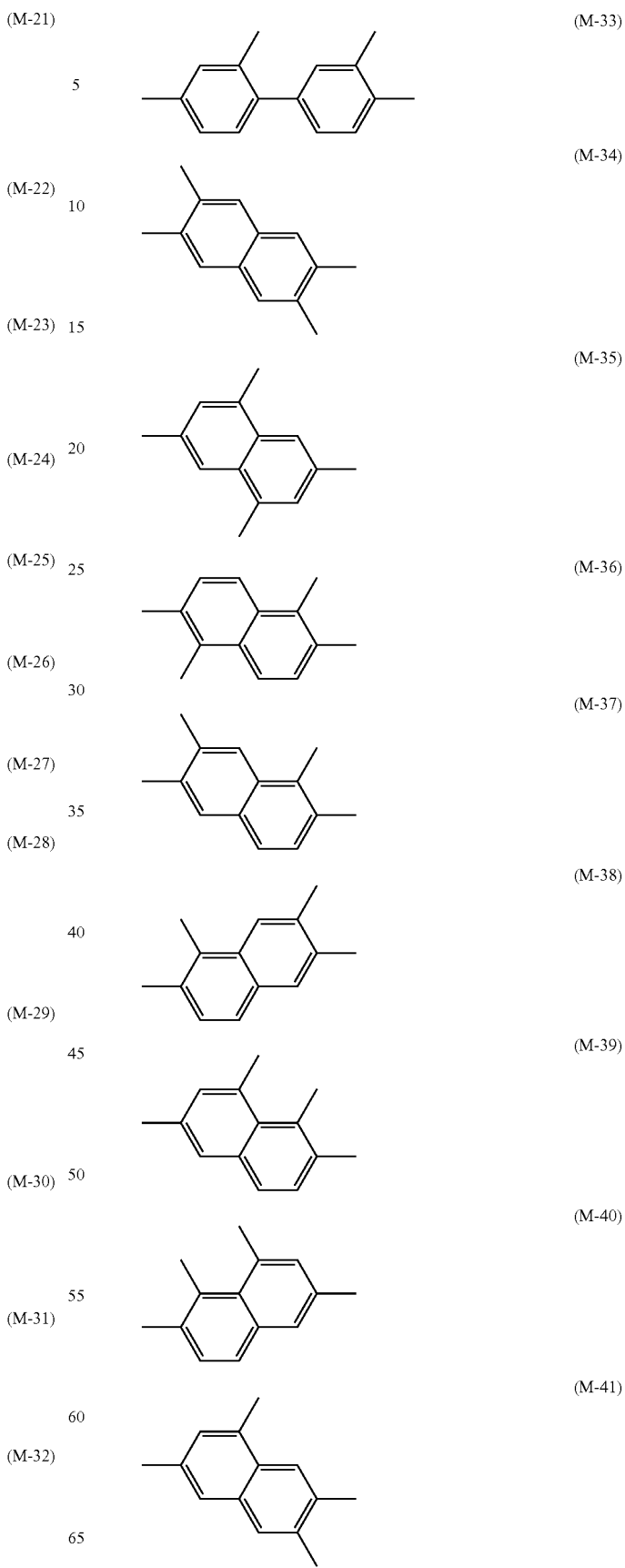

(M-42)
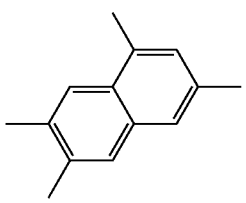
14. The compound according to claim 11, represented by any one of formulae (1a) to (1s),
(1a)
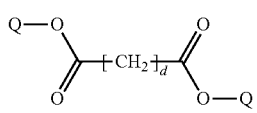
(1b)
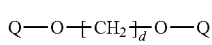
(1c)
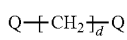
(1d)
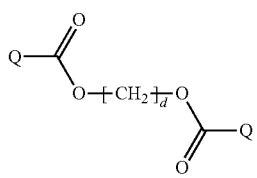
(1e)
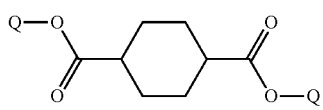
(1f)
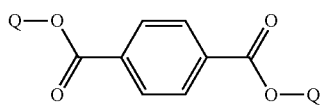
(1g)
(1h)
(1i)
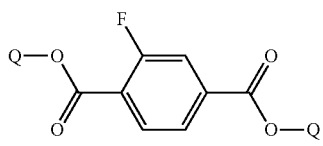
(1j)
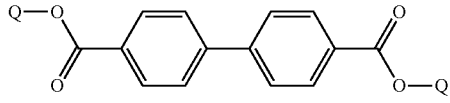
(1k)
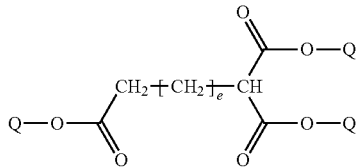
(1l)
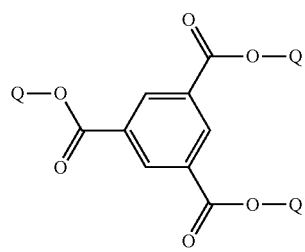
(1m)
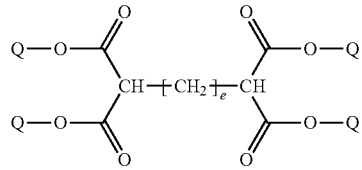
(1n)
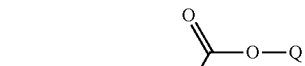
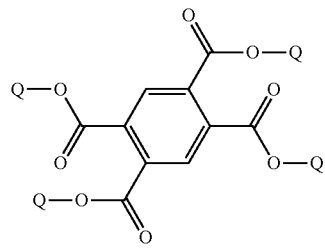
(1o)
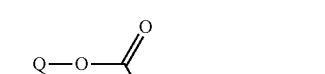
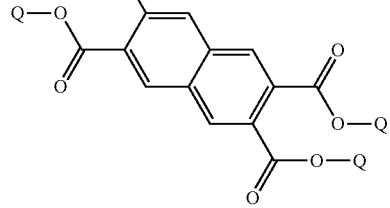
(1p)
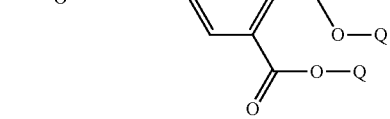
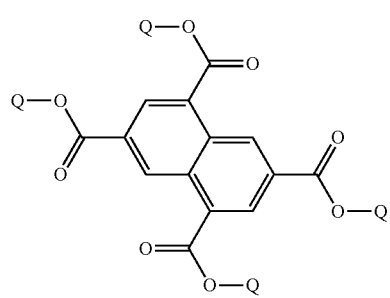
(1q)
$R^b\!-\!\!\!\overset{\displaystyle O}{\underset{}{C}}\!\!\!-\!O\!-\!Q$
(1r)
$R^b\!-\!O\!-\!Q$
(1s)
$R^4\!-\!\underset{R^5}{N}\!-\!Q$
wherein in formulae (1a) to (1s),
d is an integer of 1 to 14;
e is an integer of 0 to 13;

Q is a monovalent group represented by formula (Q-1) or (Q-2), and at least one Q is a monovalent group represented by formula (Q-2), wherein $R^a$ is hydrogen, —O., —OH, or —$R^1$;

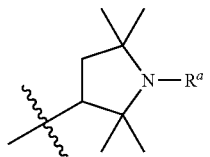
(Q-1)

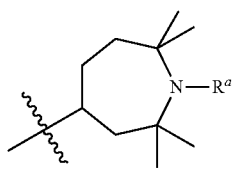
(Q-2)

$R^b$ is hydrogen or —$R^2$;
$R^1$ and $R^2$ are independently alkyl having 1 to 20 carbons, arylalkyl having 1 to 20 carbons, or aryl having 1 to 20 carbons, wherein at least one —$CH_2$— in the alkyl is optionally replaced with —O—; and $R^4$ and $R^5$ are independently alkyl having 1 to 10 carbons.

15. The compound according to claim 14, wherein in formulae (Q-1) and (Q-2) of claim 14, $R^a$ is hydrogen, —O., —OH, alkyl having 1 to 10 carbons, or alkoxy having 1 to 10 carbons.

16. The compound according to claim 11, represented by any one of formulae (1a-1), (1f), (1h), and (1n),

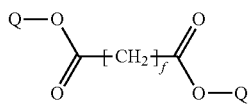
(1a-1)

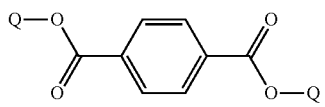
(1f)

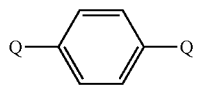
(1h)

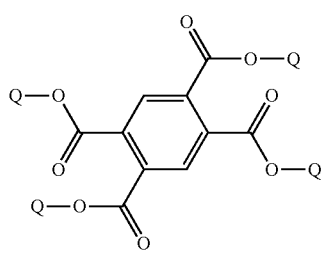
(1n)

wherein in formulae (1a-1), (1f), (1h), and (1n),
f is an integer of 1 to 12; and
Q is a monovalent group represented by formula (Q-1) or (Q-2), and at least one Q is a monovalent group represented by formula (Q-2), wherein $R^a$ is hydrogen or alkyl having 1 to 15 carbons;

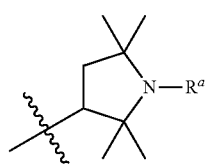
(Q-1)

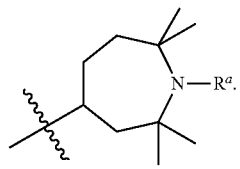
(Q-2)

17. A liquid crystal composition, containing at least one compound according to claim 11.

18. A liquid crystal display device, containing at least one liquid crystal composition according to claim 1.

* * * * *